US011932864B2

(12) United States Patent
Raab et al.

(10) Patent No.: US 11,932,864 B2
(45) Date of Patent: Mar. 19, 2024

(54) IMMUNOMODULATING TRANSGENIC PLANTS AND RELATED METHODS

(71) Applicant: AGRIVIDA, INC., Woburn, MA (US)

(72) Inventors: R. Michael Raab, Arlington, MA (US); Oleg Bougri, Winchester, MA (US); Matthew Parker, Cambridge, MA (US); Philip A. Lessard, Framingham, MA (US)

(73) Assignee: AGRIVIDA INC., Woburn, MA (US)

( * ) Notice: Subject to any disclaimer, the term of this patent is extended or adjusted under 35 U.S.C. 154(b) by 112 days.

(21) Appl. No.: 17/748,507

(22) Filed: May 19, 2022

(65) Prior Publication Data

US 2022/0282269 A1 Sep. 8, 2022

Related U.S. Application Data

(63) Continuation of application No. 16/609,633, filed as application No. PCT/US2018/034856 on May 29, 2018, now Pat. No. 11,390,879.

(60) Provisional application No. 62/512,444, filed on May 30, 2017.

(51) Int. Cl.

| | |
|---|---|
| ***C12N 15/82*** | (2006.01) |
| ***A61P 33/00*** | (2006.01) |
| ***C07K 14/54*** | (2006.01) |
| ***C07K 16/24*** | (2006.01) |
| *A61K 39/00* | (2006.01) |

(52) U.S. Cl.

CPC .......... *C12N 15/8258* (2013.01); *A61P 33/00* (2018.01); *C07K 14/5428* (2013.01); *C07K 16/244* (2013.01); *A61K 2039/505* (2013.01); *A61K 2039/542* (2013.01); *C07K 2317/13* (2013.01); *C07K 2317/22* (2013.01); *C07K 2317/23* (2013.01); *C07K 2317/569* (2013.01); *C07K 2317/76* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 8,652,457 | B2 | 2/2014 | Sand et al. |
| 8,802,825 | B2 | 8/2014 | Ludevid Mugica et al. |
| 2015/0208693 | A1 | 7/2015 | Gilbert et al. |
| 2016/0280778 | A1 | 9/2016 | Cook et al. |

FOREIGN PATENT DOCUMENTS

| | | | |
|---|---|---|---|
| CN | 103571796 | B | 4/2015 |
| WO | 2017059397 | A1 | 4/2017 |

OTHER PUBLICATIONS

Sand et al, 2016, Poultry Science, 95:439-446.*
Tschofen et al, 2016, Annu. Rev. Anal. Chem., 9:271-94.*
Rothwell et al, 2004, Journal of Immunology, 173:2675-2682.*
Arbabi Ghahroudi et al., 1997, Selection and identification of single domain antibody fragments from camel heavy-chain antibodies. FEBS Letters, 414(3), pp. 521-526.
Asadullah, Sterry and Volk, 2003, Interleukin-10 Theraphy—Review of a New Approach, Pharmacological Reviews, 55(2), pp. 241-269.
Bartlett, Snape and Harwood, 2009, Intron-mediated enhancement as a method for increasing transgene expression levels in barley, Plant Biotechnology Journal, 7, pp. 856-866.
Bombarely, Rosli, Vrebalov, Moffett, Mueller, and Martin, 2012, A draft genome sequence of *Nicotiana benthamiana* to enhance molecular plant-microbe biology research. Molecular Plant-Microbe Interactions 25, pp. 1523-1530.
Callis, Fromm, and Walbot, 1987, Introns increase gene expression in cultured maize cells, Genes Dev., 1, pp. 1183-1200 ; doi:10.1101/gad.1.10.1183.
Cervantes, 2002, Incidence of pathological conditions in clinically normal broilers from different regions of the USA. 51st Western Poultry Disease Conference, May 1-4, Casa Magna Marriott Resort, Puerto Vallart, Jalisco, Mexico, 220-223.
Cervantes, 2006, Incidence of subclinical diseases and pathological conditions in clinically normal broilers from 3 production complexes sorted by sex and age. 143rd Annual Convention of the American Veterinary Medical Association and 50th Annual Meeting of the American Association of Avian Pathologists, Jul. 15-19, Hawaii Convention Center, Honolulu, Hawaii.
Conley et al., 2009, Induction of protein body formation in plant leaves by elastin-like polypeptide fusions, BMC Biology, 7:48 doi:10.1186/1741-7007-7-48.
Couper, Blount, and Riley, 2008, IL-10: The master regulator of immunity to infection, The Journal of Immunology, 180, pp. 5771-5777.
Diaz-Valdes, Manterola, Belsue, Riezu-Boj, Larrea, Echeverria, LLopiz, Lopez-Sagaseta, Lerat, Pawlotsky, Prieto, Lasarte, Borras-Cuesta, and Sarobe, 2011, Improved dendritic cell-based immunization against hepatitis C virus using peptide inhibitors of Interleukin 10, Hepatology, 53, pp. 23-31.
Goldman et al., 2006, Facile generation of heat stable antiviral and antitoxin aingle domain antibodies from a semi-synthetic llama library, 78(24), pp. 8245-8255.

(Continued)

*Primary Examiner* — Jason Deveau Rosen
(74) *Attorney, Agent, or Firm* — Volpe Koenig

(57) ABSTRACT

The transgenic plants expressing one or more antagonist IL-10R peptides and anti-IL-10 single domain antibodies that stimulate or modulate the immune system and improve gastrointestinal physiology of an animal fed the transgenic plants or tissues thereof and the genes encoding the antagonist IL-10R peptides and anti-IL-10 single domain antibodies are described. The animal feed additives and animal feed incorporating the transgenic plants or tissues thereof are also described. Methods of stimulating or modulating an animal's immune system, improving an animal's gastrointestinal physiology, improving animal performance by using the transgenic plants or tissues thereof, and treating animals infected with a gastrointestinal pathogen are provided.

19 Claims, 23 Drawing Sheets

Specification includes a Sequence Listing.

(56) References Cited

OTHER PUBLICATIONS

Jacquet et al., 2014, Hydrophobin fusion of an influenza virus Hemagglutinin allows high transient expression in Nicotiana benthamiana, easy purification and immune response with neutralizing activity, PLOS One, DOI:10.1371/journal.pone. 0115944.
Johnson and Reid, 1970, Anticoccidial drugs: lesion scoring techniques in battery and floor-pen experiments with chickens, Experimental Parasitology, 28, pp. 30-36.
Josephson, Logsdon, and Walter, 2001, Crystal structure of the IL-10/IL-10R1 complex reveals a shared receptor binding site, Immunity 14, pp. 35-46.
Joensuu et al., 2010, Hydrophobin fusions for high-level transient protein expression and purification in Nicotiana benthamiana, Plant Physiology, vol. 152, pp. 622-633.
Lin et al., 2006, Functional expression of a biologically active fragment of soluble gp130 as an ELP-fusion protein in transgenic plants: purification via inverse transition cycling, Biochem. J., 398, pp. 577-583.
Liu et al., 2013, Selection and evaluation of single domain antibodies toward MS2 phage and coat protein. Molecular Immunology, 53(1-2), pp. 118-125.
Llop-Tous et al., 2011, The expression of a xylanase targeted to ER-protein bodies provides a simple strategy to produce active insoluble enzyme polymers in tobacco plants, PLoS One 6(4): e19474. doi:10.1371/journal.pone.0019474.
Mainieri et al., 2004, Zeolin. A New Recombinant Storage Protein Constructed Using Maize g-Zein and Bean Phaseolin, Plant Physiology, , vol. 136, pp. 3447-3456.
Nakasugi, Crowhurst, Bally, Wood, Hellens, Waterhouse, 2013, De Novo transcriptome sequence assembly and analysis of RNA silencing genes of *Nicotiana benthamiana*. PLoS One 8(3): e59534. https://doi.org/10.1371/ journal.pone.0059534.
Naiyer, Saha, Hemke, Roy, Singh, Musti, and Saha, 2013, Identification and characterization of a human IL-10 receptor antagonist, Human Immunology, 74, pp. 28-31.
Ni, Chen, Yang, Cummins, Zhan, Li, Zhu, Mounsey, Walton, Wei, Wang, Zhou, Wang, and Liu, 2016, Investigation the possibility of using peptides with a helical repeating pattern of hydrophobic and hydrophilic residues to inhibit IL-10, PLS One, 11(4): e0153939. doi:10.1371/journal.pone.0153939.
Patel et al., 2007, Elastin-like polypeptide fusions enhance the accumulation of recombinant protein in tobacco leaves, Transgenic Res, 16, pp. 239-249.
Reina et al. 1990, DNA sequence of the gene encoding the Zcl protein from *Zea mays* W64 A, Nucleic Acids Research, vol. 18, No. 21., p. 6425.
Reineke, Sabat, Volk, and Schneider-Mergener, 1998, Mapping of the interleukin-10/interleukin-10 receptor combining site, Protein Sci. 7, pp. 951-960.
Rothwell, Young, Zoorob, Whittaker, Hesketh, Archer, Smith, and Kaiser, 2004, Cloning and characterization of chicken IL-10 and its role in the immune response to Eimeria maxima, J. Immunol. 173, pp. 2675-2682.
Smith, and Waterman, 1981, Identification of Common Molecular Subsequences, J Mol Biol 147, pp. 195-197.
Urry et al. , 1992, Hydrophobicity-induced pK shifts in elastin protein-based polymers, Biopolymers, vol. 32, pp. 373-379.
Vasil, Clancy, Ferl, Vasil, and Hannah, 1989, Increased Gene Expression by the First Intron of Maize Shrunken-1 Locus in Grass Species, Plant Physiol. 9, pp. 1575-1579.
Wu, Hu, Rothwell, Vervelde, Kaiser, Boulton, Nolan, Tomley, Blake, and Hume, 2016, Analysis of the function of IL-10 in chickens using specific neutralizing antibodies and a sensitive capture ELISA, Devel. Comp. Immunol. 63, pp. 206-212.
Yoon, Jones, Logsdon, and Walter, 2005, Same structure, different function: crystal structure of the Epstein-Barr virus IL-10 bound to the soluble IL-10R1 chain, Structure 13, pp. 551-564.
Zdanov, Schalk-Hihi, and Wlodawer, 1996, Crystal structure of human interleukin-10 at 1.6 A resolution and a model of a complex with its soluble receptor, Protein Sci. 5, pp. 1955-1962.
Arendt et al., 2016 "Interleukin-10 neutralizing antibody for detection of intestinal luminal levels and as a dietary additive in Eimeria challenged broiler chicks," Poult Sci, vol. 95, No. 2 pp. 430-438.
De Meyer et al., 2015, "Comparison of VHH-Fc antbody production in *Arabidopsis thaliana*, Nicotiana benthamiana, and Pichia pastoris," Plant Biotechnol J., vol. 13, No. 7, pp. 938-947.
Lizuka et al., 2014, "Prophylactic effect of the oral administration of transgenic rice seeds containing altered peptide ligands of type II collagen on rheumatoid arthritis," Biosci Biotechnol Biochem, vol. 87, No. 10, pp. 1662-1668.
Piazzon et al., 2016, "A tale of an evolutionary conserved cytokine across vertebrates," Crit Rev Immunol, vol. 36, No. 2, pp. 99-129.
International Search Report and Written Opinion issued in corresponding International Patent Appln. No. PCT/US2018/34856 dated Oct. 30, 2018.
Sand et al., 2016, Oral antibody to interleukin-10 reduces growth rate depression due to *Eimeria* spp. infection in broiler chickens, Poultry Science, vol. 95(2), pp. 439-446.
Lessard et al., 2020, Improved performance of Eimeria-infected chickens fed corn expressing a single-domain antibody against interleukin-10, Nature Food , pp. 119-126.
Office Action issued for European. Patent Application No. 8808980.9 dated Feb. 5, 2021.
Anonymous: "IL-10-Interleukin-10 precursor—*Gallu gallus* (chicken)—IL 10 gene & protein," Jul. 27, 2007, Retrieved from Internet: URL:https://uniprot.org (UniProtKQ6A2H4(IL10_Chick).
Office Action issued for European. Patent Application No. 8808980.9 dated May 31, 2021.
Walter, 2014, The Molecular Basis of IL-10 Function: From Receptor Structure to the Onset of Signaling, Curr Top Microbiol Immunology, 380: 191-212.
Rothwell et al., 2004, Cloning and Characterization of Chicken IL-10 and Its Role in the Immune Response to Eimeria maxima Journal of Immunology, 173: 2675-2682.
Tschofen et al., 2016, Plant Molecular Farming: Much More than Medicines, Annu. Rev. Anal Chem, 9: 271-94.
Otvos Jr. et al. 2014, Current Challenges in peptide-based drug discovery, Frontiers in Chemistry, 2:1-4.
Office Action issued for Chinese Patent Application No. 201880036216.X dated Mar. 1, 2022.
Pan Hong et al. 2011, Role and Application of Cytokines against Chicken Coccidiosis, China Animal Husbandry & Veterinary Medicine, vol. 38 » Issue (7): 176-179. Abstract in English.
Gao Jun-Feng et al. Dec. 22, 2016, Development and Identification of monoclonal antibodies against chIL-10, Chinese Journal of Veterinary Medicine, No. 10. Abstract in English.
Yang Cheng-huai et al. May 20, 2003, Reserach progress of edible vaccine from transgenic plants, Advances in Animal Medicine, No. 3. Abstract in English.

* cited by examiner

IMMUNOMODULATING TRANSGENIC PLANTS AND RELATED METHODS

CROSS REFERENCE TO RELATED APPLICATION

This application is a continuation of U.S. patent application Ser. No. 16/609,633 filed on Oct. 30, 2019 as US National Stage of International Patent Application No. PCT/US2018/034856, which was filed on May 29, 2018, and claimed the benefit of U.S. provisional application No. 62/512,444 filed May 30, 2017; all of which are incorporated herein by reference as if fully set forth.

The sequence listing electronically filed with this application titled "Sequence Listing," which was created on May 19, 2022 and had a size of 485,841 bytes is incorporated by reference herein as if fully set forth.

FIELD OF INVENTION

This disclosure relates to antagonist IL-10 receptor (IL-10R) peptides and anti-IL-10 antibodies, including anti-IL-10 single domain antibodies. This disclosure relates to transgenic plants that express and accumulate antagonist IL-10R peptides and anti-IL-10 single domain antibodies that stimulate or modulate the immune system and improve gastrointestinal physiology of an animal fed the transgenic plants or tissues thereof. This disclosure also relates to the genes encoding these peptides and antibodies.

This disclosure relates to animal feed additives and animal feed that incorporates the transgenic plants or tissues thereof including the peptides and antibodies. This disclosure also relates to animal feed additives and animal feed that incorporates the peptides and antibodies.

This disclosure relates to methods of treating animals infected with a gastrointestinal pathogen by administering to them antagonist IL-10R peptides and anti-IL-10 single domain antibodies, transgenic plants expressing the peptides and antibodies disclosed herein, or feeding animals with animal feed that includes these transgenic plants, peptides or antibodies. The disclosure also relates to methods of stimulating or modulating an animal's immune system, methods of improving an animal's gastrointestinal physiology, methods of improving animal performance by using the disclosed transgenic plants or tissues thereof, antagonist IL-10R peptides, or anti-IL-10 single domain antibodies.

This disclosure relates to methods of making antagonist IL-10R peptides and anti-IL-10 single domain antibodies, and methods of making transgenic plants expressing the peptides and antibodies disclosed herein.

The sequence listing electronically filed with this application titled "Sequence Listing," created on May 30, 2017, and having a file size of 210,215 bytes is incorporated herein by reference as if fully set forth.

BACKGROUND

Coccidiosis is a common poultry disease caused by protozoan parasites that infect the gastrointestinal tract (Cervantes, H., 2002; Cervantes, H., 2006).

The disease spreads from one animal to another by contact with infected feces or ingestion of infected tissue. Coccidiosis in chickens is caused by infection of the intestinal lining cells by parasitic protozoa of the genus *Eimeria*, and commonly by *Eimeria tenella*. The most common medications used to treat coccidial infections are anti-Coccidial drugs, antibiotics, and vaccines.

Anti-Coccidial drugs and Coccidiostats are used in poultry production to control Coccidiosis and maintain animal productivity, which generally decreases when animals are infected by *Eimeria*, and develop subclinical or clinical Coccidiosis. Clinical Coccidiosis results in disruption of the digestive tract, and symptoms include weight loss, growth suppression, diarrhea, bloody droppings and increased mortality. Subclinical Coccidiosis is common in poultry production, even when employing current Coccidiostats or vaccines, and does not present many of the same symptoms as clinical Coccidiosis, but still decreases animal productivity. The reduced animal productivity from Coccidiosis results in significant losses for the poultry industry, estimated at over one billion US dollars per year.

Anti-Coccidial drugs, antibiotics, and vaccines are important for efficient poultry production, but are being phased out in many countries due to consumer concerns over their use and safety. Vaccine use is challenged by incomplete immunity within the flock, and anti-Coccidial drugs are costly, need to be administered at the right time and dose, and can lead to the development of resistant *Eimeria* strains. Industry has witnessed a rise in the number of drug-resistant strains, which lowers the value of these products and necessitates the development of other methods for controlling Coccidiosis.

*Eimeria* stimulates production of an anti-inflammatory cytokine interleukin 10 (IL-10). IL-10 interacts with its receptor IL-10R in the intestinal lining to suppress the immune response. In turn, this allows *Eimeria* infection to proceed without interference from the immune system. IL-10 is a potent anti-inflammatory cytokine that helps animals control inflammation responses. IL-10 also controls the immune system to prevent hyper immune responses. Blocking IL-10 to prevent its interaction with IL-10R would prevent immune suppression, and thus, helps the animal's normal immune response to reduce and clear *Eimeria* infection. In contrast to other prophylactic or therapeutic approaches to controlling Coccidiosis, blocking IL-10 suppression of the immune system should not lead to the development of resistant *Eimeria* strains because such intervention focuses on stimulating the host's immune response and not on attenuating or killing the infectious agent itself.

As previously described, this approach currently suffers from significant limitations that have prevented widespread commercial adoption and industrial use. First, the antibodies used thus far have been generated by inoculating either a maternal hen, or eggs, with the target peptide. In the case of the former, only chicks from the inoculated hen may be used, requiring the inoculation of many hens for chick production, and full protection is not guaranteed due to inadequate immunity, an ineffective peptide (stimulating antigen), or an unprolonged response. Peptide effectiveness may also be challenged since it is well known that small peptides often do not mobilize an effective immune response, and because IL-10 (or IL-10 homologs) is produced by the host, it may be difficult to generate adequate antibodies without the use of adjuvants or conjugates, which further increases the cost and complexity of this approach. Furthermore, because IL-10 is known to dimerize in vivo, selected peptides may generate antibodies to epitopes that are not normally exposed by the IL-10 dimer and therefore may be ineffective in binding IL-10 in the host animal. Likewise, inoculating eggs (or collecting eggs from inoculated hens) is cumbersome and increases costs, suffers from many of the same issues that challenge hen inoculation, and adds additional costs when the antibodies must be harvested from the yolks. In the case where the antibodies are harvested from the eggs, the material must be dried, stabilized, and then mixed into feed to deliver to chicks. While the added processing steps (including harvesting the eggs, drying, formulating and packaging for feed addition), add extra cost, it is unclear how consistent this production method will be, how susceptible it is to contamination by other infectious agents, or whether the antibodies generated in this manner will be thermally stable enough to survive the pelleting processes used in preparing animal feed. Many full-length antibodies do not possess the thermal stability required to maintain their solubility, structure, and affinity for IL-10, when combined with animal feed and processed through a pellet mill. Antibodies delivered in pelleted feed will be exposed to pelleting temperatures that may be 65° C., 70° C., 75° C., 80° C., 82° C., 85° C., 90° C., 95° C., or even greater. For these reasons, using eggs to produce antibodies for animal feed is a very challenging, high-cost practice, and because the antibodies are never fully sequenced or characterized, this production method precludes the use of biotechnology to improve antibody properties and the cost, efficiency, and efficacy of production. Therefore, new technologies are greatly needed if modulation of the IL-10 signaling pathway is to achieve any market relevance in the animal production industry. To address these shortcomings, there exists a need for a novel, low-cost feed additive that ideally is delivered in existing diet ingredients, that has increased thermal stability to endure the feed pelleting process, and that can more effectively inhibit the IL-10 signaling process.

SUMMARY

In an aspect, the invention relates to a transgenic plant or tissues thereof comprising a synthetic polynucleotide encoding at least one antagonist IL-10R peptide, or an anti-IL-10 single domain antibody.

In an aspect, the invention relates to at least one antagonist IL-10R peptide. The at least one antagonist IL-10R peptide is one peptide comprising an amino acid sequence with at least 90% identity to a reference sequence selected from the group consisting of: SEQ ID NOS: 1-13. The at least one antagonist IL-10R peptide comprises concatenated peptides comprising an amino acid sequence with at least 90% identity to a reference sequence selected from the group consisting of: SEQ ID NOS: 32-40.

In an aspect, the invention relates to a synthetic polynucleotide encoding the at least one IL-10R antagonist peptide described herein.

In an aspect, the invention relates to an anti-IL-10 single domain antibody that binds to a polypeptide comprising an amino acid sequence of SEQ ID NO: 80.

In an aspect, the invention relates to a synthetic polynucleotide encoding any one of the anti-IL-10 single domain antibodies described herein.

In an aspect, the invention relates to an animal feed comprising any one of the transgenic plants or tissues thereof described herein.

In an aspect, the invention relates to an animal feed comprising any of the antagonist IL-10R peptides, or anti-IL-10 single domain antibodies described herein.

In an aspect, the invention relates to a method of treating or preventing a gastrointestinal infection in an animal comprising feeding the animal any one of the transgenic plants or tissues thereof, antagonist IL-10R peptides, anti-IL-10 single domain antibodies, or animal feed described herein.

In an aspect, the invention relates to a method of stimulating or modulating the immune system and improving gastrointestinal physiology of an animal comprising feeding the animal any one of the transgenic plants or tissues thereof, antagonist IL-10R peptides, anti-IL-10 single domain antibodies or the animal feed described herein.

In an aspect, the invention relates to a method of improving animal performance comprising feeding an animal any one of the transgenic plants or tissues thereof, antagonist IL-10R peptides, anti-IL-10 single domain antibodies or animal feed described herein.

In an aspect, the invention relates to a method of preparing an animal feed comprising mixing any one of the transgenic plants or tissues thereof described herein with plant material to form a mixture.

In an aspect, the invention relates to a method of preparing an animal feed comprising mixing any one of the antagonist IL-10R peptides or anti-IL-10 single domain antibodies described herein with plant material to form a mixture.

In an aspect, the invention relates to a method of preparing a transgenic plant or tissues thereof comprising any of the antagonist IL-10R peptides or anti-IL-10 single domain antibodies described herein.

BRIEF DESCRIPTION OF THE DRAWINGS

The following detailed description of preferred embodiments of the present invention will be better understood when read in conjunction with the appended drawings. For the purpose of illustrating the invention, particular embodiments are shown in the drawings. It is understood, however, that the invention is not limited to the precise arrangements and instrumentalities shown. In the drawings.

DETAILED DESCRIPTION OF THE PREFERRED EMBODIMENTS

Figure 1A:
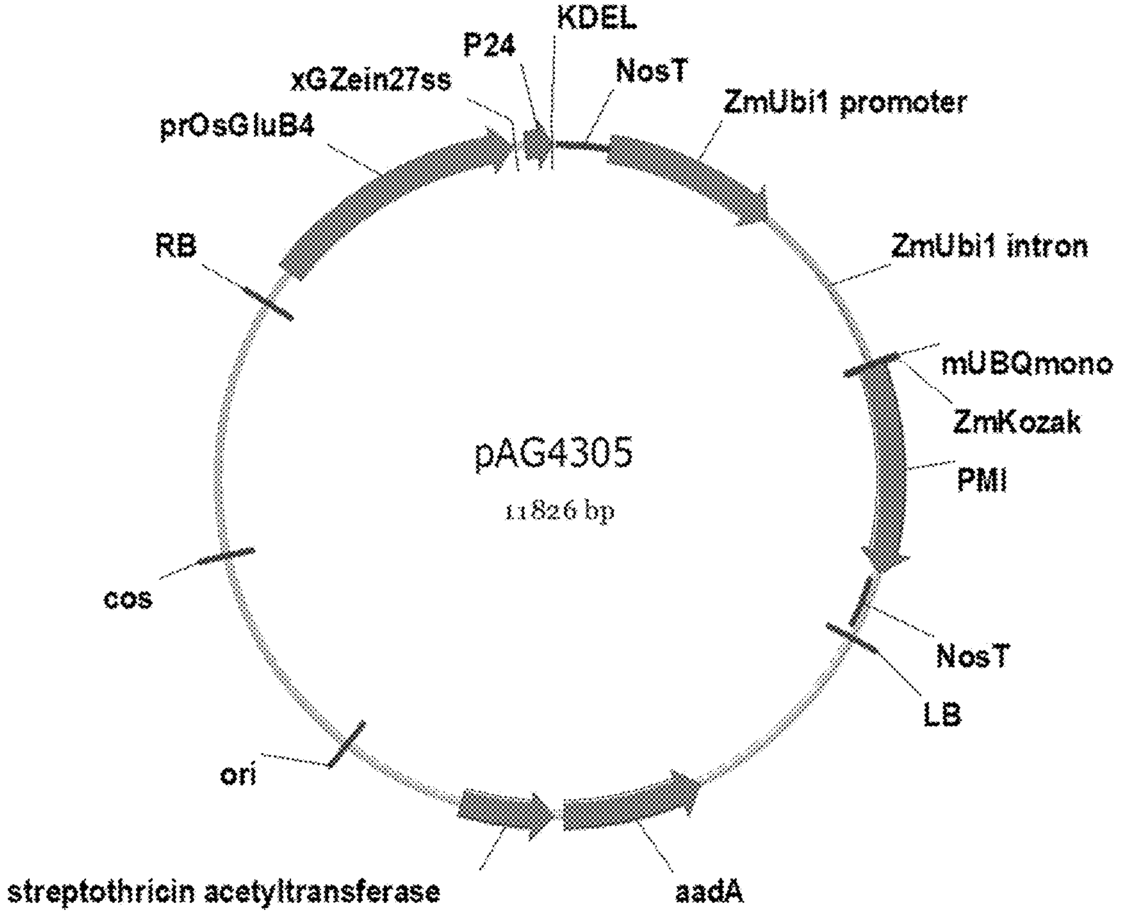
FIGS. 1A-1G are schematic drawings of the vectors pAG4305 (FIG. 1A), pAG4306 (FIG. 1B), pAG4308 (FIG. 1C), pAG4310 (FIG. 1D), pAG4311 (FIG. 1E), pAG4312 (FIG. 1F), and pAG4313 (FIG. 1G).
Figure 1B:
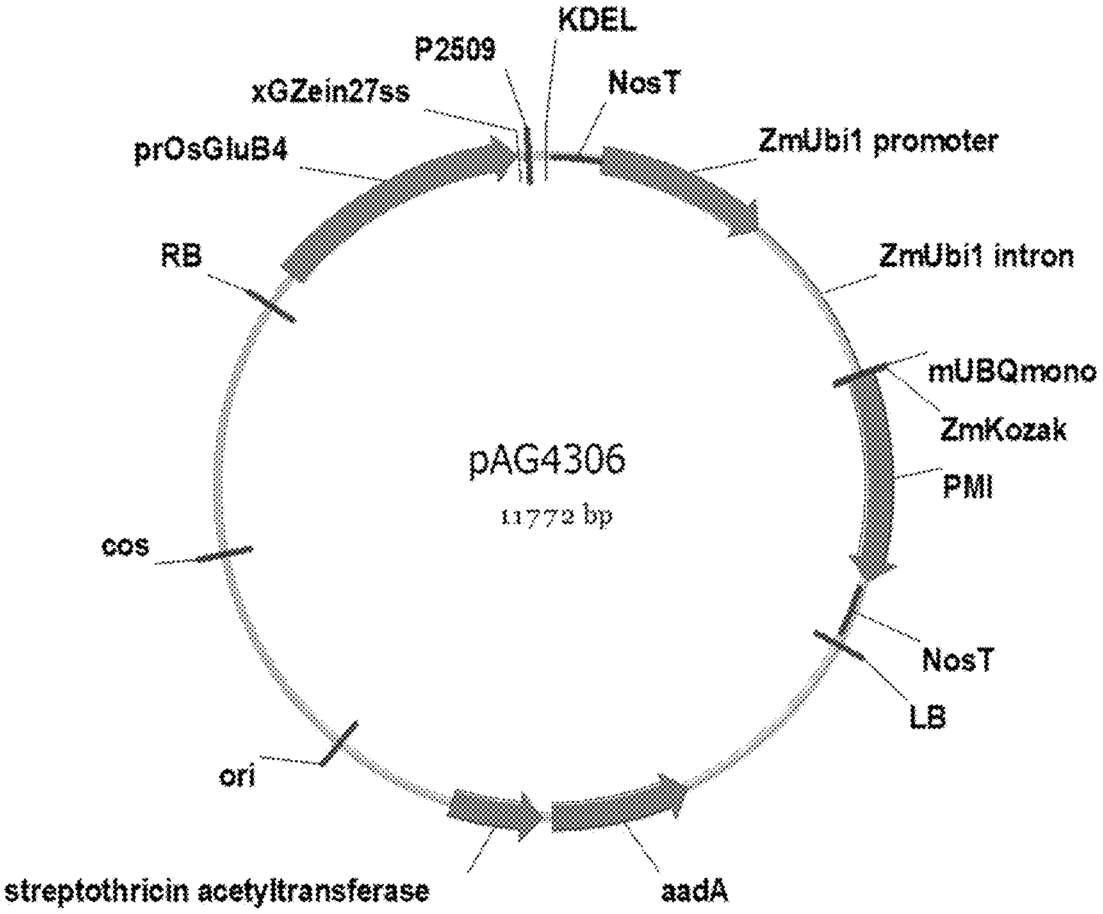
Figure 1C:
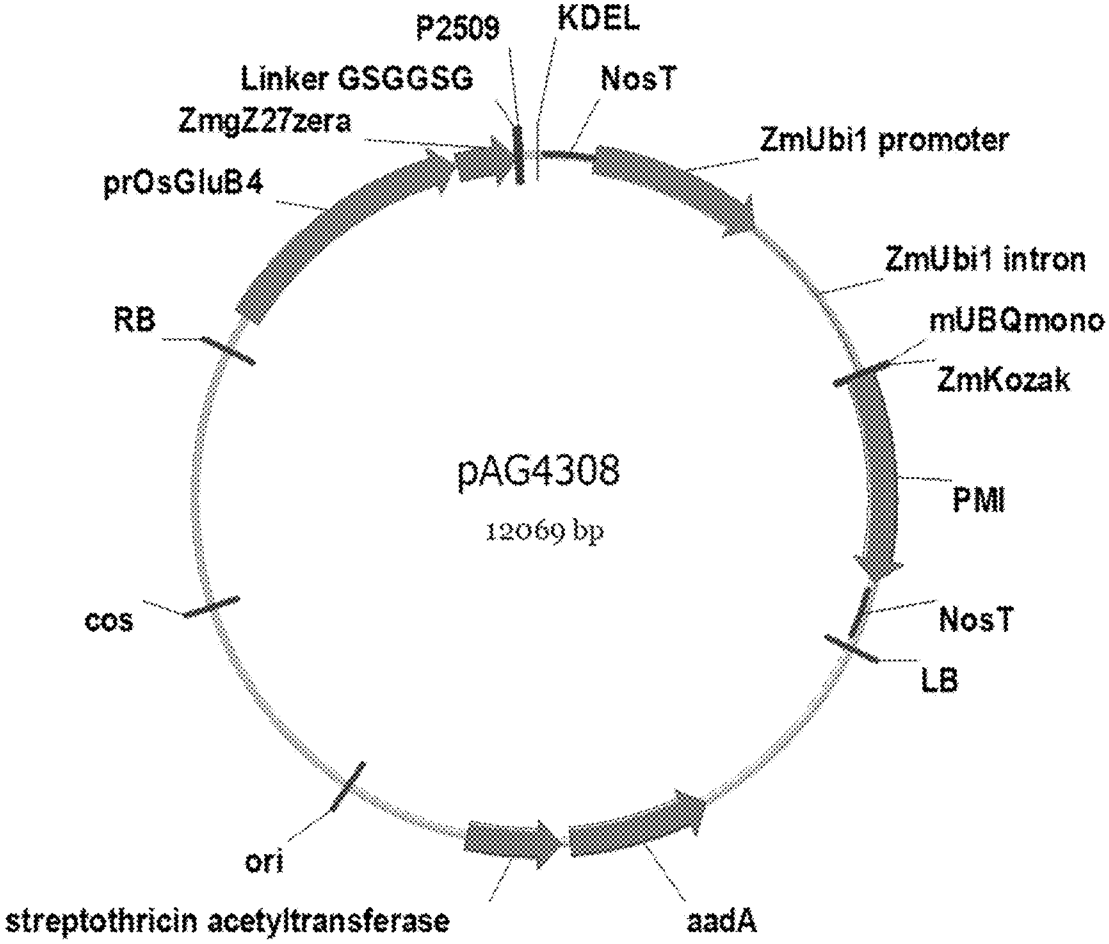
Figure 1D:
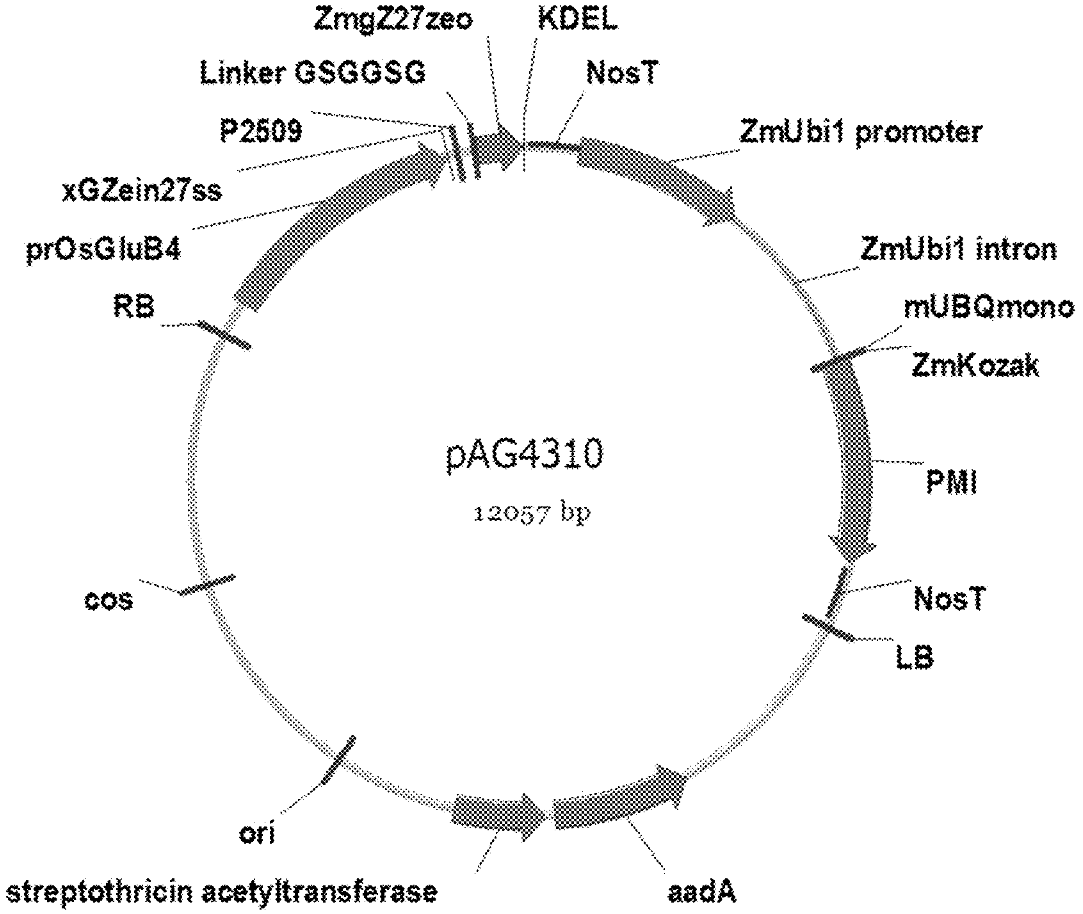
Figure 1E:
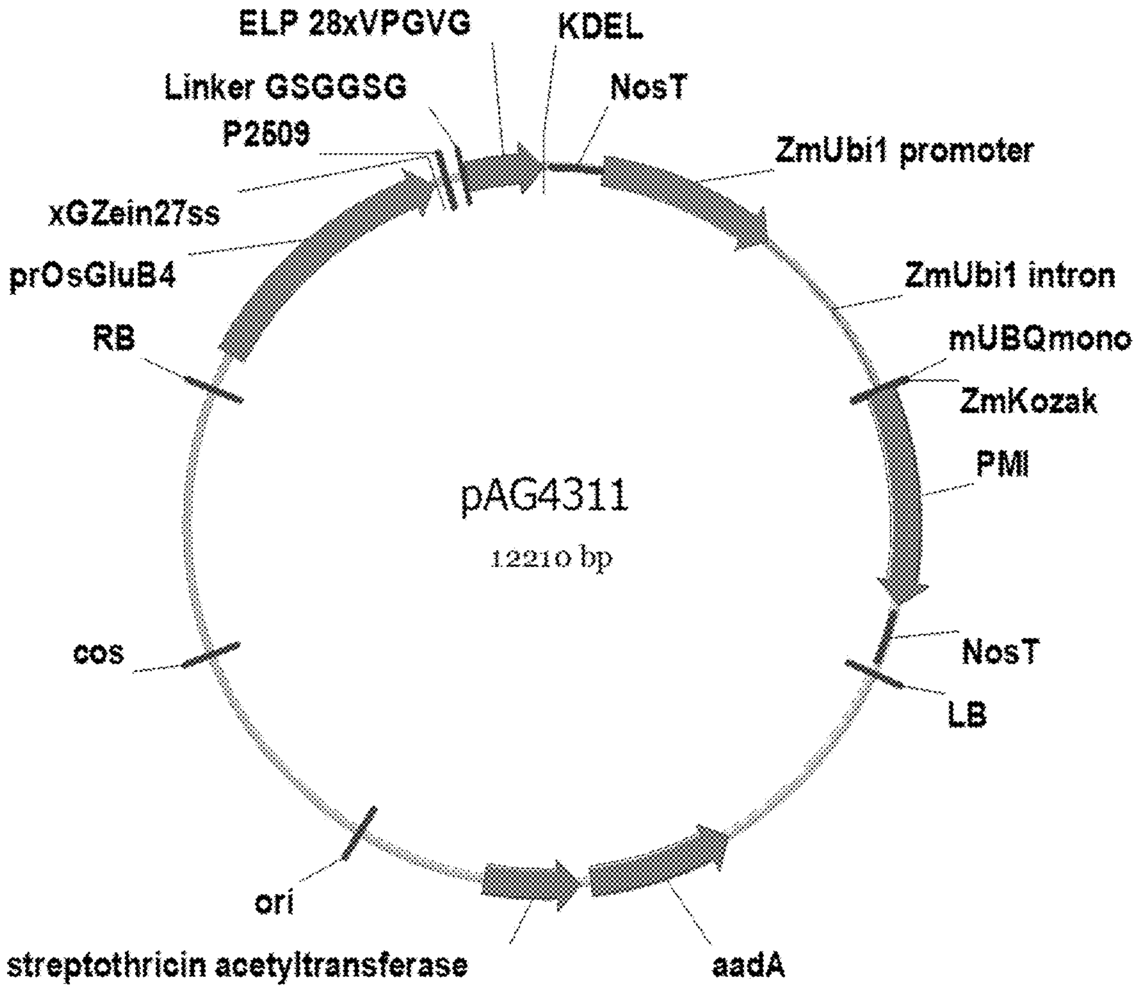
Figure 1F:
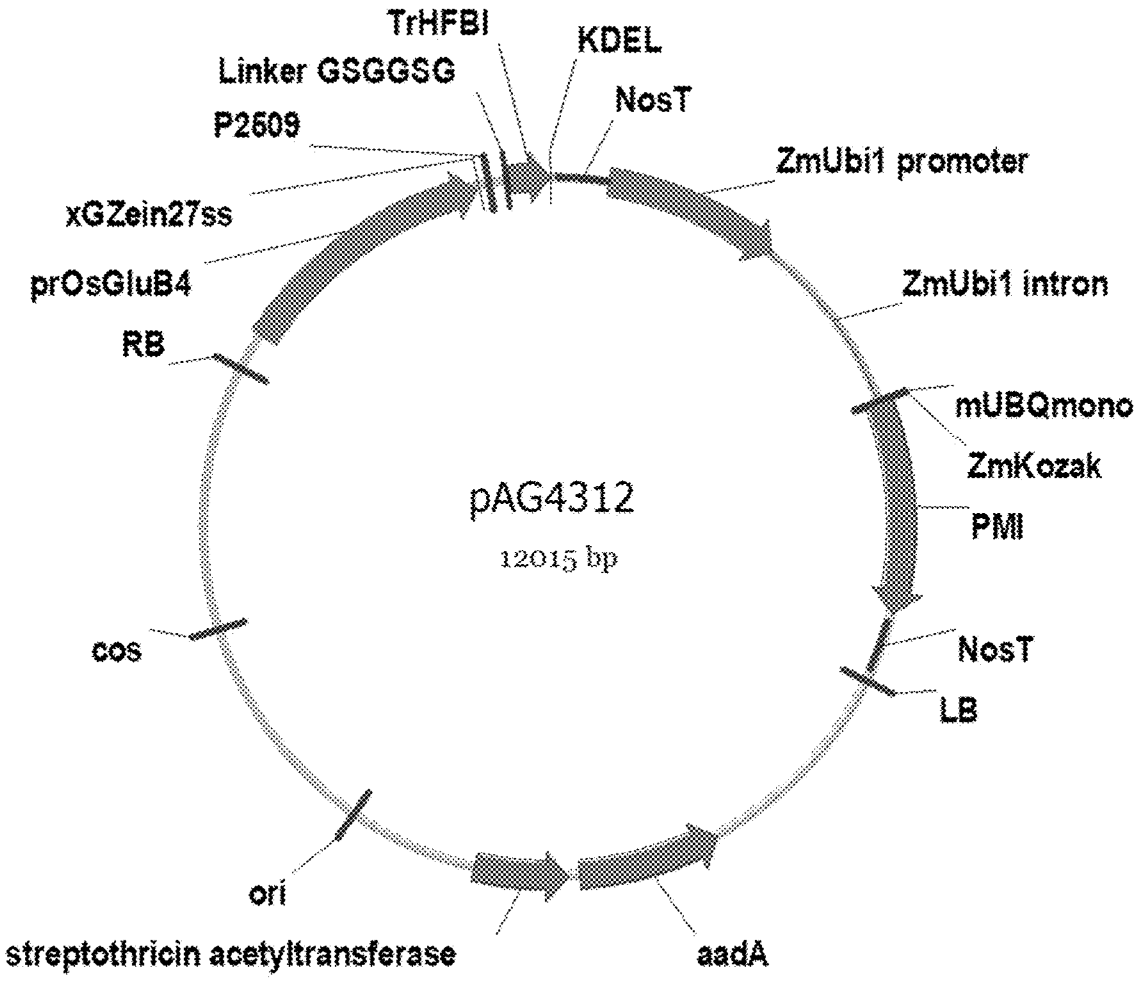

Certain terminology is used in the following description for convenience only and is not limiting.

"Synthetic nucleic acid sequence," "synthetic polynucleotide," "synthetic oligonucleotide," "synthetic DNA," or "synthetic RNA" as used herein refers to a nucleic acid sequence, a polynucleotide, an oligonucleotide, DNA, or RNA that differs from one found in nature by having a different sequence that one found in nature or a chemical modification not found in nature. The definition of synthetic nucleic acid includes but is not limited to a DNA sequence created using biotechnology tools. Such tools include but are not limited to recombinant DNA technology, chemical synthesis, or directed use of nucleases (so called "genome editing" or "gene optimizing" technologies).

"Synthetic protein," "synthetic polypeptide," "synthetic oligopeptide," or "synthetic peptide" as used herein refers to a protein, polypeptide, oligopeptide or peptide that was made through a synthetic process. The synthetic process includes but is not limited to chemical synthesis or recombinant technology.

As used herein, the terms "interleukin 10," "IL10" and "IL-10" are used interchangeably, and refer to cytokine synthesis inhibitory factor, i.e., an anti-inflammatory cytokine. The terms "cIL-10," "cIL10", "chIL10", and "chIL-10" refer to the chicken interleukin 10.

As used herein, the terms "antagonist IL-10R peptide," "antagonist IL10R," "IL10R antagonist peptide," and "IL-10R antagonist peptide" are used interchangeably, and refer to peptides that are inhibitors of IL-10 receptors (IL-10R). The IL-10R antagonist peptides may be fragments of IL-10, or may differ from the fragments of IL-10. The IL-10R antagonist peptide may be an antagonist derived from the IL-10R. The IL-10R antagonist peptide may be fusion of the peptides, concatenation of the peptides, or any other peptides that are capable of blocking or antagonizing IL-10 receptors. The IL-10R antagonist peptides can block or antagonize receptors in any way, e.g., by blocking the IL-10 binding pockets of the IL-10 receptors, preventing IL-10 from binding to the receptors, blocking IL-10 dimerization, or IL-10 receptor assembly, or allowing IL-10 binding to the receptors but blocking subsequent signal transduction. The IL-10R antagonist peptides can block or antagonize IL-10 receptors by any mechanism or mode of action.

"Antibody" as used herein refers to an immunoglobulin molecule which specifically binds with an antigen.

"Synthetic antibody" as used herein refers to an antibody which is generated using recombinant DNA technology, such as, for example, an antibody expressed by a host engineered to produce the antibody, such as a mammalian cell, microbial cell, or plant as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. A "synthetic antibody" described herein may include fragments and hybrids of antibodies. A "synthetic antibody" described herein may be generated by an organism that is dosed with a specific antigen, and the antibody generated by the organism is isolated and propagated in a second organism.

A "single domain antibody," or sdAB, refers to a synthetic antibody that is a small monomeric antigen-binding fragment of an antibody, i.e., the variable region of an antibody heavy or light chain. sdABs can be derived from antibodies that occur naturally or are generated in camelids, e.g., camels, and llamas, and may be produced by immunizing a camelid with a target antigen, isolating peripheral blood mononucleocytes, isolating their nucleic acids, and cloning sdAB coding regions from specific nucleic acid fragments.

sdABs may be also produced in cell culture, by microbial hosts in a fermentation process, or by plants. An antibody described herein may be a sdAB comprising a VHH domain substantially as set out herein. A single domain antibody is a synthetic antibody.

"Antigen" as used herein is defined as a molecule that triggers an immune response. The immune response may involve either antibody production, or the activation of specific immunologically active cells, or both. The antigen may refer to any molecule capable of stimulating an immune response, including macromolecules such as proteins or peptides. The antigen may be synthesized, produced recombinantly in a mammalian, insect, microbial or plant cell, or may be derived from a biological sample, including but not limited to a tissue sample, a cell, or a biological fluid.

"Binding affinity" refers to the sum total noncovalent interaction between members of binding pairs, e.g., an antibody and antigen. The binding affinity of the antibody can be determined based on apparent binding EC50 value. As used herein, the term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing chicken IL-10, as determined by, e.g., an ELISA assay. Thus, reduced or weaker binding is observed with an increased $EC_{50}$, or half maximal effective concentration value.

As used herein, "variant" refers to a protein or DNA molecule that has an amino acid or nucleic acid sequence that differs from the original sequence but retains a biological activity that is the same or substantially similar to that of the original sequence. The variant may be from the same or different species or be a synthetic sequence based on a natural or prior molecule.

The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

In an embodiment, one or more antagonist IL-10R peptides is provided. The antagonist IL-10R peptide may be expressed separately as one antagonist IL-10R peptide. The antagonist IL-10R peptide may include an amino acid sequence with at least 70, 72, 75, 80, 85, 90, 91, 92, 93, 94, 95, 96, 97, 98, 99 or 100% identity to a reference sequence selected from the group consisting of: SEQ ID NO: 1 [P21], SEQ ID NO: 2 [P22], SEQ ID NO: 3 [P23], SEQ ID NO: 4 [P24], SEQ ID NO: 5 [P25], SEQ ID NO: 6 [P26], SEQ ID NO: 7 [P27], SEQ ID NO: 8 [P28], SEQ ID NO: 9 [P29], SEQ ID NO: 10 [P11], SEQ ID NO: 11 [P30], SEQ ID NO: 12 [P31], and SEQ ID NO: 13 [P32].

An antagonist IL-10R peptide may be expressed in the form of concatenated antagonist IL-10R peptides. The concatenated antagonist IL-10R peptides may comprise a first antagonist IL-10R peptide having an amino acid sequence with at least 70, 72, 75, 80, 85, 90, 91, 92, 93, 94, 95, 96, 97, 98, 99 or 100% identity to a reference sequence selected from the group consisting of SEQ ID NOS: 1-13 fused to a second antagonist IL-10R peptide having an amino acid sequence with at least 70, 72, 75, 80, 85, 90, 91, 92, 93, 94, 95, 96, 97, 98, 99 or 100% identity to a reference sequence selected from the group consisting of SEQ ID NOS: 1-13. The first antagonist IL-10R peptide may differ from the second antagonist IL-10R peptide. The first antagonist IL-10R peptide may be similar to the second antagonist IL-10R peptide. The concatenated antagonist IL-10R peptides may have more than two antagonist IL-10R peptides. Each of the first antagonist IL-10R peptide and the second antagonist IL-10R peptide included in the concatenated antagonist IL-10R peptides may have an amino acid sequence with at least 70, 72, 75, 80, 85, 90, 91, 92, 93, 94, 95, 96, 97, 98, 99 or 100% identity to a reference sequence selected from the group consisting of SEQ ID NOS: 1-13. Subsequent antagonist IL-10R peptides may differ from the first and second antagonist IL-10R peptides and from each other. Subsequent antagonist IL-10R peptides may be similar to the first and the second antagonist IL-10R peptide and to each other. The concatenated antagonist IL-10R peptides may comprise an amino acid sequence with at least 70, 72, 75, 80, 85, 90, 91, 92, 93, 94, 95, 96, 97, 98, 99 or 100% identity to a reference sequence selected from the group consisting of SEQ ID NO: 32 [P2501], SEQ ID NO: 33 [P2502], SEQ ID NO: 34 [P2503], SEQ ID NO: 35 [P2504], SEQ ID NO: 36 [P2505], SEQ ID NO: 37 [P2506], SEQ ID NO: 38 [P2507], SEQ ID NO: 39 [P2508], and SEQ ID NO: 40 [P2509]. The first antagonist IL-10R peptide may be linked to the second antagonist IL-10R peptide by a linker. Each of the first, the second and the subsequent antagonist IL-10R peptides may be linked to each other by one or more linkers. The one or more linker may be selected from the group consisting of SEQ ID NOS: 41-44, and 65. The antagonist IL-10R peptide or the concatenated antagonist IL-10R peptides may comprise a signal peptide. The signal peptide may be but is not limited to an amyloplast targeting signal, a cell wall targeting peptide, a mitochondrial targeting peptide, a cytosol localization signal, a chloroplast targeting signal, a nuclear targeting peptide, or a vacuole targeting peptide. The signal peptide may an N-terminal signal peptide or a C-terminal signal peptide. The N-terminal signal peptide may be but is not limited to OsGluB4sp (rice Glu-B4 glutelin signal peptide), BAASS (barley alpha amylase signal sequence), PR1 (pathogenesis related protein), or zein 27 (xGZm27ss) signal peptide. The C-terminal signal peptide may be but is not limited to KDEL (SEQ ID NO: 29), HDEL (SEQ ID NO: 30), SEKDEL (SEQ ID NO: 31), HvVSD from barley polyamine oxidase, or HvAle from barley aleurone (thiol protease). The IL-10R antagonist peptide or the concatenated IL-10R antagonist peptides may be fused to the N-terminal signal peptide or C-terminal signal peptide, or both.

The antagonist IL-10R peptide, or the concatenated antagonist IL-10R peptides may be capable of reducing IL-10 binding to the IL-10R. The antagonist IL-10R peptide, or the concatenated antagonist IL-10R peptides may decrease the production of interferon gamma or nitric oxide when used in a cellular assay comprising cells that are stimulated by IL-10 to increase production of interferon gamma or nitric oxide.

In an embodiment, the antagonist IL-10R peptide having less than 100% identity to its corresponding amino acid sequence of SEQ ID NO: 1-13 or 32-40 may be a variant of the referenced peptide or amino acid. In an embodiment, an isolated peptide having a sequence with at least 70, 75, 80, 85, 90, 91, 92, 93, 94, 95, 96, 97, 98, 99, or 100% identity to a peptide having the sequence of any one of SEQ ID NOS: 1-13 and 32-40 along 7 to 10, 7 to 15, 7 to 30, 7 to 40, 7 to 50, or 7 to all amino acids of a protein having the sequence of any of one any one of SEQ ID NOS: 1-13 and 32-40 is provided. This list of sequence lengths encompasses every full length peptide in SEQ ID NOS: 1-13 and 32-40 and every smaller length within the list, even for peptides that do not include over 50 amino acids. For example, the lengths of 7 to 10, 7 to 20, 7 to 30, and 7 to all amino acids would apply to a sequence with 50 amino acids. A range of amino acid sequence lengths recited herein includes every length of amino sequence within the range, endpoints inclusive. The recited length of amino acids may start at any single position within a reference sequence where enough amino acids follow the single position to accommodate the recited length. The fragment of the antagonist IL-10R peptide may be a subsequence of the polypeptides herein that retain at least 40% of the antagonist IL-10R peptide $EC_{50}$ value when used in a cellular assay comprising cells that are inhibited by IL-10 (in the presence of ConA or PHA) to decrease production of interferon gamma or nitric oxide. The fragment may have 5, 7, 8, 9, 10, 15, 20, 25, 30, 35, 40, 45 or 50 amino acids. The fragments may include 5, 7, 8, 9, 10, 15, 20, 25, 30, 35, 40, 45 or 50 contiguous amino acids. Embodiments also include nucleic acids or polynucleotides, encoding said amino acid sequences. A less than full length amino acid sequence may be selected from any portion of one of the sequences of SEQ ID NOS: 1-13 and 32-40 corresponding to the recited length of amino acids. A less than full length amino acid sequence may be selected from a portion of any one of SEQ ID NOS: 1-13 and 32-40.

In an embodiment, an antagonist IL-10R peptide or concatenated antagonist IL-10R peptides may maintain or improve the body weight, and, or the feed conversion ratio, of poultry fed the peptides relative to poultry fed the same feed lacking the peptides. The antagonist IL-10R peptide or concatenated antagonist IL-10R peptides may be dosed at less than 500 mg per kg of pelleted feed, or more preferably at less than 50 mg per kg of pelleted feed, or even more preferably at less than 5 mg per kg of pelleted feed, or even more preferably at less than 1 mg per kg of pelleted feed. The antagonist IL-10R peptide or concatenated antagonist IL-10R peptides may also improve the body weight or feed conversion ratio of poultry when used in mash (non-pelleted) feed. The antagonist IL-10R peptide or concatenated antagonist IL-10R peptides may maintain their affinity for the IL-10R following incubation in liquid for at least 60 seconds at a temperature less than or equal to 65° C., or 70° C., or 75° C., or 80° C., or 85° C., or 90° C., or 95° C., or 100° C. The antagonist IL-10R peptide or concatenated antagonist IL-10R peptides may maintain their affinity for the IL-10R when heated to a temperature of 70° C. to 90° C. The antagonist IL-10R peptide or concatenated antagonist IL-10R peptides may maintain their affinity for the IL-10R when heated to a temperature in a range between any two of the following values: 70° C., 75° C., 80° C., 85° C., or 90° C.

In an embodiment, the antagonist IL-10R peptide or concatenated antagonist IL-10R peptides may be a peptide or concatenated peptides that are stable to pepsin digestion, may have an increased stability in the animal digestive tract, and may be produced by a microbial host. The antagonist IL-10R peptide or concatenated antagonist IL-10R peptides may be a peptide or concatenated peptides that are readily degradable by pepsin. The readily degradable peptide or concatenated peptides may completely degrade in a time period from 45 minutes to 40 minutes, from 40 minutes to 35 minutes, from 35 minutes to 30 minutes, from 30 minutes to 25 minutes, from 25 minutes to 20 minutes, from 20 minutes to 15 minutes, from 15 minutes to 10 minutes, from 10 minutes to 8 minutes, from 8 minutes to 6 minutes, from 6 minutes to 4 minutes, from 4 minutes to 2 minutes of the pepsin treatment. The time period for degradation may be in a range between any two integer value between 2 minutes and 45 minutes. The complete degradation of the peptide or concatenated peptides by pepsin may occur in 10 minutes.

An embodiment provides an antibody that binds to IL-10, and is referred herein as anti-IL-10 antibody. The anti-IL-10 antibody may bind to the *Gallus gallus* (chicken) IL-10, and is referred herein as an anti-chIL-10 antibody, or chIl10AB. The anti-IL-10 antibody may be a single domain anti-IL-10 antibody (sdAB). Both “single domain anti-IL-10 antibody” and “anti-IL-10 single domain antibody” refer to the same type of antibody and may be used interchangeably herein. An anti-IL-10 single domain antibody may bind to a polypeptide comprising an amino acid sequence of SEQ ID NO: 80. The anti-IL-10 single domain antibody may be capable of reducing IL-10 binding to the IL-10 receptor (IL-10R).

In an embodiment, the anti-IL-10 single domain antibody may have a binding $EC_{50}$ for chicken I1-10 of 30 nM, or less. The anti-IL-10 single domain antibody may have a binding EC50 for chicken IL-10 of about 30 nM, or less, about 25 nM, or less, about 20 nM, or less, about 15 nM, or less, about 10 nM, or less, about 5 nM, or less, or about 1 nM, or less. The anti-IL-10 single domain antibody may have a binding $EC_{50}$ for chicken I1-10 in a range between any two of the following $EC_{50}$ values: 30, 20, 10, 5, or 1 nM. In an embodiment, the $EC_{50}$ of the anti-IL-10 single domain antibody provided herein may be measured by ELISA or any other assay known in the art. The $EC_{50}$ of the anti-IL-10 single domain antibody value may be measured by an ELISA assay described in Example 9 herein.

Without limitations, the anti-IL-10 single domain antibody may be a single domain antibody of any length and of any molecular mass that is capable of reducing IL-10 binding to the IL-10 receptor (IL-10R). The anti-IL-10 single domain antibody may have a molecular mass of 10, 11, 12, 13, 14, 15, 16, 17, 18, 19, or 20 kDa. The anti-IL-10 single domain antibody may have a molecular mass of 14, 15, 16, 17, 18, 19, or 20 kDa. The anti-IL-10 single domain antibody may have a molecular mass in a range between any two of the following molecular masses: 10, 11, 12, 13, 14, 15, 16, 17, 18, 19, or 20 kDa. The anti-Il-10 single domain antibody may have a molecular mass in a range between any two of the following molecular masses: 14, 15, 16, 17, 18, 19, or 20 kDa.

The anti-IL-10 single domain antibody may include an amino acid sequence with at least 70, 72, 75, 80, 85, 90, 91, 92, 93, 94, 95, 96, 97, 98, 99 or 100% identity to a reference sequence selected from the group consisting of: SEQ ID NO: 87 [chIL10sdAB1H5], SEQ ID NO: 88 [chIL10sdAB1E9], SEQ ID NO: 89 [chIL10sdAB1H1], SEQ ID NO: 90 [chIL10sdAB1G6], SEQ ID NO: 91 [chIL10sdAB1C10], SEQ ID NO: 92 [chIL10sdAB1B6], SEQ ID NO: 93 [chIL10sdAB1D12], SEQ ID NO:947 [chIL10sdAB1C2], SEQ ID NO: 95 [chIL10sdAB1B5], SEQ ID NO: 96 [chIL10sdAB1E2], SEQ ID NO: 97 [chIL10sdAB1G7], SEQ ID NO: 98 [chIL10sdAB1G9], SEQ ID NO: 99 [chIL10sdAB1H12], SEQ ID NO: 100 [chIL10sdAB2A9], SEQ ID NO: 101 [chIL10sdAB1E12], SEQ ID NO: 102 [chIL10sdAB1E10], SEQ ID NO: 103 [chIL10sdAB1F12], SEQ ID NO: 104 [chIL10sdAB1A8], SEQ ID NO: 105 [chIL10sdAB1C8], SEQ ID NO: 106 [chIL10sdAB1C12], SEQ ID NO: 107 [chIL10sdAB1B1], SEQ ID NO: 108 [chIL10sdAB1F1], SEQ ID NO: 109 [chIL10sdAB1D11], SEQ ID NO: 110 [chIL10sdAB1E6], SEQ ID NO: 111 [chIL10sdAB1B9], SEQ ID NO: 112 [chIL10sdAB1B10], SEQ ID NO: 113 [chIL10sdAB1F5], SEQ ID NO: 114 [chIL10sdAB1A6], SEQ ID NO: 115 [chIL10sdAB1D5], SEQ ID NO: 116 [chIL10sdAB1D8], SEQ ID NO: 117 [chIL10sdAB1B4], SEQ ID NO: 118 [chIL10sdAB1C7], SEQ ID NO: 119 [chIL10sdAB1B3], SEQ ID NO: 120 [chIL10sdAB1D7], SEQ ID NO: 121 [chIL10sdAB1F7], SEQ ID NO: 122 [chIL10sdAB1F10], SEQ ID NO: 123 [chIL10sdAB1F2], SEQ ID NO: 124 [chIL10sdAB1F3], SEQ ID NO: 125 [chIL10sdAB1F8], SEQ ID NO: 126 [chIL10sdAB1C9], SEQ ID NO: 127 [chIL10sdAB1A12], SEQ ID NO: 128 [chIL10sdAB1C3], SEQ ID NO: 129 [chIL10sdAB1E7], SEQ ID NO: 130 [chIL10sdAB1D9], SEQ ID NO: 131 [chIL10sdAB1A9], SEQ ID NO: 132 [chIL10sdAB1H10], SEQ ID NO: 133 [chIL10sdAB1C1], SEQ ID NO: 134 [chIL10sdAB1D1], SEQ ID NO: 135 [chIL10sdAB1A11], SEQ ID NO: 136 [chIL10sdAB1G8], SEQ ID NO: 137 [chIL10sdAB1A5], SEQ ID NO: 138 [chIL10sdAB1C5], SEQ ID NO: 139 [chIL10sdAB1H6], SEQ ID NO: 140 [chIL10sdAB2A8], SEQ ID NO: 141 [chIL10sdAB1F9], SEQ ID NO: 142 [chIL10sdAB1E11], SEQ ID NO: 143 [chIL10sdAB1D6], SEQ ID NO: 144 [chIL10sdAB1C4], SEQ ID NO: 145 [chIL10sdAB1H4], SEQ ID NO: 146 [chIL10sdAB1F11], SEQ ID NO: 147 [chIL10sdAB1D3], SEQ ID NO: 148 [chIL10sdAB1A7], SEQ ID NO: 149 [chIL10sdAB1H8], SEQ ID NO: 150 [chIL10sdAB1H3], SEQ ID NO: 151 [chIL10sdAB1B8], SEQ ID NO: 152 [chIL10sdAB1B2], SEQ ID NO: 153 [chIL10sdAB1D2], and SEQ ID NO: 154 [chIL10sdAB1D10]. The anti-IL-10 single domain antibody may be fused to a signal peptide. The signal peptide may be but is not limited to an amyloplast targeting signal, a cell wall targeting peptide, a mitochondrial targeting peptide, a cytosol localization signal, a chloroplast targeting signal, a nuclear targeting peptide, an endoplasmic reticulum retention signal, or a vacuole targeting peptide. The signal peptide may an N-terminal signal peptide or a C-terminal signal peptide. The N-terminal signal peptide may be but is not limited to OsGluB4sp (rice Glu-B4 glutelin signal peptide), BAASS (barley alpha amylase signal sequence), PR1 (pathogenesis related protein), or zein 27 (xGZm27ss) signal peptide. The C-terminal signal peptide may be but is not limited to KDEL (SEQ ID NO: 29), HDEL (SEQ ID NO: 30), SEKDEL (SEQ ID NO: 31), HvVSD from barley polyamine oxidase, or HvAle from barley aleurone (thiol protease). The anti-IL-10 single domain antibody may be fused to the N-terminal signal peptide or C-terminal signal peptide, or both.

In an embodiment, the anti-IL-10 single domain antibody having less than 100% identity to its corresponding amino acid sequence of one of SEQ ID NO: 87-154 may be a variant of the referenced peptide or amino acid. In an embodiment, an isolated peptide having a sequence with at least 70, 75, 80, 85, 90, 91, 92, 93, 94, 95, 96, 97, 98, 99, or 100% identity to a peptide having the sequence of any one of SEQ ID NOS: 87-154 along 10 to 20, 10 to 25, 10 to 30, 10 to 40, 10 to 50, 10 to 60, 10 to 70, 10 to 80, 10 to 90, 10 to 100, 10 to 110, 10 to 115, 10 to 116, 10 to 117, 10 to 118, 10 to 119, 10 to 120, 10 to 121, 10 to 122, 10 to 123, 10 to 124, 10 to 125, 10 to 126, or 10 to all amino acids of a protein having the sequence of any of one any one of SEQ ID NOS: 87-154 is provided. This list of sequence lengths encompasses every full length peptide in SEQ ID NOS: 87-154 and every smaller length within the list, even for peptides that do not include over 126 amino acids. For example, the lengths of 10 to 20, 10 to 25, 10 to 30, 10 to 40, 10 to 50, 10 to 60, 10 to 70, 10 to 80, 10 to 90, 10 to 100, 10 to 110, 10 to 115, 10 to 116, 10 to 117, 10 to 118, 10 to 119, 10 to 120, 10 to 121, 10 to 122, 10 to 123, 10 to 124, 10 to 125, 10 to 126, or 10 to all amino acids would apply to a sequence with 126 amino acids. A range of amino acid sequence lengths recited herein includes every length of amino sequence within the range, endpoints inclusive. The recited length of amino acids may start at any single position within a reference sequence where enough amino acids follow the single position to accommodate the recited length. The fragment of the anti-IL-10 single domain antibody may be a subsequence of the polypeptides herein that retain at least 40% of the anti-IL-10 single domain antibody's $EC_{50}$ value when used in a cellular assay comprising cells that are inhibited by IL-10 to decrease production of interferon gamma in the presence of ConA, which is described herein in Example 9. The fragment may have 10, 15, 20, 25, 30, 35, 40, 45, 50, 55, 60, 65 70, 75, 80, 85, 90, 95, 100, 115, 116, 117, 118, 19, 120, 121, 122, 123, 124, 124, or 126 amino acids. The fragments may include 10, 15, 20, 25, 30, 35, 40, 45, 50, 55, 60, 65 70, 75, 80, 85, 90, 95, 100, 115, 116, 117, 118, 19, 120, 121, 122, 123, 124, 124, or 126 contiguous amino acids. Embodiments also include nucleic acids or polynucleotides, encoding said amino acid sequences. A less than full length amino acid sequence may be selected from any portion of one of the sequences of SEQ ID NOS: 87-154 corresponding to the recited length of amino acids. A less than full length amino acid sequence may be selected from a portion of any one of SEQ ID NOS: 87-154.

The anti-IL-10 single domain antibody may increase the production of interferon gamma or nitric oxide when used in a cellular assay comprising cells that are inhibited by IL-10 to decrease production of interferon gamma or nitric oxide.

The anti-IL-10 single domain antibody may maintain or improve the body weight, and, or the feed conversion ratio, of poultry fed the antibodies relative to poultry fed the same feed lacking the antibodies. The anti-IL-10 single domain antibody may be dosed at less than 500 mg per kg of pelleted feed, or more preferably at less than 50 mg per kg of pelleted feed, or even more preferably at less than 5 mg per kg of pelleted feed, or even more preferably at less than 1 mg per kg of pelleted feed. The anti-IL-10 single domain antibody may also improve the body weight or feed conversion ratio of poultry when used in mash (non-pelleted) feed. The anti-IL-10 single domain antibody may maintain its affinity for IL-10 following exposure to pelleting process temperature less than or equal to 65° C., or 70° C., or 75° C., or 80° C., or 85° C., or 90° C., or 95° C., or 100° C. The anti-IL-10 single domain antibody may maintain its affinity for IL-10 following incubation in liquid for at least 60 seconds at a temperature less than or equal to 65° C., or 70° C., or 75° C., or 80° C., or 85° C., or 90° C., or 95° C., or 100° C. The anti-IL-10 single domain antibody may have activity when heated to a temperature of 70° C. to 90° C. The anti-IL-10 single domain antibody may have activity when heated to a temperature in a range between any two of the following values: 70° C., 75° C., 80° C., 85° C., or 90° C. The anti-IL-10 single domain antibody may be active following exposure of a temperature of 70° C. to 90° C., or any value in between the foregoing values. The anti-IL-10 single domain antibody may be an antibody stable to pepsin digestion, may have an increased stability in the animal digestive tract, and may be produced by a microbial host. The anti-IL-10 single domain antibody may be an antibody that is readily degradable by pepsin. The readily degradable antibody may completely degrade in a time period from 45 minutes to 40 minutes, from 40 minutes to 35 minutes, from 35 minutes to 30 minutes, from 30 minutes to 25 minutes, from 25 minutes to 20 minutes, from 20 minutes to 15 minutes, from 15 minutes to 10 minutes, from 10 minutes to 8 minutes, from 8 minutes to 6 minutes, from 6 minutes to 4 minutes, from 4 minutes to 2 minutes of the pepsin treatment. The time period for degradation may be in a range between any two integer value between 2 minutes and 45 minutes. The complete degradation of the antibody by pepsin may occur in 10 minutes.

An embodiment provides one or more synthetic polynucleotides encoding the anti-IL-10 single domain antibody or their variants described herein. The one or more synthetic polynucleotides may comprise, consist essentially of, or consist of a sequence with at least 70, 72, 75, 80, 85, 90, 91, 92, 93, 94, 95, 96, 97, 98, 99, or 100% identity to a reference sequence of SEQ ID NO: 173 [chIL101A11 coding seq], SEQ ID NO: 174 [chIL101A11B coding seq], SEQ ID NO: 175 [chIL101F11A coding seq], SEQ ID NO: 176 [chIL101F11B coding seq], SEQ ID NO: 177 [chIL101H1A coding seq], or SEQ ID NO: 178 [chIL101H1B coding seq]. The one or more synthetic polynucleotides may be included in the expression cassette to be expressed in a host. The host may be but is not limited to a microorganism, a plant cell, a phage, a virus, a mammalian cell, or an insect cell.

An embodiment provides an expression cassette. The expression cassette may comprise one or more synthetic polynucleotide encoding the antagonist IL-10R peptide, concatenated IL-10R antagonist peptides, anti-IL-10 single domain antibody or their variants described herein.

A polynucleotide sequence in an expression cassette, isolated nucleic acid, vector, or any other DNA construct herein, or utilized in a method herein may be operably connected to one or more regulatory elements. A regulatory element included may be a promoter. The promoter may be a constitutive promoter which provides transcription of the polynucleotide sequences throughout the plant in most cells, tissues and organs and during many but not necessarily all stages of development. The promoter may be an inducible promoter, which initiates transcription of the polynucleotide sequences only when exposed to a particular chemical or environmental stimulus. The promoter may be specific to a host. The promoter may be suitable for expression of the polynucleotide in a plant, a bacterium, yeast, a mammalian cell, or an insect cell. The promoter may be a plant specific promoter. The promoter may be specific to a particular developmental stage, organ or tissue. A tissue specific promoter may be capable of initiating transcription in a particular plant tissue. Plant tissue that may be targeted by a tissue specific promoter may be but is not limited to a stem, leaves, trichomes, anthers, seed, embryo, or endosperm. A constitutive promoter herein may be the maize Ubiquitin promoter, the rice Ubiquitin 3 promoter (OsUbi3P), the switchgrass ubiquitin promoter, the PEPC promoter, the maize Actin promoter, or the rice Actin 1 promoter. Other known constitutive promoters may be used, and include but are not limited to Cauliflower Mosaic Virus (CAMV) 35S promoter, the Cestrum Yellow Leaf Curling Virus promoter (CMP) or the CMP short version (CMPS), and the Rubisco small subunit promoter.

The tissue specific promoter may include the seed-specific promoter. The seed specific promoter may be but is not limited to the maize zein promoter, the rice glutelin (GluB4) promoter, the maize oleosin promoter, or the maize globulin promoter.

The promoter may be a promoter homolog to any one of the previously listed promoters derived from other species, or promoter variants to the previously listed promoters with greater than 80% identity.

The promoter may be suitable for expressing the one or more polynucleotides in a bacterium. The promoter may be the T7 RNA polymerase promoter, the LAC promoter or the arabinose promoter. The promoter may be suitable for expressing the polynucleotide in a yeast. The promoter may be the GAL promoter or the glucose promoter. The promoter may be any prokaryotic promoter. The prokaryotic promoter may be a bacterial promoter, or phage promoter that is active in bacteria. The prokaryotic promoter may be any inducible promoter that is active in bacteria, or any other promoter that is active in bacteria.

Another regulatory element that may be provided is a terminator sequence, which terminates transcription. A terminator sequence may be included at the 3' end of a transcriptional unit of the expression cassette. The terminator may be derived from a variety of genes. The terminator may be from a eukaryote, such as a plant or mammalian cell, or a prokaryote. The terminator may be a terminator sequence from the nopaline synthase or octopine synthase genes of *Agrobacterium tumefaciens*. The terminator may be maize gamma zein 27 terminator. The terminator may be any other terminator sequence.

The one or more synthetic polynucleotide may further include one or more signal polynucleotide sequence encoding any one of the signal peptides described herein. The expression cassette may comprise, consist essentially of, or consist of a synthetic polynucleotide sequence with at least 70, 72, 75, 80, 85, 90, 91, 92, 93, 94, 95, 96, 97, 98, 99, or 100% identity to a reference sequence of SEQ ID NO: 84 [xGZein27ss: chIL10sdAB1A11:KDEL], SEQ ID NO: 85 [xGZein27ss:chIL10 sdAB 1B9:KDEL], SEQ ID NO: 86 [xGZein27ss:chIL10sdAB1F11:KDEL], or SEQ ID NO: 179 [xGZein27ss:chIL10sdAB1H1:KDEL].

The expression cassette including the one or more synthetic polynucleotides may be included in a vector.

An embodiment comprises a vector containing the expression cassette including one or more synthetic polynucleotides encoding the antagonist IL-10R peptide, the concatenated antagonist IL-10R peptides, or the anti-IL-10 single domain antibody of any of the above embodiments. The vector may contain any one of the expression cassettes described in any of the embodiments herein. The vector may be a vector used in plant transformation and that is capable of delivering its DNA into the genome of plant cells. The vector may be a vector used for yeast and fungal expression. The vector may be a vector for expression of the peptides, concatenated peptides or antibodies described herein used in bacterial expression. The vector may be a vector used for mammalian or insect cell expression.

The vector may comprise the expression cassette including synthetic polynucleotides encoding the antagonist IL-10R peptide or concatenated antagonist IL-10R peptides. The vector may comprise a nucleic acid sequence with at least 70, 72, 75, 80, 85, 90, 91, 92, 93, 94, 95, 96, 97, 98, 99, or 100% identity to a reference sequence of SEQ ID NO: 69 [pAG4305], SEQ ID NO: 70 [pAG4306], SEQ ID NO: 71 [pAG4308], SEQ IS NO: 72 [pAG4310], SEQ ID NO: 73 [pAG4311], SEQ ID NO: 74 [pAG4312], SEQ ID NO: 75 [pAG4313], SEQ ID NO: 76 [pAG4981], SEQ ID NO: 77 [pAG4982], SEQ ID NO: 78 [pAG4983], and SEQ ID NO: 79 [pAG4984].

The vector may comprise the expression cassette including the synthetic polynucleotide encoding an anti-IL-10 single domain antibody. The vector may comprise a nucleic acid sequence with at least 70, 72, 75, 80, 85, 90, 91, 92, 93, 94, 95, 96, 97, 98, 99, or 100% identity to a reference sequence of SEQ ID NO: 155 [pAG4314], SEQ ID NO: 156 [pAG4315], SEQ ID NO: 157 [pAG4316], SEQ ID NO: 158 [pAG4317], SEQ ID NO: 159 [pAG4985], SEQ ID NO: 160 [pAG4986], SEQ ID NO: 161 [pAG4987], SEQ ID NO: 162 [pAG4988], SEQ ID NO: 163 [pAG4989], SEQ ID NO: 164 [pAG4990], SEQ ID NO: 165 [pAG4991], SEQ ID NO: 166 [pAG4992], SEQ ID NO: 167 [pAG4993], SEQ ID NO: 168 [pAG4994], SEQ ID NO: 169 [pAG4995], SEQ ID NO: 170 [pAG4996], SEQ ID NO: 171 [pAG4997], or SEQ ID NO: 172 [pAG4998].

An embodiment comprises a polynucleotide comprising, consisting essentially of, or consisting of a sequence that has at least 70, 72, 75, 80, 85, 90, 91, 92, 93, 94, 95, 96, 97, 98, 99, or 100% identity along its length to a contiguous portion of a polynucleotide having any one of the sequences set forth herein or the complements thereof. The contiguous portion may be any length up to the entire length of a sequence set forth herein or the complement thereof.

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity is measured by the Smith Waterman algorithm (Smith T F, Waterman M S 1981 "Identification of Common Molecular Subsequences," J Mol Biol 147: 195-197, which is incorporated herein by reference as if fully set forth).

In an embodiment, a transgenic plant comprising any one of synthetic polynucleotides described herein and expressing any one of the antagonist IL-10R peptides, concatenated antagonist IL-10R peptides or anti-IL-10 single domain antibodies described herein is provided. As used herein, the term "transgenic plants" describes plants transformed with DNA that enables the plant containing the transformed DNA to perform a novel function; usually the transcription of the DNA, potentially at a level different from the level in wild-type plants, and potentially the translation of the transcript into a protein, which may be a novel protein to the plant. The transgenic plant may refer to a whole transgenic plant or tissues thereof. The tissues of transgenic plants may be any portion of a transgenic plant, including but not limited to leaves, stems, flowers, buds, petals, grain, seed, embryo, endosperm, leaves, stalks, roots, pollen, or anthers. The tissues may also refer to liquid extracts made by fractionating any portion of a transgenic plant in an organic or aqueous liquid (for example, extracting protein from transgenic seeds and using the extract as a source of the transgenic protein) and using the separated liquid to feed an animal, or in animal feed, or an animal feed additive. The tissue may be callus from a transgenic plant. The tissue may be seeds from a transgenic plant that accumulate peptides, antagonist IL-10R peptides, concatenated antagonist IL-10R peptides, or anti-IL-10 single domain antibodies described herein. A transgenic plant may be regenerated from tissues of a transgenic plant. A transgenic plant may be a product of sexual crossing of a first transgenic plant and a second transgenic plant or a non-transgenic plant where the product plant retains a synthetic nucleic acid introduced to the first transgenic plant. A transgenic plant may be a product of self-pollination of a first transgenic plant with itself.

An embodiment provides a progeny of any one of the transgenic plants described herein. The transgenic plant may express any one of the antibodies described herein. The antibodies may target endogenous molecules produced by the host animal ingesting the transgenic plant or tissues thereof. The targeted endogenous molecules may be but are not limited to interleukins, cytokines, hormones, peptides, cellular receptors, clusters of differentiation, or related molecules. The transgenic plants of the present disclosure may express other peptides or proteins that impact immune response of an animal fed with the transgenic plant or tissues thereof. The transgenic plant may contain at least one of the expression cassettes that are described herein. The transgenic plant may be produced using the vectors described herein. The transgenic plant may be capable of producing any one of the peptides, antagonist IL-10R peptides, concatenated antagonist IL-10R peptides, or anti-IL-10 single domain antibodies described herein. The transgenic plant expressing peptides, antagonist IL-10R peptides, concatenated antagonist IL-10R peptides, or anti-IL-10 single domain antibodies described herein, may be but is not limited to tobacco plant, corn plants, soy bean plants, or any other plant commonly eaten by animals.

The transgenic plants may express peptides and proteins that modulate, stimulate, or augment the immune system, or immune response of an animal fed the transgenic plants or tissues thereof. The transgenic plants may express antibodies targeting endogenous molecules produced by the host animal ingesting the transgenic plants or tissues thereof. The antibodies expressed by the transgenic plant may bind to molecules such as interleukins, cytokines, hormones, peptides, cellular receptors, clusters of differentiation, or similar molecules. The transgenic plants may express other peptides or proteins that modulate various endogenous immune system pathways, endocrine pathways, or other physiological systems. More specifically, the transgenic plants may express express one or more antibodies that bind to interleukin 10 (IL-10), or one or more peptide or protein antagonists that interfere or block the IL-10 receptor complex (IL-10R), or one or more peptide or protein molecules that otherwise inhibit IL-10 signaling pathways.

The transgenic plants, or tissue thereof may modulate, stimulate, or augment the immune system, or immune response of an animal fed the transgenic plant or tissues thereof. The transgenic plants or tissues thereof may improve the gastrointestinal physiology of an animal eating the plants. The transgenic plants or tissues thereof may decrease the binding of IL-10 with the IL-10 receptor (IL-10R) when fed to poultry. The transgenic plants or tissues thereof may maintain or improve the body weight, and, or the feed conversion ratio, of poultry fed the transgenic plants or tissues thereof, relative to poultry fed the same feed lacking the transgenic plants or tissues thereof. The transgenic plants or tissues thereof may be dosed at less than 700 kg per ton of pelleted feed, or more preferably at less than 5 kg per ton of pelleted feed, or more preferably at less than 1 kg per ton of pelleted feed, or even more preferably at less than 500 g per ton of pelleted feed, or even more preferably at less than 50 g per ton of pelleted feed, or yet even more preferably at less than 5 g per ton of pelleted feed. The transgenic plants and tissues thereof may also improve the body weight or feed conversion ratio of poultry when used in mash (non-pelleted) feed.

In an embodiment, a method of making any one of the transgenic plants described herein is provided. The method may comprise culturing explants from a target plant and contacting them with a vector that contains at least one expression cassette described herein. The target plant may be a corn or soy bean plant, or it may be wheat, rice, sorghum, tobacco, canola, cotton, switchgrass, or another plant. The method may include contacting the vector with the plant explant, for example, by using biolistic transformation or by using *Agrobacterium* transformation. Once the explant has been contacted by the vector, methods of selecting and regenerating whole plants may be used that are known in the art.

In an embodiment, any one of the antagonist IL-10R peptides, concatenated antagonist IL-10R peptides or anti-IL-10 single domain antibodies may be isolated from the transgenic plant or plant tissue.

In an embodiment, the specific recombinant, engineered or synthetic molecules described herein may be expressed by other hosts and may be isolated from the hosts.

In an embodiment, the transgenic plants or tissues thereof, or the isolated antagonist IL-10R peptides, concatenated antagonist IL-10R peptides or anti-IL-10 single domain antibodies may be included in an animal feed.

In an embodiment, an animal feed that includes any one of the transgenic plants, or tissues thereof described herein is provided. The term "animal feed" refers to any food, feed, feed composition, preparation, additive, supplement, or mixture suitable and intended for intake by animals for their nourishment and growth. The animal feed comprising transgenic plants, or plant tissues, may decrease the binding of IL-10 with the IL-10R when fed to poultry. The animal feed comprising transgenic plants, or plant tissues, may maintain or improve the body weight, and, or the feed conversion ratio, of poultry fed the transgenic plants or tissues thereof, relative to poultry fed the same feed lacking the transgenic plants or tissues thereof. The animal feed may comprise transgenic plants or tissues thereof at less than 700 kg per ton of pelleted feed, or more preferably at less than 5 kg per ton of pelleted feed, or more preferably at less than 1 kg per ton of pelleted feed, or even more preferably at less than 500 g per ton of pelleted feed, or even more preferably at less than 50 g per ton of pelleted feed, or yet even more preferably at less than 5 g per ton of pelleted feed. The animal feed or animal feed additives comprising transgenic plants and tissues thereof may also improve the body weight or feed conversion ratio of poultry when used in mash (non-pelleted) feed. The animal feed may include an isolated antagonist IL-10R peptide, concatenated antagonist IL-10R peptides or anti-IL-10 single domain antibody. The antagonist IL-10R peptide, concatenated antagonist IL-10R peptides or anti-IL-10 single domain antibodies included in the animal feed may be active in the gastrointestinal environment of animals. The antagonist IL-10R peptide, concatenated antagonist IL-10R peptides or anti-IL-10 single domain antibody included the animal feed may be a peptide or antibody that is stable to pepsin digestion. The antagonist IL-10R peptide, concatenated antagonist IL-10R peptides, anti-IL-10 single domain antibodies included the animal feed may be a peptide or antibody that is digested by pepsin. The animal may be a monogastric animal. The monogastric animal may be but is not limited to a chicken, a turkey, or a duck. The antagonist IL-10R peptide, concatenated antagonist IL-10R peptides or anti-IL-10 single domain antibody may be active after preparation of the animal feed. The temperatures which feeds are exposed to during preparation may be within the range of 20° C. to 70° C., endpoints inclusive. The temperature may be 20° C., 25° C., 30° C., 35° C., 40° C., 45° C., 50° C., 55° C., 60° C., 65° C., 70° C., 20° C. to 25° C., 20° C. to 30° C., 2° C. to 35° C., 20° C. to 40° C., 20° C. to 45° C., 20° C. to 50° C., 20° C. to 55° C., 20° C. to 60° C., 20° C. to 65° C., 20° C. to 70° C., 30° C. to 70° C., 40° C. to 70° C., 50° C. to 70° C., 60° C. to 60° C., or less than 70° C. The temperatures which feeds are exposed to during pelleting may be within the range of 70° C. to 130° C., endpoints inclusive. The temperature may be 70° C., 75° C., 80° C., 85° C., 90° C., 95° C., 100° C., 105° C., 110° C., 115° C., 120° C., 125° C., 130° C., 0° C. to 75° C., 70° C. to 80° C., 70° C. to 85° C., 70° C. to 90° C., 70° C. to 95° C., 70° C. to 100° C., 70° C. to 105° C., 70° C. to 110° C., 70° C. to 115° C., 70° C. to 120° C., 70° C. to 125° C., 70° C. to 130° C., 80° C. to 130° C., 90° C. to 130° C., 100° C. to 130° C., 110° C. to 130° C., 120° C. to 130° C., or less than 130° C.

The antagonist IL-10R peptide, concatenated antagonist IL-10R peptides or anti-IL-10 single domain antibody may have improved thermal stability and may retain activity after being exposed to high temperatures during feed pelleting.

In an embodiment, the animal feed may further include a feed supplement. The feed supplement may be any plant material. The plant material may be a non-transgenic plant or a transgenic plant. The plant material may include a transgenic plant or a mutant plant. The plant material may be a grain that contains starch. The plant material may be a grain that contains fiber. The plant material may be a chemically treated forage. The plant material may be a non-transgenic plant or part thereof. The plant material may include at least one component selected from the group consisting of: barley, wheat, rye, oat, corn, rice, triticale, beet, sugar beet, spinach, cabbage, quinoa, corn meal, corn pellets, corn oil, distillers grains, forage, wheat meal, wheat pellets, wheat grain, barley grain, barley pellets, soybean meal, soybean oilcake, lupin meal, rapeseed meal, sorghum grain, sorghum pellets, rapeseed, sunflower seed, and cotton seed.

The feed supplement may be a mineral. The mineral may be a trace mineral. The mineral may be a macro mineral. The mineral may be rock phosphate or a phosphate salt. The mineral may be calcium phosphate. The feed supplement may be at least one vitamin. The at least one vitamin may be a fat-soluble vitamin. The feed supplement may be an amino acid. The feed supplement may include one or more exogenous enzymes. The one or more exogenous enzymes may include a phytase enzyme. The one or more exogenous enzymes may include a hydrolytic enzyme. The hydrolytic enzyme may be an enzyme classified under EC3.4 as hydrolase. The hydrolytic enzymes may be, but are not limited to, xylanases, mannanases, carbohydrases, proteases, peptidases, glucanases, cellulases, lipases, phospholipases, pectinases, galactosidases, laccases, amylases, hemicellulases, or cellobiohydrolases. The enzymes may be expressed in the transgenic plants or parts thereof included in the feed supplement. The feed supplement may include purified enzymes. The feed supplements may be but are not limited to growth improving additives, coloring agents, flavorings, stabilizers, limestone, stearine, starch, saccharides, fatty acids, or a gum. The coloring agents may be carotenoids. The carotenoids may be but are not limited to cantaxanthin, beta-carotene, astaxanthin, or lutein. The fatty acids may be polyunsaturated fatty acids. The polyunsaturated fatty acids may include but are not limited to arachidonic acid, docosohexaenoic acid (DHA), eicosapentaenoic acid (EPA) or gamma-linoleic acid.

The feed supplement may include at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix. The feed supplement may include fish meal, fish oil, bone meal, feather meal and animal fat. The feed supplement may include yeast or yeast extract.

In an embodiment, a method of preparing an animal feed is provided. The method may include producing any one of the antagonist IL-10R peptides, concatenated antagonist IL-10R peptides or anti-IL-10 single domain antibodies described herein by any one of the methods described herein.

An embodiment provides a method of producing an animal feed. The method may include mixing any one of the transgenic plants or tissues thereof described herein, or the progeny thereof with plant material. The transgenic plant may be a progeny of the transgenic plant that include one or more synthetic polynucleotides encoding peptides and antibodies described herein. The one or more polynucleotides may be included in a genetic construct(s) or an expression cassette(s). The method may comprise making any transgenic plant herein. The transgenic plant or its progeny may be the plant expressing a peptide or protein produced by the method herein. The method may further include pelletizing the mixture. The method may further include adding a feed supplement to the mixture. The feed supplement may include at least one exogenous enzyme. The at least one exogenous enzyme may be selected from the group consisting of: phytase, xylanase, mannanase, protease, glucanase, and cellulase. Preparing the animal feed may include combining one or more transgenic plants described herein with any other feed supplement.

An expression cassette having one or more polynucleotides encoding an antagonist IL-10R peptide, concatenated antagonist IL-10R peptides or anti-IL-10 single domain antibody in a plant may be expressed prior to the step of step of mixing the plant, or prior to the step of pelletizing the plant. The expression may be constitutive or the expression may be induced. Upon the expression of the nucleic acid(s), the transgenic plant may have an increased level of the antagonist IL-10R peptide, concatenated antagonist IL-10R peptides or anti-IL-10 single domain antibodies compared to the level of antagonist IL-10R peptide, concatenated antagonist IL-10R peptides or anti-IL-10 single domain antibodies in a non-transgenic plant of the same genetic background but lacking the one or more expression cassettes.

The antagonist IL-10R peptide, concatenated antagonist IL-10R peptides or anti-IL-10 single domain antibodies may be isolated, purified and added to the animal feed as a pure antagonist IL-10R peptide, concatenated antagonist IL-10R peptides or anti-IL-10 single domain antibodies. The antagonist IL-10R peptide, concatenated antagonist IL-10R peptides or anti-IL-10 single domain antibodies may be isolated from the intact host organism and added to the animal feed as an antagonist IL-10R peptide, concatenated antagonist IL-10R peptides or anti-IL-10 single domain antibodies composition. The antagonist IL-10R peptide, concatenated antagonist IL-10R peptides or anti-IL-10 single domain antibodies may be added to the animal feed in admixture with other feed supplements. The transgenic plant including the antagonist IL-10R peptide, concatenated antagonist IL-10R antagonist peptides or anti-IL-10 single domain antibodies or the purified antagonist IL-10R peptide, concatenated antagonist IL-10R peptides or anti-IL-10 single domain antibodies may be combined with other feed supplements to form premixes.

An animal feed may be produced as mash feed. The animal feed may be produced as pelleted feed. The milled feed stuffs may be mixed with the premix that includes any one of the transgenic plants that include an antagonist IL-10R peptide, concatenated antagonist IL-10R peptides or anti-IL-10 single domain antibody. The antagonist IL-10R peptide, concatenated antagonist IL-10R peptides or anti-IL-10 single domain antibody may be an antagonist IL-10R peptide, concatenated antagonist IL-10R peptides or anti-IL-10 single domain antibody that is/are stable to pepsin digestion. The antagonist IL-10R peptide, concatenated antagonist IL-10R peptides or anti-IL-10 single domain antibody may be an antagonist IL-10R peptide, concatenated antagonist IL-10R peptides or anti-IL-10 single domain antibody that is/are digestible by pepsin. The milled feed stuffs may include the plant material and the feed supplements described herein. The feed supplements may include one or more exogenous enzymes described herein. Enzymes may be added as liquid or solid formulations. For mash feed, a solid or liquid peptide formulation may be added before or during the mixing step. For pelleted feed, the peptide preparation may be added before or after the pelleting step. The antagonist IL-10R peptide, concatenated antagonist IL-10R peptides or anti-IL-10 single domain antibody may be included in premix. The premix may also include vitamins and trace minerals. Macro minerals may be added separately to animal feedstock.

An embodiment comprises a method of treating or preventing a gastrointestinal infection in an animal. The gastrointestinal infection may be caused by a gastrointestinal pathogen. As used herein, a gastrointestinal pathogen may include a bacterium, yeast, fungi, archaea, virus, protozoa, or other infectious agent that is capable of replication inside or outside of the infected host animal, and causes irritation, necrosis, cellular disruption, or cellular damage within the infected host animal, or otherwise stimulates or modulates the immune system of the infected host animal. The gastrointestinal pathogen may belong to the genus *Eimeria*. The gastrointestinal pathogen may be but is not limited to *Eimeria tenella, Eimeria acervulina*, or *Eimeria maxima*. The method may include administering to an animal any one of the antagonist IL-10R peptides or anti-IL-10 single domain antibodies described herein. Administering may be performed by any known route, for example, by injection. Administering may be performed by feeding the infected animal with the transgenic plant expressing one or more antibodies that bind to IL-10, or one or more peptide or protein antagonists to the IL-10R, or plant tissues thereof, or animal feed or feed compositions containing the transgenic plants and tissues thereof. The method comprises administering any one of the antagonist IL-10R peptides or anti-IL-10 single domain antibodies described herein in a therapeutically effective amount. As used herein, a therapeutically effective amount of an antagonist IL-10 peptide, concatenated antagonist IL-10 peptides or anti-IL-10 single domain antibody is an amount effective to reduce the symptoms of the gastrointestinal disease in the animal when administered daily for a period of from one week to two months. The therapeutically effective amounts of the antagonist IL-10R peptide or concatenated antagonist IL-10R peptides may be a dose of less than 500 mg per kg of pelleted feed, or more preferably less than 50 mg per kg of pelleted feed, or even more preferably less than 5 mg per kg of pelleted feed, or even more preferably less than 1 mg per kg of pelleted feed.

The therapeutically effective amounts of the anti-IL-10 single domain antibody may be at a dose of less than 500 mg per kg of pelleted feed, or more preferably at a dose of less than 50 mg per kg of pelleted feed, or even more preferably at a dose of less than 5 mg per kg of pelleted feed, or even more preferably at a dose of less than 1 mg per kg of pelleted feed.

The therapeutically effective amounts of the transgenic plants or tissues thereof may be at a dose of less than 700 kg per ton of pelleted feed, or more preferably at a dose of less than 5 kg per ton of pelleted feed, or more preferably at a dose of less than 1 kg per ton of pelleted feed, or even more preferably at a dose of less than 500 g per ton of pelleted feed, or even more preferably at a dose of less than 50 g per ton of pelleted feed, or yet even more preferably at a dose less than 5 g per ton of pelleted feed.

The therapeutically effective amounts of the animal feed may comprise transgenic plants or tissues thereof at less than 700 kg per ton of pelleted feed, or more preferably at less than 5 kg per ton of pelleted feed, or more preferably at less than 1 kg per ton of pelleted feed, or even more preferably at less than 500 g per ton of pelleted feed, or even more preferably at less than 50 g per ton of pelleted feed, or yet even more preferably at less than 5 g per ton of pelleted feed.

An embodiment comprises a method of stimulating or modulating the immune system and improving gastrointestinal physiology of an animal comprising feeding the animal with the transgenic plants or tissues thereof. As used herein, the term "modulate" means to change, or respond to a stimulus. In this context "modulate" could mean to increase a response or decrease a response. With regards to modulating an immune response, it means to stimulate or to decrease an immune response. Words that are used synonymously with decrease as it relates to modulation of a response include blocking, interfering, antagonizing, lowering, alleviating, shutting down, or removing. The term gastrointestinal physiology describes the biological state of an animal's gastrointestinal tract, including the foregut, midgut, and hindgut. The actual anatomical features of the gastrointestinal tract may vary among animal species, but in poultry include the esophagus, crop, proventriculus, ventriculous, gizzard, duodenum, jejunum, ileum, small intestine, large intestine, cloaca, and ceca. The biological state of the gastrointestinal tract may be described as healthy or normal, lacking any abnormal visual or pathological observation, or aberrant histological evaluation. The biological state of the gastrointestinal tract may be described as inflamed, infected, or necrotic, all of which describe a physiological state that is impaired and could be improved to a normal or healthy state.

In an embodiment, a method of improving the gastrointestinal physiology of an animal is provided. The method may comprise feeding the animal any of the transgenic plants, or plant parts, described herein. In an embodiment, the method may comprise feeding the animal any of the anti-IL-10 single domain antibodies, peptides, or antagonist IL-10R s described herein.

In an embodiment, a method of improving animal performance or animal gastrointestinal physiology is provided. The method may comprise feeding the animals any of the transgenic plants expressing one or more antibodies that bind to IL-10, or one or more peptide or protein antagonists to the IL-10R, or plant tissues thereof, or feed, or feed compositions containing the transgenic plants or tissues thereof, or anti-IL-10 single domain antibodies, or the IL-10R antagonists. The method may comprise feeding the animals any one of the transgenic plants, or plant parts described herein. As used herein, animal performance is synonymous with animal growth or animal productivity, and each term can be used interchangeably. Animal performance relates to the weight gain of the animal over time, and to the animal's feed conversion ratio, which is defined as the mass of feed eaten by the animal divided by the weight gain of the animal. These terms may be used to describe either, or both, weight gain and feed conversion ratio, so an improvement in animal performance may indicate an increase in weight gain relative to control animals, and, or, a decrease (less feed eaten per mass of animal growth) in feed conversion ratio. In an embodiment, the method may comprise feeding an animal any of the animal feed or animal feed additives comprising any of the anti-IL-10 single domain antibodies, peptides, IL-10R antagonists, or transgenic plants or tissues thereof, described herein.

The following list includes particular embodiments of the present invention. But the list is not limiting and does not exclude alternate embodiments, or embodiments otherwise described herein. Percent identity described in the following embodiments list refers to the identity of the recited sequence along the entire length of the reference sequence.

EMBODIMENTS

1. At least one antagonist IL-10R peptide, wherein (i) the at least one antagonist IL-10R peptide is one peptide comprising an amino acid sequence with at least 90% identity to a reference sequence selected from the group consisting of: SEQ ID NOS: 1-13, or (ii) the at least one antagonist IL-10R peptide comprises concatenated peptides comprising an amino acid sequence with at least 90% identity to a reference sequence selected from the group consisting of: SEQ ID NOS: 32-40.

2. The at least one antagonist IL-10R peptide of embodiment 1, wherein each of the concatenated peptides are linked to each other by one or more linkers.

3. The at least one antagonist peptide of any one or both of embodiments 1 and 2, wherein the one or more linkers comprise a sequence selected from the group consisting of SEQ ID NOS: 41-44, and 65.

4. The at least one antagonist IL-10R peptide of any one or more of embodiments 1-3, wherein the at least one peptide or each one of the concatenated peptides comprise an N-terminal signal peptide or C-terminal signal peptide, or both.

5. The at least one antagonist IL-10R peptide of any one or more of embodiments 1-4, wherein the N-terminal signal peptide is selected from a group consisting of: OsGluB4sp (rice Glu-B4 glutelin signal peptide), BAASS (barley alpha amylase signal sequence), PR1 (pathogenesis related protein), or zein 27 (xGZm27ss) signal peptide.

6. The at least one antagonist IL-10R peptide of any one or more of embodiments 1-5, wherein the peptide is stable at a temperature in a range from 70° C. to 90° C.

7. The at least one antagonist IL-10R peptide of any one or more of embodiments 1-6, wherein the peptide is digestible by pepsin.

8. The at least one antagonist IL-10R peptide of any one or more of embodiments 1-6, wherein the peptide is stable to digestion by pepsin.

9. The at least one antagonist IL-10R peptide of any one or more of embodiments 1-8, wherein the C-terminal signal peptide is selected from a group consisting of: KDEL (SEQ ID NO: 29), HDEL (SEQ ID NO: 30), SEKDEL (SEQ ID NO: 31), HvVSD from barley polyamine oxidase, or HvAle from barley aleurone (thiol protease).

10. A synthetic polynucleotide encoding the at least one antagonist IL-10R peptide of any one or more of embodiments 1-9.

11. The synthetic polynucleotide of embodiment 10, wherein the synthetic polynucleotide comprises a sequence with at least 90% identity to a reference sequence selected from the group consisting of: 16-28, and 56.

12. An anti-IL-10 single domain antibody that binds to a polypeptide comprising an amino acid sequence of SEQ ID NO: 80.

13. The anti-IL-10 single domain antibody of embodiment 12, wherein the antibody has a molecular mass in a range of 10 kDa to 20 kDa.

14. The anti-IL-10 single domain antibody of any one or both of embodiments 12 and 13, wherein the antibody is stable at a temperature in a range from 70° C. to 90° C.

15. The anti-IL-10 single domain antibody of any one or more of embodiments 12-14, wherein the antibody binds to chicken I1-10 with an $EC_{50}$ of 30 nM or less in a cell ELISA assay.

16. The anti-IL-10 single domain antibody of any one or more of embodiments 12-15, wherein the antibody comprises an amino acid sequence with at least 90% identity to a sequence selected from the group consisting of SEQ ID NOs: 87-154.

17. The anti-IL-10 single domain antibody of any one or more of embodiments 12-16, wherein the antibody comprises the amino acid sequence with at least 90% identity to a sequence selected from the group consisting of SEQ ID NOs: 89, 135, and 146.

18. The anti-IL-10 single domain antibody of any one or more of embodiments 12-17, wherein the antibody is fused to an N-terminal signal peptide or C-terminal signal peptide, or both.

19. The anti-IL-10 single domain antibody of any one or more of embodiments 12-18, wherein the N-terminal signal peptide is selected from a group consisting of: OsGluB4sp (rice Glu-B4 glutelin signal peptide), BAASS (barley alpha amylase signal sequence), PR1 (pathogenesis related protein), or zein 27 (xGZm27ss) signal peptide.

20. The anti-IL-10 single domain antibody of any one or more of embodiments 12-19, wherein the C-terminal signal peptide is selected from a group consisting of: KDEL (SEQ ID NO: 29), HDEL (SEQ ID NO: 30), SEKDEL (SEQ ID NO: 31), HvVSD from barley polyamine oxidase, or HvAle from barley aleurone (thiol protease).

21. The anti-IL-10 single domain antibody of any one or more of embodiments 12-20, wherein the anti-IL-10 single domain antibody is digestible by pepsin.

22. The anti-IL-10 single domain antibody of any one or more of embodiments 12-20, wherein the anti-IL-10 single domain antibody is stable to digestion by pepsin.

23. The anti-IL-10 single domain antibody of any one or more of embodiments 12-22, wherein the anti-IL-10 single domain antibody is stable to a temperature exposure of greater than 70° C. and less than 100° C.

24. A synthetic polynucleotide encoding the anti-IL-10 single domain antibody of any one or more of embodiments 12-23.

25. The synthetic polynucleotide of embodiment 24, wherein the synthetic polynucleotide comprises a sequence with at least 90% identity to a reference sequence selected from the group consisting of: SEQ ID NOs: 173-178.

26. A transgenic plant or tissues thereof comprising one or more polynucleotides encoding the at least one antagonist IL-10R peptide of any one or more of embodiments 1-9, or the anti-IL-10 single domain antibody of any one or more of embodiments 12-23.

27. A transgenic plant or tissues thereof comprising one or more polynucleotides encoding the at least one antagonist IL-10R peptide, or the anti-IL-10 single domain antibody.

28. The transgenic plant or tissues thereof of embodiment 27, wherein the antagonist IL-10R peptide is one peptide comprising an amino acid sequence with at least 90% identity to a reference sequence selected from the group consisting of: SEQ ID NOS: 1-13.

29. The transgenic plant or tissues thereof of any one or both embodiments 27 and 28, wherein the antagonist IL-10R peptide comprises concatenated antagonist IL-10R peptides comprising an amino acid with at least 90% identity to a reference sequence selected from the group consisting of SEQ ID NOS: 32-40.

30. The transgenic plant or tissues thereof of any one or more of embodiments 27-29, wherein the anti-IL-10 single domain antibody binds to a polypeptide comprising an amino acid sequence of SEQ ID NO: 80.

31. The transgenic plant or tissues thereof of any one or more of embodiments 27-30, wherein the anti-IL-10 single domain antibody has a molecular mass in a range of 10 kDa to 20 kDa.

32. The transgenic plant or tissues thereof of any one or more of embodiments 27-31, wherein the anti-IL-10 single domain antibody is stable at a temperature in a range from 70° C. to 90° C.

33. The transgenic plant or tissues thereof of any one or more of embodiments 27-32, wherein the anti-IL-10 single domain antibody binds to chicken I1-10 with an EC50 of 30 nM or less in a cell ELISA assay.

34. The transgenic plant or tissues thereof of any one or more of embodiments 27-33, wherein the anti-IL-10 single domain antibody comprises an amino acid sequence with at least 90% identity to a sequence selected from the group consisting of SEQ ID NOs: 87-154.

35. The transgenic plant or tissues thereof of any one or more of embodiments 27-34, wherein the anti-IL-10 single domain antibody comprises the amino acid sequence with at least 90% identity to a sequence selected from the group consisting of SEQ ID NOs: 89, 135, and 146.

36. The transgenic plant or tissues thereof of any one or more of embodiments 27-35, wherein the one or more polynucleotides comprise a sequence with at least 90% identity to a reference sequence selected from the group consisting of SEQ ID NOS: 16-28, and 56.

37. The transgenic plant or tissues thereof of any one or more of embodiments 27-36, wherein the one or more polynucleotides comprise a sequence with at least 90% identity to a reference sequence selected from the group consisting of SEQ ID NOS: 173-178.

38. The transgenic plant or tissues thereof of any one or more of embodiments 27-37, wherein the anti-IL-10 single domain antibody is digestible by pepsin.

39. The transgenic plant or tissues thereof of any one or more of embodiments 27-37, wherein the anti-IL-10 single domain antibody is stable to digestion by pepsin.

40. The transgenic plant or tissues thereof of any one or more of embodiments 27-39, wherein a plant is selected from the group consisting of: corn, soybean, wheat, rice, sorghum, canola, cotton, and switchgrass.

41. An animal feed comprising the transgenic plant or tissues thereof of any one or more of embodiments 26-40.

42. An animal feed comprising at least one antagonist IL-10R peptide of any one or more of embodiments 1-9, or an anti-IL-10 single domain antibody of any one or more of embodiments 12-23.

43. The animal feed of embodiment 42, wherein the at least one IL-10R antagonist IL-10R peptide, or the anti-IL-10 single domain antibody is active upon expression in the plant and exposure to a temperature in the range from 25° C. to 130° C.

44. The animal feed of any one or more of embodiments 41, or 42-43 further comprising a feed supplement.

45. The animal feed of any one or more of embodiments 41, or 42-44, wherein the feed supplement is plant material.

46. The animal feed of any one or more of embodiments 41, or 42-45, wherein the plant material is a non-transgenic plant or a transgenic plant.

47. The animal feed of any one or more of embodiments 41, or 42-46, wherein the plant material includes at least one component selected from the group consisting of: corn meal, corn pellets, wheat meal, wheat pellets, wheat grain, barley grain, barley pellets, soybean meal, soybean oilcake, sorghum grain and sorghum pellets.

48. The animal feed of any one or more of embodiments 41, or 42-47, wherein the feed supplement includes one or more exogenous enzymes.

49. The animal feed of any or more of embodiments 41, or 42-48, wherein the one or more exogenous enzymes includes a hydrolytic enzyme selected from the group consisting of: xylanase, endoglucanase, cellulase, protease, phytase, amylase and mannanase.

50. The animal feed of any one or more of embodiments 41, or 42-49, wherein the feed supplement includes at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix.

51. A method of treating or preventing a gastrointestinal infection in an animal comprising feeding the animal the at least one antagonist IL-10R peptide of any one or more of embodiments 1-9, the anti-IL-10 single domain antibody of any or more of embodiments 12-23, the transgenic plant or tissues thereof of any one or more of embodiments 26-40, or the animal feed of any one more of embodiments 41-50.

52. The method of embodiment 51, wherein the gastrointestinal infection is caused by a gastrointestinal pathogen selected from the group consisting of: bacteria, yeast, fungi, archae, virus, and protozoa.

53. The method of any one or both of embodiments 51 and 52, wherein the gastrointestinal pathogen belongs to the genus *Eimeria.*

54. The method any one or more of embodiments 51-53, wherein the gastrointestinal pathogen is selected from the group consisting of: *Eimeria tenella, Eimeria acervulina*, and *Eimeria maxima.*

55. A method of stimulating or modulating the immune system and improving gastrointestinal physiology of an animal comprising feeding the animal the at least one antagonist IL-10R peptide of any one or more of embodiments 1-9, the anti-IL-10 single domain antibody of any or more of embodiments 12-23, the transgenic plant or tissues thereof of any one or more of embodiments 26-40, or the animal feed of any one or more of embodiments 41-50.

56. A method of improving animal performance comprising feeding an animal the at least one antagonist IL-10R peptide of any one or more of embodiments 1-9, the anti-IL-10 single domain antibody of any one or more of embodiments 12-23, the transgenic plant or tissues thereof of any one or more of embodiments 26-40, or the animal feed of any one or more of embodiments 41-50.

57. A method of preparing an animal feed comprising mixing the antagonist IL-10R peptide of any one or more of embodiments 1-9, the anti-IL-10 single domain antibody of any one or more of embodiments 12-23, or the transgenic plant or tissues thereof of any one or more of embodiments 26-40 with plant material to form a mixture.

58. The method of embodiment 57, wherein the method further comprises pelletizing the mixture.

59. The method of any one or both of embodiments 57 and 58, wherein the method further comprises adding a feed supplement to the mixture.

60. The method of any one or more of embodiments 57-59, wherein the plant material is a non-transgenic plant or a transgenic plant.

61. The method of any one or more of embodiments 57-60, wherein the plant material includes at least one component selected from the group consisting of: corn meal, corn pellets, wheat meal, wheat pellets, wheat grain, barley grain, barley pellets, soybean meal, soybean oilcake, sorghum grain and sorghum pellets.

62. The method of any one or more of embodiments 57-61, wherein the feed supplement includes one or more exogenous enzymes.

63. The method of any or more of embodiments 57-62, wherein the one or more exogenous enzymes includes a hydrolytic enzyme selected from the group consisting of: xylanase, endoglucanase, cellulase, protease, phytase, amylase and mannanase.

64. The method of any one or more of embodiments 57-63, wherein the feed supplement includes at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix.

Further embodiments herein may be formed by supplementing an embodiment with one or more elements from any one or more other embodiments herein, and/or substituting one or more elements from one embodiment with one or more elements from one or more other embodiments

EXAMPLES

The following non-limiting examples are provided to illustrate particular embodiments. The embodiments throughout may be supplemented with one or more details from one or more examples below, and/or one or more elements from an embodiment may be substituted with one or more details from one or more examples below.

Example 1. Strategies for Engineering Peptides and Antibodies

While reducing IL-10 levels prior to and during *Eimeria* infection can help control the negative effects of Coccidiosis, the mechanisms known in the art that have been employed to reduce IL-10 levels are expensive and have questionable robustness to be employed broadly in industry. The shortcomings of the existing technologies (using isolated, or partially purified, peptides or antibodies) to control Coccidiosis can be addressed in several important ways using biotechnology to design novel products that target the IL-10 signaling pathway. First, by broadening antibody discovery and development beyond the common target chicken production system, as is currently done by inoculating maternal hens or eggs with conjugated IL-10 peptides, novel antibodies and peptides can be developed that have been specifically tailored to controlling Coccidiosis. The peptides and synthetic antibodies developed herein were engineered to have high affinity (thus reducing dosing levels), improved thermal stability (to survive pelleting when mixed into animal feed), and low molecular weight to promote high-levels of expression (to maximize production economics), properties that are not found in naturally occurring peptides and antibodies and that could not be simply selected for in nature, nor could these properties be efficiently replicated in a hen or egg production system without undue experimentation. Second, by engineering the genes encoding the peptides and antibodies developed herein into plants, their delivery can be made by directly feeding the plants or plant tissues without additional isolation, or purification, or formulation, into the diet. This greatly benefits production and animal administration economics. That such a combination of technologies works effectively in controlling Coccidiosis was unexpected. It was anticipated that antibodies and peptides delivered in whole grain or meal, with no isolation, would either not survive the pelleting process when being mixed in feed (which is often the case when using larger antibodies, such as IgG's or IgY's, and peptides), not diffuse adequately from the plant matrix and be readily available to the animal at sufficient concentrations to modulate the IL-10 signaling pathway, or would be rapidly degraded in the digestive tract. Unexpectedly, the combination of technologies used to make the products described herein, was able to overcome these challenges and address the challenges confronting current methods used in the art for controlling Coccidiosis.

Plant expression of heterologous peptides and proteins is one of the least expensive recombinant protein production systems on the planet. By engineering corn or soy beans to produce anti-IL-10 antibodies, IL-10R peptide antagonists, or other molecules that inhibit IL-10 signaling, these molecules can be made at high concentrations, e.g., a concentration in a range from 0.01 mg of heterologous protein (anti-IL-10 antibodies, IL-10R peptide antagonists, or other proteins or peptides that inhibit IL-10 signaling) per gram of milled grain up to as much as 20 mg of heterologous protein per gram of milled grain. Heterologous proteins and peptides produced in seed tissue are naturally stabilized in the seed as it progresses through its desiccation process following seed development. Antibodies and peptide antagonists produced in corn or soy beans can be delivered directly into poultry diets by simply milling the grain and mixing it with the other ingredients. While other processing and formulation steps may be used, there is no need for additional processing steps that would be required if these products were produced by fermentation or by inoculating eggs, both of which are more expensive processes. Further, because these molecules are encoded by DNA that is stably integrated into the plants' genome, there is the opportunity to further engineer these molecules and endow them with beneficial properties that cannot be implemented when generating antibodies in maternal hens or by inoculating eggs.

Figure 3:
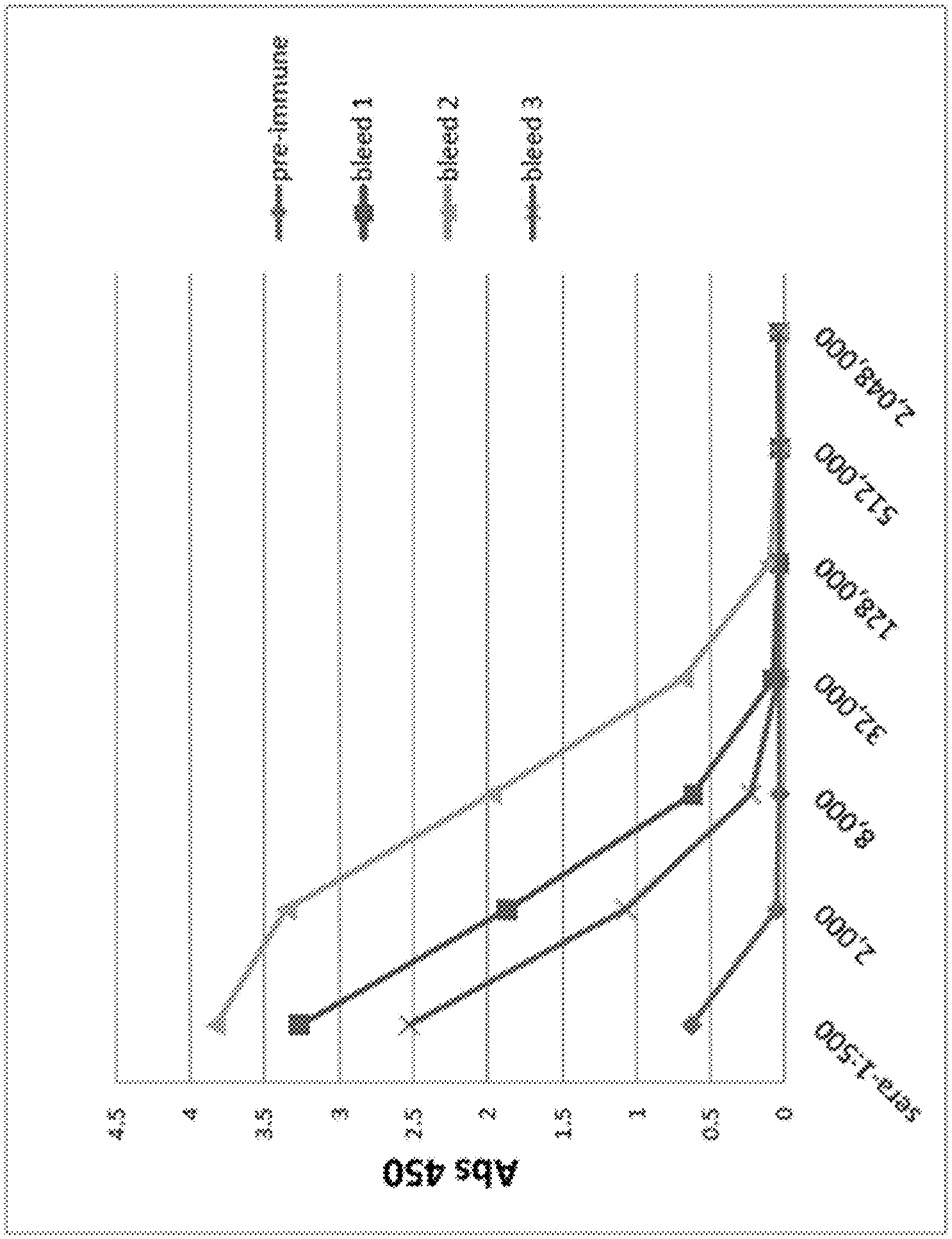
FIG. 3 illustrates the antibody response generated by a llama injected with full-length chicken IL-10. It demonstrates that specific antibodies are produced by the animal that increases the binding of chicken IL-10 post-injection, relative to the pre-immune (that is, pre-injection) state of the animal.

Engineering of antibodies, proteins, and peptides provides additional opportunities to address industry needs in modulating IL-10 signaling pathways. Anti-IL-10 antibodies can be generated by any number of hosts, including camels, calves, chickens, goats, horses, humans, llamas, mice, rabbits, rats, sharks, and many other species. The particular choice of host for generating an antibody may depend on a variety of considerations including the choice of antigen (will the antigen be recognized as self by the host or recognized as foreign and generate an appropriate immune response), the choice of antibody (IgG, IgY, a polyclonal, monoclonal, etc.), ease of working with the host, the amount of antibody desired, the intended species the antibody will be used in, and the type of antibody desired (full length (approximately 120-160 kDa), antibody fragments (Fab that can be approximately 50 kDa, or scFv that can be approximately 25 kDa), or single domain antibodies (that can be approximately 10-20 kDa)). Single domain antibodies are small synthetic antibodies abbreviated by sdAb, sdAB, VHH, or VNAR, and have specific features that make them suitable for targeting IL-10 when delivered through feed into an animal's digestive tract. In particular, sdAbs are generally recognized as having improved thermal stability relative to full length and other antibody fragments, and are very susceptible to molecular engineering, which provides the possibility of further improving their thermal stability and affinity, both of which may help in reducing the necessary dose required in the animal feed to modulate the IL-10 signaling pathway (E. R. Goldman, G. P. Anderson, J. L. Liu, J. B. Delehanty, L. J. Sherwood, L. E. Osborn, L. B. Cummins, and A. Hayhurst, 2006, Facile Generation of Heat-Stable Antiviral and Antitoxin Single Domain Antibodies from a Semisynthetic Llama Library, Annal. Chem., 78:8245-8255, which is incorporated herein by reference as if fully set forth). Chicken IL-10 (amino acid residues in positions 2 to 151 of SEQ ID NO: 80) was compared with llama IL-10 (SEQ ID NO: 207). Sequence alignment analysis showed the sequences to be only 48% identical. Based on this analysis, the full-length *Gallus gallus* IL-10 (chicken IL-10 or cIL-10) was selected as the target antigen for generating sdAbs in camels or llamas. Because llamas are not exposed to cIL-10, an endogenous chicken interleukin, and it's only through a biotechnology process that cIL-10 can be made, isolated and dosed into a llama, llamas are naive to cIL-10 and it was found that it's possible to generate a significant immune response as shown in FIG. 3. Further, given that IL-10 is known to dimerize in vivo (K. Asadullah, W. Sterry, H. D. Volk, "Interleukin-10 Theraphy—Review of a New Approach", Pharmacological Reviews, 55(2):241-269, 2003), using IL-10 peptides as target antigens is challenging because peptide epitopes may be selected that are not normally exposed in the IL-10 dimer in vivo. Thus, library generation and antibody screening may be more readily optimized, and synthetic antibodies developed, using full-length cIL-10. Another advantage of developing a single molecule for expression is that it can be selected from a diversity of molecules made by the inoculated host, allowing for screening and selection of a highly optimized sdAb that can be reproducibly made with great efficiency in corn or another host. In this way, many of the current challenges with modulating the IL-10 pathway in poultry can be addressed to bring this innovation into the marketplace.

Example 2. Peptide Selection

Synthetic peptides were designed by analyzing the crystal structures of human IL-10/IL-10R1 complexes, determining portions of the sequences of the human proteins that contribute to binding, and finding the analogous sequences in the chicken proteins by aligning the sequences of human and chicken IL-10 and IL-10R1, respectively, with Clustal Omega (Diaz-Valdez et al., 2011, Josephson et al., 2001, Naiyer et al., 2013, Ni et al., 2016, Reineke et al., 1998, Yoon et al., 2005, Zdanov et al., 1996). Amino acid sequences were obtained from Pub Med; and the presumed signal peptide, transmembrane, and intracellular sequences were removed from the alignments. All peptide sequences were checked for known allergenic epitopes using the Allergen Online Database.

Human IL-10 residues involved in binding to its receptor as determined by peptide mapping are as follows:

```
Chicken ------ LEPTCLHFSELLPARLRELRVKFEEIKDYFQSRDD
Huma    SPGQGTQSENSCTHFPGNLPNMLRDLRDAFSRVKTFFQMKDQ
        .   .    * :* **   **  **:**  *..:* :** :*:
Chicken ELNIQLLSSELLDEFKGTFGCQSVSEMLRFYTDEVLPRAMQTSTSHQQSMGDLGNMLLGL

Human    -LDNLLLKESLLEDFKGYLGCQALSEMIQFYLEEVMPQAENQDPDIKAHVNSLGENLKTL
          *:  **...**::*** :***::***::** :**:*:* : . . :  :..**: *  *

Chicken KATMRRCHRFFTCEKRSKAIKQIKETFEKMDENGIYKAMGEFDIFINYIEEYLLMRRR- (SEQ ID NO: 80)

Human    RLRLRRCHRFLPCENKSKAVEQVKNAFNKLQEKGIYKAMSEFDIFINYIEAYMTMKIRN (SEQ ID NO: 81)
         :  :*****:  **::***::*:*::*:*::*:*****.**********  *: * : *
```

Human (AAA63207.1; SEQ ID NO: 81) and chicken (NP_001004414.2; SEQ ID NO: 80) sequences were obtained and edited as described above. Human IL-10 residues that are involved in binding to human IL-10R1 are in boldface and colored gray (Reineke et. al., 1998). Chicken IL-10 sequence alignment with the human IL-10 sequence is also shown.

Human IL-10 residues that bury >5 Å$^2$ surface area in the complex with the receptor (Yoon, et, al., 2005).

```
Chicken ------ LEPTCLHFSELLPARLRELRVKFEEIKDYFQSRDD

Human    SPGQGTQSENSCTHFPGNLPNMLRDLRDAFSRVKTFFQMKDQ
         .   .    * :* **   **  **: **  *..:* :** :*:

Chicken ELNIQLLSSELLDEFKGTFGCQSVSEMLRFYTDEVLPRAMQTSTSHQQSMGDLGNMLLGL

Human    -LDNLLLKESLLEDFKGYLGCQALSEMIQFYLEEVMPQAENQDPDIKAHVNSLGENLKTL
          *:  **...**:: *** : ***::***::** : **:*:* : . . :  :..**: *  *

Chicken KATMRRCHRFFTCEKRSKAIKQIKETFEKMDENGIYKAMGEFDIFINYIEEYLLMRRR- (SEQ ID NO: 80)

Human    RLRLRRCHRFLPCENKSKAVEQVKNAFNKLQEKGIYKAMSEFDIFINYIEAYMTMKIRN (SEQ ID NO: 81)
         :  :*****:  **::***::*:*::*:*::*:*****.**********  *: * : *
```

Chicken IL-10 sequence (SEQ ID NO: 80) alignment with the human IL-10 sequence (SEQ ID NO: 81) is shown, with the two segments of the human IL-10 sequence that contribute the majority of binding surface (Diaz-Valdez et al., 2011; Josephson et al., 2001; Naiyer et al., 2013; Ni et al., 2016; Reineke et al., 1998; Yoon et al., 2005; and Zdanov et al., 1996), are indicated in boldface and colored gray. Helical regions are underlined.

Examples of peptide design based on alignment with predicted sequence regions of binding interactions:

```
Chicken  ------ LEPTCLHFSELLPARLRELRVKFEEIKDYFQSRDD
Human    SPGQGTQSENSCTHFPGNLPNMLRDLRDAFSRVKTFFQMKDQ
         .   .    * :* **   **  **:**  *...* :** :*:

Chicken  ELNIQLLSSELLDEFKGTFGCQSVSEMLRFYTDEVLPRAMQTSTSHQQSMGDLGNMLLGL

Human   -LDNLLLKESLLEDFKGYLGCQALSEMIQFYLEEVMPQAENQDPDIKAHVNSLGENLKTL
         *: **...**::*** :***::***::** :**:*:* : . . :  :..**: *  *
Chicken KATMRRCHRFFTCEKRSKAIKQIKETFEKMDENGIYKAMGEFDIFINYIEEYLLMRRR- (SEQ ID NO: 80)
Human   RLRLRRCHRFLPCENKSKAVEQVKNAFNKLQEKGIYKAMSEFDIFINYIEAYMTMKIRN (SEQ ID NO: 81)
        :   : ** *** *:  ** : : * ** : : * : * : : * : * : : * : * *** **. ** ** ***
        ** * * :  *:  *
```

Binding hot spots and helical regions of human IL-10 are designated as shown previously. Sequences within the chicken IL-10 sequence that encompass peptides P25 (SEQ ID NO: 5) and P26 (SEQ ID NO: 6) are designated by boldface italics and colored gray. Peptide P21 (SEQ ID NO: 1) consists of P25, P26, and all of the chicken IL-10 residues between them in the sequence.

Examples of peptide design based on alignment with binding hot spots:

```
Chicken  ------ LEPTCLHFSELLPARLRELRVKFEEIKDYFQSRDD
Human    SPGQGTQSENSCTHFPGNLPNMLRDLRDAFSRVKTFFQMKDQ
         .    .     *  : *  **     **    ** * *    * . . : *   : * * : * :
Chicken  ELNIQLLSSELLDEFKGTFGCQSVSEMLRFYTDEVLPRAMQTSTSHQQSMGDLGNMLLGL
Human    -LDNLLLKESLLEDFKGYLGCQALSEMIQFYLEEVMPQAENQDPDIKAHVNSLGENLKTL
          *:  **...**::*** :***::***::** :**:*:* :  .  . :  :..**: *  *

Chicken   KATMRRCHRFFTCEKRSKAIKQIKETFEKMDENGIYKAMGEFDIFINYIEEYLLMRRR- (SEQ ID NO: 80)

Human    RLRLRRCHRFLPCENKSKAVEQVKNAFNKLQEKGIYKAMSEFDIFNYIEAYMTMKIRN (SEQ ID NO: 81)
         :    : ** *** *:  ** : : * ** : : * : * : : * : * : : * : * *** **. ** ** *** **
         * * :  *:  *
```

Binding hot spots and helical regions of human IL-10 are designated as previously shown. Peptide P27 (SEQ ID NO: 7) is designated by boldface, italicized and is colored in gray. Peptide P22 (SEQ ID NO: 2) is designated in boldface and included in a frame. Peptide 27 is the region within the P22 sequence.

Alignment of human (SEQ ID NO: 83) and chicken (SEQ ID NO: 82) IL-10R1 soluble domain sequences:

```
Human IL-10R1    HGTELPSPPSVWFEAEFFHHILHWTPIPNQSESTCYEVALLRYGIE-SWNSISNCSQTLS
Chicken IL-10r1  --ELRLKPTRVRFVAEMVYHLLQWEPGPDAPSDTRYDVEHKIYGTNSPWTAIPNCMKIHG
                       .*  * * **:.:*:*:* *  :  ..* *:*    ** :  *.:* ** :  .

Human IL-10R1    YDLTAVTLDLYHSNGYRARVRAVDGSRHSNWTVTNTRFSVDEVTLTVGSVNLEIHNGFIL
Chicken IL-10R1  HSCDLTYYTLDPSLRYYARVRAVVGNHTSDWKRTNA-FSPQEASLRLSGHSLAVTDNSIH
                 :.   .   *  *  * ****** *.: *:*. **: ** :*.:* :.. .* : :. *

Human IL-10R1    GKIQLPRPKMAPANDTYESIFSHFREYEIAIRKVPGNFTFTHKKVKHENFSLLTSGEVGE
Chicken IL-10R1  VQLQLLL-RAGNRTVKYDDIQKHARRYRVYIRRARDNQTYEVWETAS-EFYIRNLFWNTE
                  ::**   : .  . .*:.* .* *.*.: **:. .* *:   :.   :* : .     *

Human IL-10R1    FCVQVKPSVASRSNKGMWSKEECISLTRQYFTVTN---VIIFFAFVLL---LSGALAYCL (SEQ ID NO: 83)
Chicken IL-10R1  YCISVEPDVASRHIPAMRTAEQCVTIGHRDESAEL (SEQ ID NO: 82)
                 :*:.*:*.****   .* : *:*::: ::  :.
```

Human (NP_001549.2) and chicken (NP_001034686.1) sequences were obtained and edited as described above. Human IL-10R1 residues that are involved in binding to human IL-10 (FIG. 5 of Reineke et. al., 1998) are designated by boldface. Chicken IL-10R1 sequence alignment with the human IL-10R1 sequence is also shown; intracellular and transmembrane domains are omitted for clarity.

Example 3. Peptide Screening

Peptides were chemically synthesized, desalted, and purified to >98% purity by Watsonbio, Inc., Houston TX Peptide stock solutions were prepared at 10 mM in DMSO and diluted in assay buffer to 0.05 mM. Peptides were screened at Marin Biologic Laboratories, Inc., Novato, CA, by determining their effectiveness at blocking the inhibitory effect of chicken IL-10 on the induction of interferon gamma (IFN-γ) induced by concanavalin A (ConA) (or alternatively phytohemagglutinin (PHA) may be used) in chicken spleen cells (Wu et al. (2016) and Rothwell et al. (2004)). Briefly, lymphocytes and mononuclear cells were isolated from chicken spleens by differential centrifugation on Ficoll-Hypaque. Cells were cultured at $5\times10^6$ cells/mL in wells of a 96-well plate for 72 hours in the presence of peptide, 1.2 μg/mL ConA (or alternatively 12.5 μg/mL PHA), and with or without cIL-10. Spleen cells were also incubated without peptides and/or without ConA (or PHA) as controls. Levels of IFN-γ in the supernatants were determined by ELISA.

The use of peptides derived from IL-10s of several species that can be added to feed to reduce respiratory and intestinal illness in these animals is known in the art. See U.S. Pat. No. 8,652,457 B2 and U.S. patent application publication No. US2016/0280778 A1, which are incorporated by reference herein as if fully set forth. These peptides were designed to elicit an immune response in the animals, which would lead to the production of anti-IL-10 antibodies. In contrast, peptides described herein were designed with the goal of directly interfering with binding of chicken IL-10 to its receptor (that is, as IL-10R antagonists). As a result, the peptides described here were designed in part to mimic sections of either cIL-10 or the R1 subunit of the cIL-10 receptor and to compete with either cIL-10 or cIL-10R for binding to the other species, as opposed to the peptides in the previous patents that were designed to incorporate antigenic features of IL-10.

TABLE 1

Amino acid sequences of peptides

| SEQ ID NO | Description | Sequence |
|---|---|---|
| 1 | P21 | PARLRELRVKFEEIKDYFQSRDDELNIQLLSSEL LDEFKG |

TABLE 1-continued

Amino acid sequences of peptides

| SEQ ID NO | Description | Sequence |
|---|---|---|
| 2 | P22 | ENGIYKAMGEFDIFINYIEEYLLMRRR |
| 3 | P23 | PARLRELRVKFEEIKDYFQGGGSGGGSQQSMGDLGNMLLGLKATMRR |
| 4 | P24 | GCQSVSEMLRFYTDEVLPRAMQGGGSGGGSKAMGEFDIFINYIEEYLLMR |
| 5 | P25 | PARLRELR |
| 6 | P26 | LSSELLDEFKG |
| 7 | P27 | GEFDIFNYIE |
| 8 | P28 | SLRYYARVRA |
| 9 | P29 | TNAFSPQ |
| 10 | P11 | YDDIQKHARRYRVYIRRARDNQTYEVWET |
| 11 | P30 | IQKHARRY |
| 12 | P31 | NQTYEVWE |
| 13 | P32 | VASRHIPAM |
| 14 | P9* | FFKKFFKKFFKKFFKK |
| 15 | P6* | GTELPSPPSVWFEAEF |

*P9 and P6 are control peptides (Ni et al.)

Example 4. Basic Plant Expression Constructs for Production of IL-10R Antagonist Peptides in Maize The amino acid sequences for IL-10R antagonist peptides and all other sequences in this document have been back translated and codon optimized for expression in the desired host organism. As an example, for plant expression, maize codon usage was used to demonstrate codon optimization, expression cassette assembly, vector assembly, and plant transformation, but other host organisms could also be used. All IL-10R antagonist peptides and antibodies were back translated and codon optimized for expression in maize using the computer program Vector NTI (ThermoFisher Scientific, Waltham, MA). The resulting DNA sequences are presented in Table 2 and at the end of the document.

TABLE 2

IL-10R antagonist peptides and their maize codon optimized DNA coding sequences

| Peptide name | IL-10R antagonist peptide sequence | Maize codon optimized DNA sequence |
|---|---|---|
| P21 | PARLRELRVKFEEIKDYFQSRDDELNIQLLSSELLDEFKG (SEQ ID NO: 1) | CCGGCCAGGCTGAGGGAGCTGAGGGTGAAGTTCGAGGAGATCAAGGACTACTTCCAGAGCAGGGACGACGAGCTGAACATCCAGCTGCTGAGCAGCGAGCTGCTGGACGAGTTCAAGGGC (SEQ ID NO: 16) |
| P22 | ENGIYKAMGEFDIFINYIEEYLLMRRR (SEQ ID NO: 2) | GAGAACGGCATCTACAAGGCCATGGGCGAGTTCGACATCTTCATCAACTACATCGAGGAGTACCTGCTGATGAGGAGGAGG (SEQ ID NO: 17) |
| P23 | PARLRELRVKFEEIKDYFQGGGSGGGSQQSMGDLGNMLLGLKATMRR (SEQ ID NO: 3) | CCGGCCAGGCTGAGGGAGCTGAGGGTGAAGTTCGAGGAGATCAAGGACTACTTCCAGGGCGGCGGCAGCGGCGGCGGCAGCCAGCAGAGCATGGGCGACCTGGGCAACATGCTGCTGGGCCTGAAGGCCACCATGAGGAGG (SEQ ID NO: 18) |
| P24 | GCQSVSEMLRFYTDEVLPRAMQGGGSGGGSKAMGEFDIFINYIEEYLLMR (SEQ ID NO: 4) | GGCTGCCAGAGCGTGAGCGAGATGCTGAGGTTCTACACCGACGAGGTGCTGCCGAGGGCCATGCAGGGCGGCGGCAGCGGCGGCGGCAGCAAGGCCATGGGCGAGTTCGACATCTTCATCAACTACATCGAGGAGTACCTGCTGATGAGG (SEQ ID NO: 19) |
| P25 | PARLRELR (SEQ ID NO: 5) | CCGGCCAGGCTGAGGGAGCTGAGG (SEQ ID NO: 20) |
| P26 | LSSELLDEFKG (SEQ ID NO: 6) | CTGAGCAGCGAGCTGCTGGACGAGTTCAAGGGC (SEQ ID NO: 21) |
| P27 | GEFDIFNYIE (SEQ ID NO: 7) | GGCGAGTTCGACATCTTCAACTACATCGAG (SEQ ID NO: 22) |
| P28 | SLRYYARVRA (SEQ ID NO: 8) | AGCCTGAGGTACTACGCCAGGGTGAGGGCC (SEQ ID NO: 23) |

TABLE 2-continued

| IL-10R antagonist peptides and their maize codon optimized DNA coding sequences | | |
|---|---|---|
| Peptide name | IL-10R antagonist peptide sequence | Maize codon optimized DNA sequence |
| P29 | TNAFSPQ (SEQ ID NO: 9) | ACCAACGCCTTCAGCCCGCAG (SEQ ID NO: 24) |
| P11 | YDDIQKHARRYRVYIRR ARDNQTYEVWET (SEQ ID NO: 10) | TACGACGACATCCAGAAGCACGCCAGGAGG TACAGGGTGTACATCAGGAGGGCCAGGGAC AACCAGACCTACGAGGTGTGGGAGACC (SEQ ID NO: 25) |
| P30 | IQKHARRY (SEQ ID NO: 11) | ATCCAGAAGCACGCCAGGAGGTAC (SEQ ID NO: 26) |
| P31 | NQTYEVWE (SEQ ID NO: 12) | AACCAGACCTACGAGGTGTGGGAG (SEQ ID NO: 27) |
| P32 | VASRHIPAM (SEQ ID NO: 13) | GTGGCCAGCAGGCACATCCCGGCCATG (SEQ ID NO: 28) |

Examples of basic cloning vectors containing individual expression cassettes for P24 IL-10R antagonist peptide are given in Table 3. Analogous vectors could be made for any of the other IL-10R antagonist peptides listed in Table 2, or antibodies, by substituting the P24 peptide transgene with a different peptide or antibody sequence.

TABLE 3

| P24 basic expression vectors | | | |
|---|---|---|---|
| Vector | Promoter | N-terminal signal | C-terminal signal |
| pAG4305 | prOsGluB4 | xGZein27ss | KDEL (SEQ ID NO: 29) |
| pAG4981 | prZmgZ27 | xGZein27ss | KDEL (SEQ ID NO: 29) |
| pAG4982 | prGtl1 | xGZein27ss | KDEL (SEQ ID NO: 29) |
| pAG4983 | prZmGlb1 | xGZein27ss | KDEL (SEQ ID NO: 29) |
| pAG4984 | prZmOle16 | xGZein27ss | KDEL (SEQ ID NO: 29) |

Figure 1G:
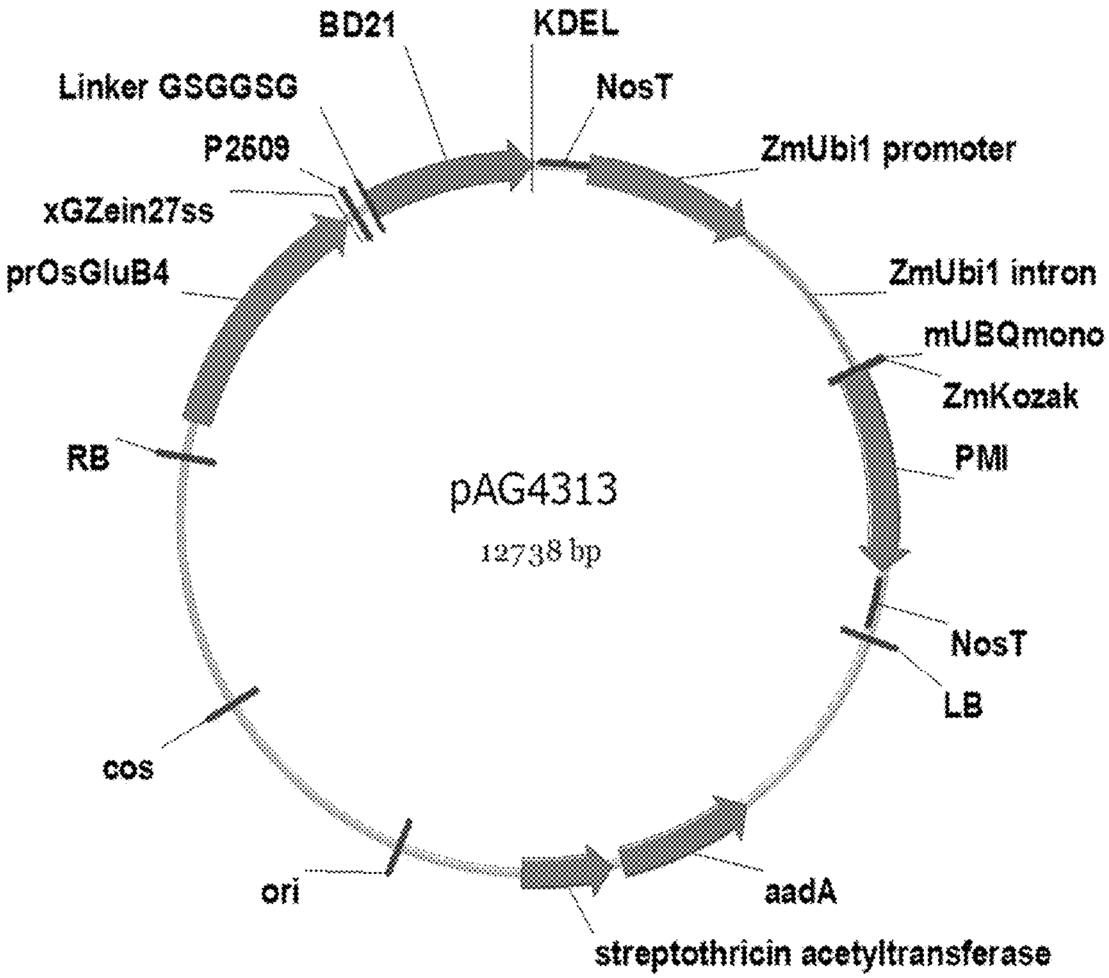

FIGS. 1A-1G illustrate the schematic drawings of the vectors pAG4305 (FIG. 1A), pAG4306 (FIG. 1B), pAG4308 (FIG. 1C), pAG4310 (FIG. 1D), pAG4311 (FIG. 1E), pAG4312 (FIG. 1F), and pAG4313 (FIG. 1G).

Figure 2A:
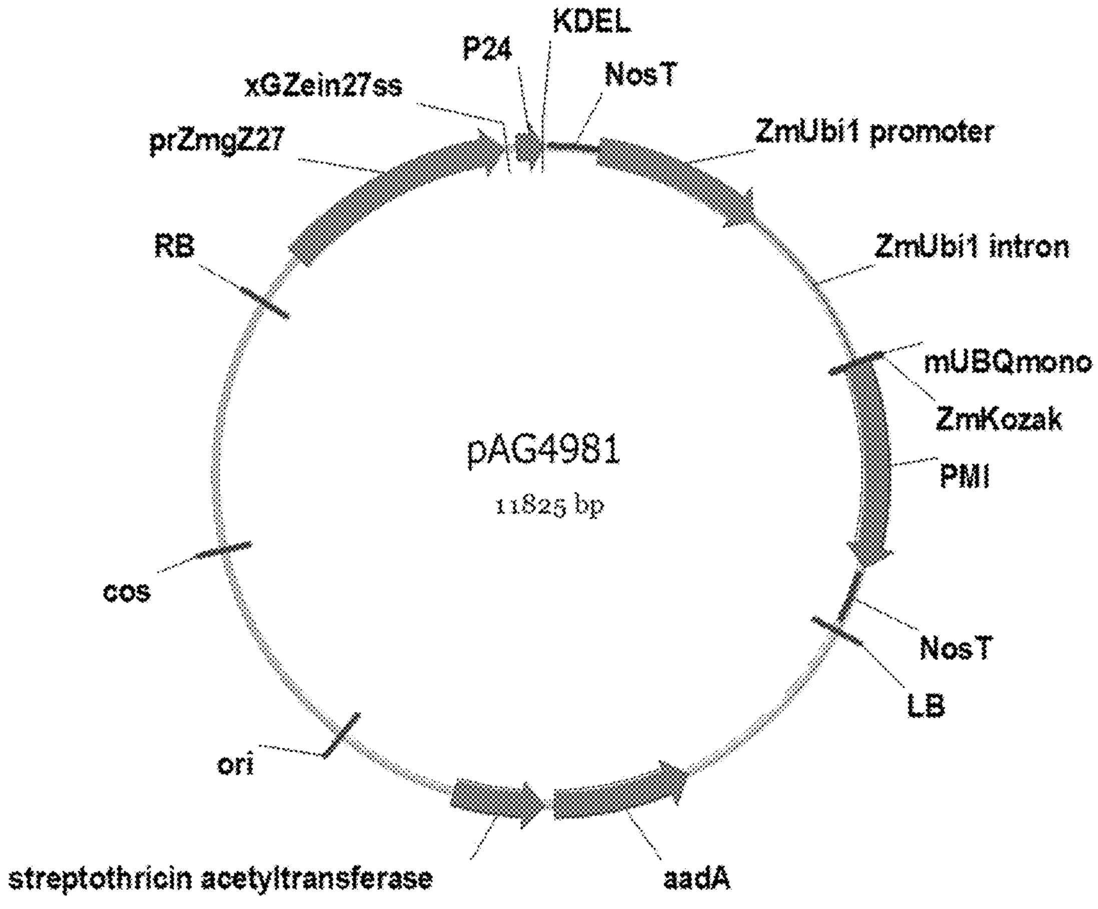
FIGS. 2A-2D are schematic drawings of the vectors pAG4981 (FIG. 2A), pAG4982 (FIG. 2B), pAG4983 (FIG. 2C), and pAG4984 (FIG. 2D).
Figure 2B:
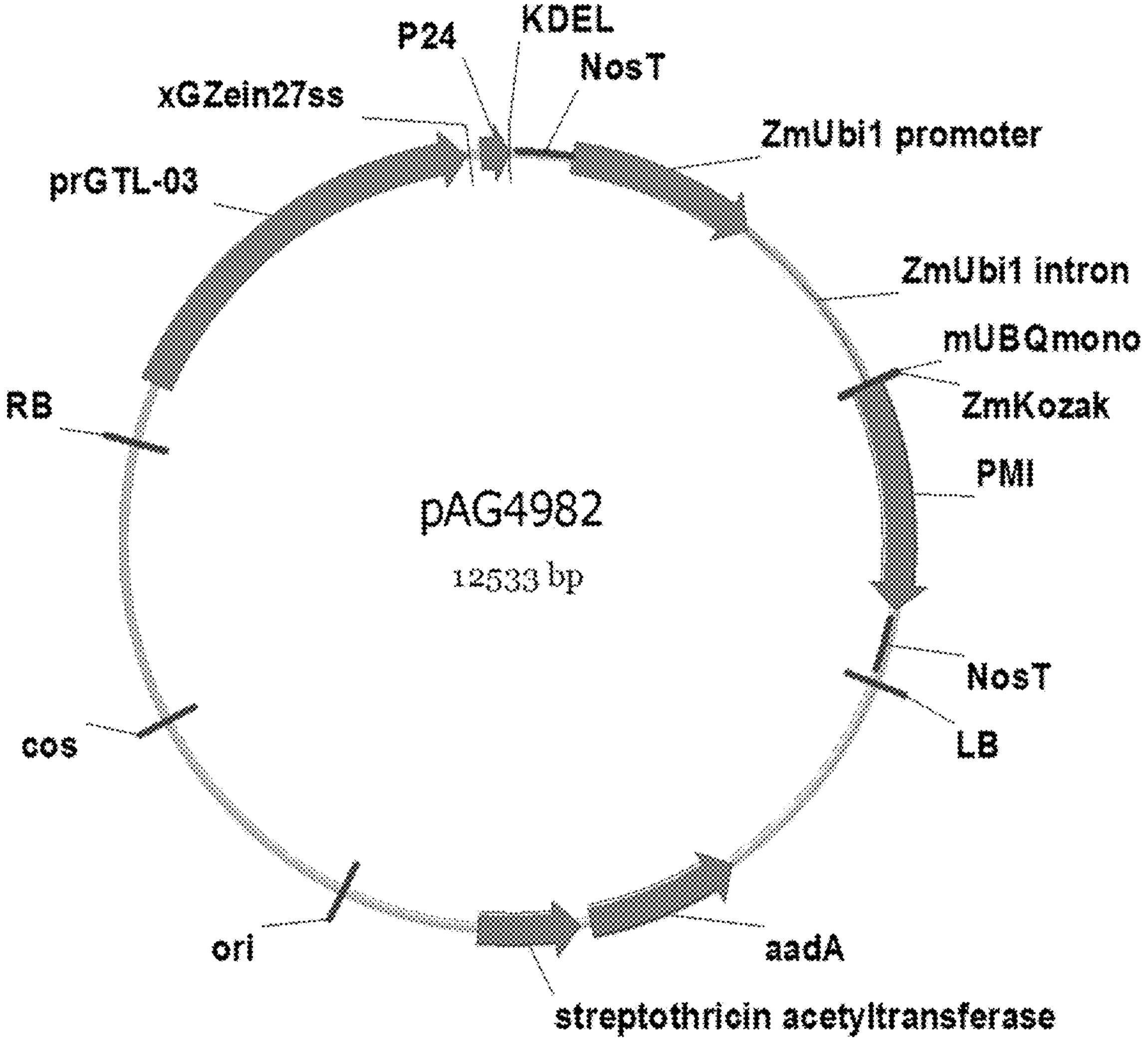
Figure 2C:
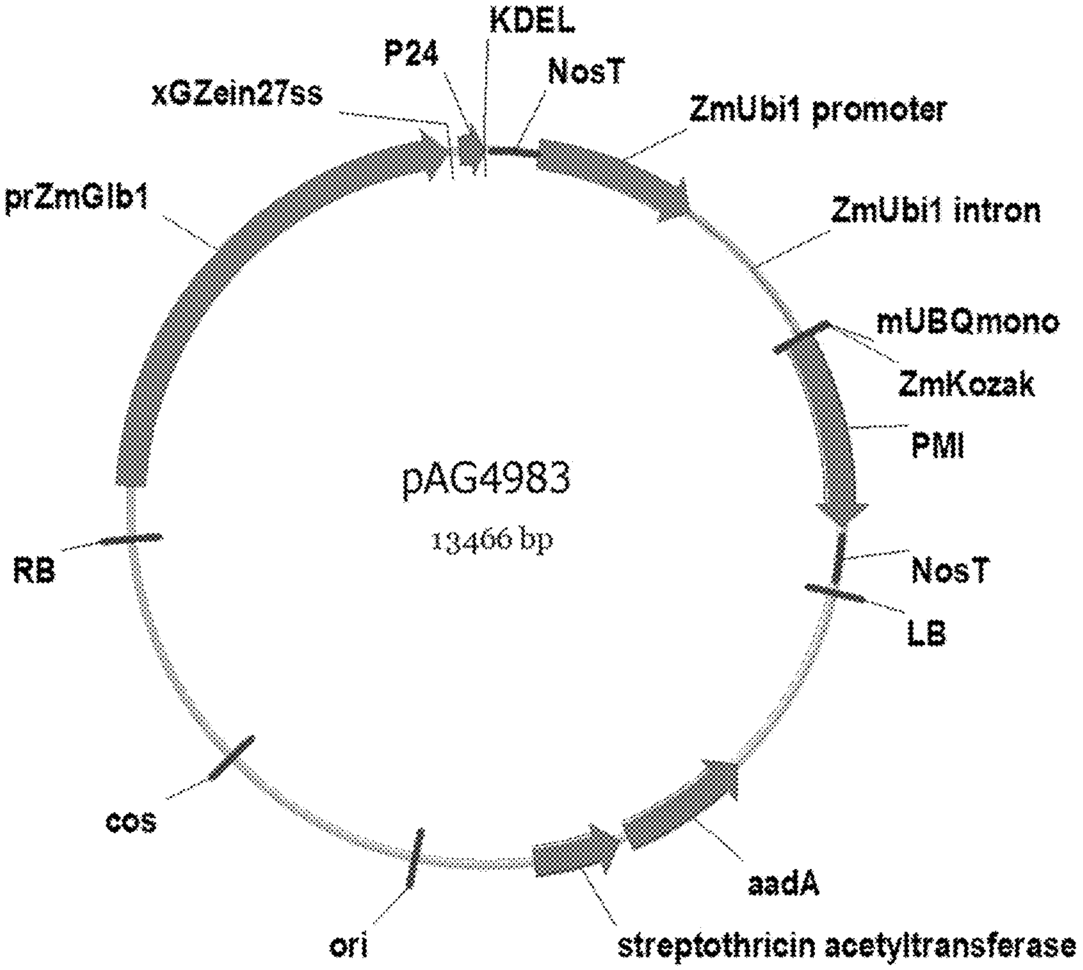
Figure 2D:
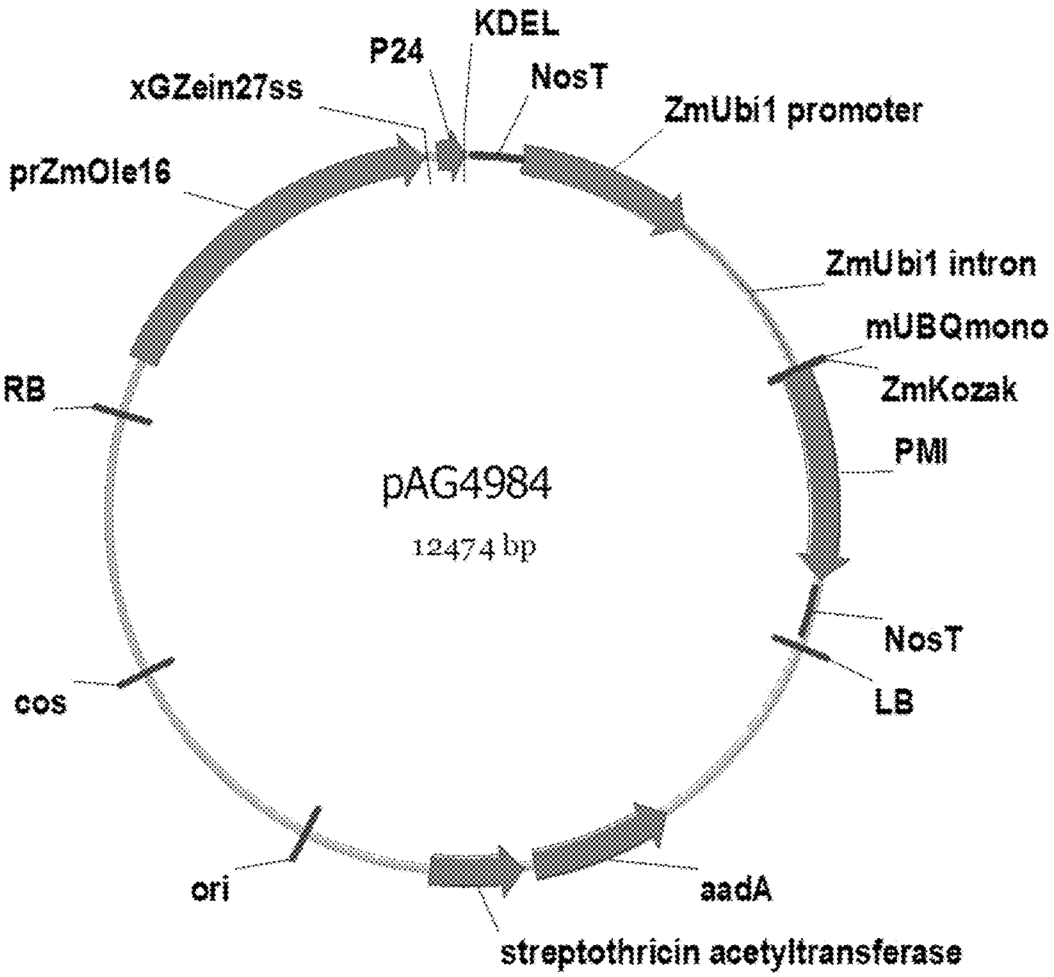

FIGS. 2A-2D illustrate the schematic drawings of the vectors pAG4981 (FIG. 2A), pAG4982 (FIG. 2B), pAG4983 (FIG. 2C), and pAG4984 (FIG. 2D).

Any DNA fragments encoding IL-10R antagonist peptides listed in Table 2, or anti-IL-10 single domain antibodies, can be cloned between desirable promoter and Nos terminator sequence in the basic P24 peptide expression vectors (Table 3), in order to generate required expression cassettes. In addition, amino terminal (N) signal sequences, such as xGZein27ss in maize expression vectors, can be replaced by other signal sequences in order to modulate specific expression and accumulation of IL-10R antagonist peptides or antibodies to desired levels. N-terminal signal sequences include, but not limited to, for example by OsGluB4sp (rice GluB-4 glutelin signal peptide), BAASS (barley alpha amylase signal sequence), or PR1 (pathogenesis related protein). The IL-10R antagonist peptides, or anti-IL-10 single domain antibodies, can be expressed to endoplasmic reticulum (ER) for improved accumulation and glycosylation using carboxyl terminal (C) retention signal sequences such KDEL (SEQ ID NO: 29), HDEL (SEQ ID NO: 30), or SEKDEL. Furthermore, IL-10R antagonist peptides, or anti-IL-10 single domain antibodies, can be expressed and directed to protein storage vacuoles with the help of signal sequences attached to either N-terminal or C-terminal part of the sequence. These storage vacuole signal sequences include HvAle from barley aleurone (thiol protease) or HvVSD from barley polyamine oxidase. If necessary, IL-10R antagonist peptides, or anti-IL-10 singe domain antibodies, can be also expressed from basic P24 vectors without signal sequences for accumulating expressed products in apoplast or cytoplasm. All those mentioned above and other signal sequences of similar functions can be added to or removed from the basic plant expression vectors. Signal sequences described above can be found in the "List of sequences" at the end of this document.

Example 5. Additional Strategies for Expressing IL-10R Antagonist Peptides in Transgenic Maize Peptide Concatenation.

This strategy represents expression of a chimeric IL-10R antagonist sequence that contains multiple, contiguously linked, copies of DNA sequences encoding IL-10R antagonist peptides. The peptide coding sequences in a concatemer could be fused directly to one another or separated by intervening sequences such as AGPA hinges for stabilizing chimeric molecule for expression. Examples of possible variants of concatenated peptide sequences for the eight amino acid long peptide P25 are provided in Table 4. Each P25 concatemer can be synthesized as DNA molecule and cloned into any P24 basic expression vectors thus effectively replacing P24 coding sequence for subsequent expression in maize. In this way, new maize transformation vectors can be developed, such as for example pAG4306, where P2509 concatemer that is composed of three P25 units separated by AGPA hinges is expressed from the rice GluB4 promoter into ER. Nucleotide sequence for P2509 is available in the "List of sequences" section. A similar approach can be used for expressing all other short or all IL-10R antagonist peptides that are listed in Table 2.

TABLE 4

Examples of the P25 IL-10R antagonist peptide and concatemers for expression in maize

| Peptide | Sequence for maize expression |
|---|---|
| P25 | PARLRELR (SEQ ID NO: 5) |
| P2501 | PARLRELRKDEL (SEQ ID NO: 32) |
| P2502 | PARLRELRPARLRELR (SEQ ID NO: 33) |
| P2503 | PARLRELRPARLRELRKDEL (SEQ ID NO: 34) |
| P2504 | PARLRELR**AGPA**PARLRELR (SEQ ID NO: 35) |
| P2505 | PARLRELR**AGPA**PARLRELRKDEL (SEQ ID NO: 36) |
| P2506 | PARLRELRPARLRELRPARLRELR (SEQ ID NO: 37) |
| P2507 | PARLRELRPARLRELRPARLRELRKDEL (SEQ ID NO: 38) |
| P2508 | PARLRELR**AGPA**PARLRELR**AGPA**PARLRELR (SEQ ID NO: 39) |
| P2509 | PARLRELR**AGPA**PARLRELR**AGPA**PARLRELRKDEL (SEQ ID NO: 40) |

Gene Fusions.

Another strategy for expressing IL-10R antagonist peptides in plants can employ chimeric enlargement or gene fusion approach. In this strategy, target peptides can be expressed, for example, as chimeric fusions with parts of the maize gamma-zein 27 kDa. This strategy was used for expressing zeolin and Zera fusion proteins (Mainieri et al., 2007; U.S. Pat. No. 8,802,825; Llop-Tous, 2010, all of which are incorporated herein by reference as if fully set forth). Co-expression of target sequences as gamma-zein fusions allows high level protein accumulation in ER-derived protein bodies. The IL-10R antagonist peptide sequences selected for expression can be fused to maize gamma-zein sequences with the help of linker sequences such as, for example linker GSGGSG (SEQ ID NO: 41). Additional linker sequences, for example linkers similar to those in zeolin fusion protein (GGGGS; SEQ ID NO: 42), Zera fusions (GGGGG; SEQ ID NO: 43), or other linkers can also be exploited (Table 5). All IL-10R antagonist peptides can be expressed with or without C-terminal sequence such as KDEL (SEQ ID NO: 29), HDEL (SEQ ID NO: 30), SEKDEL (SEQ ID NO: 31), HvVSD, or other such sequences. Furthermore, gamma-zein sequences as fusion components of chimeric protein enlargements can be substituted for other protein sequences such as, for example, elastin-like polypeptides (ELP) (Urry, 1992), which were used for expressing human IL-10 in tobacco (Patel et al., 2007) or hydrophobins that were used for transient protein expression in *Nicotiana benthamiana* (Joensuu et al., 2010; Jacquet et al., 2014). When either of the latter two approaches is used, expressed protein fusions form protein bodies. Two constructs that serve as examples for expressing P2509 concatemer fused with maize gamma-zein components are represented by the vectors pAG4308 and pAG4310. The pAG4311 vector is an example of expressing P2509 as a fusion with 28×VPGVG (SEQ ID NO: 44) elasting-like polypeptide (Conley et al., 2009). Variable number of repeats and sequences such as VPGXG in ELP fusion partner could be used for expressing IL-10R antagonist peptides. The ELP fusion proteins can be purified by nonchromatographic bioseparation of recombinant proteins (Lin et al., 2006). The pAG4312 construct provides an example of expressing P2509 peptide fused to the mature chain of *Trichoderma reesei* HFBI hydrophobin (GenBank Accession #P52754.1). Hydrophobins fusions can be purified by efficient surfactant-based aqueous two-phase system (ATPS) (Joensuu et al., 2010). Other fusion partners for IL-10R antagonist peptides could additionally be exploited such as, fusing P2509 to a thermal stable glucanase enzyme, which is presented in vector pAG4313.

TABLE 5

Linker sequences for developing protein fusions

| Linker sequence | Nucleotide | Description |
|---|---|---|
| GSGGSG (SEQ ID NO: 41) | ggcagcggcggcagcggc (SEQ ID NO: 45) | Linker for expression Phy02opt: BD21 |
| GGGGS (SEQ ID NO: 42) | ggcggcggcggcagc (SEQ ID NO: 46) | Linker used for Zeolin expression (Mainieri et al., 2004) |
| GGGGG (SEQ ID NO: 43) | ggcggcggcggcggc (SEQ ID NO: 47) | Linker used for expressing Zera fusions (Llop-Tous et al., 2011) |

Example 6. Production of Single-Domain Antibodies to IL-10

Camelid single-domain antibodies (sdABs; also known as $V_HH$ antibodies) with affinity for cIL-10 were generated by immunizing a llama with full-length, purified recombinant cIL-10 (IBI Scientific, Peosta IA). Full-length IL-10 was selected, as opposed to individual cIL-10 peptides, because cIL-10 is only 48% identical to the llama IL-10 homologue. It was previously unknown whether cIL-10 would generate an adequate immune response in llamas, but given the limited sequence identity, cIL-10 was used to test whether llamas would be naïve, and that the full-length molecule could be used to generate an adequate immune response. Furthermore, IL-10 is known to dimerize, thus using the full-length molecule would bias the generated antibodies towards epitopes that are present in the dimerized molecule. That llamas would not otherwise be exposed to cIL-10, except through injection of isolated or recombinant cIL-10, provided a novel process for generating anti-cIL-10 antibodies. Pre-immune serum was collected from a single llama prior to injection with cIL-10. The first immunization was carried out with 200 μg of cIL-10 in the presence of Complete Freund's Adjuvant (CFA). Subsequent booster immunizations were carried out, each with 100 μg cIL-10, in the presence of Incomplete Freund's Adjuvant (IFA) three weeks, seven weeks and eleven weeks after the initial immunization. Blood samples ("bleeds") were collected from the animal one week after each of the booster immunizations. FIG. 3 illustrates the llama's immune response prior to (pre-immune), and after being dosed with cIL-10.

Figure 4:
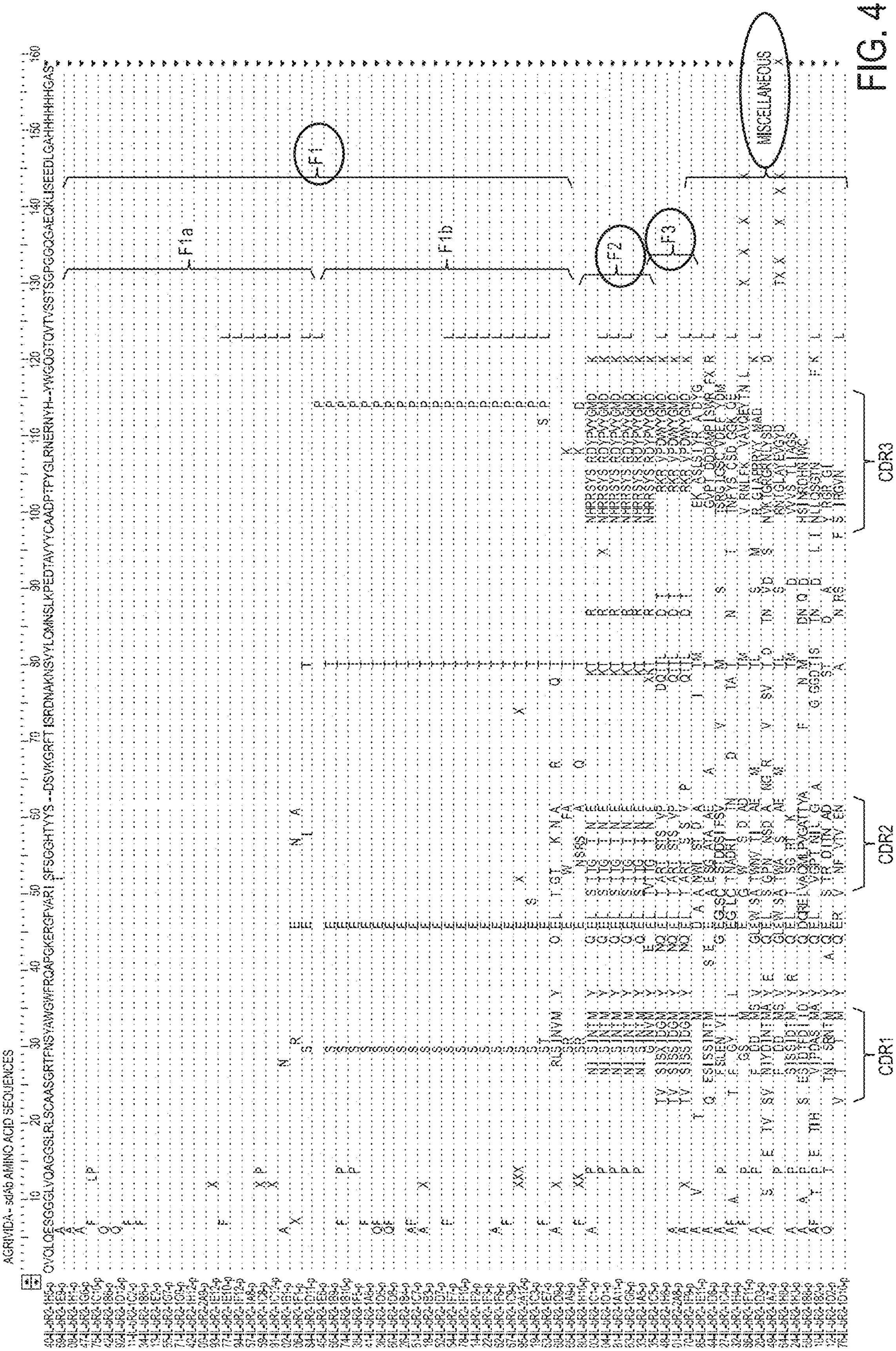
FIG. 4 illustrates the sequencing results from the anti-IL-10 antibody development and inter-relationship among the identified sequences. In this figure, sequences of sdAbs according to embodiments herein are aligned and compared to the sequence of sdAbs 40-IL-bR2-1115 set forth as SEQ ID NO: 208. The amino acid (AA) positions replaced in the sequence of SEQ ID NO: 208 are as follows: for 68-IL-bR2-1D9, AA 26 to 34 (SEQ ID NO: 209); for 80-IL-bR2-1H10, AA 54 to 57 (SEQ ID NO: 210); for 03-IL-bR2-1C1, 04-IL-bR2-1D1, 81-IL-bR2-1A11, 63-IL-bR2-1G8, and 33-IL-bR2-1A5, AA 30 to 34 (SEQ ID NO: 211), AA 97 to 103 (SEQ ID NO: 212), and AA 105 to 112) SEQ ID NO: 213); for 35-IL-bR2-1C5, AA 30 to 34 (SEQ ID NO: 214), AA 50 to 54 (SEQ ID NO: 215), and AA 97 to 103 (SEQ ID NO: 212); for 48-IL-bR2-1E16, AA 27 to 34 (SEQ ID NO: 216), AA 75 to 79 (SEQ ID NO: 217), and AA 105 to 112 (SEQ ID NO: 218); for 01-IL-bR2-2A8 and 70-IL-bR2-1F9, AA 27 to 34 (SEQ ID NO: 216), AA 105 to 112 (SEQ ID NO: 218), and AA 76 to 79 (SEQ ID NO: 219); for 85-IL-bR2-1E11, AA 102 to 108 (SEQ ID NO: 220); for 44-IL-bR2-1D6, AA 26 to 34 (SEQ ID NO: 221), AA 99 to 102 (SEQ ID NO: 222), and AA 104 to 113 (SEQ ID NO: 223); for 27-IL-bR2-1C4, AA 27 to 31 (SEQ ID NO: 224), AA 46 to 50 (SEQ ID NO: 225), AA 53 to 61 (SEQ ID NO: 226), and AA 98 to 105 (SEQ ID NO: 227); for 32-IL-bR2-1114, AA 52 to 57 (SEQ ID NO: 228), and AA 98 to 102 (SEQ ID NO: 229); for 86-IL-bR2-1F11, AA 100 to 104 (SEQ ID NO: 230), and AA 107 to 110 (SEQ ID NO: 231); for 20-IL-bR2-ID3, AA 44 to 47 (SEQ ID NO: 232), AA 52 to 55 (SEQ ID NO: 233), and AA 100 to 107 (SEQ ID NO: 234); for 49-IL-bR2-1A7, AA 27 to 35 (SEQ ID NO: 235), and AA 97 to 109 (SEQ ID NO: 236); for 24-IL-bR2-1113, AA 24 to 37 (SEQ ID NO: 237), AA 98 to 101 (SEQ ID NO: 238), and AA 103 to 108 (SEQ ID NO: 239); for 58-IL-bR2-1B8, AA 26 to 35 (SEQ ID NO: 240), AA 46 to 61 (SEQ ID NO: 241), and AA 97 to 107 (SEQ ID NO: 242); for 10-IL-bR2-1B2, AA 27 to 32 (SEQ ID NO: 243), AA 52 to 59 (SEQ ID NO: 244), AA 75 to 80 (SEQ ID NO: 245), and AA 97 to 104 (SEQ ID NO: 246); for 12-IL-bR2-1D2, AA 30 to 34 (SEQ ID NO: 247), and AA 55 to 58 (SEQ ID NO: 248); and for 76-IL-bR2-1D10, AA 99 to 103 (SEQ ID NO: 249).

The production of antibodies targeting cIL-10 in the animal during this immunization process was evaluated via ELISA using each of the bleeds as shown in FIG. 3, and the bleeds were then used to develop single-domain antibodies. The alignment of the chicken and llama IL-10 homologs shows 48% identity (68% similarity). The preparation of sdABs has been described elsewhere (Goldman et al. 2006; Arbabi Ghahroudi et al. 1997; Liu et al. 2013). Briefly, peripheral blood mononuclear cells (PBMCs) were isolated from the bleeds that were collected during weeks eight and 12 of the immunization protocol. RNA was purified from the PBMCs and used to create phagemid cDNA libraries for expression and screening of sdABs. Notably, sdABs represent only the heavy chain variable region (VHH) from the llama antibodies produced when the host was injected with recombinant cIL-10, and therefore the RNA-derived, DNA coding sequence of sdABs represents a synthetic nucleotide that is produced through a novel process that does not occur in nature. Two rounds of panning against purified recombinant cIL-10 were used to enrich the library for phage displaying sdAB with affinity for the antigen. From the enriched libraries, individual clones were generated, isolated and sequenced. FIG. 4 illustrates the results of the anti-IL-10 sdAB screening and sequencing. FIG. 4 demonstrates that the isolated sdAB amino acid sequences reside in four distinct groups, with a fifth miscellaneous group. The complementarity-determine regions (CDRs) are designated in FIG. 4.

Example 7. Anti-IL-10 sdAbEC50 Measurements and Thermal Stability

Figure 5:
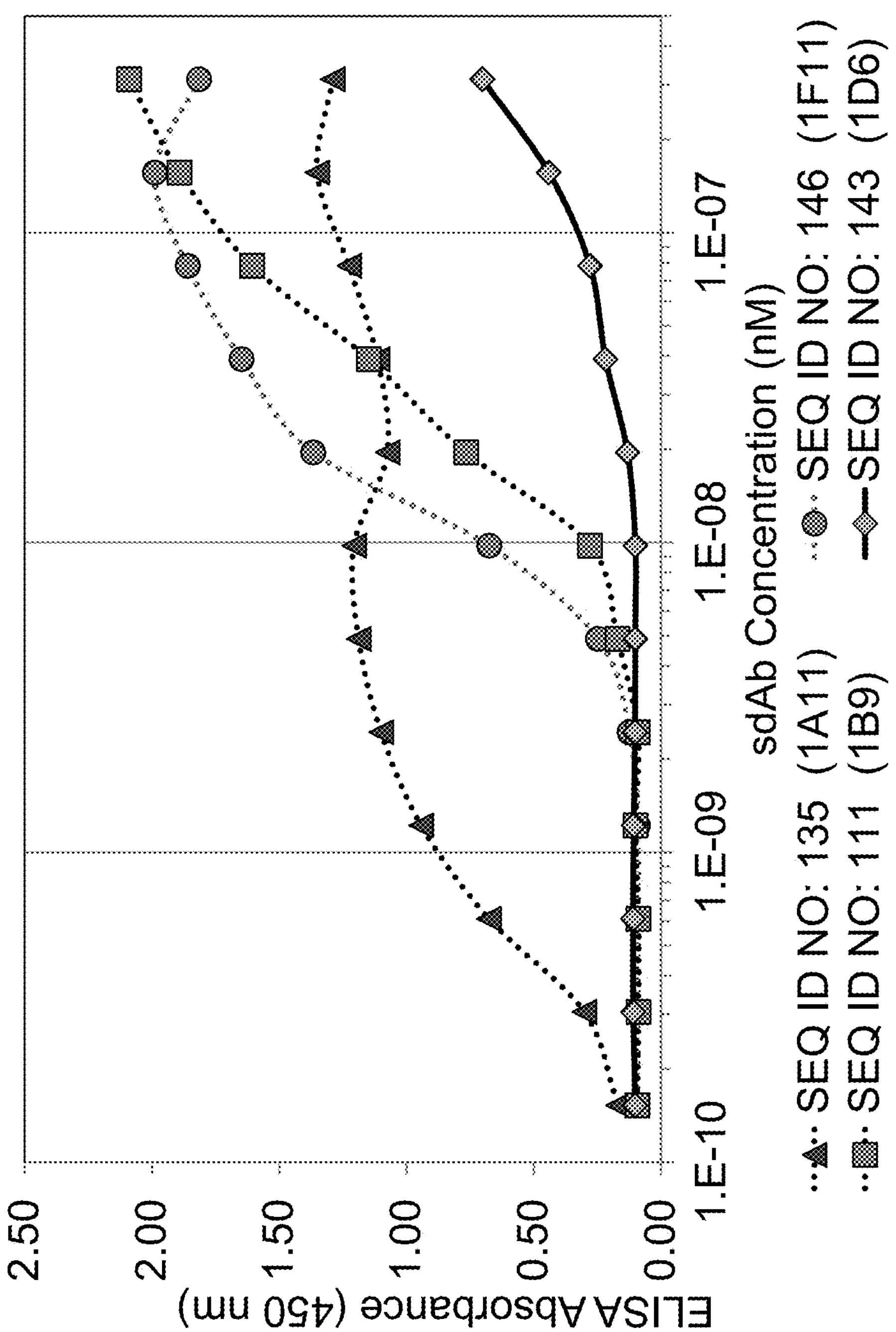
FIG. 5 illustrates apparent binding affinity of anti-IL-10 antibodies to chicken IL-10.

Candidate sdABs were evaluated for their apparent binding affinity against purified cIL-10, as measured by ELISA. Different concentrations of individual isolated sdABs were incubated on cIL-10 ELISA plates, with increasing signals indicative of higher levels of sdAB binding to cIL-10. Apparent EC50 values were estimated by determining the sdAB concentration at which 50% of the maximum signal was observed. FIG. 5 illustrates the ELISA measurements and apparent binding affinity of selected sdAB candidates to chicken IL-10. Among the candidates tested, chIL10sdAB1A11 (SEQ ID NO: 135), chIL10sdAB1F11 (SEQ ID NO: 146), and chIL10sdAB1B9 (SEQ ID NO: 111), had EC50 values of less than 100 nM, with estimated values of 1 nM, 15 nM, and 35 nM, respectively. Another sdAB, chIL10sdAB1D6 (SEQ ID NO: 143), had an estimated EC50 value of 100 nM. Additional sdABs were evaluated in this way for their EC50 values, including chIL10sdAB1H1 (SEQ ID NO: 89) with an EC50 value of 20 nM. Since higher binding affinity is reflected by lower EC50 values, sdABs with low EC50 values, and more divergent sequences were selected for further assessment and development.

Although sdABs are considered to have high specificity for their antigenic target, and do not bind strongly to non-specific peptides, it is often desirable to demonstrate binding specificity to individual epitopes or peptides. The sdABs were prepared using the full-length chIL-10 protein, however individual peptides could also be used in our method. Likewise, counter selecting sdABs that bind the full length chIL-10, but had little or no affinity to specific peptides was also used to identify sdABs that bound desired antigenic peptides, but not others. Counter selection can be made using several different methods, including an ELISA or dot-blot, where the peptides for counter selection are immobilized on a surface and the anti-cIL-10 sdAB are incubated to allow binding, washed to remove unbound sdAB, then incubated with a labeled anti-llama antibody to detect any bound sdAB. Any sdAB that does not bind the immobilized peptides used for counter selection but still bind the full length IL-10, can be further developed with the confidence that they possess the desired binding criteria. Some peptides that were used for counter selection include: DDELNIQL [peptide 1; SEQ ID NO: 180], VLPRAMQT [peptide 2; SEQ ID NO: 181], EKMDENGI [peptide 3; SEQ ID NO: 182], EPTCLHFS [peptide 4; SEQ ID NO: 183], DQMGDLL [peptide 5; SEQ ID NO: 184], DQLHSLL [peptide 6; SEQ ID NO: 185], VMPKAESD [peptide 7; SEQ ID NO: 186], VMPQAENH [peptide 8; SEQ ID NO: 187], SKLQERGV [peptide 9; SEQ ID NO: 188], SELQERGV [peptide 10; SEQ ID NO; 189], ENSCIHFP [peptide 11; SEQ ID NO: 190], DSSCIHLP [peptide 12; SEQ ID NO: 191], DQLNSML [peptide 13; SEQ ID NO: 192], NMLQERGV [peptide 14; SEQ ID NO: 193], DSSCTHFP [peptide 15; SEQ ID NO: 194], DDLEIGL [peptide 16; SEQ ID NO: 195], VLPTAIADMTEE peptide 17; SEQ ID NO: 196], TQMEGKGP [peptide 18; SEQ ID NO: 197], and NQCCRFV [peptide 19; SEQ ID NO: 198].

Internal screening for thermal stability was performed to determine the heat tolerance of sdABs, which may be important for their use in animal feed processing. In particular, thermal stability is a highly desirable property in animal feed pelleting processes, where the molecules may be exposed to temperatures over 70° C., and up to 125° C., depending on the specific process and pelleting equipment used. In order to evaluate the thermal stability, heat treated sdABs were prepared by incubating the sdABs at 70° C., 75° C., 80° C., 85° C., and 90° C. for 30 seconds, 60 seconds, 90 seconds, 120 seconds, 300 seconds and 600 seconds, and were then allowed to equilibrate to room temperature. Control sdABs were incubated at 37° C. or room temperature, for the same period of time that the heat treated sdABs and also allowed to equilibrate to room temperature. The EC50 values of the sdABs were then compared between the control (37° C. or room temperature treated) and treatment (those heated between 70° C. and 90° C. for various amounts of time) sdABs by ELISA. Thermal stability, as expressed by the ratio of the EC50 values of the heat treated sdABs and control sdABs, ranged between 30% to 90%, with higher thermal stability values correlating to lower temperatures and lower exposure times.

Example 8. Anti-IL-10 sdAb Gastric Stability

Simulated gastric fluid (SGF) consisted of 0.084 M HCl, 35 mM NaCl, pH 1.2, containing 2630 Units of pepsin per milliliter. Reaction stop solution was 200 mM sodium carbonate. Protein samples, including bovine serum albumin (BSA), chIL10sdAB1A11 (SEQ ID NO: 135), chIL10sdAB1F11 (SEQ ID NO: 146), chIL10sdAB1H1 (SEQ ID NO: 89), chIL10sdAB1B9 (SEQ ID NO: 111), chIL10sdAB1D6 (SEQ ID NO: 143), chIL10sdAB1E11 (SEQ ID NO: 142) chIL10sdAB1F7 (SEQ ID NO: 121) chIL10sdAB1F9 (SEQ ID NO: 141), and chIL10sdAB2A8 (SEQ ID NO: 140), to be tested were brought to a concentration of 5 mg/mL in storage buffer (50 mM MES, 150 mM NaCl, 40% (v/v) glycerol, pH 6.3).

Figure 6:
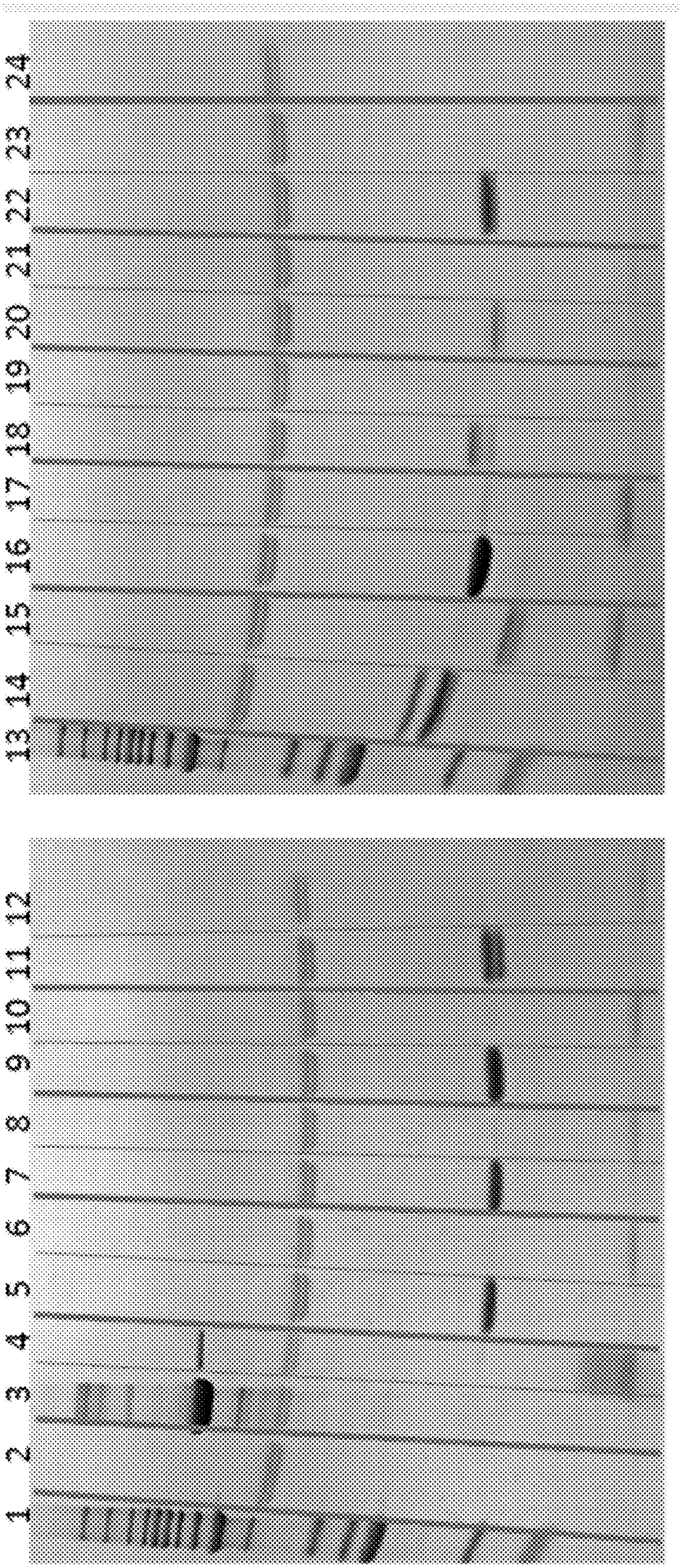
FIG. 6 illustrates results of the anti-IL-10 antibody digestion in the simulated gastric fluid (SGF) test.

Single domain antibody samples (2.5 μL) were dispensed into 200 μL thin-walled PCR tubes and prewarmed on a PCR thermal cycler set to 37° C. Aliquots (100 μL) of SGF were placed into PCR tubes and also prewarmed. For 0 minute digestion samples, 17.5 μL of stop solution was added to the protein samples before adding SGF. Digestions were initiated by the addition of 47.5 μL of prewarmed SGF to the sdAB samples. After 1 minute, 2 minutes, 5 minutes, 10 minutes, and 30 minutes, reactions were terminated by the addition of 17.5 μL stop solution. SDS-PAGE sample-loading buffer (17.5 μL; ThermoFisher catalog #NP0007, with dithiothreitol added to a concentration of approximately 50 mM) was added to each sample. After heating for 10 minutes at 70° C., 15 μL of each sample was loaded onto a protein electrophoresis gel (ThermoFisher catalog #NP0321 or similar) and electrophoresis was performed as directed by the manufacturer. Gels were then stained with Coomassie Blue dye using standard methods. Results are shown in FIG. 6 for the 0 and 10 minute time points. In this figure, lane 1—molecular weight standards; lane 2—pepsin only; lane 3—BSA 0 min; lane 4—BSA 10 min; lane 5—1A11 0 min; lane 6—1A11 10 min; lane 7—1F11 0 min; lane 8—1F11 10 min; lane 9—1H1 0 min; lane 10-1E11 10 min; lane 11-1B9 0 min; lane 12-1B9 10 min; lane 13—molecular weight standards; lane 14-1D6 0 min; lane 15-1D6 10 min; lane 16-1E11 0 min; lane 17-1E11 10 min; lane 18-1F7 0 min; lane 19-1F7 10 min; lane 20-1F9 0 min; lane 21-1F9 10 min; lane 22-2A8 0 min; lane 23-2A8 10 min; and lane 24—pepsin only. FIG. 6 shows that BSA is significantly degraded within a 10 minute digestion in SGF, as are all of the sdABs tested. Given the inherent rapid digestibility of the sdABs, it is unexpected that the sdABs perform well in controlling Coccidiosis and binding IL-10 when dosed into feed. It may have been anticipated that rapid digestion in SGF would underlie poor performance of sdABs in controlling Coccidiosis as they should be quickly degraded and therefore have a limited ability to bind IL-10 and block IL-10 signaling. Given that the sdABs described herein are effective in controlling Coccidiosis suggests that gastric stability is not a dominating factor in oral antibody administration and is a beneficial trait as proteins that are rapidly degraded in SGF pose a lower allergenicity risk than those that are stable in SGF. Given the increased thermal stability of sdABs (see discussion in Example 1, above), it is unusual that the developed sdABs are readily digestible by pepsin, as it is widely regarded that high thermal stability, as demonstrated by sdABs, correlates with high SGF stability, in contrast to the measured digestibility of the developed anti-IL-10 sdABs. The anti-IL-10 sdABs developed herein have good thermal stability and are readily digested in pepsin, which are attributes that support the product's performance and safety profile, which should aid in its regulatory evaluation and eventual customer acceptance.

Example 9. Chicken IL-10 Ligand-Receptor Assay and sdAB IC50 Measurement

An assay was developed to measure how the sdABs bind their target cIL-10, and prevent cIL-10 from binding to its receptor. The soluble domain of the cIL-10 receptor was expressed and immobilized on a biacore probe surface. It was then incubated with cIL-10 and different mixtures of sdABs and cIL-10, and the binding of cIL-10 to the soluble domain of the cIL-10 receptor was measured by surface plasmon resonance.

The amino acid sequence of the soluble domain of the chicken interleukin-10 receptor subunit 1 (cIL-10R1) was deduced by alignment of the amino acid sequence of the human IL-10R alpha receptor subunit (UniProtKB/SwissProt accession number Q13651) with the analogous chicken IL-10 receptor subunit 1 (NCBI reference sequence NP_001034686).

For this assay, the gene coding for the chicken receptor soluble domain (residues 22-231) was synthesized as an upstream fusion to the human $IgG_1$ Fc domain (residues 100-330 of UniProtKB/SwissProt accession number P01857) connected by a linker consisting of IEGRMD [SEQ ID NO: 199] (the final, aggregate expressed molecule comprising the cIL-10R1 fused to IEGRMD [SEQ ID NO: 199] fused to the Fc residues 100-330 will be referred to as "cIL-10R1-Fc"). cIL-10R1-Fc could be directly immobilized to facilitate the surface plasmon resonance binding assay on a biacore instrument. To produce cIL-10R1-Fc, the gene encoding cIL-10R1-Fc was cloned into pGAPZaB (ThermoFisher) via the EcoRI and NotI restriction sites. *Pichia pastoris* strain GS115 was transformed with the plasmid as directed in the pGAPZaB instruction manual. A high-expressing clone was grown in a 2.5 L fermenter using a fed-batch protocol. Growth medium in the batch phase consisted of 1.5 L of 20 g/L peptone, 10 g/L yeast extract, 13.4 g/L yeast nitrogen base, 10 g/L casamino acids, 10 g/L glycerol, and 100 mM sodium phosphate monobasic. Temperature was maintained at 28° C., pH was maintained at 6.0 by addition of 50% ammonium hydroxide, and dissolved oxygen ($pO_2$) was maintained at 30%. After glycerol was exhausted, as indicated by a spike in dissolved oxygen, temperature was lowered to 25° C. and feeding of 750 mL of 100 g/L glucose, 50 g/L peptone, 25 g/L yeast extract, 10 g/L casamino acids, 0.5% (v/v) Antifoam 204, and 100 μg/mL zeocin was initiated.

Culture supernatant was isolated by centrifugation and sterile filtered through a 0.22 μm filter. Supernatant was taken to 1M ammonium sulfate by the addition of 0.5 volume of 3M ammonium sulfate, 20 mM Tris.HCl, 1 mM EDTA, pH 8. After filtering, the receptor fusion was purified by hydrophobic interaction chromatography (Phenyl Sepharose), affinity chromatography (Protein G Sepharose), anion-exchange chromatography (MonoQ), and size-exclusion chromatography.

Chicken IL-10 was obtained from Kingfisher Biotech, Inc. Camelid VHH domains fused to C-terminal myc- and his-tags were expressed in *E. coli* with expression directed to the periplasmic space by an N-terminal signal peptide. Protein was extracted from the periplasm by osmotic shock and then purified by metal chelation chromatography and size-exclusion chromatography. Protein concentrations were determined by measuring the absorbance at 280 nm, using extinction coefficients calculated from the amino acid sequences.

Affinity and inhibition were measured using a BIAcore T200 surface plasmon resonance instrument (GE Healthcare). Approximately 7000 response units of the cIL-10R1-Fc fusion was covalently coupled to a CM5 sensor chip using EDC/NHS chemistry as directed by the manufacturer. All experiments were conducted at 37° C. in HBS-EP buffer (10 mM HEPES, 150 mM NaCl, 3 mM EDTA, 0.005% [v/v] Tween-20, pH 7.4). Binding affinity ($K_d$) for cIL-10 to immobilized cIL-10R1-Fc was determined by injecting five concentrations of cIL-10 over the sensor chip for 120 seconds at 20 μL/second. After 300 seconds of dissociation, the sensor chip was regenerated with a 10 second pulse of 10 mM sodium acetate, 0.5 mM EDTA, pH 4 followed by a 120 second stabilization phase before making the next injection. The BIAcore evaluation software was used to calculate the maximum bound material ($R_{max}$) for each cIL-10 concentration. $R_{max}$ values were plotted against cIL-10 concentration and fit to the equation for a rectangular hyperbola to calculate $K_d$.

Inhibition of cIL-10 binding to cIL-10R1-Fc by the sdABs was measured by preincubating 10 nM cIL-10 with six concentrations of each sdAB in HBS-EP for at least 20 minutes, followed by injection onto the sensor chip as described above. Calculated $R_{max}$ values for each sdAB concentration were plotted against the sdAB concentration to determine $IC_{50}$ values.

Figure 7:
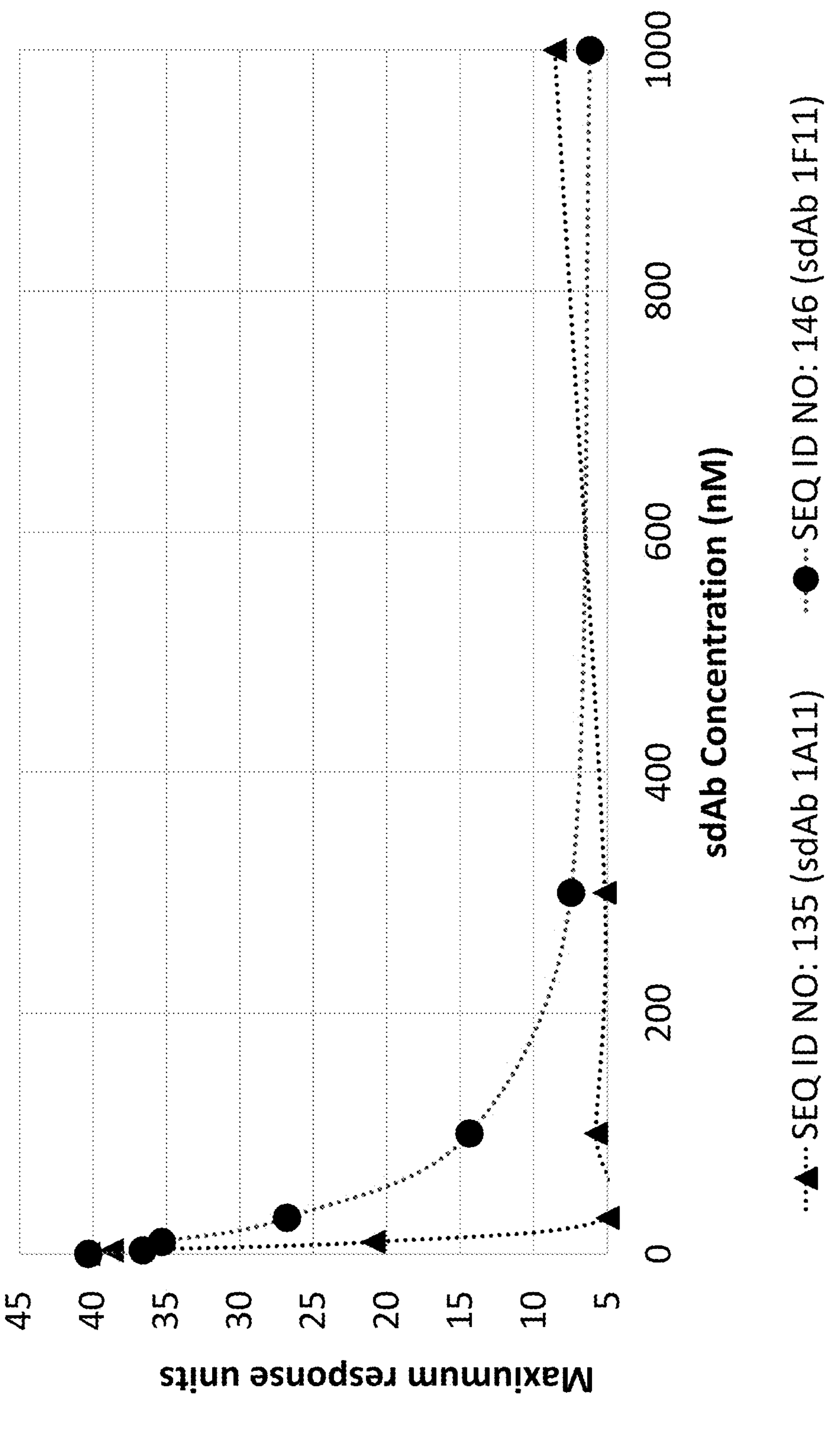
FIG. 7 illustrates the apparent inhibition of IL-10 binding to the IL-10 receptor in the presence of anti-IL10 antibodies chIL10sdAB1A11 (SEQ ID NO: 135) and chIL10sdAB1F11 (SEQ ID NO: 146).

FIG. 7 illustrates anti-IL-10 sdAb IC50 values measured for chIL10sdAB1A11 (SEQ ID NO: 135) and chIL10sdAB1F11 (SEQ ID NO: 146).

Figure 8:
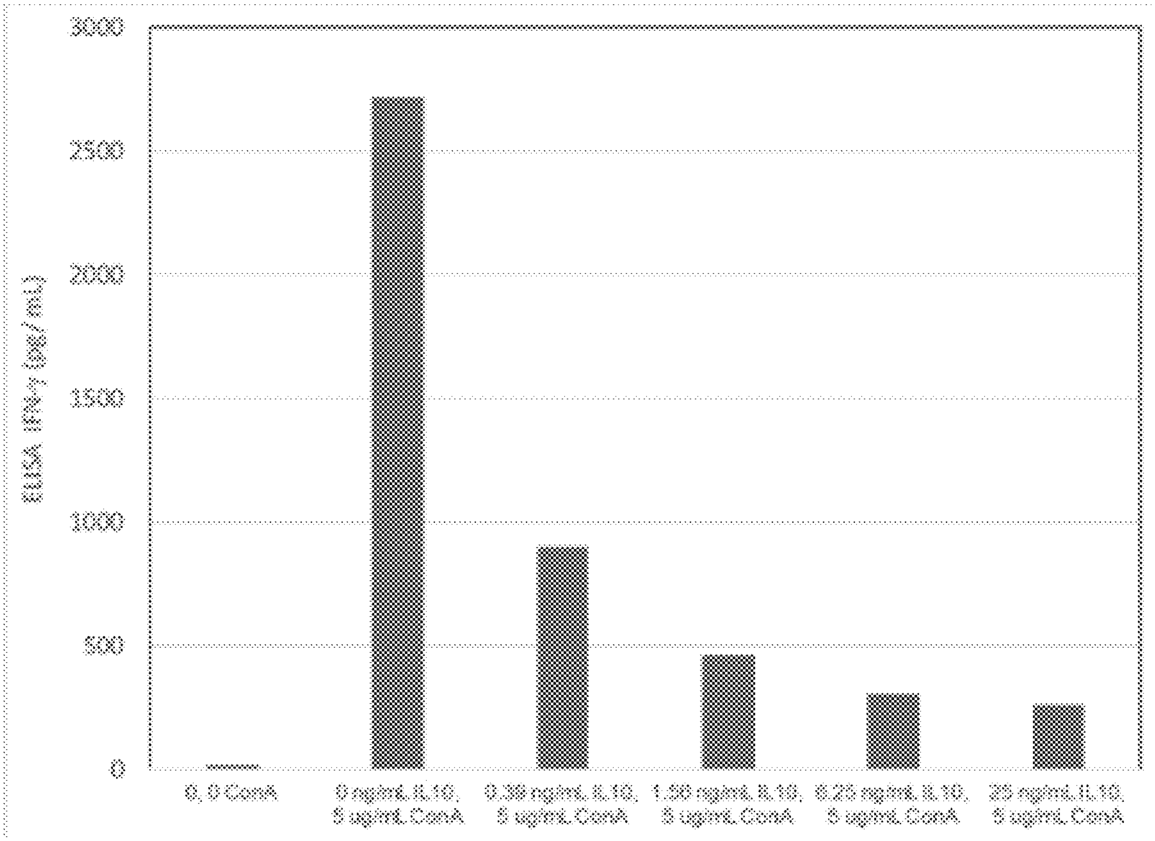
FIG. 8 illustrates IL-10 suppression of Concanavalin A-induced secretion of IFN-γ secretion in primary chicken spleen cells.

Example 10. Cell-Based Assay to Measure the Biological Activity of cIL-10 on Interferon Gamma (IFN-γ) Production and Inhibition of cIL-10 by Anti-IL-10 sdAB in Stimulated Primary Chicken Spleenocytes IL-10 is known to be a potent regulator of the immune system that affects many cell types and generally acts to attenuate inflammation and the immune response (Kevin N. Couper, Daniel G. Blount, Eleanor M. Riley, "IL-10: The Master Regulator of Immunity to Infection," The Journal of Immunology, 180:5771-5777, 2008). Primary chicken spleen cells were used to evaluate the use of sdABs in blocking the biological activity of IL-10 in cellular signaling on a relevant target cell type. A cell-based assay was developed to study the inhibitory effect of cIL-10 on the concanavalin A (ConA) dependent induction (or phytohemagglutinin (PHA) dependent induction, both stimulators work with these cells) of interferon gamma (IFN-γ) production in chicken spleen cells (Wu et al. (2016) and Rothwell et al. (2004)). Briefly, lymphocytes and mononuclear cells were isolated from chicken spleens by differential centrifugation on Ficoll-Hypaque. Freshly isolated cells were cultured at $5\times10^6$ cells/mL in wells of a 96-well plate for 72 hours in the presence of 1.2 μg/mL ConA (or 12.5 μg/mL PHA) with, or without, cIL-10 at concentrations of 0-25 mg/mL. Levels of IFN-γ in the supernatants of treated cells were determined by ELISA. FIG. 8 shows the IFN-γ response of the cells in the absence of ConA, ConA with no cIL-10, and ConA with 0.39, or 1.56, or 6.25, or 25 ng/mL cIL-10). As seen in FIG. 8, IL-10 suppresses of ConA-induced secretion of IFN-γ in primary chicken spleen cells. FIG. 8 also shows that spleen cells have a dose dependent response in IFN-γ production to chIL-10, as increasing cIL-10 lowers IFN-γ production in a dose-dependent manner.

To test how effective sdABs were in interrupting cIL-10 stimulated production of IFN-γ, primary chicken spleen cells were incubated with and without different concentrations of sdABs ranging from 0.1 nM up to 10 μM, with ConA, and with or without cIL-10. Levels of IFN-γ in the culture supernatants were determined by ELISA. Included in these studies, as control treatments, were spleen cells treated only with 5 μg/mL ConA (positive control for IFN-γ production), cells treated with 5 μg/mL of ConA and 1.5 ng/mL of cIL-10 (positive control for cIL-10 inhibition of ConA-dependent IFN-g production), and cells treated with 5 μg/mL of ConA, 1.5 ng/mL of cIL-10, and either an anti-IL-10 polyclonal antibody ("aIL10 pAb", positive control antibody) or a non-specific sdAB that did not bind cIL-10 ("aMOP pAb (NC)", a negative control antibody to demonstrate that non-specific binding cannot provide the same effect observed with antibodies that specifically bind cIL-10). Experimental treatments contained 5 μg/mL ConA, 1.5 ng/mL of cIL-10, and varying concentrations of anti-IL-10 sdABs. In these experiments, sdABs were dose at 1 nM, 30 nM, and 1000 nM.

Figure 9:
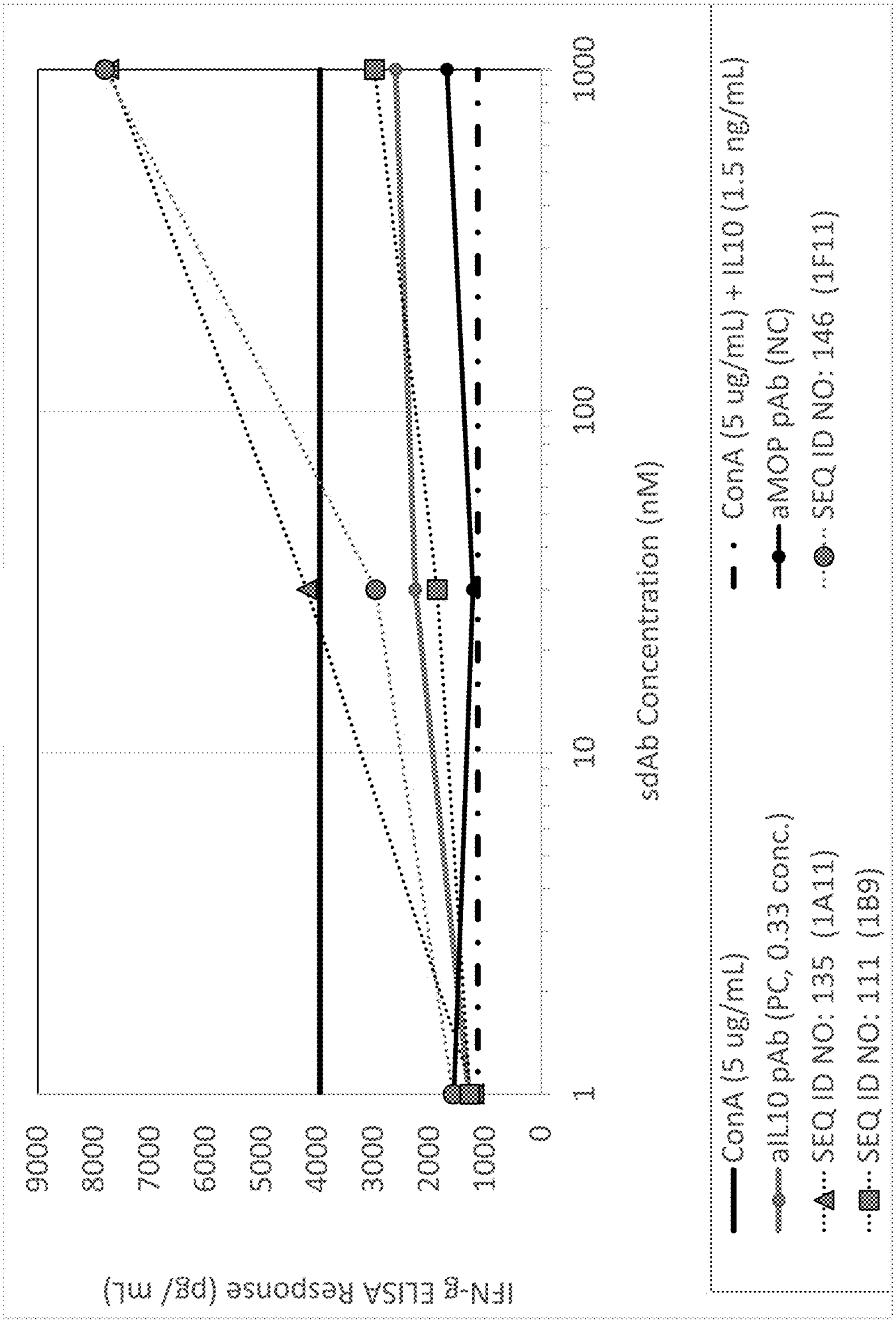
FIG. 9 illustrates recovery of IFN-γ secretion from primary chicken spleen cells treated with Concanavalin A and chicken IL-10, when also treated with the anti-IL-10 antibodies (chIL10sdAB1A11 (SEQ ID NO: 135), chIL10sdAB1B9 (SEQ ID NO: 111), and chIL10sdAB1F11 (SEQ ID NO: 146)).

FIG. 9 illustrates the anti-IL-10 antibodies (chIL10sdAB1A11 (SEQ ID NO: 135), chIL10sdAB1B9 (SEQ ID NO: 111), chIL10sdAB1F11 (SEQ ID NO: 146) effect on the IFN-γ secretion in primary chicken spleen cells. Based on these results, the apparent EC50 values for chIL10sdAB1A11 (SEQ ID NO: 135), chIL10sdAB1B9 (SEQ ID NO: 111), chIL10sdAB1F11 (SEQ ID NO: 146) were measured to be 25 nM, 40 nM, and 60 nM, respectively. Although higher than the $EC_{50}$ and $IC_{50}$ values measured for binding of the anti-IL-10 sdABs to cIL-10, they are still in relative agreement with these values and further demonstrate the biological efficacy of the anti-IL-10 sdABs in blocking IL-10 signaling and decrease immune system suppression.

Example 11. Plant Expression of Anti-IL-10 Single Domain Antibodies

Antibody expression was demonstrated in transient expression using tobacco and in transgenic corn events. Other plant species can be used to express the anti-IL-10 sdABs, including rice, sorghum, soy beans, and canola. Depending on the final product and intended use, a particular plant species may be more suited for production than other species.

Expression cassettes containing the sequences of anti-IL-10 sdAbs for expression in maize are included in Table 6. In Table 6, some vectors contain single expression cassettes, while other vectors contain multiple expression cassettes, which usually helps increase expression of the sdAB. The DNA sequence of each chicken anti-IL-10 sdAB contained in the expression cassettes listed in Table 6 has been codon optimized for maize gene expression, however, the genes may be optimized for other plant (or microbial) species to improve their expression when a different expression host is desired.

TABLE 6

Plant expression vectors for expression of chicken anti-IL-10 sdABs:

| Vector | Chicken anti-IL-10 sdAb expression cassette(s) |
|---|---|
| pAG4314 | OsGluB4P:xGZein27ss:chIL10sdAB1A11A:KDEL |
| pAG4315 | OsGluB4P:xGZein27ss:chIL10sdAB1B9:KDEL |
| pAG4316 | OsGluB4P:xGZein27ss:chIL10sdAB1F11A:KDEL |
| pAG4317 | OsGluB4P:xGZein27ss:chIL10sdAB1H1A:KDEL |
| pAG4985 | ZmZ27P:xGZein27ss:chIL10sdAB1A11A:KDEL |
| pAG4986 | ZmZ27P:xGZein27ss:chIL10sdAB1B9:KDEL |
| pAG4987 | ZmZ27P:xGZein27ss:chIL10sdAB1F11A:KDEL |
| pAG4988 | ZmZ27P:xGZein27ss:chIL10sdAb1A11A:KDEL + OsGluB4P:xGZein27ss: chIL10sdAB1A11A:KDEL |
| pAG4989 | ZmZ27P:xGZein27ss:chIL10sdAB1B9:KDEL + OsGluB4P:xGZein27ss: chIL10sdAB1B9:KDEL |
| pAG4990 | ZmZ27P:xGZein27ss:chIL10sdAB1F11A:KDEL + OsGluB4P:xGZein27ss: chIL10sdAB1F11A:KDEL |
| pAG4991 | ZmZ27P:xGZein27ss:chIL10sdAB1H1A:KDEL |
| pAG4992 | ZmZ27P:xGZein27ss:chIL10sdAB1H1A:KDEL + OsGluB4P:xGZein27ss: chIL10sdAB1H1A:KDEL |
| pAG4993 | ZmZ27P:xGZein27ss:chIL10sdAB1A11B:KDEL |
| pAG4994 | ZmZ27P:xGZein27ss:chIL10sdAB1F11B:KDEL |
| pAG4995 | ZmZ27P:xGZein27ss:chIL10sdAB1H1B:KDEL |
| pAG4996 | ZmZ27P:xGZein27ss:chIL10sdAB1A11B:KDEL + OsGluB4P:xGZein27ss: chIL10sdAB1A11A:KDEL |
| pAG4997 | ZmZ27P:xGZein27ss:chIL10sdAB1F11B:KDEL + OsGluB4P:xGZein27ss: chIL10sdAB1F11A:KDEL |
| pAG4998 | ZmZ27P:xGZein27ss:chIL10sdAB1H1B:KDEL + OsGluB4P:xGZein27ss: chIL10sdAB1H1A:KDEL |

Figure 10A:
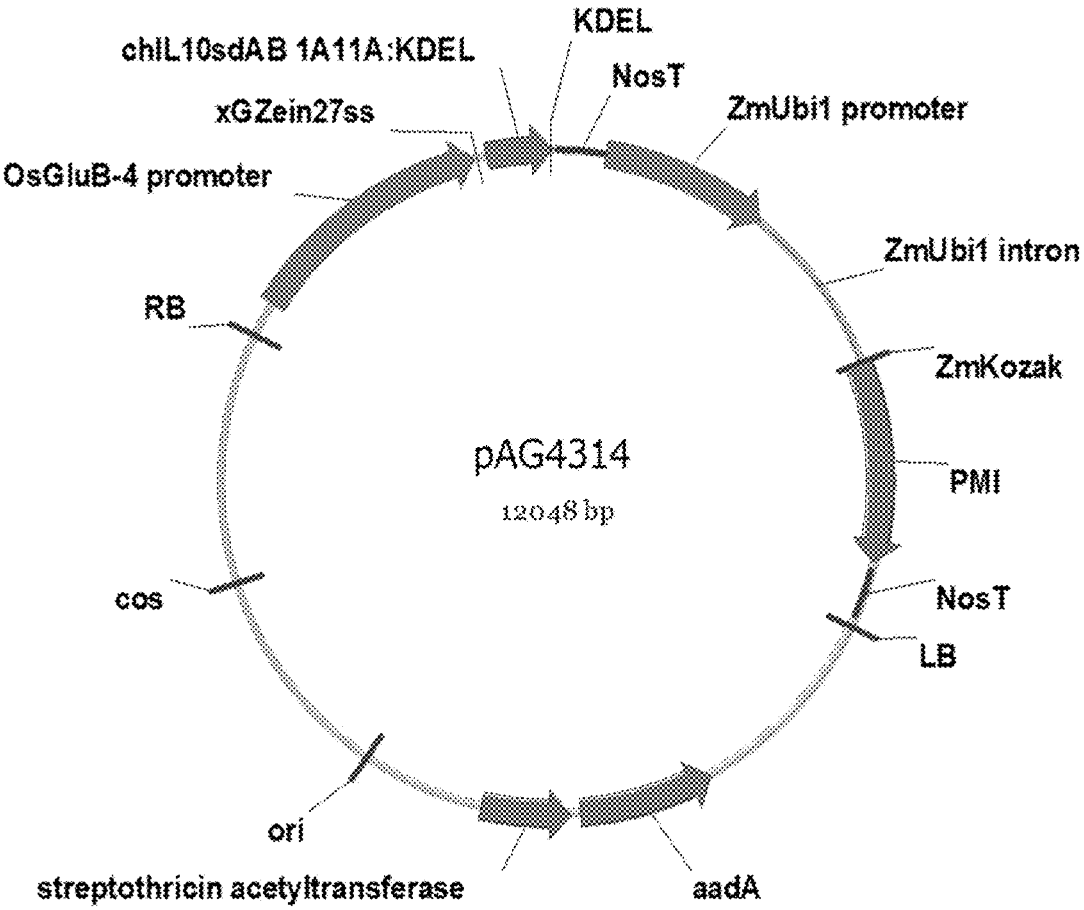
FIG. 10A is a schematic drawing of the vector pAG4314.
Figure 10B:
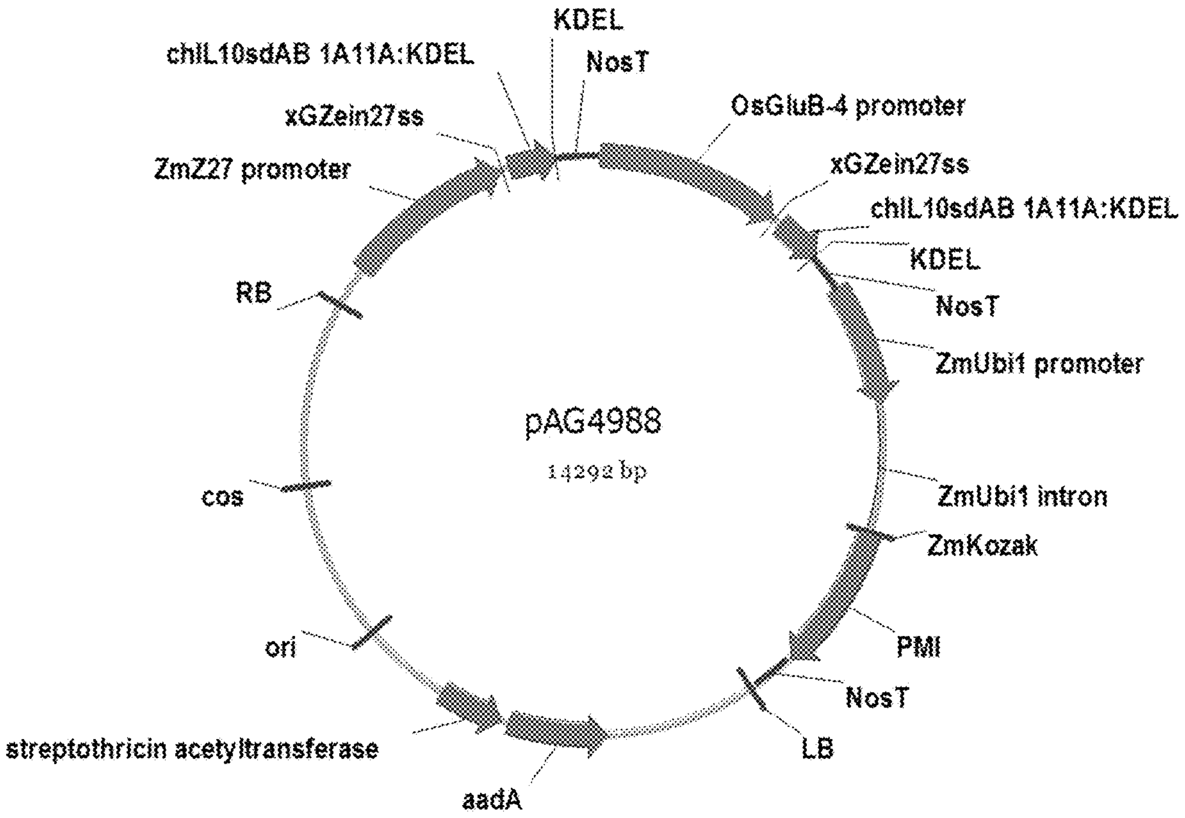
FIG. 10B is a schematic drawing of the vector pAG4988.

FIG. 10A is a schematic drawing of a vector pAG4314 that includes a single expression cassette for an anti-IL-10 sdAB (OsGluB4P:xGZein27ss:chIL10sdAB1A11A:KDEL) and the PMI expression cassette for selection in plants. FIG. 10B is a schematic drawing of a vector pAG4988 that increases the transgene dosage by including two expression cassettes for the same anti-IL-10 sdAB (ZmZ27P: xGZein27ss:chIL10sdAb1A11A:KDEL+OsGluB4P: xGZein27ss:chIL10sdAB1A11A:KDEL). Vector pAG4988 also includes the PMI expression cassette for selection in plant tissues. The T-DNA sequences for the vectors listed in the table are provided below in such a way that each sequence starts with the right border repeat and ends with the left border repeat.

Deduced protein sequences for selected chicken IL10 sdAb are provided with the maize gamma zein 27 signal sequence and KDEL signal sequence, which are underlined at N-terminal and C-terminal ends of the protein, respectively.

Protein Sequences of chIL10 sdABs Encoded by Plant Expression Cassettes

```
>xGZein27ss:chIL10sdAb1A11:KDEL
                                        (SEQ ID NO: 84)
MRVLLVALALLALAASATSQVQLQESGGGLVQPGGSLRLSCASGNIFSIN

TMGWYRQAPGKQRELVASITTGGTTNYEDSVKGRFTISRDNAKKTVYLQM

NRLKPEDTAVYYCNHRRSYSGRDYPVYGMDYWGKGTLVTVSSKDEL

>xGZein27ss:chIL10sdAb1B9:KDEL
                                        (SEQ ID NO: 85)
MRVLLVALALLALAASATSQVQLQESGGGLVQAGGSLRLSCAASGRTFSS

YAWGWFRQAPGKEREFVARISFSGGHTYYSDSVKGRFTISRDNAKNTVYL
```

-continued

```
QMNSLKPEDTAVYYCAADPTPYGLRNERNYPYWGQGTQVTVSSKDEL

>xGZein27ss:chIL10sdAb1F11:KDEL
                                        (SEQ ID NO: 86)
MRVLLVALALLALAASATSQVQLQEFGGGLVQPGGSLRLSCASGRTGSSY

AMGWFRQAPGKEREFVAAISWSGGSTDYADSVKGRFTISRDNAKNTMYLQ

MNSLKPEDTAVYYCAVDRNLFKLRVAVQEYTNLGQGTQVTVSSKDEL

>xGZein27ss:chIL10sdAb1H1:KDEL
                                        (SEQ ID NO: 179)
MRVLLVALALLALAASATSQVQLQASGGGLVQAGGSLRLSCAASGRTFNS

YAWGWFRQAPGKERGFVARISFSGGHTYYSDSVKGRFTISRDNAKNSVYL

QMNSLKPEDTAVYYCAADPTPYGLRNERNYHYWGQGTQVTVSSKDEL
```

The nucleotide sequences encoding chIL10sdAB1A11, chIL10sdAB1F11, and chIL10sdAB1H1 antibodies in vectors and nucleotide sequences were named 1A11A (chIL101A11A), 1F11A (chIL101F11A), and 1H1A (chIL101H1A), respectively, to reflect different coding sequences with altered codon usage. This modification was made in order to avoid any possible confusion in the future due to availability of different variants (for example, “variant A” and “variant B”) of the maize codon optimized sequences for maize expression. The deduced protein sequences encoded by the variants “A” and “B” are identical.

Nucleotide sequence alignments of the maize codon optimized variants “A' and “B” of the selected chIL10 sdABs:

CLUSTAL O(1.2.4) multiple sequence alignments

```
1A11A    CAGGTTCAGCTGCAGGAAAGCGGTGGCGGACTGGTGCAGCCAGGTGGCAGCCTCAGGCTG    60
1A11B    CAGGTGCAGCTCCAGGAGTCCGGCGGCGGCCTCGTGCAGCCGGGCGGCTCCCTCCGCCTG    60
         ***** ***** *****   *** ***** ** ******** ** ***  **** * ***

1A11A    AGCTGCGCTGCTAGCGGCAATATTTTTAGCATTAACACAATGGGTTGGTATAGACAGGCT   120
1A11B    AGCTGCGCCGCGTCCGGCAACATCTTCAGCATCAACACGATGGGCTGGTACAGGCAGGCC   120
         ******** **   ****** ** ** ***** ***** ***** ***** ** *****

1A11A    CCTGGCAAGCAGCGTGAGCTCGTTGCCAGCATTACCACGGGTGGTACAACCAATTATGAA   180
1A11B    CCCGGCAAGCAGCGGGAGCTCGTGGCCTCCATCACCACGGGCGGCACCACGAACTACGAG   180
         ** *********** ******** ***  *** ******** ** ** ** ** ** **

1A11A    GATAGCGTGAAGGGTCGTTTTACCATTAGCAGGGACAATGCTAAGAAGACCGTTTACCTC   240
1A11B    GACAGCGTCAAGGGCCGCTTCACCATCTCCAGGGACAACGCCAAGAAGACGGTGTACCTC   240
         ** ***** ***** ** ** *****   ********* ** ******** ** ******

1A11A    CAGATGAACAGGCTGAAGCCAGAAGATACCGCCGTGTATTACTGCAACCACAGGAGAAGC   300
1A11B    CAGATGAACCGCCTGAAGCCGGAGGACACGGCGGTCTACTACTGCAACCACCGCAGGTCC   300
         ********* * ******** ** ** ** ** ** ** ************ * **   *

1A11A    TATAGCGGAAGAGATTATCCTGTTTACGGTATGGACTACTGGGGCAAGGGAACCCTGGTT   360
1A11B    TACAGCGGCAGGGACTACCCCGTGTACGGCATGGACTACTGGGGCAAGGGCACCCTCGTG   360
         ** ***** ** ** ** ** ** ***** ******************** ***** **

1A11A    ACCGTGAGCAGC 372 [SEQ ID NO: 173]
1A11B    ACCGTGTCCTCC 372 [SEQ ID NO: 174]
         ******  *  *

1F11A    CAGGTTCAGCTCCAGGAGTTTGGTGGCGGACTGGTGCAGCCAGGTGGCAGCCTCAGGCTG    60
1F11B    CAGGTGCAGCTCCAGGAGTTCGGCGGCGGCCTCGTGCAGCCGGGCGGCTCCCTCCGCCTG    60
         ***** ************** ** ***** ** ******** ** ***  **** * ***

1F11A    AGCTGCGCTGCTAGCGGTAGAACCGGCAGCAGCTATGCTATGGGATGGTTTAGACAGGCT   120
1F11B    AGCTGCGCCGCGTCCGGCAGGACGGGCTCCAGCTACGCGATGGGCTGGTTCAGGCAGGCG   120
         ******** **   *** ** ** ***  ****** ** ***** ***** ** *****

1F11A.   CCAGGCAAGGAGCGTGAATTTGTTGCTGCCATTAGCTGGAGCGGAGGTAGCACCGATTAT   180
1F11B    CCCGGCAAGGAGAGGGAGTTCGTGGCGGCCATCTCGTGGAGCGGCGGCAGCACCGACTAC   180
         ** ********* * ** ** ** ** *****    ******** ** ******** **
```

-continued

CLUSTAL O(1.2.4) multiple sequence alignments

```
1F11A    GCTGACAGCGTGAAGGGCAGGTTTACCATTAGCAGAGATAATGCCAAGAACACCATGTAC   240
1F11B    GCTGACTCCGTCAAGGGCCGCTTCACCATCAGCAGGGACAACGCGAAGAACACGATGTAC   240
         ******  *** ****** * ** ***** ***** ** ** ** ******** ******

1F11A    CTCCAGATGAATAGCCTGAAGCCAGAGGATACCGCTGTTTATTACTGCGCCGTGGACCGT   300
1F11B    CTCCAGATGAACTCCCTGAAGCCGGAGGACACCGCCGTGTACTACTGCGCGGTCGACCGC   300
         ***********   ********* ***** ***** ** ** ******** ** *****

1F11A    AATCTCTTTAAGCTGAGGGTTGCTGTGCAGGAATACACCAACCTCGGCCAGGGAACCCAG   360
1F11B    AACCTCTTCAAGCTGAGGGTGGCCGTCCAGGAGTACACCAACCTCGGCCAGGGCACCCAG   360
         ** ***** *********** ** ** ***** ******************** ******

1F11A    GTTACCGTGAGCAGC 373 [SEQ ID NO: 173]
1F11B    GTGACCGTGTCCTCC 373 [SEQ ID NO: 176]
         ** ******  *  *

1H1A     CAGGTTCAGCTCCAGGCTTCGGGCGGCGGGCTCGTCCAGGCGGGCGGCTCGCTCAGGCTC    60
1H1B     CAGGTGCAGCTCCAGGCCTCCGGCGGCGGCCTCGTGCAGGCGGGCGGCTCCCTCCGCCTG    60
         ***** *********** ** ******** ***** ************** *** * **

1H1A     TCGTGCGCGGCGTCGGGGCGGACTTTCAACAGCTACGCTTGGGGCTGGTTCAGGCAGGCG   120
1H1B     AGCTGCGCCGCGTCCGGCAGGACCTTCAACAGCTACGCTTGGGGCTGGTTCAGGCAGGCG   120
            ***** ***** **  **** ************************************

1H1A     CCGGGCAAGGAGCGCGGCTTCGTGGCCAGGATCTCCTTCAGCGGCGGCCACACCTACTAC   180
1H1B     CCGGGCAAGGAGCGCGGCTTCGTGGCCAGGATCTCCTTCAGCGGCGGCCACACCTACTAC   180
         ************************************************************

1H1A     TCCGACAGCGTCAAGGGCCGCTTCACGATCTCCAGGGACAACGCCAAGAACAGCGTGTAC   240
1H1B     TCCGACAGCGTCAAGGGCCGCTTCACGATCAGCAGGGACAACGCCAAGAACTCCGTGTAC   240
         ******************************  *******************  *******

1H1A     CTCCAGATGAACTCCCTGAAGCCCGAGGACACGGCCGTCTACTACTGCGCGGCGGACCCG   300
1H1B     CTCCAGATGAACAGCCTGAAGCCCGAGGACACGGCCGTCTACTACTGCGCGGCGGACCCG   300
         ************  **********************************************

1H1A     ACGCCCTACGGCCTCAGGAACGAGCGGAACTACCATTACTGGGGGCAGGGCACGCAGGTC   360
1H1B     ACCCCATACGGCCTCCGCAACGAGAGGAACTACCACTACTGGGGCCAGGGCACCCAGGTG   360
         ** ** ********* * ****** ********** ******** ******** *****

1H1A     ACTGTCTCTTCG 372 [SEQ ID NO: 177]
1H1B     ACCGTGTCCTCC 372 [SEQ ID NO: 178]
         ** ** ** **
```

TABLE 7

The percentage of nucleotide sequence identity between "A" and "B" variants

| Sequence "A" | Sequence "B" | Sequence identity, % |
|---|---|---|
| 1A11A | 1A11B | 78.2 |
| 1F11A | 1F11B | 79.7 |
| 1H1A | 1H1B | 90.3 |

Figure 11:
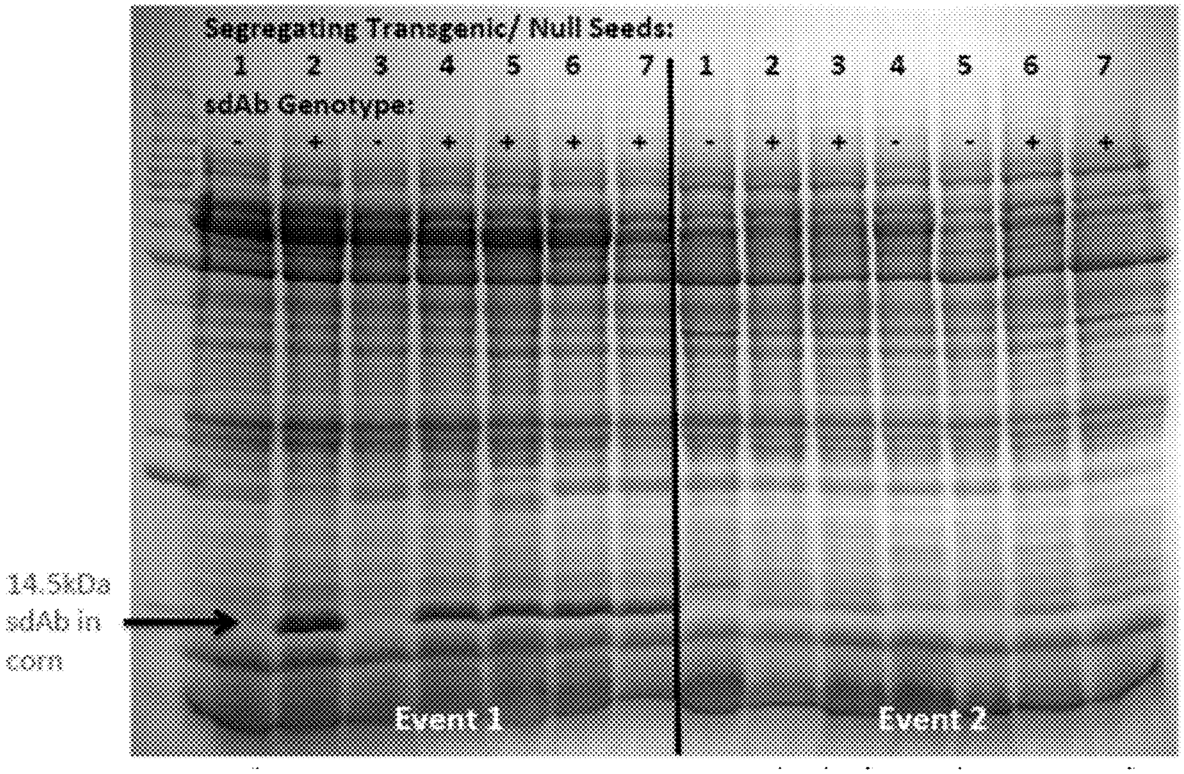
FIG. 11 illustrates that single domain antibodies express at high level in individual corn grain. In both transgenic events, individual grain were genotyped and protein extracted. The presence of the sdAB band in the gel image correlates perfectly with the presence of the sdAB gene as represented at the top of the figure with a "+" if the sdAB gene is present and a "−" if the sdAB gene is absent.

Any polynucleotides encoding anti-IL10 antibodies can be cloned between desirable promoter and terminator sequences in the plant expression vectors described herein (Table 6), in order to generate expression cassettes. In addition, amino terminal (N) signal sequences, such as xGZein27ss in maize expression vectors, can be replaced by other signal sequences in order to modulate specific expression and accumulation of anti-IL-10 antibodies to desired levels. N-terminal signal sequences include, but not limited to, for example by OsGluB4sp (rice GluB-4 glutelin signal peptide), BAASS (barley alpha amylase signal sequence), or PR1 (pathogenesis related protein). The anti-IL-10 antibodies can be expressed to endoplasmic reticulum (ER) for improved accumulation and potential glycosylation using carboxyl terminal (C) retention signal sequences such KDEL (SEQ ID NO: 29), HDEL (SEQ ID NO: 30), or SEKDEL (SEQ ID NO: 31). Furthermore, anti-IL10 antibodies can be expressed and directed to protein storage vacuoles with the help of signal sequences attached to either N-terminal or C-terminal part of the sequence. These storage vacuole signal sequences include HvAle from barley aleurone (thiol protease) or HvVSD from barley polyamine oxidase. If necessary, anti-IL-10 antibodies can be also expressed from expression vectors without signal sequences for accumulating expressed products in apoplast, chloroplast, or cytoplasm. All of the genetic elements mentioned above, including other signal sequences with similar functions, can be added to or removed from the basic plant expression vectors to tailor the expression properties of the anti-IL-10 sdAB. FIG. 11 illustrates that using the genetic elements described herein, sdABs can be expressed at high level in corn grain. In FIG. 11, sdABs expressed in corn were extracted from individual seed from a hemizygous parent, where 50% of the seed contained the expression cassette and 50% of the seed did not contain the expression cassette. In FIG. 11, individual seed from two different transgenic events were genotyped and analyzed for the presence of the expressed sdAB by SDS-PAGE electrophoresis and coomassie staining. As shown in FIG. 11, the presence of the sdAB correlated perfectly with the genotyping result, that is, only seed that tested positive for the gene by PCR produced a protein band at the right size of the sdAB. Further, expression levels of the sdAB in event 1 were estimated at 3 mg per gram of corn grain, which would result in an expression level of 9 mg of sdAB per gram of corn for the fully homozygous event. Expression levels for recombinant proteins, including sdABs, up to 21 mg per gram of corn grain have been observed using the expression cassettes and genetic elements described herein.

Example 12. Transient Expression of Chicken IL10 sdAb 1A11 in Leaves of Tobacco *Nicotiana benthamiana*

Transient protein expression in plants has been used by multiple groups for production of therapeutic proteins and vaccine antigens. Among various plant species, tobacco *Nicotiana benthamiana*, is one of the most suitable production hosts because it can achieve a high level of protein expression in a short timeframe by using a leaf infiltration procedure. Such production attributes are required for economical heterologous protein production.

Genetic Elements and Construction of Vectors

For expression in *N. benthamiana*, the chicken IL-10 sdAb 1A11 (referred to herein as Nb1A11; SEQ ID NO: 202) sequence was codon optimized for *Nicotiana* codon usage and synthesized by GenScript as either an 868 bp NcoI-AvrII DNA fragment, which at 5' end contained 90 bp tobacco PR1a gene sequence [SEQ ID NO: 205] encoding transit peptide, 304 bp first intron of *Arabidopsis* ubiquitin 10 gene (AtUBQ10i) in Nb1a11 coding region, and at 3' end myc tag, 6×His, and KDEL sequences [SEQ ID NO: 206], or as 564 bp NcoI-AvrII fragment without the AtUBQ10i intron. The Nb1A11:AtUBQ10i sequence is shown below as SEQ ID NO: 203, and the intron sequence is indicated by the bold characters and is underlined.

[SEQ ID NO: 203]

CAAGTTCAGTTACAGGAAAGCGGGGGAGGTTTAGTTCAGCCTGGGGGTTCATTGAGGTTGAGTTG

TGCAGCAAGTGGAAATATTTTTTCTATTAATACTATGGGATGGTATAGACAAGCTCCAGGTAAATTTCTGTGTTCCT

TATTCTCTCAAAATCTTC GATTTTGTTTTCGTTCG ATCCCAATTTCGTATATGTTCTTTGGTTTAGATTCTGTTAAT

CTTAGATCGAAGACGATTTT CTGGGTTTGATCGTTAGATA CATCTTAATTCTCGATTAGGGTTTCATAGATATCAT

CCGATTTGTTCAAATAATTT GAGTTTTGTCGAATAATTACT CTTCGATTTGTGATTTCTATCTAGATCTGGTGTTAG

TTTCTAGTTTGTGCGATC GAATTTGTCGATTAATCT GAGTTTTTCTGATTAACAGGAAAGCAAAGAGAACTTGTTGC

AAGTATTACTACTGGAGGAACTACAAATTACGAAGATAGTGTTAAAGGAAGATTCACTATTTCAAGAGATAATGCTA

AGAAAACAGTTTATCTTCAGATGAATAGATTGAAGCCAGAAGATACAGCAGTTTACTACTGTAATCATAGAAGATCA

TACTCTGGTAGAGATTATCCTGTTTATGGTATGGATTATTGGGGAAAAGGGACATTAGTTACAGTTAGCAGC

The AtUBQ10i was inserted into Nb1A11 coding region between nucleotides 124 and 125 for dual purpose: 1) monitoring expression of Nb1A11 from plant cells rather than from *Agrobacterium;* 2) potentially enhancing expression of Nb1A11 in tobacco, since positive effects of heterologous introns on gene transcription in plants and other species are well documented in the literature ("Introns increase gene expression in cultured maize cells," J. Callis, M. Fromm, V. Walbot, Genes Dev., 1:1183-1200, 1987; doi:10.1101/gad.1.10.1183; "Increased Gene Expression by the First Intron of Maize Shrunken-1 Locus in Grass Species," V. Vasil, M. Clancy, R. J. Ferl, I. K. Vasil, L. C. Hannah, Plant Physiol. 91:1575-1579, 1989; "Intron-mediated enhancement as a method for increasing transgene expression levels in barley," J. G. Bartlett, J. W. Snape, W. A. Harwood, Plant Biotechnology Journal, 7:856-866, 2009, all of which are incorporated herein by reference as if fully set forth). The sequences of myc tag and 6×His were included to facilitate Nb1A11 sdAB detection and purification. The KDEL sequence was added for retaining the expressed 1A11 sdAb in endoplasmic reticulum (ER) for improving accumulation levels of the protein. For transient expression of Nb1A11 sdAB in *N. benthamiana*, a new and previously uncharacterized constitutive ubiquitin 1 gene promoter (prNbUbi1) was used. The sequence of the prNbUbi1 is shown below as SEQ ID NO: 204, wherein the sequence of the intron sequence is indicated by the bold characters and is underlined.

[SEQ ID NO: 204]

CATGAAAGTCCACATCATCAGCTCGTCCCAAACATCACTACTAGACCCAACTCGTTCAATCTTCT

CGACTACAACAAATGAAATCCGCTCATCAAGGTGTCTGAGGCTGATCTCAATAAATGGAGGGACTAATTGTATGGAT

CGAAATCTGCCCCAAAATATTTAGGGTAAGGTACATTGAAGAAAGAGTCATCGAGGTCGATCAGGAAACGATCGAGA

TGTTAACAATGGTCGATGTCGAGCACCGCATGTAGAGTTGTAACACCTAGTTTTTAGAATAGGATAATACAAAGAAT

ATTCTATTGGATATCCTTTACACTTATATTATTAGAGTTTGTTAGGAAAATGACCCACATAAATAGGAAAAAAGACA

ATGAATGGAGACAGGTGACATTTATCTGATGAGAACAGACTTTTGATAGAAGATATTTTCTCTCTCACTAAGATACA

AACACTACATTTTCATCAAGATTCTTGTTCATATCATTGTACACTTTTCTATCAAATCTGAAATAATTTAAATATTC

TAGGATTTGTCTGTCACTCATCATTGTCAGACGGGATAATCATGTACTCATCCTTTTTTGGCAAACCACTTTTTCTA

TTTACTTAAATGCCATTTATTGATATCTATTGCTAGTCATTCCTCCACCGTTGCTCATACTTTTTTGCAATAGTATG

CATGTTGATATCAATCCACCACCAAATCTTCTAACATTAATCATATTTTCACAACTTACATTTATAAATATTATTAT

TAACTAAGTTTAACTCACTATTATATAAACTCAATTGTTTTACTCGAAAGTTACACTATTATATTGAGAATTACGTT

TCCAAACTTTTTAAGCATTTATTGTGTAACCATAAGAGACTTTGATTTTTTAAAAATTATTTAGATTTTATTAATGA

GAATGGCACAACATTATGGTCAACTATGTATTTCATCATTAACTAAATAGTTAGCACTTTGATTCTTTCACATGAAT

TATGAATTTATGATGGGCTCAAATTAAAATTAAATTATTCACAAAAACTTATTTTTATATTCTACGACACCCACTTT

TCTAGCTTTTTCCCGAAGGGGCGTGAGAGTGTCACACACGCTCCAAATTTCCCAACCAAACAAGGAAAGGGCAGAGA

AAGATAGCTTTAGCGTGTTGTTTTGGTGCACTACACGTCATTAGGACACGTGTCATGATATAATAGGCCAATCCCAC

GAGGCGGTTTCGTCTTGAGTCGGCCATAGTGTCCATAAATGAGGGCTCTCCGTCGGTTTCCCCATCATTCATCAGAT

TTATCTTCTATACTTCATCGCCTTCATATTTCTCTCTCAAGGTTTGAGAATTTCTTCAATTTCTCGCTTTAGCAGTT

CTTTTTTATTGAATCAACGA TTTCGGCATCTAAAGTCCTA ATTTTGAAGTTCATTGCTTTAATTGTTTGTTGTTGAT

TTTATATTATTACAG

This promoter was identified by screening *N. benthamiana* Expressed Sequence Tag (EST) database for the most abundant in leaf tissue ubiquitin gene transcript. The database is maintained by the *Nicotiana benthamiana* Genome and Transcriptome Sequencing Consortium (Nakasugi K, Crowhurst R N, Bally J, Wood C C, Hellens R P, Waterhouse P M (2013) De Novo Transcriptome Sequence Assembly and Analysis of RNA Silencing Genes of *Nicotiana benthamiana*. PLoS ONE 8(3): e59534, which is incorporated by reference herein as if fully set forth). The transcript Nbv6.1trP26199, annotated as putative ubiquitin 1, appeared to contain significantly larger number of ESTs (1196) than other ubiquitin related transcripts. The Nbv6.1trP26199 specific 1466 bp upstream genomic sequence, which included 128 bp 3'UTR positioned intron, was identified in *N. benthamiana* draft genome sequence (v1.0.1) that is available at the Sol Genomics Network at Boyce Thompson Institute for Plant Research (Bombarely, A., H. G. Bosh, J. Vrebalov, P. Moffett, L. A. Mueller, and G. B. Martin (2012), A draft genome sequence of *Nicotiana benthamiana* to enhance molecular plant-microbe biology research. Molecular Plant-Microbe Interactions 25:1523-1530, which is incorporated by reference herein as if fully set forth).

Figure 12:
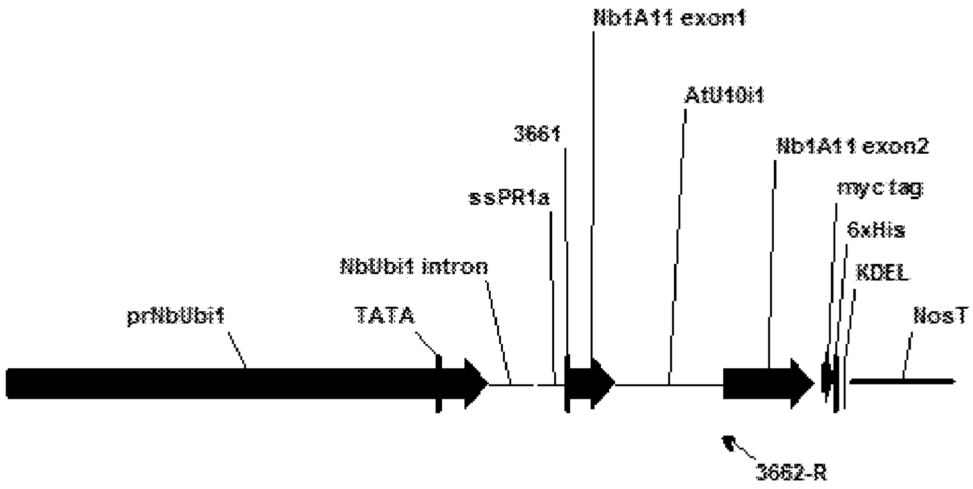
FIG. 12 is a schematic drawing of the pLH1A11int expression cassette.
Figure 13:
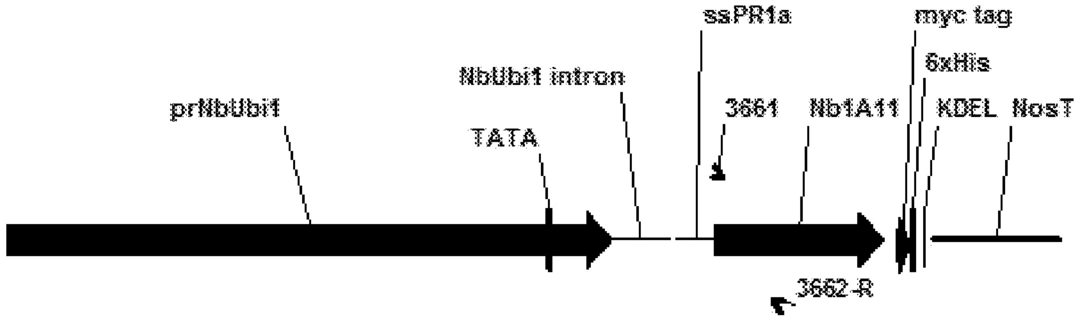
FIG. 13 is a schematic drawing of the pLH1A11 expression cassette.

This 1466 bp sequence in *N. benthamiana* genome has nucleotide coordinates 74703-76169 in the Scaffold No: 5041 and is fused to coding region of a putative ubiquitin gene that encodes five 76 amino acid long identical ubiquitin monomers. The 1466 bp prNbUbi1 was synthesized by GenScript as NotI-NcoI fragment. The entire Nb1A11+AtUBQ10i or Nb1A11 expression cassettes were cloned into NotI-KpnI sites of the pLH9000 vector, which was kindly provided by Dr. I. Lernomtova (IPK Gatersleben, Germany), and the final constructs were designated as pLH1A11int or pLH1A11 respectively. FIG. 12 illustrates pLH1A11int expression cassette. FIG. 13 illustrates pLH1A11 expression cassette. Subsequently, pLH9000, pLH1A11int and pLH1A11 were electroporated into electrocompetent cells of the *Agrobacterium* strain GV3101. *Agrobacterium* colonies carrying pLH9000, pLH1A11int or pLH1A11 constructs were validated by PCR.

*N. benthamiana* Plant Growing and Inoculation with *Agrobacterium*

The seeds of *N. benthamiana* were acquired from The US *Nicotiana* Germplasm Collection (NC State University). The seeds were sowed into 4"×4' pots containing ProMix soil. After germination the seedlings and the plants were kept at 16 h day and 8 h night light regime. Five weeks old healthy *N. benthamiana* plants were used for syringe infiltration with *Agrobacterium* strains GV3101 harboring either pLH9000 as a negative control, pLH1A11int or pLH1A11 expressing Nb1A11 (chicken IL-10 sdAb1A11 for *N. benthamiana* expression as described above), or with the mixture of two *Agrobacterium* strains, such as GV3101 with pLH1A11int and C58C1 with p19. As used herein, 1A11 sdAB is synonomous with anti-chicken IL-10 sdAB and chicken IL-10 sdAb1A11. The p19 is a tomato bushy stunt virus protein, which is involved into suppression of RNA-dependent gene silencing thus improving expression of heterologous proteins. *Agrobacterium* strains GV3101 and C58C1 with p19 were kindly provided by Dr. I. Lernomtova (IPK Gatersleben, Germany). The *Agrobacterium* strains containing plasmids were grown from single colonies overnight in LB medium supplemented with corresponding antibiotics, the cells were harvested by centrifugation and resuspended to $OD_{600}$=0.4 in 10 mM $MgCl_2$, 10 mM MES-K (pH 5.6). Prior to syringe infiltration of *N. benthamiana* leaves 100 μM Acetosyringone was added to each *Agrobacterium* strain. The leaf tissues for expression analysis of Nb1A11 were harvested on day 4 post infiltration.

RNA Analysis of Nb1A11 Expression

The total plant RNA from *Agrobacterium* infiltrated *N. benthamiana* leaf tissues was isolated with NucleoSpin RNA Plant Kit (Takara) according to manufacturer's protocol. Subsequently, 1 μg of the total RNA was converted into cDNA using iScript cDNA Synthesis Kit (Bio-Rad) and 1.5 μl of each cDNA was used as template in PCR reactions with the following primers:

forward primer 3661 (5'-CGTGCCCAAGTTCAGTTACA-3' [SEQ ID NO: 200]), and reverse primer 3662 (5'-TTGCAACAAGTTCTCTTTGCTT-3' [SEQ ID NO: 201]).

Figure 14:
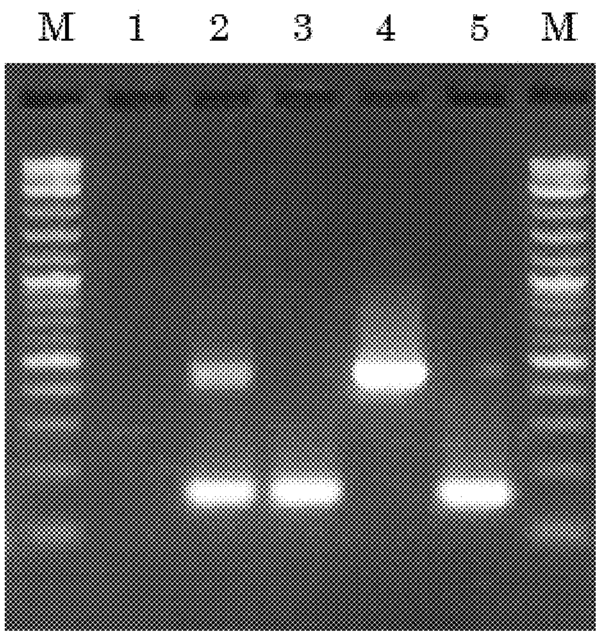
FIG. 14 illustrates end point RT-PCR analysis of transiently expressed Nb1A11 in *N. benthamiana* leaves. Lanes 1-5 contain the following samples: lane 1—GV3101+pLH9000 (negative control); lane 2—GV3101+pLH1A11int; lane 3—GV3101+pLH1A11; lane 4—plasmid pLH1A11int; and lane 5—plasmid pLH1A11.

The primers were positioned to flank intron AtUBQ10i within the coding region of Nb1A11 and allow unambiguous identification of the plant cell expressed 1A11 transcript with the fully spliced out intron. The Platinum Taq DNA Polymerase (Invitrogen) was used to amplify PCR products under conditions recommended by manufacturer with 36 cycles of amplification and primer annealing temperature of 55° C. The PCR products were resolved on 2% agarose gel. FIG. 14 illustrates end point RT-PCR analysis of transiently expressed Nb1A11 in *N. benthamiana* leaves. In this figure, lanes 1-5: lane 1—GV3101+pLH9000 (negative control); lane 2—GV3101+pLH1A11int; lane 3—GV3101+pLH1A11; lane 4—plasmid pLH1A11int; and lane 5—plasmid pLH1A11.

In *N. benthamiana* leaf tissues infiltrated with the negative control plasmid pLH9000 no 1A11 transcripts were amplified (lane 1). Distinct PCR products of the expected 1A11 transcript sizes were amplified from *N. benthamiana* leaf tissues infiltrated with either pLH1A11int or pLH1A11 (lanes 2 and 3 respectively).

Amplified PCR products from plasmids pLH1A11int and pLH1A11 were uses as positive controls and run in lanes 4 and 5. The resulting products in lanes 4 and 5 were observed to have identical sizes to the products in lanes 2 and 3. A lower intensity PCR band corresponding in size to the expected 458 bp fragment containing AtUBQ10i was also detected in lane 2. This fragment could have been amplified from either *N. benthamiana* genomic DNA, which was still lingering in total RNA preparation of the sample despite of its removal by DNase digestion as suggested by manufacturer's instructions, or alternatively, the amplification product is indicative of a fraction of isolated total RNA containing Nb1A11 transcripts with still unspliced AtUBQ10i.

1A11 sdAb Transient Protein Expression Analysis

Figure 15:
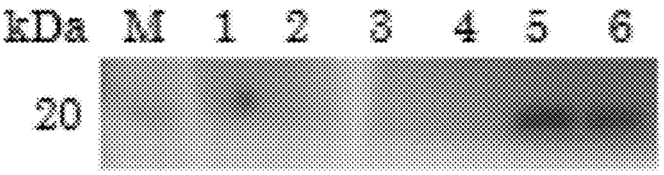
FIG. 15 illustrates sdAB1A11 expression in *Agrobacterium* infiltrated leaves of *N. benthamiana*. The Western blot shows detection of sdAB1A11 in samples 5 and 6.

Based on the results of Nb1A11 RNA transcript analysis in leaves of *N. benthamiana*, the leaf tissue samples that were infiltrated with pLH1A11int and pLH1A11int+p19 were selected for protein isolation and Western blot analysis. *Agrobacterium*-infiltrated leaf tissues were ground in liquid nitrogen and the total protein was isolated using extraction buffer composed of 1 M NaCl, 50 mM Sodium Phosphate p118.0, 10 mM Imidazole. The extraction buffer was supplemented with 1× Halt Protease Inhibitor Cocktail (ThermoFisher) and 2 mM β-mercaptoethanol. Protein extraction was performed at 4° C. for 1 h with agitation, samples were centrifuged twice to remove plant debris. The 1A11 sdAB containing 6×His tag at its C-terminal end was isolated from the cleared supernatant of the total *N. benthamiana* leaf protein using Ni-NTA spin columns (QIAGEN) according to manufacturer's protocol for native conditions. The 1A11 sdAB was further concentrated using Amicon Ultra-2 centrifugal filters (Millipore-Sigma) and protein concentration was determined by NanoDrop spectrophotometer. Subsequently, 15 μg of 1A11 containing concentrated protein fraction was resolved on 4-12% gradient NuPAGE polyacrylamide gels (ThermoFisher) using 1×MOPS SDS gel running buffer. Biotynylated Protein Ladder (Cell Signalling Technologies) and Precision Plus Protein Kaleidoscope (Bio-Rad) were used as molecular weight standards. The proteins were separated in a polyacrylamide gel and transferred onto PVDF membrane using semi-dry Western blotting procedure. The PVDF membrane bound 1A11 protein was detected using Rabbit Anti-VHH HRP (Invitrogen) as the primary antibody at 1:2500 dilution followed by Anti-Rabbit IgG Peroxidase Goat (Sigma) as the secondary antibody at 1:5000 dilution. Detection of the biotinylated proteins in the protein molecular weight ladder was accomplished by Anti-biotin HRP-liked Ab at 1:15000 dilution (Cell Signaling Technology). The signal detection was achieved using Super Signal West Pico Plus chemiluminescent substrate (ThermoFisher). FIG. 15 illustrates 1A11 protein expression in *Agrobacterium* infiltrated leaves of *N. benthamiana*. The Western blot shows detection of 1A11 sdAb in samples 5, 6. It was demonstrated that the lanes 5 and 6 contain a protein of expected molecular weight of 17.4 kDa that is cross reactive with the Anti-VHH primary antibody, indicating the protein is indeed 1A11 sdAB.

Example 13. Anticoccidial Efficacy of IL-10R Peptide Antagonists and sdABs in Commercial Broiler Chickens Infected with a Mixture of *Eimeria acervulina, E. maxima*, and *E. tenella* Field Isolates The same study design was used to measure the anticoccidial efficacy/sensitivity anti-IL10 antibodies, or IL-10R antagonists against a mixture of *Eimeria acervulina, E. maxima*, and *E. tenella*. In these trials, chickens were separated into multiple control groups that were either exposed to *Eimeria* (Infected, I) or not exposed to *Eimeria* (Non-Infected, NI), and treatment groups that were exposed to *Eimeria* and treated with various diets. The control groups included a negative control group receiving normal feed with and without anti-IL-10 sdAB (or with and without IL-10R antagonist) in the feed, and a positive control group receiving a standard chemical Coccidiostat. Treatment groups were fed diets containing from 50 g to four kilograms of milled grain expressing anti-IL-10 sdAB per kilogram of feed (or IL-10R antagonist peptide doses ranging from 1 milligram of peptide per kilogram of feed to 40 milligrams of IL-10R antagonist peptide per kilogram of feed. Anti-IL-10 sdABs, including SEQ ID NO: 87 (chIL10sdAB1115), SEQ ID NO: 88 (chIL10sdAB1E9), SEQ ID NO: 89 (chIL10sdAB1H1), SEQ ID NO: 90 (chIL10sdAB1G6), SEQ ID NO: 91 (chIL10sdAB1C10), SEQ ID NO: 92 (chIL10sdAB1B6), SEQ ID NO: 93 (chIL10sdAB1D12), SEQ ID NO: 94 (chIL10sdAB1C2), SEQ ID NO: 95 (chIL10sdAB1B5), SEQ ID NO: 96 (chIL10sdAB1E2), SEQ ID NO: 97 (chIL10sdAB1G7), SEQ ID NO: 98 (chIL10sdAB1G9), SEQ ID NO: 99 (chIL10sdAB1H12), SEQ ID NO: 100 (chIL10sdAB2A9), SEQ ID NO: 101 (chIL10sdAB1E12), SEQ ID NO: 102 (chIL10sdAB1E10), SEQ ID NO: 103 (chIL10sdAB1F12), SEQ ID NO: 104 (chIL10sdAB1A8), SEQ ID NO: 105 (chIL10sdAB1C8), SEQ ID NO: 106 (chIL10sdAB1C12), SEQ ID NO: 107 (chIL10sdAB1B1), SEQ ID NO: 108 (chIL10sdAB1F1), SEQ ID NO: 109 (chIL10sdAB1D11), SEQ ID NO: 110 (chIL10sdAB1E6), SEQ ID NO: 111 (chIL10sdAB1B9), SEQ ID NO: 112 (chIL10sdAB1B10), SEQ ID NO: 113 (chIL10sdAB1F5), SEQ ID NO: 114 (chIL10sdAB1A6), SEQ ID NO: 115 (chIL10sdAB1D5), SEQ ID NO: 116 (chIL10sdAB1D8), SEQ ID NO: 117 (chIL10sdAB1B4), SEQ ID NO: 118 (chIL10sdAB1C7), SEQ ID NO: 119 (chIL10sdAB1B3), SEQ ID NO: 120 (chIL10sdAB1D7), SEQ ID NO: 121 (chIL10sdAB1F7), SEQ ID NO: 122 (chIL10sdAB1F10), SEQ ID NO: 123 (chIL10sdAB1F2), SEQ ID NO: 124 (chIL10sdAB1F3), SEQ ID NO:125 (chIL10sdAB1F8), SEQ ID NO: 126 (chIL10sdAB1C9), SEQ ID NO: 127 (chIL10sdAB1A12), SEQ ID NO: 128 (chIL10sdAB1C3), SEQ ID NO: 129 (chIL10sdAB1E7), SEQ ID NO: 130 (chIL10sdAB1D9), SEQ ID NO: 131 (chIL10sdAB1A9), SEQ ID NO: 132 (chIL10sdAB1H10), SEQ ID NO: 133 (chIL10sdAB1C1), SEQ ID NO: 134 (chIL10sdAB1D1), SEQ ID NO: 135 (chIL10sdAB1A11), SEQ ID NO: 136 (chIL10sdAB1G8), SEQ ID NO: 137 (chIL10sdAB1A5), SEQ ID NO: 138 (chIL10sdAB1C5), SEQ ID NO: 139 (chIL10sdAB1H6), SEQ ID NO: 140 (chIL10sdAB2A8), SEQ ID NO: 141 (chIL10sdAB1F9), SEQ ID NO: 142 (chIL10sdAB1E11), SEQ ID NO: 143 (chIL10sdAB1D6), SEQ ID NO: 144 (chIL10sdAB1C4), SEQ ID NO: 145 (chIL10sdAB1H4), SEQ ID NO: 146 (chIL10sdAB1F11), SEQ ID NO: 147 (chIL10sdAB1D3), SEQ ID NO: 148 (chIL10sdAB1A7), SEQ ID NO: 149 (chIL10sdAB1H8), SEQ ID NO: 150 (chIL10sdAB1H3), SEQ ID NO: 151 (chIL10sdAB1B8), SEQ ID NO: 152 (chIL10sdAB1B2), SEQ ID NO: 153 (chIL10sdAB1D2), or SEQ ID NO: 154 (chIL10sdAB1D10), or peptides of SEQ ID NO: 1 [P21], SEQ ID NO: 2 [P22], SEQ ID NO: 3 [P23], SEQ ID NO: 4 [P24], SEQ ID NO: 5 [P25], SEQ ID NO: 6 [P26], SEQ ID NO: 7 [P27], SEQ ID NO: 8 [P28], SEQ ID NO: 9 [P29], SEQ ID NO: 10 [P11], SEQ ID NO: 11 [P30], SEQ ID NO: 12 [P31], SEQ ID NO: 13 [P32] SEQ or concatenated peptides SEQ ID NO: 32 [P2501], SEQ ID NO: 33 [P2502], SEQ ID NO: 34 [P2503], SEQ ID NO: 35 [P2504], SEQ ID NO: 36 [P2505], SEQ ID NO: 37 [P2506], SEQ ID NO: 38 [P2507], SEQ ID NO: 39 [P2508], or SEQ ID NO: 40 [P2509] were tested in this manner.

These feeding trials are eight days in length and consist of 96 cages, each starting with 8 male chicks. The treatments will be replicated in 8 blocks, randomized within blocks of 8 cages each. A randomization procedure for pen assignment for treatments and blocks was used by the contracting facility.

TABLE 8

Treatment design to test chIL10sdAB expressing corn grain

| Trt | Description | Infected/ Non-Infected | Additive inclusion, g additive/kg feed | Cages/ Trt | Birds/ Cage |
|---|---|---|---|---|---|
| T1 | Nonmedicated (NMNI) | NI | 0 | 8 | 8 |
| T2 | Nonmedicated (NMI, NC) | I | 0 | 8 | 8 |
| T3 | Coccidiostat (PC) | NI | 0.010 | 8 | 8 |
| T4 | Coccidiostat (PC) | I | 0.010 | 8 | 8 |
| T5 | SEQ ID NO: 135 (chIL10sdAB1A11) | I | 4000 | 8 | 8 |
| T6 | SEQ ID NO: 135 (chIL10sdAB1A11) | I | 4000 | 8 | 8 |
| T7 | SEQ ID NO: 135 (chIL10sdAB1A11) | I | 1 | 8 | 8 |
| T8 | SEQ ID NO: 135 (chIL10sdAB1A11) | I | 40 | 8 | 8 |
| T9 | SEQ ID NO: 135 (chIL10sdAB1A11) | I | 500 | 8 | 8 |
| T10 | SEQ ID NO: 135 (chIL10sdAB1A11) | I | 300 | 8 | 8 |
| T11 | SEQ ID NO: 135 (chIL10sdAB1A11) | I | 150 | 8 | 8 |
| T12 | SEQ ID NO: 135 (chIL10sdAB1A11) | I | 50 | 8 | 8 |

Other sdABs were tested using the same trial design, same grain loadings, but different chIL10sdAB expressing corn grain. In a similar way, the same trial design was used to test IL-10R peptide antagonists as shown in Table 9.

TABLE 9

Treatment design to test IL-10R antagonist peptides

| Trt | Description | Infected/ Non-Infected | Additive inclusion, g additive/kg feed | Cages/ Trt | Birds/ Cage |
|---|---|---|---|---|---|
| T1 | Nonmedicated (NMNI, NC) | NI | 0 | 8 | 8 |
| T2 | Nonmedicated (NMI, NC) | I | 0 | 8 | 8 |
| T3 | Coccidiostat (PC) | NI | 0.010 | 8 | 8 |
| T4 | Coccidiostat (PC) | I | 0.010 | 8 | 8 |
| T5 | P21 | NI | 0.070 | 8 | 8 |

TABLE 9-continued

Treatment design to test IL-10R antagonist peptides

| Trt | Description | Infected/ Non-Infected | Additive inclusion, g additive/kg feed | Cages/ Trt | Birds/ Cage |
|---|---|---|---|---|---|
| T6 | P21 | I | 0.070 | 8 | 8 |
| T7 | P21 | I | 0.050 | 8 | 8 |
| T8 | P21 | I | 0.035 | 8 | 8 |
| T9 | P21 | I | 0.020 | 8 | 8 |
| T10 | P21 | I | 0.015 | 8 | 8 |
| T11 | P21 | I | 0.010 | 8 | 8 |
| T12 | P21 | I | 0.001 | 8 | 8 |

At the start of every trial, the facility was checked to ensure that all cages have water and feed available in each cage, which was provided to animal ad libitum. The building temperature was maintained as appropriate for the age of the birds. Even, continuous illumination was provided by fluorescent lamps hung vertically along the wall. Cages will be checked twice daily, and observations including availability of feed, water, temperature and any unusual conditions were recorded. Mortality birds were removed from cages, and the cage number, date, weight of the bird, sex and probable cause of death were recorded.

As part of the trial, an unmedicated commercial starter ration compounded with basal feedstuffs was formulated. This ration was used to formulate the study's negative and positive control rations, and experimental diets, which were all fed ad libitum from the date of chick arrival until completion of the study. Quantities of all basal feed and test articles used to prepare treatment batches were documented and tested as part of the trial quality control procedures. Treatment diets were mixed to a uniform distribution of test article. The mixer was flushed between control and treatment diets, and in between each treatment diet. Each treatment feed was then distributed among cages of the corresponding treatment.

Day of hatch male chicks (Cobb 500) were used in the study. Upon arrival, chicks will be colony raised in Coccidia free battery cages. At 12 days of age (trial day 0) chicks will grouped into sets of 8, weighed, and placed into an assigned cage. Birds were weighed by cage on day of trial 0 and 8.

On day of trial 2, all non-infected birds received 1 ml of distilled water by oral pipette. All other birds will receive the coccidial inoculum diluted to a 1 ml volume and dosed by oral pipette. The inoculum was a mixture of *Eimeria acervulina, E. maxima*, and *E. tenella* field isolates, which produces a mild infection with all species.

Data were collected after starting the study on days 0, 2, 7, and 8. On day 0, birds were weighed and allocated to their cages for the study. On Day 2, designated birds were inoculated with coccidian. On Day 7, dropping pans were cleaned to prepare for droppings collection on Day 8, and subsequent analysis. On Day 8, birds were weighed by cage, along with the remaining feed, and fecal matter. Feces collected from each cage were thoroughly mixed and prepared for fecal floatation, and each sample was examined to determine the number of oocysts per gram of fecal matter. All birds were scored for coccidian lesions on day 8 using the method of Johnson and Reid (1970). During the trial death weights were recorded and clinical observations were recorded twice each day throughout the study.

Feed in-take, body weight gain, feed conversion, opgs, coccidian lesion scores, and mortality were measured for each group and analyzed by standard statistical methods. The effect of sdAB (or peptide) supplementation was compared between groups treated with *Eimeria* and not treated with *Eimeria*, between treatment groups treated with *Eimeria* and antibody (or peptide) and control groups treated and not treated with *Eimeria*, control groups treated with *Eimeria* and no antibody (or peptide) or Coccidiostat, and control groups treated with *Eimeria* and also treated with a Coccidiostat.

Additionally the minimum effective dose was determined by seeing which antibody (or peptide) dose reduced fecal oocyst counts or lesion scores relative to the control birds that were infected but not treated with antibody (or peptide) or Coccidiostat. Using this design the extent of oocyst and lesion scoring reduction were determined as a function of dose.

REFERENCES

Arbabi Ghahroudi, M. et al., 1997. Selection and identification of single domain antibody fragments from camel heavy-chain antibodies. *FEBS Letters,* 414(3), pp. 521-526.

Cervantes, H., 2002. Incidence of pathological conditions in clinically normal broilers from different regions of the USA. $51^{st}$ Western Poultry Disease Conference, May 1-4, Casa *Magna* Marriott Resort, Puerto Vallart, Jalisco, Mexico, 220-223.

Cervantes, H., 2006. Incidence of subclinical diseases and pathological conditions in clinically normal broilers from 3 production complexes sorted by sex and age. $143^{rd}$ Annual Convention of the American Veterinary Medical Association and $50^{th}$ Annual Meeting of the American Association of Avian Pathologists, July 15-19, Hawaii Convention Center, Honolulu, Hawaii Cook, M. E., Sand, J. M., McGuirk, S. M., Rieman, J. E., and Raabis, S. M. (2015), U. S. patent application No. US2016/0280778 A1

Diaz-Valdes, N., Manterola, L., Belsue, V., Riezu-Boj, J. I., Larrea, E., Echeverria, I., LLopiz, D., Lopez-Sagaseta, J., Lerat, H., Pawlotsky, J.-M., Prieto, J., Lasarte, J. J., Borras-Cuesta, F., and Sarobe, P. (2011), Hepatology 53, 23-31.

Goldman, E. R. et al., 2006. Facile Generation of Heat Stable Antiviral and Antitoxin Single Domain Antibodies from a Semi-synthetic Llama Library., 78(24), pp. 8245-8255.

Josephson, K., Logsdon, N. J., and Walter, M. W. (2001), Immunity 14, 35-46.

Liu, J. L. et al., 2013. Selection and evaluation of single domain antibodies toward MS2 phage and coat protein. *Molecular Immunology,* 53(1-2), pp. 118-125.

Naiyer, M. M., Saha, S., Hemke, V., Roy, S., Singh, S., Musti, K. V., and Saha, B. (2013), Human Immunology 74, 28-31.

Ni, G., Chen, S., Yang, Y., Cummins, S. F., Zhan, J., Li, Z., Zhu, B., Mounsey, K., Walton, S., Wei, M. Q., Wang, Y., Zhou, Y., Wang, T., and Liu, X. (2016), PLOSOne, Apr. 21, 2016.

Reineke, U., Sabat, R., Volk, H.-D., and Schneider-Mergener, J. (1998), Protein Sci. 7, 951-960.

Rothwell, L., Young, J. R., Zoorob, R., Whittaker, C. A., Hesketh, P., Archer, A., Smith, A. L., and Kaiser, P. (2004), J. Immunol. 173, 2675-2682.

Sand, J. M, and Cook, M. E. (2014), U.S. Pat. No. 8,652,457 B2.

Wu, Z., Hu, T., Rothwell, L., Vervelde, L., Kaiser, P., Boulton, K., Nolan, M. J., Tomley, F. M., Blake, D. P., and Hume, D. A. (2016), Devel. Comp. Immunol. 63, 206-212.

Yoon, I. L., Jones, B. C., Logsdon, N. J., and Walter, M. R. (2005), Structure 13, 551-564.

Zdanov, A., Schalk-Hihi, C., and Wlodawer, A. (1996), Protein Sci. 5, 1955-1962.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A transgenic plant or tissues thereof comprising a synthetic polynucleotide encoding an anti-IL-10 single domain antibody, wherein the anti-IL-10 single domain antibody comprises an amino acid sequence of SEQ ID NO: 146, and binds a polypeptide comprising an amino acid sequence of SEQ ID NO: 80 with an $EC_{50}$ of 60 nM or less, as measured by ELISA.

2. The transgenic plant or tissues thereof of claim 1, wherein the synthetic polynucleotide comprises a sequence to of SEQ ID NO: 175 or 176.

3. The transgenic plant or tissue thereof of claim 1, wherein a plant is selected from the group consisting of: corn, soybean, wheat, rice, sorghum, canola, cotton, and switchgrass.

4. An animal feed comprising the transgenic plant or tissue thereof of claim 1.

5. The animal feed of claim 1, wherein the anti-IL-10 single domain antibody is active upon expression in the plant and exposure to a temperature in the range from 25° C. to 130° C.

6. The animal feed of claim 4 further comprising a feed supplement.

7. The animal feed of claim 6, wherein the feed supplement is plant material.

8. The animal feed of claim 7, wherein the plant material is a non-transgenic plant or a transgenic plant.

9. The animal feed of claim 7, wherein the plant material includes at least one component selected from the group consisting of: corn meal, corn pellets, wheat meal, wheat pellets, wheat grain, barley grain, barley pellets, soybean meal, soybean oilcake, sorghum grain and sorghum pellets.

10. The animal feed of claim 6, wherein the feed supplement includes one or more exogenous enzymes.

11. The animal feed of claim 10, wherein the one or more exogenous enzymes includes a hydrolytic enzyme selected from the group consisting of: xylanase, endoglucanase, cellulase, protease, phytase, amylase and mannanase.

12. The animal feed of claim 6, wherein the feed supplement includes at least one component selected from the group consisting of: soluble solids, fat and vermiculite, limestone, plain salt, DL-methionine, L-lysine, L-threonine, monensin, vitamin premix, dicalcium phosphate, selenium premix, choline chloride, sodium chloride, and mineral premix.

13. A method of treating or preventing a gastrointestinal infection in the animal comprising administering to an animal the transgenic plant or tissue thereof of claim 1.

14. The method of claim 13, wherein the step of administering is performed by feeding or injecting.

15. The method of claim 13, wherein the gastrointestinal infection is caused by a gastrointestinal pathogen selected from the group consisting of: a bacteria, yeast, fungi, archae, virus, and protozoa.

16. The method of claim 15, wherein the gastrointestinal pathogen belongs to the genus *Eimeria*.

17. The method of claim 16, wherein the gastrointestinal pathogen is selected from the group consisting of: *Eimeria tenella, Eimeria acervulina*, and *Eimeria maxima*.

18. The method of claim 13, wherein treating stimulates the immune system and enhances growth of the animal.

19. The method of claim 18, wherein the animal is selected from the group consisting of: a chicken, a turkey, or a duck.

* * * * *

SEQUENCE LISTING

```
<160> NUMBER OF SEQ ID NOS: 249

<210> SEQ ID NO 1
<211> LENGTH: 40
<212> TYPE: PRT
<213> ORGANISM: Artificial Sequence
<220> FEATURE:
<223> OTHER INFORMATION: Synthetic construct, P21

<400> SEQUENCE: 1

Pro Ala Arg Leu Arg Glu Leu Arg Val Lys Phe Glu Glu Ile Lys Asp
1               5                   10                  15

Tyr Phe Gln Ser Arg Asp Asp Glu Leu Asn Ile Gln Leu Leu Ser Ser
            20                  25                  30

Glu Leu Leu Asp Glu Phe Lys Gly
        35                  40


<210> SEQ ID NO 2
<211> LENGTH: 27
<212> TYPE: PRT
<213> ORGANISM: Artificial Sequence
<220> FEATURE:
<223> OTHER INFORMATION: Synthetic construct, P22

<400> SEQUENCE: 2

Glu Asn Gly Ile Tyr Lys Ala Met Gly Glu Phe Asp Ile Phe Ile Asn
1               5                   10                  15

Tyr Ile Glu Glu Tyr Leu Leu Met Arg Arg Arg
            20                  25


<210> SEQ ID NO 3
<211> LENGTH: 47
<212> TYPE: PRT
<213> ORGANISM: Artificial Sequence
<220> FEATURE:
<223> OTHER INFORMATION: Synthetic construct, P23

<400> SEQUENCE: 3

Pro Ala Arg Leu Arg Glu Leu Arg Val Lys Phe Glu Glu Ile Lys Asp
1               5                   10                  15

Tyr Phe Gln Gly Gly Gly Ser Gly Gly Gly Ser Gln Gln Ser Met Gly
            20                  25                  30

Asp Leu Gly Asn Met Leu Leu Gly Leu Lys Ala Thr Met Arg Arg
```

35 40 45

<210> SEQ ID NO 4
<211> LENGTH: 50
<212> TYPE: PRT
<213> ORGANISM: Artificial Sequence
<220> FEATURE:
<223> OTHER INFORMATION: Synthetic construct, P24

<400> SEQUENCE: 4

```
Gly Cys Gln Ser Val Ser Glu Met Leu Arg Phe Tyr Thr Asp Glu Val
1               5                   10                  15

Leu Pro Arg Ala Met Gln Gly Gly Gly Ser Gly Gly Gly Ser Lys Ala
            20                  25                  30

Met Gly Glu Phe Asp Ile Phe Ile Asn Tyr Ile Glu Glu Tyr Leu Leu
        35                  40                  45

Met Arg
    50
```

<210> SEQ ID NO 5
<211> LENGTH: 8
<212> TYPE: PRT
<213> ORGANISM: Artificial Sequence
<220> FEATURE:
<223> OTHER INFORMATION: Synthetic construct, P25

<400> SEQUENCE: 5

```
Pro Ala Arg Leu Arg Glu Leu Arg
1               5
```

<210> SEQ ID NO 6
<211> LENGTH: 11
<212> TYPE: PRT
<213> ORGANISM: Artificial Sequence
<220> FEATURE:
<223> OTHER INFORMATION: Synthetic construct, P26

<400> SEQUENCE: 6

```
Leu Ser Ser Glu Leu Leu Asp Glu Phe Lys Gly
1               5                   10
```

<210> SEQ ID NO 7
<211> LENGTH: 10
<212> TYPE: PRT
<213> ORGANISM: Artificial Sequence
<220> FEATURE:
<223> OTHER INFORMATION: Synthetic construct, P27

<400> SEQUENCE: 7

```
Gly Glu Phe Asp Ile Phe Asn Tyr Ile Glu
1               5                   10
```

<210> SEQ ID NO 8
<211> LENGTH: 10
<212> TYPE: PRT
<213> ORGANISM: Artificial Sequence
<220> FEATURE:
<223> OTHER INFORMATION: Synthetic construct, P28

<400> SEQUENCE: 8

```
Ser Leu Arg Tyr Tyr Ala Arg Val Arg Ala
1               5                   10
```

<210> SEQ ID NO 9
<211> LENGTH: 7

-continued

<212> TYPE: PRT
<213> ORGANISM: Artificial Sequence
<220> FEATURE:
<223> OTHER INFORMATION: Synthetic construct, P29

<400> SEQUENCE: 9

Thr Asn Ala Phe Ser Pro Gln
1               5

<210> SEQ ID NO 10
<211> LENGTH: 29
<212> TYPE: PRT
<213> ORGANISM: Artificial Sequence
<220> FEATURE:
<223> OTHER INFORMATION: Synthetic construct, P11

<400> SEQUENCE: 10

Tyr Asp Asp Ile Gln Lys His Ala Arg Arg Tyr Arg Val Tyr Ile Arg
1               5                   10                  15

Arg Ala Arg Asp Asn Gln Thr Tyr Glu Val Trp Glu Thr
            20                  25

<210> SEQ ID NO 11
<211> LENGTH: 8
<212> TYPE: PRT
<213> ORGANISM: Artificial Sequence
<220> FEATURE:
<223> OTHER INFORMATION: Synthetic construct, P30

<400> SEQUENCE: 11

Ile Gln Lys His Ala Arg Arg Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic construct, P31

<400> SEQUENCE: 12

Asn Gln Thr Tyr Glu Val Trp Glu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic construct, P32

<400> SEQUENCE: 13

Val Ala Ser Arg His Ile Pro Ala Met
1               5

<210> SEQ ID NO 14
<211> LENGTH: 16
<212> TYPE: PRT
<213> ORGANISM: Artificial Sequence
<220> FEATURE:
<223> OTHER INFORMATION: Synthetic construct, P9

<400> SEQUENCE: 14

Phe Phe Lys Lys Phe Phe Lys Lys Phe Phe Lys Lys Phe Phe Lys Lys
1               5                   10                  15

-continued

<210> SEQ ID NO 15
<211> LENGTH: 16
<212> TYPE: PRT
<213> ORGANISM: Artificial Sequence
<220> FEATURE:
<223> OTHER INFORMATION: Synthetic construct, P6

<400> SEQUENCE: 15

Gly Thr Glu Leu Pro Ser Pro Pro Ser Val Trp Phe Glu Ala Glu Phe
1 5 10 15

<210> SEQ ID NO 16
<211> LENGTH: 120
<212> TYPE: DNA
<213> ORGANISM: Artificial Sequence
<220> FEATURE:
<223> OTHER INFORMATION: Synthetic construct, P21 coding sequence

<400> SEQUENCE: 16
ccggccaggc tgagggagct gagggtgaag ttcgaggaga tcaaggacta cttccagagc 60
agggacgacg agctgaacat ccagctgctg agcagcgagc tgctggacga gttcaagggc 120

<210> SEQ ID NO 17
<211> LENGTH: 81
<212> TYPE: DNA
<213> ORGANISM: Artificial Sequence
<220> FEATURE:
<223> OTHER INFORMATION: Synthetic construct, P22 coding sequence

<400> SEQUENCE: 17
gagaacggca tctacaaggc catgggcgag ttcgacatct tcatcaacta catcgaggag 60
tacctgctga tgaggaggag g 81

<210> SEQ ID NO 18
<211> LENGTH: 141
<212> TYPE: DNA
<213> ORGANISM: Artificial Sequence
<220> FEATURE:
<223> OTHER INFORMATION: Synthetic construct, P23 coding sequence

<400> SEQUENCE: 18
ccggccaggc tgagggagct gagggtgaag ttcgaggaga tcaaggacta cttccagggc 60
ggcggcagcg gcggcggcag ccagcagagc atgggcgacc tgggcaacat gctgctgggc 120
ctgaaggcca ccatgaggag g 141

<210> SEQ ID NO 19
<211> LENGTH: 150
<212> TYPE: DNA
<213> ORGANISM: Artificial Sequence
<220> FEATURE:
<223> OTHER INFORMATION: Synthetic construct, P24 coding sequence

<400> SEQUENCE: 19
ggctgccaga gcgtgagcga gatgctgagg ttctacaccg acgaggtgct gccgagggcc 60
atgcagggcg gcggcagcgg cggcggcagc aaggccatgg gcgagttcga catcttcatc 120
aactacatcg aggagtacct gctgatgagg 150

<210> SEQ ID NO 20
<211> LENGTH: 24
<212> TYPE: DNA
<213> ORGANISM: Artificial Sequence
<220> FEATURE:
<223> OTHER INFORMATION: Synthetic construct, P25 coding sequence

<400> SEQUENCE: 20
ccggccaggc tgagggagct gagg 24

<210> SEQ ID NO 21
<211> LENGTH: 33
<212> TYPE: DNA
<213> ORGANISM: Artificial Sequence
<220> FEATURE:
<223> OTHER INFORMATION: Synthetic construct, P26 coding sequence

<400> SEQUENCE: 21
ctgagcagcg agctgctgga cgagttcaag ggc 33

<210> SEQ ID NO 22
<211> LENGTH: 30
<212> TYPE: DNA
<213> ORGANISM: Artificial Sequence
<220> FEATURE:
<223> OTHER INFORMATION: Synthetic construct, P27 coding sequence

<400> SEQUENCE: 22
ggcgagttcg acatcttcaa ctacatcgag 30

<210> SEQ ID NO 23
<211> LENGTH: 30
<212> TYPE: DNA
<213> ORGANISM: Artificial Sequence
<220> FEATURE:
<223> OTHER INFORMATION: Synthetic construct, P28 coding sequence

<400> SEQUENCE: 23
agcctgaggt actacgccag ggtgagggcc 30

<210> SEQ ID NO 24
<211> LENGTH: 21
<212> TYPE: DNA
<213> ORGANISM: Artificial Sequence
<220> FEATURE:
<223> OTHER INFORMATION: Synthetic construct, P29 coding sequence

<400> SEQUENCE: 24
accaacgcct tcagcccgca g 21

<210> SEQ ID NO 25
<211> LENGTH: 87
<212> TYPE: DNA
<213> ORGANISM: Artificial Sequence
<220> FEATURE:
<223> OTHER INFORMATION: Synthetic construct, P11 coding sequence

<400> SEQUENCE: 25
tacgacgaca tccagaagca cgccaggagg tacagggtgt acatcaggag ggccagggac 60
aaccagacct acgaggtgtg ggagacc 87

<210> SEQ ID NO 26
<211> LENGTH: 24
<212> TYPE: DNA
<213> ORGANISM: Artificial Sequence
<220> FEATURE:
<223> OTHER INFORMATION: Synthetic construct, P30 coding sequence

<400> SEQUENCE: 26
atccagaagc acgccaggag gtac 24

<210> SEQ ID NO 27
<211> LENGTH: 24
<212> TYPE: DNA
<213> ORGANISM: Artificial Sequence
<220> FEATURE:
<223> OTHER INFORMATION: Synthetic construct, P31 coding sequence

<400> SEQUENCE: 27
aaccagacct acgaggtgtg ggag 24

<210> SEQ ID NO 28
<211> LENGTH: 27
<212> TYPE: DNA
<213> ORGANISM: Artificial Sequence
<220> FEATURE:
<223> OTHER INFORMATION: Synthetic construct, P32 coding sequence

<400> SEQUENCE: 28
gtggccagca ggcacatccc ggccatg 27

<210> SEQ ID NO 29
<211> LENGTH: 4
<212> TYPE: PRT
<213> ORGANISM: Artificial Sequence
<220> FEATURE:
<223> OTHER INFORMATION: Synthetic construct, KDEL

<400> SEQUENCE: 29

Lys Asp Glu Leu
1

<210> SEQ ID NO 30
<211> LENGTH: 4
<212> TYPE: PRT
<213> ORGANISM: Artificial Sequence
<220> FEATURE:
<223> OTHER INFORMATION: Synthetic construct, HDEL

<400> SEQUENCE: 30

His Asp Glu Leu
1

<210> SEQ ID NO 31
<211> LENGTH: 6
<212> TYPE: PRT
<213> ORGANISM: Artificial Sequence
<220> FEATURE:
<223> OTHER INFORMATION: Synthetic construct, SEKDEL

<400> SEQUENCE: 31

Ser Glu Lys Asp Glu Leu
1 5

<210> SEQ ID NO 32
<211> LENGTH: 12
<212> TYPE: PRT
<213> ORGANISM: Artificial Sequence
<220> FEATURE:
<223> OTHER INFORMATION: Synthetic construct, P2501

<400> SEQUENCE: 32

Pro Ala Arg Leu Arg Glu Leu Arg Lys Asp Glu Leu
1 5 10

<210> SEQ ID NO 33
<211> LENGTH: 16

-continued

<212> TYPE: PRT
<213> ORGANISM: Artificial Sequence
<220> FEATURE:
<223> OTHER INFORMATION: Synthetic construct, P2502

<400> SEQUENCE: 33

Pro Ala Arg Leu Arg Glu Leu Arg Pro Ala Arg Leu Arg Glu Leu Arg
1               5                   10                  15

<210> SEQ ID NO 34
<211> LENGTH: 20
<212> TYPE: PRT
<213> ORGANISM: Artificial Sequence
<220> FEATURE:
<223> OTHER INFORMATION: Synthetic construct, P2503

<400> SEQUENCE: 34

Pro Ala Arg Leu Arg Glu Leu Arg Pro Ala Arg Leu Arg Glu Leu Arg
1               5                   10                  15

Lys Asp Glu Leu
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic construct, P2504

<400> SEQUENCE: 35

Pro Ala Arg Leu Arg Glu Leu Arg Ala Gly Pro Ala Pro Ala Arg Leu
1               5                   10                  15

Arg Glu Leu Arg
            20

<210> SEQ ID NO 36
<211> LENGTH: 24
<212> TYPE: PRT
<213> ORGANISM: Artificial Sequence
<220> FEATURE:
<223> OTHER INFORMATION: Synthetic construct, P2505

<400> SEQUENCE: 36

Pro Ala Arg Leu Arg Glu Leu Arg Ala Gly Pro Ala Pro Ala Arg Leu
1               5                   10                  15

Arg Glu Leu Arg Lys Asp Glu Leu
            20

<210> SEQ ID NO 37
<211> LENGTH: 24
<212> TYPE: PRT
<213> ORGANISM: Artificial Sequence
<220> FEATURE:
<223> OTHER INFORMATION: Synthetic construct, P2506

<400> SEQUENCE: 37

Pro Ala Arg Leu Arg Glu Leu Arg Pro Ala Arg Leu Arg Glu Leu Arg
1               5                   10                  15

Pro Ala Arg Leu Arg Glu Leu Arg
            20

<210> SEQ ID NO 38
<211> LENGTH: 28
<212> TYPE: PRT
<213> ORGANISM: Artificial Sequence
<220> FEATURE:
<223> OTHER INFORMATION: Syntheict construct, P2507

<400> SEQUENCE: 38

Pro Ala Arg Leu Arg Glu Leu Arg Pro Ala Arg Leu Arg Glu Leu Arg
1               5                   10                  15

Pro Ala Arg Leu Arg Glu Leu Arg Lys Asp Glu Leu
            20                  25

<210> SEQ ID NO 39
<211> LENGTH: 32
<212> TYPE: PRT
<213> ORGANISM: Artificial Sequence
<220> FEATURE:
<223> OTHER INFORMATION: Synthetic construct, P2508

<400> SEQUENCE: 39

Pro Ala Arg Leu Arg Glu Leu Arg Ala Gly Pro Ala Pro Ala Arg Leu
1               5                   10                  15

Arg Glu Leu Arg Ala Gly Pro Ala Pro Ala Arg Leu Arg Glu Leu Arg
            20                  25                  30

<210> SEQ ID NO 40
<211> LENGTH: 36
<212> TYPE: PRT
<213> ORGANISM: Artificial Sequence
<220> FEATURE:
<223> OTHER INFORMATION: Synthetic construct, P2509

<400> SEQUENCE: 40

Pro Ala Arg Leu Arg Glu Leu Arg Ala Gly Pro Ala Pro Ala Arg Leu
1               5                   10                  15

Arg Glu Leu Arg Ala Gly Pro Ala Pro Ala Arg Leu Arg Glu Leu Arg
            20                  25                  30

Lys Asp Glu Leu
        35

<210> SEQ ID NO 41
<211> LENGTH: 6
<212> TYPE: PRT
<213> ORGANISM: Artificial Sequence
<220> FEATURE:
<223> OTHER INFORMATION: Synthetic construct, GSGGSG linker

<400> SEQUENCE: 41

Gly Ser Gly Gly Ser Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic construct, zeolin linker

<400> SEQUENCE: 42

Gly Gly Gly Gly Ser
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic construct, Zera fusion -continued

<400> SEQUENCE: 43

Gly Gly Gly Gly Gly
1 5

<210> SEQ ID NO 44
<211> LENGTH: 5
<212> TYPE: PRT
<213> ORGANISM: Artificial Sequence
<220> FEATURE:
<223> OTHER INFORMATION: Synthetic construct, VPGVG

<400> SEQUENCE: 44

Val Pro Gly Val Gly
1 5

<210> SEQ ID NO 45
<211> LENGTH: 18
<212> TYPE: DNA
<213> ORGANISM: Artificial Sequence
<220> FEATURE:
<223> OTHER INFORMATION: Synthetic construct, GSSGGSG coding seq

<400> SEQUENCE: 45
ggcagcggcg gcagcggc 18

<210> SEQ ID NO 46
<211> LENGTH: 15
<212> TYPE: DNA
<213> ORGANISM: Artificial Sequence
<220> FEATURE:
<223> OTHER INFORMATION: Synthetic construct, zeolin linker coding seq

<400> SEQUENCE: 46
ggcggcggcg gcagc 15

<210> SEQ ID NO 47
<211> LENGTH: 15
<212> TYPE: DNA
<213> ORGANISM: Artificial Sequence
<220> FEATURE:
<223> OTHER INFORMATION: Synthetic construct, Zera linker coding seq

<400> SEQUENCE: 47
ggcggcggcg gcggc 15

<210> SEQ ID NO 48
<211> LENGTH: 72
<212> TYPE: DNA
<213> ORGANISM: Artificial Sequence
<220> FEATURE:
<223> OTHER INFORMATION: Synthetic construct, BAAS coding seq

<400> SEQUENCE: 48
atggcgaaca aacatttgtc cctctccctc ttcctcgtcc tccttggcct gtcggccagc 60
ttggcctccg gg 72

<210> SEQ ID NO 49
<211> LENGTH: 72
<212> TYPE: DNA
<213> ORGANISM: Artificial Sequence
<220> FEATURE:
<223> OTHER INFORMATION: Synthetic construct, OsGluB4sp coding seq

<400> SEQUENCE: 49

-continued

```
atggccacca tcgctttctc ccgcttgtcc atctacttct gcgtgcttct cctgtgccac     60

ggctccatgg cc                                                         72


<210> SEQ ID NO 50
<211> LENGTH: 93
<212> TYPE: DNA
<213> ORGANISM: Artificial Sequence
<220> FEATURE:
<223> OTHER INFORMATION: Synthetic construct, PR1 coding seq

<400> SEQUENCE: 50

atgggcttcg tgctcttctc ccagctgcct tccttccttc ttgtctccac cctgctcttg     60

ttcctcgtga tctcccactc ctgccgcgcc cag                                  93


<210> SEQ ID NO 51
<211> LENGTH: 12
<212> TYPE: DNA
<213> ORGANISM: Artificial Sequence
<220> FEATURE:
<223> OTHER INFORMATION: Synthetic construct, KDEL coding seq

<400> SEQUENCE: 51

aaggacgagc tg                                                         12


<210> SEQ ID NO 52
<211> LENGTH: 12
<212> TYPE: DNA
<213> ORGANISM: Artificial Sequence
<220> FEATURE:
<223> OTHER INFORMATION: Synthetic construct, HDEL coding seq

<400> SEQUENCE: 52

cacgacgagc tg                                                         12


<210> SEQ ID NO 53
<211> LENGTH: 18
<212> TYPE: DNA
<213> ORGANISM: Artificial Sequence
<220> FEATURE:
<223> OTHER INFORMATION: Synthetic construct, SEKDEL coding seq

<400> SEQUENCE: 53

tccgagaagg acgagctg                                                   18


<210> SEQ ID NO 54
<211> LENGTH: 129
<212> TYPE: DNA
<213> ORGANISM: Artificial Sequence
<220> FEATURE:
<223> OTHER INFORMATION: Synthetic construct, HvAle coding seq

<400> SEQUENCE: 54

atggcccacg cccgcgtcct cctcctggcg ctcgccgtcc tggccaccgc cgccgtcgcc     60

gtcgcctcct cctcctcctt cgccgactcc aacccgatcc gcccggtgac cgaccgcgcc    120

gcctccacc                                                            129


<210> SEQ ID NO 55
<211> LENGTH: 24
<212> TYPE: DNA
<213> ORGANISM: Artificial Sequence
<220> FEATURE:
<223> OTHER INFORMATION: Synthetic construct, HvVSD coding seq

<400> SEQUENCE: 55
```

gacgagctga aggccgaggc caag 24

<210> SEQ ID NO 56
<211> LENGTH: 108
<212> TYPE: DNA
<213> ORGANISM: Artificial Sequence
<220> FEATURE:
<223> OTHER INFORMATION: Synthetic construct, P2509 coding seq

<400> SEQUENCE: 56
ccggccaggc tgagggagct gagggccggc ccggccccgg ccaggctgag ggagctgagg 60
gccggcccgg ccccggccag gctgagggag ctgaggaagg acgagctg 108

<210> SEQ ID NO 57
<211> LENGTH: 223
<212> TYPE: PRT
<213> ORGANISM: Artificial Sequence
<220> FEATURE:
<223> OTHER INFORMATION: Synthetic construct, ZmZ27

<400> SEQUENCE: 57

Met Arg Val Leu Leu Val Ala Leu Ala Leu Leu Ala Leu Ala Ala Ser
1 5 10 15

Ala Thr Ser Thr His Thr Ser Gly Gly Cys Gly Cys Gln Pro Pro Pro
20 25 30

Pro Val His Leu Pro Pro Pro Val His Leu Pro Pro Pro Val His Leu
35 40 45

Pro Pro Pro Val His Leu Pro Pro Pro Val His Leu Pro Pro Pro Val
50 55 60

His Leu Pro Pro Pro Val His Val Pro Pro Pro Val His Leu Pro Pro
65 70 75 80

Pro Pro Cys His Tyr Pro Thr Gln Pro Pro Arg Pro Gln Pro His Pro
85 90 95

Gln Pro His Pro Cys Pro Cys Gln Gln Pro His Pro Ser Pro Cys Gln
100 105 110

Leu Gln Gly Thr Cys Gly Val Gly Ser Thr Pro Ile Leu Gly Gln Cys
115 120 125

Val Glu Phe Leu Arg His Gln Cys Ser Pro Thr Ala Thr Pro Tyr Cys
130 135 140

Ser Pro Gln Cys Gln Ser Leu Arg Gln Gln Cys Cys Gln Gln Leu Arg
145 150 155 160

Gln Val Glu Pro Gln His Arg Tyr Gln Ala Ile Phe Gly Leu Val Leu
165 170 175

Gln Ser Ile Leu Gln Gln Gln Pro Gln Ser Gly Gln Val Ala Gly Leu
180 185 190

Leu Ala Ala Gln Ile Ala Gln Gln Leu Thr Ala Met Cys Gly Leu Gln
195 200 205

Gln Pro Thr Pro Cys Pro Tyr Ala Ala Ala Gly Gly Val Pro His
210 215 220

<210> SEQ ID NO 58
<211> LENGTH: 672
<212> TYPE: DNA
<213> ORGANISM: Artificial Sequence
<220> FEATURE:
<223> OTHER INFORMATION: Synthetic construct, ZmZ27 coding seq

<400> SEQUENCE: 58

-continued

```
atgagggtgt tgctcgttgc cctcgctctc ctggctctcg ctgcgagcgc cacctccacg     60

catacaagcg gcggctgcgg ctgccagcca ccgccgccgg ttcatctacc gccgccggtg    120

catctgccac ctccggttca cctgccacct ccggtgcatc tcccaccgcc ggtccacctg    180

ccgccgccgg tccacctgcc accgccggtc catgtgccgc cgccggttca tctgccgccg    240

ccaccatgcc actaccctac tcaaccgccc cggcctcagc ctcatcccca gccacaccca    300

tgcccgtgcc aacagccgca tccaagcccg tgccagctgc agggaacctg cggcgttggc    360

agcaccccga tcctgggcca gtgcgtcgag ttcctgaggc atcagtgcag cccgacggcg    420

acgccctact gctcgcctca gtgccagtcg ttgcggcagc agtgttgcca gcagctcagg    480

caggtggagc cgcagcaccg gtaccaggcg atcttcggct tggtcctcca gtccatcctg    540

cagcagcagc cgcaaagcgg ccaggtcgcg gggctgttgg cggcgcagat agcgcagcaa    600

ctgacggcga tgtgcggcct gcagcagccg actccatgcc cctacgctgc tgccggcggt    660

gtcccccact ga                                                         672
```

<210> SEQ ID NO 59
<211> LENGTH: 89
<212> TYPE: PRT
<213> ORGANISM: Artificial Sequence
<220> FEATURE:
<223> OTHER INFORMATION: Synthetic construct, ZmZ27_AA24-112

<400> SEQUENCE: 59

```
Gly Gly Cys Gly Cys Gln Pro Pro Pro Pro Val His Leu Pro Pro Pro
1               5                   10                  15

Val His Leu Pro Pro Pro Val His Leu Pro Pro Pro Val His Leu Pro
            20                  25                  30

Pro Pro Val His Leu Pro Pro Pro Val His Leu Pro Pro Pro Val His
        35                  40                  45

Val Pro Pro Pro Val His Leu Pro Pro Pro Pro Cys His Tyr Pro Thr
    50                  55                  60

Gln Pro Pro Arg Pro Gln Pro His Pro Gln Pro His Pro Cys Pro Cys
65                  70                  75                  80

Gln Gln Pro His Pro Ser Pro Cys Gln
                85
```

<210> SEQ ID NO 60
<211> LENGTH: 267
<212> TYPE: DNA
<213> ORGANISM: Artificial Sequence
<220> FEATURE:
<223> OTHER INFORMATION: Synthetic construct, ZmZ27_AA24-112 coding seq

<400> SEQUENCE: 60

```
ggcggctgcg gctgccagcc accgccgccg gttcatctac cgccgccggt gcatctgcca     60

cctccggttc acctgccacc tccggtgcat ctcccaccgc cggtccacct gccgccgccg    120

gtccacctgc caccgccggt ccatgtgccg ccgccggttc atctgccgcc gccaccatgc    180

cactacccta ctcaaccgcc ccggcctcag cctcatcccc agccacaccc atgcccgtgc    240

caacagccgc atccaagccc gtgccag                                        267
```

<210> SEQ ID NO 61
<211> LENGTH: 112
<212> TYPE: PRT
<213> ORGANISM: Artificial Sequence
<220> FEATURE:
<223> OTHER INFORMATION: Synthetic construct, Zera_AA1-112

<400> SEQUENCE: 61

Met Arg Val Leu Leu Val Ala Leu Ala Leu Leu Ala Leu Ala Ala Ser
1 5 10 15

Ala Thr Ser Thr His Thr Ser Gly Gly Cys Gly Cys Gln Pro Pro Pro
20 25 30

Pro Val His Leu Pro Pro Pro Val His Leu Pro Pro Pro Val His Leu
35 40 45

Pro Pro Pro Val His Leu Pro Pro Pro Val His Leu Pro Pro Pro Val
50 55 60

His Leu Pro Pro Pro Val His Val Pro Pro Pro Val His Leu Pro Pro
65 70 75 80

Pro Pro Cys His Tyr Pro Thr Gln Pro Pro Arg Pro Gln Pro His Pro
85 90 95

Gln Pro His Pro Cys Pro Cys Gln Gln Pro His Pro Ser Pro Cys Gln
100 105 110

<210> SEQ ID NO 62
<211> LENGTH: 336
<212> TYPE: DNA
<213> ORGANISM: Artificial Sequence
<220> FEATURE:
<223> OTHER INFORMATION: Synthetic construct, Zera coding seq

<400> SEQUENCE: 62
atgagggtgt tgctcgttgc cctcgctctc ctggctctcg ctgcgagcgc cacctccacg 60
catacaagcg gcggctgcgg ctgccagcca ccgccgccgg ttcatctacc gccgccggtg 120
catctgccac ctccggttca cctgccacct ccggtgcatc tcccaccgcc ggtccacctg 180
ccgccgccgg tccacctgcc accgccggtc catgtgccgc cgccggttca tctgccgccg 240
ccaccatgcc actaccctac tcaaccgccc cggcctcagc ctcatcccca gccacaccca 300
tgcccgtgcc aacagccgca tccaagcccg tgccag 336

<210> SEQ ID NO 63
<211> LENGTH: 450
<212> TYPE: DNA
<213> ORGANISM: Artificial Sequence
<220> FEATURE:
<223> OTHER INFORMATION: Synthetic construct, ZeraP2508 coding seq

<400> SEQUENCE: 63
atgagggtgt tgctcgttgc cctcgctctc ctggctctcg ctgcgagcgc cacctccacg 60
catacaagcg gcggctgcgg ctgccagcca ccgccgccgg ttcatctacc gccgccggtg 120
catctgccac ctccggttca cctgccacct ccggtgcatc tcccaccgcc ggtccacctg 180
ccgccgccgg tccacctgcc accgccggtc catgtgccgc cgccggttca tctgccgccg 240
ccaccatgcc actaccctac tcaaccgccc cggcctcagc ctcatcccca gccacaccca 300
tgcccgtgcc aacagccgca tccaagcccg tgccagggca gcggcggcag cggcccggcc 360
aggctgaggg agctgagggc cggcccggcc ccggccaggc tgagggagct gagggccggc 420
ccggccccgg ccaggctgag ggagctgagg 450

<210> SEQ ID NO 64
<211> LENGTH: 462
<212> TYPE: DNA
<213> ORGANISM: Artificial Sequence
<220> FEATURE:
<223> OTHER INFORMATION: Synthetic construct, ZeraP2509KDEL coding seq

<400> SEQUENCE: 64
atgagggtgt tgctcgttgc cctcgctctc ctggctctcg ctgcgagcgc cacctccacg 60
catacaagcg gcggctgcgg ctgccagcca ccgccgccgg ttcatctacc gccgccggtg 120
catctgccac ctccggttca cctgccacct ccggtgcatc tcccaccgcc ggtccacctg 180
ccgccgccgg tccacctgcc accgccggtc catgtgccgc cgccggttca tctgccgccg 240
ccaccatgcc actaccctac tcaaccgccc cggcctcagc ctcatcccca gccacaccca 300
tgcccgtgcc aacagccgca tccaagcccg tgccagggca gcggcggcag cggcccggcc 360
aggctgaggg agctgagggc cggcccggcc ccggccaggc tgagggagct gagggccggc 420
ccggccccgg ccaggctgag ggagctgagg aaggacgagc tg 462

<210> SEQ ID NO 65
<211> LENGTH: 140
<212> TYPE: PRT
<213> ORGANISM: Artificial Sequence
<220> FEATURE:
<223> OTHER INFORMATION: Synthetic construct, 28xVPGVG

<400> SEQUENCE: 65

```
Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Val Pro Gly Val Gly Val Pro
            100                 105                 110

Gly Val Gly Val Pro Gly Val Gly Val Pro Gly Val Gly Val Pro Gly
        115                 120                 125

Val Gly Val Pro Gly Val Gly Val Pro Gly Val Gly
    130                 135                 140
```

<210> SEQ ID NO 66
<211> LENGTH: 420
<212> TYPE: DNA
<213> ORGANISM: Artificial Sequence
<220> FEATURE:
<223> OTHER INFORMATION: Synthetic construct, 28xVPGVG coding seq

<400> SEQUENCE: 66
gtgccgggcg tgggcgtgcc gggcgtgggc gtgccgggcg tgggcgtgcc gggcgtgggc 60
gtgccgggcg tgggcgtgcc gggcgtgggc gtgccgggcg tgggcgtgcc gggcgtgggc 120
gtgccgggcg tgggcgtgcc gggcgtgggc gtgccgggcg tgggcgtgcc gggcgtgggc 180
gtgccgggcg tgggcgtgcc gggcgtgggc gtgccgggcg tgggcgtgcc gggcgtgggc 240
gtgccgggcg tgggcgtgcc gggcgtgggc gtgccgggcg tgggcgtgcc gggcgtgggc 300
gtgccgggcg tgggcgtgcc gggcgtgggc gtgccgggcg tgggcgtgcc gggcgtgggc 360
gtgccgggcg tgggcgtgcc gggcgtgggc gtgccgggcg tgggcgtgcc gggcgtgggc 420

<210> SEQ ID NO 67
<211> LENGTH: 75
<212> TYPE: PRT
<213> ORGANISM: Artificial Sequence
<220> FEATURE:
<223> OTHER INFORMATION: Synthetic construct, HFBI

<400> SEQUENCE: 67

Ser Asn Gly Asn Gly Asn Val Cys Pro Pro Gly Leu Phe Ser Asn Pro
1 5 10 15

Gln Cys Cys Ala Thr Gln Val Leu Gly Leu Ile Gly Leu Asp Cys Lys
20 25 30

Val Pro Ser Gln Asn Val Tyr Asp Gly Thr Asp Phe Arg Asn Val Cys
35 40 45

Ala Lys Thr Gly Ala Gln Pro Leu Cys Cys Val Ala Pro Val Ala Gly
50 55 60

Gln Ala Leu Leu Cys Gln Thr Ala Val Gly Ala
65 70 75

<210> SEQ ID NO 68
<211> LENGTH: 225
<212> TYPE: DNA
<213> ORGANISM: Artificial Sequence
<220> FEATURE:
<223> OTHER INFORMATION: Synthetic construct, HFBI coding seq

<400> SEQUENCE: 68
agcaacggca acggcaacgt gtgcccgccg ggcctgttca gcaacccgca gtgctgcgcc 60
acccaggtgc tgggcctgat cggcctggac tgcaaggtgc cgagccagaa cgtgtacgac 120
ggcaccgact tcaggaacgt gtgcgccaag accggcgccc agccgctgtg ctgcgtggcc 180
ccggtggccg gccaggccct gctgtgccag accgccgtgg gcgcc 225

<210> SEQ ID NO 69
<211> LENGTH: 11826
<212> TYPE: DNA
<213> ORGANISM: Artificial Sequence
<220> FEATURE:
<223> OTHER INFORMATION: Synthetic construct, pAG4305

<400> SEQUENCE: 69
ctaggtcccc gaatttcccc gatcgttcaa acatttggca ataaagtttc ttaagattga 60
atcctgttgc cggtcttgcg atgattatca tataatttct gttgaattac gttaagcatg 120
taataattaa catgtaatgc atgacgttat ttatgagatg ggtttttatg attagagtcc 180
cgcaattata catttaatac gcgatagaaa acaaaatata gcgcgcaaac taggataaat 240
tatcgcgcgc ggtgtcatct atgttactag atcgggaatt ggaattcctg cagtgcagcg 300
tgacccggtc gtgcccctct ctagagataa tgagcattgc atgtctaagt tataaaaaat 360
taccacatat ttttttgtc acacttgttt gaagtgcagt ttatctatct ttatacatat 420
atttaaactt tactctacga ataatataat ctatagtact acaataatat cagtgtttta 480
gagaatcata taaatgaaca gttagacatg gtctaaagga caattgagta ttttgacaac 540
aggactctac agttttatct ttttagtgtg catgtgttct cctttttttt tgcaaatagc 600
ttcacctata taatacttca tccattttat tagtacatcc atttagggtt tagggttaat 660
ggtttttata gactaatttt tttagtacat ctattttatt ctattttagc ctctaaatta 720
agaaaactaa aactctattt tagttttttt atttaataat ttagatataa aatagaataa 780

```
aataaagtga ctaaaaatta aacaaatacc ctttaagaaa ttaaaaaaac taaggaaaca    840
tttttcttgt ttcgagtaga taatgccagc ctgttaaacg ccgtcgacga gtctaacgga    900
caccaaccag cgaaccagca gcgtcgcgtc gggccaagcg aagcagacgg cacggcatct    960
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc cccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
ttttttgtct tggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
tttcactgcg tgatgtgatt gagagtgata aatcgactct gctcggagag gccgttgcca   2520
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
gtatcccgat ggatgccgcc gagcgtaact ataaagatcc taaccacaag ccggagctgg   2700
tttttgcgct gacgcctttc cttgcgatga acgcgtttcg tgaattttcc gagattgtct   2760
ccctactcca gccggtcgca ggtgcacatc cggcgattgc tcacttttta caacagcctg   2820
atgccgaacg tttaagcgaa ctgttcgcca gcctgttgaa tatgcagggt gaagaaaaat   2880
cccgcgcgct ggcgatttta aaatcggccc tcgatagcca gcagggtgaa ccgtggcaaa   2940
cgattcgttt aatttctgaa ttttacccgg aagacagcgg tctgttctcc ccgctattgc   3000
tgaatgtggt gaaattgaac cctggcgaag cgatgttcct gttcgctgaa acaccgcacg   3060
cttacctgca aggcgtggcg ctggaagtga tggcaaactc cgataacgtg ctgcgtgcgg   3120
```

-continued

```
gtctgacgcc taaatacatt gatattccgg aactggttgc caatgtgaaa ttcgaagcca   3180
aaccggctaa ccagttgttg acccagccgg tgaaacaagg tgcagaactg gacttcccga   3240
ttccagtgga tgattttgcc ttctcgctgc atgaccttag tgataaagaa accaccatta   3300
gccagcagag tgccgccatt ttgttctgcg tcgaaggcga tgcaacgttg tggaaaggtt   3360
ctcagcagtt acagcttaaa ccgggtgaat cagcgtttat tgccgccaac gaatcaccgg   3420
tgactgtcaa aggccacggc cgtttagcgc gtgtttacaa caagctgtaa gagcttactg   3480
aaaaaattaa catctcttgc taagctggga gctctagatc cccgaatttc cccgatcgtt   3540
caaacatttg gcaataaagt ttcttaagat tgaatcctgt tgccggtctt gcgatgatta   3600
tcatataatt tctgttgaat tacgttaagc atgtaataat taacatgtaa tgcatgacgt   3660
tatttatgag atgggttttt atgattagag tcccgcaatt atacatttaa tacgcgatag   3720
aaaacaaaat atagcgcgca aactaggata aattatcgcg cgcggtgtca tctatgttac   3780
tagatcggga attggcgagc tcgaattaat tcagtacatt aaaaacgtcc gcaatgtgtt   3840
attaagttgt ctaagcgtca atttgtttac accacaatat atcctgccac cagccagcca   3900
acagctcccc gaccggcagc tcggcacaaa atcaccactc gatacaggca gcccatcagt   3960
ccgggacggc gtcagcggga gagccgttgt aaggcggcag actttgctca tgttaccgat   4020
gctattcgga agaacggcaa ctaagctgcc gggtttgaaa cacggatgat ctcgcggagg   4080
gtagcatgtt gattgtaacg atgacagagc gttgctgcct gtgatcaaat atcatctccc   4140
tcgcagagat ccgaattatc agccttctta ttcatttctc gcttaaccgt gacaggctgt   4200
cgatcttgag aactatgccg acataatagg aaatcgctgg ataaagccgc tgaggaagct   4260
gagtggcgct atttctttag aagtgaacgt tgacgatcgt cgaccgtacc ccgatgaatt   4320
aattcggacg tacgttctga acacagctgg atacttactt gggcgattgt catacatgac   4380
atcaacaatg tacccgtttg tgtaaccgtc tcttggaggt tcgtatgaca ctagtggttc   4440
ccctcagctt gcgactagat gttgaggcct aacattttat tagagagcag gctagttgct   4500
tagatacatg atcttcaggc cgttatctgt cagggcaagc gaaaattggc catttatgac   4560
gaccaatgcc ccgcagaagc tcccatcttt gccgccatag acgccgcgcc cccttttgg    4620
ggtgtagaac atccttttgc cagatgtgga aaagaagttc gttgtcccat tgttggcaat   4680
gacgtagtag ccggcgaaag tgcgagaccc atttgcgcta tatataagcc tacgatttcc   4740
gttgcgacta ttgtcgtaat tggatgaact attatcgtag ttgctctcag agttgtcgta   4800
atttgatgga ctattgtcgt aattgcttat ggagttgtcg tagttgcttg gagaaatgtc   4860
gtagttggat ggggagtagt catagggaag acgagcttca tccactaaaa caattggcag   4920
gtcagcaagt gcctgccccg atgccatcgc aagtacgagg cttagaacca ccttcaacag   4980
atcgcgcata gtcttcccca gctctctaac gcttgagtta agccgcgccg cgaagcggcg   5040
tcggcttgaa cgaattgtta gacattattt gccgactacc ttggtgatct cgcctttcac   5100
gtagtgaaca aattcttcca actgatctgc gcgcgaggcc aagcgatctt cttgtccaag   5160
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
```

```
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
agtcgatact tcggcgatca ccgcttccct catgatgttt aactcctgaa ttaagccgcg   5880
ccgcgaagcg gtgtcggctt gaatgaattg ttaggcgtca tcctgtgctc ccgagaacca   5940
gtaccagtac atcgctgttt cgttcgagac ttgaggtcta gttttatacg tgaacaggtc   6000
aatgccgccg agagtaaagc cacattttgc gtacaaattg caggcaggta cattgttcgt   6060
ttgtgtctct aatcgtatgc caaggagctg tctgcttagt gcccactttt tcgcaaattc   6120
gatgagactg tgcgcgactc ctttgcctcg gtgcgtgtgc gacacaacaa tgtgttcgat   6180
agaggctaga tcgttccatg ttgagttgag ttcaatcttc ccgacaagct cttggtcgat   6240
gaatgcgcca tagcaagcag agtcttcatc agagtcatca tccgagatgt aatccttccg   6300
gtaggggctc acacttctgg tagatagttc aaagccttgg tcggataggt gcacatcgaa   6360
cacttcacga acaatgaaat ggttctcagc atccaatgtt tccgccacct gctcagggat   6420
caccgaaatc ttcatatgac gcctaacgcc tggcacagcg gatcgcaaac ctggcgcggc   6480
ttttggcaca aaaggcgtga caggtttgcg aatccgttgc tgccacttgt taaccctttt   6540
gccagatttg gtaactataa tttatgttag aggcgaagtc ttgggtaaaa actggcctaa   6600
aattgctggg gatttcagga aagtaaacat caccttccgg ctcgatgtct attgtagata   6660
tatgtagtgt atctacttga tcgggggatc tgctgcctcg cgcgtttcgg tgatgacggt   6720
gaaaacctct gacacatgca gctcccggag acggtcacag cttgtctgta agcggatgcc   6780
gggagcagac aagcccgtca gggcgcgtca gcgggtgttg gcgggtgtcg gggcgcagcc   6840
atgacccagt cacgtagcga tagcggagtg tatactggct taactatgcg gcatcagagc   6900
agattgtact gagagtgcac catatgcggt gtgaaatacc gcacagatgc gtaaggagaa   6960
aataccgcat caggcgctct tccgcttcct cgctcactga ctcgctgcgc tcggtcgttc   7020
ggctgcggcg agcggtatca gctcactcaa aggcggtaat acggttatcc acagaatcag   7080
gggataacgc aggaaagaac atgtgagcaa aaggccagca aaaggccagg aaccgtaaaa   7140
aggccgcgtt gctggcgttt ttccataggc tccgcccccc tgacgagcat cacaaaaatc   7200
gacgctcaag tcagaggtgg cgaaacccga caggactata aagataccag gcgtttcccc   7260
ctggaagctc cctcgtgcgc tctcctgttc cgaccctgcc gcttaccgga tacctgtccg   7320
cctttctccc ttcgggaagc gtggcgcttt ctcatagctc acgctgtagg tatctcagtt   7380
cggtgtaggt cgttcgctcc aagctgggct gtgtgcacga accccccgtt cagcccgacc   7440
gctgcgcctt atccggtaac tatcgtcttg agtccaaccc ggtaagacac gacttatcgc   7500
cactggcagc agccactggt aacaggatta gcagagcgag gtatgtaggc ggtgctacag   7560
agttcttgaa gtggtggcct aactacggct acactagaag gacagtattt ggtatctgcg   7620
ctctgctgaa gccagttacc ttcggaaaaa gagttggtag ctcttgatcc ggcaaacaaa   7680
ccaccgctgg tagcggtggt ttttttgttt gcaagcagca gattacgcgc agaaaaaaag   7740
gatctcaaga agatcctttg atcttttcta cggggtctga cgctcagtgg aacgaaaact   7800
cacgttaagg gattttggtc atgagattat caaaaaggat cttcacctag atccttttaa   7860
```

```
attaaaaatg aagttttaaa tcaatctaaa gtatatatga gtaaacttgg tctgacagtt   7920
accaatgctt aatcagtgag gcacctatct cagcgatctg tctatttcgt tcatccatag   7980
ttgcctgact ccccgtcgtg tagataacta cgatacggga gggcttacca tctggcccca   8040
gtgctgcaat gataccgcga gacccacgct caccggctcc agatttatca gcaataaacc   8100
agccagccgg aagggccgag cgcagaagtg gtcctgcaac tttatccgcc tccatccagt   8160
ctattaattg ttgccgggaa gctagagtaa gtagttcgcc agttaatagt ttgcgcaacg   8220
ttgttgccat tgctgcaggg gggggggggg gggggttcca ttgttcattc cacggacaaa   8280
aacagagaaa ggaaacgaca gaggccaaaa agctcgcttt cagcacctgt cgtttccttt   8340
cttttcagag ggtattttaa ataaaaacat taagttatga cgaagaagaa cggaaacgcc   8400
ttaaaccgga aaattttcat aaatagcgaa aacccgcgag gtcgccgccc cgtaacctgt   8460
cggatcaccg gaaaggaccc gtaaagtgat aatgattatc atctacatat cacaacgtgc   8520
gtggaggcca tcaaaccacg tcaaataatc aattatgacg caggtatcgt attaattgat   8580
ctgcatcaac ttaacgtaaa aacaacttca gacaatacaa atcagcgaca ctgaatacgg   8640
ggcaacctca tgtccccccc cccccccccc tgcaggcatc gtggtgtcac gctcgtcgtt   8700
tggtatggct tcattcagct ccggttccca acgatcaagg cgagttacat gatcccccat   8760
gttgtgcaaa aaagcggtta gctccttcgg tcctccgatc gttgtcagaa gtaagttggc   8820
cgcagtgtta tcactcatgg ttatggcagc actgcataat tctcttactg tcatgccatc   8880
cgtaagatgc ttttctgtga ctggtgagta ctcaaccaag tcattctgag aatagtgtat   8940
gcggcgaccg agttgctctt gcccggcgtc aacacgggat aataccgcgc cacatagcag   9000
aactttaaaa gtgctcatca ttggaaaacg ttcttcgggg cgaaaactct caaggatctt   9060
accgctgttg agatccagtt cgatgtaacc cactcgtgca cccaactgat cttcagcatc   9120
ttttactttc accagcgttt ctgggtgagc aaaaacagga aggcaaaatg ccgcaaaaaa   9180
gggaataagg gcgacacgga aatgttgaat actcatactc ttcctttttc aatattattg   9240
aagcatttat cagggttatt gtctcatgag cggatacata tttgaatgta tttagaaaaa   9300
taaacaaata ggggttccgc gcacatttcc ccgaaaagtg ccacctgacg tctaagaaac   9360
cattattatc atgacattaa cctataaaaa taggcgtatc acgaggccct ttcgtcttca   9420
agaattggtc gacgatcttg ctgcgttcgg atattttcgt ggagttcccg ccacagaccc   9480
ggattgaagg cgagatccag caactcgcgc cagatcatcc tgtgacggaa ctttggcgcg   9540
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
```

```
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc ttttttttt   10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac cttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ggctgccaga gcgtgagcga gatgctgagg ttctacaccg  11700
acgaggtgct gccgagggcc atgcagggcg gcggcagcgg cggcggcagc aaggccatgg  11760
gcgagttcga catcttcatc aactacatcg aggagtacct gctgatgagg aaggacgagc  11820
tgtaac                                                              11826
```

```
<210> SEQ ID NO 70
<211> LENGTH: 11772
<212> TYPE: DNA
<213> ORGANISM: Artificial Sequence
<220> FEATURE:
<223> OTHER INFORMATION: Synthetic construct, pAG4306

<400> SEQUENCE: 70

ctaggtcccc gaatttcccc gatcgttcaa acatttggca ataaagtttc ttaagattga     60
atcctgttgc cggtcttgcg atgattatca tataatttct gttgaattac gttaagcatg    120
taataattaa catgtaatgc atgacgttat ttatgagatg ggtttttatg attagagtcc    180
cgcaattata catttaatac gcgatagaaa acaaaatata gcgcgcaaac taggataaat    240
tatcgcgcgc ggtgtcatct atgttactag atcgggaatt ggaattcctg cagtgcagcg    300
tgacccggtc gtgcccctct ctagagataa tgagcattgc atgtctaagt tataaaaaat    360
taccacatat ttttttgtc acacttgttt gaagtgcagt ttatctatct ttatacatat    420
```

-continued

```
atttaaactt tactctacga ataatataat ctatagtact acaataatat cagtgtttta    480
gagaatcata taaatgaaca gttagacatg gtctaaagga caattgagta ttttgacaac    540
aggactctac agttttatct ttttagtgtg catgtgttct cctttttttt tgcaaatagc    600
ttcacctata taatacttca tccattttat tagtacatcc atttagggtt tagggttaat    660
ggtttttata gactaatttt tttagtacat ctattttatt ctattttagc ctctaaatta    720
agaaaactaa aactctattt tagttttttt atttaataat ttagatataa aatagaataa    780
aataaagtga ctaaaaatta aacaaatacc ctttaagaaa ttaaaaaaac taaggaaaca    840
tttttcttgt ttcgagtaga taatgccagc ctgttaaacg ccgtcgacga gtctaacgga    900
caccaaccag cgaaccagca gcgtcgcgtc gggccaagcg aagcagacgg cacggcatct    960
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc cccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
cccttttcctt tatttcaata tatgccgtgc acttgtttgt cgggtcatct tttcatgctt   1620
ttttttgtct tggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
tttcactgcg tgatgtgatt gagagtgata aatcgactct gctcggagag gccgttgcca   2520
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
gtatcccgat ggatgccgcc gagcgtaact ataaagatcc taaccacaag ccggagctgg   2700
tttttgcgct gacgcctttc cttgcgatga acgcgtttcg tgaattttcc gagattgtct   2760
ccctactcca gccggtcgca ggtgcacatc cggcgattgc tcacttttta caacagcctg   2820
```

atgccgaacg tttaagcgaa ctgttcgcca gcctgttgaa tatgcagggt gaagaaaaat 2880
cccgcgcgct ggcgatttta aaatcggccc tcgatagcca gcagggtgaa ccgtggcaaa 2940
cgattcgttt aatttctgaa ttttacccgg aagacagcgg tctgttctcc ccgctattgc 3000
tgaatgtggt gaaattgaac cctggcgaag cgatgttcct gttcgctgaa acaccgcacg 3060
cttacctgca aggcgtggcg ctggaagtga tggcaaactc cgataacgtg ctgcgtgcgg 3120
gtctgacgcc taaatacatt gatattccgg aactggttgc caatgtgaaa ttcgaagcca 3180
aaccggctaa ccagttgttg acccagccgg tgaaacaagg tgcagaactg gacttcccga 3240
ttccagtgga tgattttgcc ttctcgctgc atgaccttag tgataaagaa accaccatta 3300
gccagcagag tgccgccatt ttgttctgcg tcgaaggcga tgcaacgttg tggaaaggtt 3360
ctcagcagtt acagcttaaa ccgggtgaat cagcgtttat tgccgccaac gaatcaccgg 3420
tgactgtcaa aggccacggc cgtttagcgc gtgtttacaa caagctgtaa gagcttactg 3480
aaaaaattaa catctcttgc taagctggga gctctagatc cccgaatttc cccgatcgtt 3540
caaacatttg gcaataaagt ttcttaagat tgaatcctgt tgccggtctt gcgatgatta 3600
tcatataatt tctgttgaat tacgttaagc atgtaataat taacatgtaa tgcatgacgt 3660
tatttatgag atgggttttt atgattagag tcccgcaatt atacatttaa tacgcgatag 3720
aaaacaaaat atagcgcgca aactaggata aattatcgcg cgcggtgtca tctatgttac 3780
tagatcggga attggcgagc tcgaattaat tcagtacatt aaaaacgtcc gcaatgtgtt 3840
attaagttgt ctaagcgtca atttgtttac accacaatat atcctgccac cagccagcca 3900
acagctcccc gaccggcagc tcggcacaaa atcaccactc gatacaggca gcccatcagt 3960
ccgggacggc gtcagcggga gagccgttgt aaggcggcag actttgctca tgttaccgat 4020
gctattcgga agaacggcaa ctaagctgcc gggtttgaaa cacggatgat ctcgcggagg 4080
gtagcatgtt gattgtaacg atgacagagc gttgctgcct gtgatcaaat atcatctccc 4140
tcgcagagat ccgaattatc agccttctta ttcatttctc gcttaaccgt gacaggctgt 4200
cgatcttgag aactatgccg acataatagg aaatcgctgg ataaagccgc tgaggaagct 4260
gagtggcgct atttctttag aagtgaacgt tgacgatcgt cgaccgtacc ccgatgaatt 4320
aattcggacg tacgttctga acacagctgg atacttactt gggcgattgt catacatgac 4380
atcaacaatg tacccgtttg tgtaaccgtc tcttggaggt tcgtatgaca ctagtggttc 4440
ccctcagctt gcgactagat gttgaggcct aacattttat tagagagcag gctagttgct 4500
tagatacatg atcttcaggc cgttatctgt cagggcaagc gaaaattggc catttatgac 4560
gaccaatgcc ccgcagaagc tcccatcttt gccgccatag acgccgcgcc cccttttgg 4620
ggtgtagaac atccttttgc cagatgtgga aaagaagttc gttgtcccat tgttggcaat 4680
gacgtagtag ccggcgaaag tgcgagaccc atttgcgcta tatataagcc tacgatttcc 4740
gttgcgacta ttgtcgtaat tggatgaact attatcgtag ttgctctcag agttgtcgta 4800
atttgatgga ctattgtcgt aattgcttat ggagttgtcg tagttgcttg gagaaatgtc 4860
gtagttggat ggggagtagt catagggaag acgagcttca tccactaaaa caattggcag 4920
gtcagcaagt gcctgccccg atgccatcgc aagtacgagg cttagaacca ccttcaacag 4980
atcgcgcata gtcttcccca gctctctaac gcttgagtta agccgcgccg cgaagcggcg 5040
tcggcttgaa cgaattgtta gacattattt gccgactacc ttggtgatct cgcctttcac 5100
gtagtgaaca aattcttcca actgatctgc gcgcgaggcc aagcgatctt cttgtccaag 5160

-continued

```
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
agtcgatact tcggcgatca ccgcttccct catgatgttt aactcctgaa ttaagccgcg   5880
ccgcgaagcg gtgtcggctt gaatgaattg ttaggcgtca tcctgtgctc ccgagaacca   5940
gtaccagtac atcgctgttt cgttcgagac ttgaggtcta gttttatacg tgaacaggtc   6000
aatgccgccg agagtaaagc cacattttgc gtacaaattg caggcaggta cattgttcgt   6060
ttgtgtctct aatcgtatgc caaggagctg tctgcttagt gcccactttt tcgcaaattc   6120
gatgagactg tgcgcgactc ctttgcctcg gtgcgtgtgc gacacaacaa tgtgttcgat   6180
agaggctaga tcgttccatg ttgagttgag ttcaatcttc ccgacaagct cttggtcgat   6240
gaatgcgcca tagcaagcag agtcttcatc agagtcatca tccgagatgt aatccttccg   6300
gtaggggctc acacttctgg tagatagttc aaagccttgg tcggataggt gcacatcgaa   6360
cacttcacga acaatgaaat ggttctcagc atccaatgtt tccgccacct gctcagggat   6420
caccgaaatc ttcatatgac gcctaacgcc tggcacagcg gatcgcaaac ctggcgcggc   6480
ttttggcaca aaaggcgtga caggtttgcg aatccgttgc tgccacttgt taaccctttt   6540
gccagatttg gtaactataa tttatgttag aggcgaagtc ttgggtaaaa actggcctaa   6600
aattgctggg gatttcagga aagtaaacat caccttccgg ctcgatgtct attgtagata   6660
tatgtagtgt atctacttga tcgggggatc tgctgcctcg cgcgtttcgg tgatgacggt   6720
gaaaacctct gacacatgca gctcccggag acggtcacag cttgtctgta agcggatgcc   6780
gggagcagac aagcccgtca gggcgcgtca gcgggtgttg gcgggtgtcg gggcgcagcc   6840
atgacccagt cacgtagcga tagcggagtg tatactggct taactatgcg gcatcagagc   6900
agattgtact gagagtgcac catatgcggt gtgaaatacc gcacagatgc gtaaggagaa   6960
aataccgcat caggcgctct tccgcttcct cgctcactga ctcgctgcgc tcggtcgttc   7020
ggctgcggcg agcggtatca gctcactcaa aggcggtaat acggttatcc acagaatcag   7080
gggataacgc aggaaagaac atgtgagcaa aaggccagca aaaggccagg aaccgtaaaa   7140
aggccgcgtt gctggcgttt ttccataggc tccgcccccc tgacgagcat cacaaaaatc   7200
gacgctcaag tcagaggtgg cgaaacccga caggactata aagataccag gcgtttcccc   7260
ctggaagctc cctcgtgcgc tctcctgttc cgaccctgcc gcttaccgga tacctgtccg   7320
cctttctccc ttcgggaagc gtggcgcttt ctcatagctc acgctgtagg tatctcagtt   7380
cggtgtaggt cgttcgctcc aagctgggct gtgtgcacga accccccgtt cagcccgacc   7440
gctgcgcctt atccggtaac tatcgtcttg agtccaaccc ggtaagacac gacttatcgc   7500
cactggcagc agccactggt aacaggatta gcagagcgag gtatgtaggc ggtgctacag   7560
```

agttcttgaa gtggtggcct aactacggct acactagaag gacagtattt ggtatctgcg 7620
ctctgctgaa gccagttacc ttcggaaaaa gagttggtag ctcttgatcc ggcaaacaaa 7680
ccaccgctgg tagcggtggt ttttttgttt gcaagcagca gattacgcgc agaaaaaaag 7740
gatctcaaga agatcctttg atcttttcta cggggtctga cgctcagtgg aacgaaaact 7800
cacgttaagg gattttggtc atgagattat caaaaaggat cttcacctag atccttttaa 7860
attaaaaatg aagttttaaa tcaatctaaa gtatatatga gtaaacttgg tctgacagtt 7920
accaatgctt aatcagtgag gcacctatct cagcgatctg tctatttcgt tcatccatag 7980
ttgcctgact ccccgtcgtg tagataacta cgatacggga gggcttacca tctggcccca 8040
gtgctgcaat gataccgcga gacccacgct caccggctcc agatttatca gcaataaacc 8100
agccagccgg aagggccgag cgcagaagtg gtcctgcaac tttatccgcc tccatccagt 8160
ctattaattg ttgccgggaa gctagagtaa gtagttcgcc agttaatagt ttgcgcaacg 8220
ttgttgccat tgctgcaggg gggggggggg gggggttcca ttgttcattc cacggacaaa 8280
aacagagaaa ggaaacgaca gaggccaaaa agctcgcttt cagcacctgt cgtttccttt 8340
cttttcagag ggtattttaa ataaaaacat taagttatga cgaagaagaa cggaaacgcc 8400
ttaaaccgga aaattttcat aaatagcgaa aacccgcgag gtcgccgccc cgtaacctgt 8460
cggatcaccg gaaaggaccc gtaaagtgat aatgattatc atctacatat cacaacgtgc 8520
gtggaggcca tcaaaccacg tcaaataatc aattatgacg caggtatcgt attaattgat 8580
ctgcatcaac ttaacgtaaa aacaacttca gacaatacaa atcagcgaca ctgaatacgg 8640
ggcaacctca tgtccccccc cccccccccc tgcaggcatc gtggtgtcac gctcgtcgtt 8700
tggtatggct tcattcagct ccggttccca acgatcaagg cgagttacat gatcccccat 8760
gttgtgcaaa aaagcggtta gctccttcgg tcctccgatc gttgtcagaa gtaagttggc 8820
cgcagtgtta tcactcatgg ttatggcagc actgcataat tctcttactg tcatgccatc 8880
cgtaagatgc ttttctgtga ctggtgagta ctcaaccaag tcattctgag aatagtgtat 8940
gcggcgaccg agttgctctt gcccggcgtc aacacgggat aataccgcgc cacatagcag 9000
aactttaaaa gtgctcatca ttggaaaacg ttcttcgggg cgaaaactct caaggatctt 9060
accgctgttg agatccagtt cgatgtaacc cactcgtgca cccaactgat cttcagcatc 9120
ttttactttc accagcgttt ctgggtgagc aaaaacagga aggcaaaatg ccgcaaaaaa 9180
gggaataagg gcgacacgga aatgttgaat actcatactc ttcctttttc aatattattg 9240
aagcatttat cagggttatt gtctcatgag cggatacata tttgaatgta tttagaaaaa 9300
taaacaaata ggggttccgc gcacatttcc ccgaaaagtg ccacctgacg tctaagaaac 9360
cattattatc atgacattaa cctataaaaa taggcgtatc acgaggccct ttcgtcttca 9420
agaattggtc gacgatcttg ctgcgttcgg atattttcgt ggagttcccg ccacagaccc 9480
ggattgaagg cgagatccag caactcgcgc cagatcatcc tgtgacggaa ctttggcgcg 9540
tgatgactgg ccaggacgtc ggccgaaaga gcgacaagca gatcacgctt ttcgacagcg 9600
tcggatttgc gatcgaggat ttttcggcgc tgcgctacgt ccgcgaccgc gttgagggat 9660
caagccacag cagcccactc gaccttctag ccgacccaga cgagccaagg gatctttttg 9720
gaatgctgct ccgtcgtcag gctttccgac gtttgggtgg ttgaacagaa gtcattatcg 9780
cacggaatgc caagcactcc cgaggggaac cctgtggttg gcatgcacat acaaatggac 9840
gaacggataa accttttcac gccctttttaa atatccgatt attctaataa acgctctttt 9900

```
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc tttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac ctttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ccggccaggc tgagggagct gagggccggc ccggccccgg  11700
ccaggctgag ggagctgagg gccggcccgg ccccggccag gctgagggag ctgaggaagg  11760
acgagctgta ac                                                      11772
```

<210> SEQ ID NO 71
<211> LENGTH: 12069
<212> TYPE: DNA
<213> ORGANISM: Artificial Sequence
<220> FEATURE:
<223> OTHER INFORMATION: Synthetic construct, pAG4308

<400> SEQUENCE: 71

```
ctaggtcccc gaatttcccc gatcgttcaa acatttggca ataaagtttc ttaagattga     60
atcctgttgc cggtcttgcg atgattatca tataatttct gttgaattac gttaagcatg    120
taataattaa catgtaatgc atgacgttat ttatgagatg ggtttttatg attagagtcc    180
```

-continued

```
cgcaattata catttaatac gcgatagaaa acaaaatata gcgcgcaaac taggataaat    240
tatcgcgcgc ggtgtcatct atgttactag atcgggaatt ggaattcctg cagtgcagcg    300
tgacccggtc gtgcccctct ctagagataa tgagcattgc atgtctaagt tataaaaaat    360
taccacatat ttttttgtc acacttgttt gaagtgcagt ttatctatct ttatacatat    420
atttaaactt tactctacga ataatataat ctatagtact acaataatat cagtgtttta    480
gagaatcata taaatgaaca gttagacatg gtctaaagga caattgagta ttttgacaac    540
aggactctac agttttatct ttttagtgtg catgtgttct ccttttttt tgcaaatagc    600
ttcacctata taatacttca tccattttat tagtacatcc atttagggtt tagggttaat    660
ggtttttata gactaatttt tttagtacat ctattttatt ctattttagc ctctaaatta    720
agaaaactaa aactctattt tagttttttt atttaataat ttagatataa aatagaataa    780
aataaagtga ctaaaaatta aacaaatacc ctttaagaaa ttaaaaaaac taaggaaaca    840
tttttcttgt ttcgagtaga taatgccagc ctgttaaacg ccgtcgacga gtctaacgga    900
caccaaccag cgaaccagca gcgtcgcgtc gggccaagcg aagcagacgg cacggcatct    960
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc ccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
tttttgtct tggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
tttcactgcg tgatgtgatt gagagtgata aatcgactct gctcggagag gccgttgcca   2520
```

```
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
gtatcccgat ggatgccgcc gagcgtaact ataaagatcc taaccacaag ccggagctgg   2700
tttttgcgct gacgcctttc cttgcgatga acgcgtttcg tgaattttcc gagattgtct   2760
ccctactcca gccggtcgca ggtgcacatc cggcgattgc tcacttttta caacagcctg   2820
atgccgaacg tttaagcgaa ctgttcgcca gcctgttgaa tatgcagggt gaagaaaaat   2880
cccgcgcgct ggcgatttta aaatcggccc tcgatagcca gcagggtgaa ccgtggcaaa   2940
cgattcgttt aatttctgaa ttttacccgg aagacagcgg tctgttctcc ccgctattgc   3000
tgaatgtggt gaaattgaac cctggcgaag cgatgttcct gttcgctgaa acaccgcacg   3060
cttacctgca aggcgtggcg ctggaagtga tggcaaactc cgataacgtg ctgcgtgcgg   3120
gtctgacgcc taaatacatt gatattccgg aactggttgc caatgtgaaa ttcgaagcca   3180
aaccggctaa ccagttgttg acccagccgg tgaaacaagg tgcagaactg gacttcccga   3240
ttccagtgga tgattttgcc ttctcgctgc atgaccttag tgataaagaa accaccatta   3300
gccagcagag tgccgccatt ttgttctgcg tcgaaggcga tgcaacgttg tggaaaggtt   3360
ctcagcagtt acagcttaaa ccgggtgaat cagcgtttat tgccgccaac gaatcaccgg   3420
tgactgtcaa aggccacggc cgtttagcgc gtgtttacaa caagctgtaa gagcttactg   3480
aaaaaattaa catctcttgc taagctggga gctctagatc cccgaatttc cccgatcgtt   3540
caaacatttg gcaataaagt ttcttaagat tgaatcctgt tgccggtctt gcgatgatta   3600
tcatataatt tctgttgaat tacgttaagc atgtaataat taacatgtaa tgcatgacgt   3660
tatttatgag atgggttttt atgattagag tcccgcaatt atacatttaa tacgcgatag   3720
aaaacaaaat atagcgcgca aactaggata aattatcgcg cgcggtgtca tctatgttac   3780
tagatcggga attggcgagc tcgaattaat tcagtacatt aaaaacgtcc gcaatgtgtt   3840
attaagttgt ctaagcgtca atttgtttac accacaatat atcctgccac cagccagcca   3900
acagctcccc gaccggcagc tcggcacaaa atcaccactc gatacaggca gcccatcagt   3960
ccgggacggc gtcagcggga gagccgttgt aaggcggcag actttgctca tgttaccgat   4020
gctattcgga agaacggcaa ctaagctgcc gggtttgaaa cacggatgat ctcgcggagg   4080
gtagcatgtt gattgtaacg atgacagagc gttgctgcct gtgatcaaat atcatctccc   4140
tcgcagagat ccgaattatc agccttctta ttcatttctc gcttaaccgt gacaggctgt   4200
cgatcttgag aactatgccg acataatagg aaatcgctgg ataaagccgc tgaggaagct   4260
gagtggcgct atttctttag aagtgaacgt tgacgatcgt cgaccgtacc ccgatgaatt   4320
aattcggacg tacgttctga acacagctgg atacttactt gggcgattgt catacatgac   4380
atcaacaatg tacccgtttg tgtaaccgtc tcttggaggt tcgtatgaca ctagtggttc   4440
ccctcagctt gcgactagat gttgaggcct aacattttat tagagagcag gctagttgct   4500
tagatacatg atcttcaggc cgttatctgt cagggcaagc gaaaattggc catttatgac   4560
gaccaatgcc ccgcagaagc tcccatcttt gccgccatag acgccgcgcc cccttttgg    4620
ggtgtagaac atccttttgc cagatgtgga aaagaagttc gttgtcccat tgttggcaat   4680
gacgtagtag ccggcgaaag tgcgagaccc atttgcgcta tatataagcc tacgatttcc   4740
gttgcgacta ttgtcgtaat tggatgaact attatcgtag ttgctctcag agttgtcgta   4800
atttgatgga ctattgtcgt aattgcttat ggagttgtcg tagttgcttg gagaaatgtc   4860
gtagttggat ggggagtagt catagggaag acgagcttca tccactaaaa caattggcag   4920
```

-continued

```
gtcagcaagt gcctgccccg atgccatcgc aagtacgagg cttagaacca ccttcaacag   4980
atcgcgcata gtcttcccca gctctctaac gcttgagtta agccgcgccg cgaagcggcg   5040
tcggcttgaa cgaattgtta gacattattt gccgactacc ttggtgatct cgcctttcac   5100
gtagtgaaca aattcttcca actgatctgc gcgcgaggcc aagcgatctt cttgtccaag   5160
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
agtcgatact tcggcgatca ccgcttccct catgatgttt aactcctgaa ttaagccgcg   5880
ccgcgaagcg gtgtcggctt gaatgaattg ttaggcgtca tcctgtgctc ccgagaacca   5940
gtaccagtac atcgctgttt cgttcgagac ttgaggtcta gttttatacg tgaacaggtc   6000
aatgccgccg agagtaaagc cacattttgc gtacaaattg caggcaggta cattgttcgt   6060
ttgtgtctct aatcgtatgc caaggagctg tctgcttagt gcccactttt tcgcaaattc   6120
gatgagactg tgcgcgactc ctttgcctcg gtgcgtgtgc gacacaacaa tgtgttcgat   6180
agaggctaga tcgttccatg ttgagttgag ttcaatcttc ccgacaagct cttggtcgat   6240
gaatgcgcca tagcaagcag agtcttcatc agagtcatca tccgagatgt aatccttccg   6300
gtaggggctc acacttctgg tagatagttc aaagccttgg tcggataggt gcacatcgaa   6360
cacttcacga acaatgaaat ggttctcagc atccaatgtt tccgccacct gctcagggat   6420
caccgaaatc ttcatatgac gcctaacgcc tggcacagcg gatcgcaaac ctggcgcggc   6480
ttttggcaca aaaggcgtga caggtttgcg aatccgttgc tgccacttgt taaccctttt   6540
gccagatttg gtaactataa tttatgttag aggcgaagtc ttgggtaaaa actggcctaa   6600
aattgctggg gatttcagga aagtaaacat caccttccgg ctcgatgtct attgtagata   6660
tatgtagtgt atctacttga tcgggggatc tgctgcctcg cgcgtttcgg tgatgacggt   6720
gaaaacctct gacacatgca gctcccggag acggtcacag cttgtctgta agcggatgcc   6780
gggagcagac aagcccgtca gggcgcgtca gcgggtgttg gcgggtgtcg gggcgcagcc   6840
atgacccagt cacgtagcga tagcggagtg tatactggct taactatgcg gcatcagagc   6900
agattgtact gagagtgcac catatgcggt gtgaaatacc gcacagatgc gtaaggagaa   6960
aataccgcat caggcgctct tccgcttcct cgctcactga ctcgctgcgc tcggtcgttc   7020
ggctgcggcg agcggtatca gctcactcaa aggcggtaat acggttatcc acagaatcag   7080
gggataacgc aggaaagaac atgtgagcaa aaggccagca aaaggccagg aaccgtaaaa   7140
aggccgcgtt gctggcgttt ttccataggc tccgcccccc tgacgagcat cacaaaaatc   7200
gacgctcaag tcagaggtgg cgaaacccga caggactata aagataccag gcgtttcccc   7260
```

-continued

```
ctggaagctc cctcgtgcgc tctcctgttc cgaccctgcc gcttaccgga tacctgtccg   7320
cctttctccc ttcgggaagc gtggcgcttt ctcatagctc acgctgtagg tatctcagtt   7380
cggtgtaggt cgttcgctcc aagctgggct gtgtgcacga accccccgtt cagcccgacc   7440
gctgcgcctt atccggtaac tatcgtcttg agtccaaccc ggtaagacac gacttatcgc   7500
cactggcagc agccactggt aacaggatta gcagagcgag gtatgtaggc ggtgctacag   7560
agttcttgaa gtggtggcct aactacggct acactagaag gacagtattt ggtatctgcg   7620
ctctgctgaa gccagttacc ttcggaaaaa gagttggtag ctcttgatcc ggcaaacaaa   7680
ccaccgctgg tagcggtggt ttttttgttt gcaagcagca gattacgcgc agaaaaaaag   7740
gatctcaaga agatcctttg atcttttcta cggggtctga cgctcagtgg aacgaaaact   7800
cacgttaagg gattttggtc atgagattat caaaaaggat cttcacctag atccttttaa   7860
attaaaaatg aagttttaaa tcaatctaaa gtatatatga gtaaacttgg tctgacagtt   7920
accaatgctt aatcagtgag gcacctatct cagcgatctg tctatttcgt tcatccatag   7980
ttgcctgact ccccgtcgtg tagataacta cgatacggga gggcttacca tctggcccca   8040
gtgctgcaat gataccgcga gacccacgct caccggctcc agatttatca gcaataaacc   8100
agccagccgg aagggccgag cgcagaagtg gtcctgcaac tttatccgcc tccatccagt   8160
ctattaattg ttgccgggaa gctagagtaa gtagttcgcc agttaatagt ttgcgcaacg   8220
ttgttgccat tgctgcaggg gggggggggg gggggttcca ttgttcattc cacggacaaa   8280
aacagagaaa ggaaacgaca gaggccaaaa agctcgcttt cagcacctgt cgtttccttt   8340
cttttcagag ggtattttaa ataaaaacat taagttatga cgaagaagaa cggaaacgcc   8400
ttaaaccgga aaattttcat aaatagcgaa aacccgcgag gtcgccgccc cgtaacctgt   8460
cggatcaccg gaaaggaccc gtaaagtgat aatgattatc atctacatat cacaacgtgc   8520
gtggaggcca tcaaaccacg tcaaataatc aattatgacg caggtatcgt attaattgat   8580
ctgcatcaac ttaacgtaaa aacaacttca gacaatacaa atcagcgaca ctgaatacgg   8640
ggcaacctca tgtccccccc cccccccccc tgcaggcatc gtggtgtcac gctcgtcgtt   8700
tggtatggct tcattcagct ccggttccca acgatcaagg cgagttacat gatcccccat   8760
gttgtgcaaa aaagcggtta gctccttcgg tcctccgatc gttgtcagaa gtaagttggc   8820
cgcagtgtta tcactcatgg ttatggcagc actgcataat tctcttactg tcatgccatc   8880
cgtaagatgc ttttctgtga ctggtgagta ctcaaccaag tcattctgag aatagtgtat   8940
gcggcgaccg agttgctctt gcccggcgtc aacacgggat aataccgcgc cacatagcag   9000
aactttaaaa gtgctcatca ttggaaaacg ttcttcgggg cgaaaactct caaggatctt   9060
accgctgttg agatccagtt cgatgtaacc cactcgtgca cccaactgat cttcagcatc   9120
ttttactttc accagcgttt ctgggtgagc aaaaacagga aggcaaaatg ccgcaaaaaa   9180
gggaataagg gcgacacgga aatgttgaat actcatactc ttcctttttc aatattattg   9240
aagcatttat cagggttatt gtctcatgag cggatacata tttgaatgta tttagaaaaa   9300
taaacaaata ggggttccgc gcacatttcc ccgaaaagtg ccacctgacg tctaagaaac   9360
cattattatc atgacattaa cctataaaaa taggcgtatc acgaggccct ttcgtcttca   9420
agaattggtc gacgatcttg ctgcgttcgg atattttcgt ggagttcccg ccacagaccc   9480
ggattgaagg cgagatccag caactcgcgc cagatcatcc tgtgacggaa ctttggcgcg   9540
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
```

-continued

```
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc tttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac cttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc acgcatacaa gcggcggctg cggctgccag ccaccgccgc  11700
cggttcatct accgccgccg gtgcatctgc cacctccggt tcacctgcca cctccggtgc  11760
atctcccacc gccggtccac ctgccgccgc cggtccacct gccaccgccg gtccatgtgc  11820
cgccgccggt tcatctgccg ccgccaccat gccactaccc tactcaaccg ccccggcctc  11880
agcctcatcc ccagccacac ccatgcccgt gccaacagcc gcatccaagc ccgtgccagg  11940
gcagcggcgg cagcggcccg gccaggctga gggagctgag ggccggcccg gccccggcca  12000
```

```
ggctgaggga gctgagggcc ggcccggccc cggccaggct gagggagctg aggaaggacg  12060

agctgtaac                                                          12069


<210> SEQ ID NO 72
<211> LENGTH: 12057
<212> TYPE: DNA
<213> ORGANISM: Artificial Sequence
<220> FEATURE:
<223> OTHER INFORMATION: Synthetic construct, pAG4310

<400> SEQUENCE: 72

ctaggtcccc gaatttcccc gatcgttcaa acatttggca ataaagtttc ttaagattga     60

atcctgttgc cggtcttgcg atgattatca tataatttct gttgaattac gttaagcatg    120

taataattaa catgtaatgc atgacgttat ttatgagatg ggtttttatg attagagtcc    180

cgcaattata catttaatac gcgatagaaa acaaaatata gcgcgcaaac taggataaat    240

tatcgcgcgc ggtgtcatct atgttactag atcgggaatt ggaattcctg cagtgcagcg    300

tgacccggtc gtgcccctct ctagagataa tgagcattgc atgtctaagt tataaaaaat    360

taccacatat ttttttgtc acacttgttt gaagtgcagt ttatctatct ttatacatat    420

atttaaactt tactctacga ataatataat ctatagtact acaataatat cagtgtttta    480

gagaatcata taaatgaaca gttagacatg gtctaaagga caattgagta ttttgacaac    540

aggactctac agttttatct ttttagtgtg catgtgttct cctttttttt tgcaaatagc    600

ttcacctata taatacttca tccattttat tagtacatcc atttagggtt tagggttaat    660

ggtttttata gactaatttt tttagtacat ctattttatt ctattttagc ctctaaatta    720

agaaaactaa aactctattt tagttttttt atttaataat ttagatataa aatagaataa    780

aataaagtga ctaaaaatta aacaaatacc ctttaagaaa ttaaaaaaac taaggaaaca    840

tttttcttgt ttcgagtaga taatgccagc ctgttaaacg ccgtcgacga gtctaacgga    900

caccaaccag cgaaccagca gcgtcgcgtc gggccaagcg aagcagacgg cacggcatct    960

ctgtcgctgc ctctggaccc ctctcgagag ttccgctcca ccgttggact tgctccgctg   1020

tcggcatcca gaaattgcgt ggcggagcgg cagacgtgag ccggcacggc aggcggcctc   1080

ctcctcctct cacggcacgg cagctacggg ggattccttt cccaccgctc cttcgctttc   1140

ccttcctcgc ccgccgtaat aaatagacac cccctccaca ccctctttcc ccaacctcgt   1200

gttgttcgga gcgcacacac acacaaccag atctccccca aatccacccg tcggcacctc   1260

cgcttcaagg tacgccgctc gtcctccccc ccccccctc tctaccttct ctagatcggc    1320

gttccggtcc atggttaggg cccggtagtt ctacttctgt tcatgtttgt gttagatccg   1380

tgtttgtgtt agatccgtgc tgctagcgtt cgtacacgga tgcgacctgt acgtcagaca   1440

cgttctgatt gctaacttgc cagtgtttct ctttggggaa tcctgggatg gctctagccg   1500

ttccgcagac gggatcgatt tcatgatttt ttttgtttcg ttgcataggg tttggtttgc   1560

ccttttcctt tatttcaata tatgccgtgc acttgtttgt cgggtcatct tttcatgctt   1620

ttttttgtct tggttgtgat gatgtggtct ggttgggcgg tcgttctaga tcggagtaga   1680

attctgtttc aaactacctg gtggatttat taattttgga tctgtatgtg tgtgccatac   1740

atattcatag ttacgaattg aagatgatgg atggaaatat cgatctagga taggtataca   1800

tgttgatgcg ggttttactg atgcatatac agagatgctt tttgttcgct tggttgtgat   1860

gatgtggtgt ggttgggcgg tcgttcattc gttctagatc ggagtagaat actgtttcaa   1920

actacctggt gtatttatta attttggaac tgtatgtgtg tgtcatacat cttcatagtt   1980
```

acgagtttaa gatggatgga aatatcgatc taggataggt atacatgttg atgtgggttt 2040
tactgatgca tatacatgat ggcatatgca gcatctattc atatgctcta accttgagta 2100
cctatctatt ataataaaca agtatgtttt ataattattt tgatcttgat atacttggat 2160
gatggcatat gcagcagcta tatgtggatt tttttagccc tgccttcata cgctatttat 2220
ttgcttggta ctgtttcttt tgtcgatgct caccctgttg tttggtgtta cttctgcaga 2280
tccagatcta aaccatgcag aaactcatta actcagtgca aaactatgcc tggggcagca 2340
aaacggcgtt gactgaactt tatggtatgg aaaatccgtc cagccagccg atggccgagc 2400
tgtggatggg cgcacatccg aaaagcagtt cacgagtgca gaatgccgcc ggagatatcg 2460
tttcactgcg tgatgtgatt gagagtgata aatcgactct gctcggagag gccgttgcca 2520
aacgctttgg cgaactgcct ttcctgttca aagtattatg cgcagcacag ccactctcca 2580
ttcaggttca tccaaacaaa cacaattctg aaatcggttt tgccaaagaa aatgccgcag 2640
gtatcccgat ggatgccgcc gagcgtaact ataaagatcc taaccacaag ccggagctgg 2700
tttttgcgct gacgcctttc cttgcgatga acgcgtttcg tgaattttcc gagattgtct 2760
ccctactcca gccggtcgca ggtgcacatc cggcgattgc tcacttttta caacagcctg 2820
atgccgaacg tttaagcgaa ctgttcgcca gcctgttgaa tatgcagggt gaagaaaaat 2880
cccgcgcgct ggcgatttta aaatcggccc tcgatagcca gcagggtgaa ccgtggcaaa 2940
cgattcgttt aatttctgaa ttttacccgg aagacagcgg tctgttctcc ccgctattgc 3000
tgaatgtggt gaaattgaac cctggcgaag cgatgttcct gttcgctgaa acaccgcacg 3060
cttacctgca aggcgtggcg ctggaagtga tggcaaactc cgataacgtg ctgcgtgcgg 3120
gtctgacgcc taaatacatt gatattccgg aactggttgc caatgtgaaa ttcgaagcca 3180
aaccggctaa ccagttgttg acccagccgg tgaaacaagg tgcagaactg gacttcccga 3240
ttccagtgga tgattttgcc ttctcgctgc atgaccttag tgataaagaa accaccatta 3300
gccagcagag tgccgccatt ttgttctgcg tcgaaggcga tgcaacgttg tggaaaggtt 3360
ctcagcagtt acagcttaaa ccgggtgaat cagcgtttat tgccgccaac gaatcaccgg 3420
tgactgtcaa aggccacggc cgtttagcgc gtgtttacaa caagctgtaa gagcttactg 3480
aaaaaattaa catctcttgc taagctggga gctctagatc cccgaatttc cccgatcgtt 3540
caaacatttg gcaataaagt ttcttaagat tgaatcctgt tgccggtctt gcgatgatta 3600
tcatataatt tctgttgaat tacgttaagc atgtaataat taacatgtaa tgcatgacgt 3660
tatttatgag atgggttttt atgattagag tcccgcaatt atacatttaa tacgcgatag 3720
aaaacaaaat atagcgcgca aactaggata aattatcgcg cgcggtgtca tctatgttac 3780
tagatcggga attggcgagc tcgaattaat tcagtacatt aaaaacgtcc gcaatgtgtt 3840
attaagttgt ctaagcgtca atttgtttac accacaatat atcctgccac cagccagcca 3900
acagctcccc gaccggcagc tcggcacaaa atcaccactc gatacaggca gcccatcagt 3960
ccgggacggc gtcagcggga gagccgttgt aaggcggcag actttgctca tgttaccgat 4020
gctattcgga agaacggcaa ctaagctgcc gggtttgaaa cacggatgat ctcgcggagg 4080
gtagcatgtt gattgtaacg atgacagagc gttgctgcct gtgatcaaat atcatctccc 4140
tcgcagagat ccgaattatc agccttctta ttcatttctc gcttaaccgt gacaggctgt 4200
cgatcttgag aactatgccg acataatagg aaatcgctgg ataaagccgc tgaggaagct 4260
gagtggcgct atttctttag aagtgaacgt tgacgatcgt cgaccgtacc ccgatgaatt 4320

-continued

```
aattcggacg tacgttctga acacagctgg atacttactt gggcgattgt catacatgac   4380
atcaacaatg tacccgtttg tgtaaccgtc tcttggaggt tcgtatgaca ctagtggttc   4440
ccctcagctt gcgactagat gttgaggcct aacattttat tagagagcag gctagttgct   4500
tagatacatg atcttcaggc cgttatctgt cagggcaagc gaaaattggc catttatgac   4560
gaccaatgcc ccgcagaagc tcccatcttt gccgccatag acgccgcgcc ccccttttgg   4620
ggtgtagaac atccttttgc cagatgtgga aaagaagttc gttgtcccat tgttggcaat   4680
gacgtagtag ccggcgaaag tgcgagaccc atttgcgcta tatataagcc tacgatttcc   4740
gttgcgacta ttgtcgtaat tggatgaact attatcgtag ttgctctcag agttgtcgta   4800
atttgatgga ctattgtcgt aattgcttat ggagttgtcg tagttgcttg gagaaatgtc   4860
gtagttggat ggggagtagt catagggaag acgagcttca tccactaaaa caattggcag   4920
gtcagcaagt gcctgccccg atgccatcgc aagtacgagg cttagaacca ccttcaacag   4980
atcgcgcata gtcttcccca gctctctaac gcttgagtta agccgcgccg cgaagcggcg   5040
tcggcttgaa cgaattgtta gacattattt gccgactacc ttggtgatct cgcctttcac   5100
gtagtgaaca aattcttcca actgatctgc gcgcgaggcc aagcgatctt cttgtccaag   5160
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
agtcgatact tcggcgatca ccgcttccct catgatgttt aactcctgaa ttaagccgcg   5880
ccgcgaagcg gtgtcggctt gaatgaattg ttaggcgtca tcctgtgctc ccgagaacca   5940
gtaccagtac atcgctgttt cgttcgagac ttgaggtcta gttttatacg tgaacaggtc   6000
aatgccgccg agagtaaagc cacattttgc gtacaaattg caggcaggta cattgttcgt   6060
ttgtgtctct aatcgtatgc caaggagctg tctgcttagt gcccactttt tcgcaaattc   6120
gatgagactg tgcgcgactc ctttgcctcg gtgcgtgtgc gacacaacaa tgtgttcgat   6180
agaggctaga tcgttccatg ttgagttgag ttcaatcttc ccgacaagct cttggtcgat   6240
gaatgcgcca tagcaagcag agtcttcatc agagtcatca tccgagatgt aatccttccg   6300
gtaggggctc acacttctgg tagatagttc aaagccttgg tcggataggt gcacatcgaa   6360
cacttcacga acaatgaaat ggttctcagc atccaatgtt tccgccacct gctcagggat   6420
caccgaaatc ttcatatgac gcctaacgcc tggcacagcg gatcgcaaac ctggcgcggc   6480
ttttggcaca aaaggcgtga caggtttgcg aatccgttgc tgccacttgt taaccctttt   6540
gccagatttg gtaactataa tttatgttag aggcgaagtc ttgggtaaaa actggcctaa   6600
aattgctggg gatttcagga aagtaaacat caccttccgg ctcgatgtct attgtagata   6660
tatgtagtgt atctacttga tcgggggatc tgctgcctcg cgcgtttcgg tgatgacggt   6720
```

-continued

```
gaaaacctct gacacatgca gctcccggag acggtcacag cttgtctgta agcggatgcc   6780
gggagcagac aagcccgtca gggcgcgtca gcgggtgttg gcgggtgtcg gggcgcagcc   6840
atgacccagt cacgtagcga tagcggagtg tatactggct taactatgcg gcatcagagc   6900
agattgtact gagagtgcac catatgcggt gtgaaatacc gcacagatgc gtaaggagaa   6960
aataccgcat caggcgctct tccgcttcct cgctcactga ctcgctgcgc tcggtcgttc   7020
ggctgcggcg agcggtatca gctcactcaa aggcggtaat acggttatcc acagaatcag   7080
gggataacgc aggaaagaac atgtgagcaa aaggccagca aaaggccagg aaccgtaaaa   7140
aggccgcgtt gctggcgttt ttccataggc tccgcccccc tgacgagcat cacaaaaatc   7200
gacgctcaag tcagaggtgg cgaaacccga caggactata aagataccag gcgtttcccc   7260
ctggaagctc cctcgtgcgc tctcctgttc cgaccctgcc gcttaccgga tacctgtccg   7320
cctttctccc ttcgggaagc gtggcgcttt ctcatagctc acgctgtagg tatctcagtt   7380
cggtgtaggt cgttcgctcc aagctgggct gtgtgcacga accccccgtt cagcccgacc   7440
gctgcgcctt atccggtaac tatcgtcttg agtccaaccc ggtaagacac gacttatcgc   7500
cactggcagc agccactggt aacaggatta gcagagcgag gtatgtaggc ggtgctacag   7560
agttcttgaa gtggtggcct aactacggct acactagaag gacagtattt ggtatctgcg   7620
ctctgctgaa gccagttacc ttcggaaaaa gagttggtag ctcttgatcc ggcaaacaaa   7680
ccaccgctgg tagcggtggt ttttttgttt gcaagcagca gattacgcgc agaaaaaaag   7740
gatctcaaga agatcctttg atcttttcta cggggtctga cgctcagtgg aacgaaaact   7800
cacgttaagg gattttggtc atgagattat caaaaaggat cttcacctag atccttttaa   7860
attaaaaatg aagttttaaa tcaatctaaa gtatatatga gtaaacttgg tctgacagtt   7920
accaatgctt aatcagtgag gcacctatct cagcgatctg tctatttcgt tcatccatag   7980
ttgcctgact ccccgtcgtg tagataacta cgatacggga gggcttacca tctggcccca   8040
gtgctgcaat gataccgcga gacccacgct caccggctcc agatttatca gcaataaacc   8100
agccagccgg aagggccgag cgcagaagtg gtcctgcaac tttatccgcc tccatccagt   8160
ctattaattg ttgccgggaa gctagagtaa gtagttcgcc agttaatagt ttgcgcaacg   8220
ttgttgccat tgctgcaggg gggggggggg gggggttcca ttgttcattc cacggacaaa   8280
aacagagaaa ggaaacgaca gaggccaaaa agctcgcttt cagcacctgt cgtttccttt   8340
cttttcagag ggtattttaa ataaaaacat taagttatga cgaagaagaa cggaaacgcc   8400
ttaaaccgga aaattttcat aaatagcgaa aacccgcgag gtcgccgccc cgtaacctgt   8460
cggatcaccg gaaaggaccc gtaaagtgat aatgattatc atctacatat cacaacgtgc   8520
gtggaggcca tcaaaccacg tcaaataatc aattatgacg caggtatcgt attaattgat   8580
ctgcatcaac ttaacgtaaa aacaacttca gacaatacaa atcagcgaca ctgaatacgg   8640
ggcaacctca tgtccccccc cccccccccc tgcaggcatc gtggtgtcac gctcgtcgtt   8700
tggtatggct tcattcagct ccggttccca acgatcaagg cgagttacat gatcccccat   8760
gttgtgcaaa aaagcggtta gctccttcgg tcctccgatc gttgtcagaa gtaagttggc   8820
cgcagtgtta tcactcatgg ttatggcagc actgcataat tctcttactg tcatgccatc   8880
cgtaagatgc ttttctgtga ctggtgagta ctcaaccaag tcattctgag aatagtgtat   8940
gcggcgaccg agttgctctt gcccggcgtc aacacgggat aataccgcgc cacatagcag   9000
aactttaaaa gtgctcatca ttggaaaacg ttcttcgggg cgaaaactct caaggatctt   9060
```

-continued

```
accgctgttg agatccagtt cgatgtaacc cactcgtgca cccaactgat cttcagcatc   9120
ttttactttc accagcgttt ctgggtgagc aaaaacagga aggcaaaatg ccgcaaaaaa   9180
gggaataagg gcgacacgga aatgttgaat actcatactc ttcctttttc aatattattg   9240
aagcatttat cagggttatt gtctcatgag cggatacata tttgaatgta tttagaaaaa   9300
taaacaaata ggggttccgc gcacatttcc ccgaaaagtg ccacctgacg tctaagaaac   9360
cattattatc atgacattaa cctataaaaa taggcgtatc acgaggccct ttcgtcttca   9420
agaattggtc gacgatcttg ctgcgttcgg atattttcgt ggagttcccg ccacagaccc   9480
ggattgaagg cgagatccag caactcgcgc cagatcatcc tgtgacggaa ctttggcgcg   9540
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc tttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac ctttttttcta ttatactttt cgcattatag gctagatatt  11460
```

atctatacat gtcaacaaac tctatcccta cgtcatatct gaagattctt ttcttcacta 11520
tataagttgg cttccctgtc attgaactca catcaaccag cccaagtttc caataacatc 11580
ctcaaatagc tggatcctaa accatgaggg tgttgctcgt tgccctcgct ctcctggctc 11640
tcgctgcgag cgccacctcc ccggccaggc tgagggagct gagggccggc ccggccccgg 11700
ccaggctgag ggagctgagg gccggcccgg ccccggccag gctgagggag ctgaggggca 11760
gcggcggcag cggcggcggc tgcggctgcc agccaccgcc gccggttcat ctaccgccgc 11820
cggtgcatct gccacctccg gttcacctgc cacctccggt gcatctccca ccgccggtcc 11880
acctgccgcc gccggtccac ctgccaccgc cggtccatgt gccgccgccg gttcatctgc 11940
cgccgccacc atgccactac cctactcaac cgccccggcc tcagcctcat ccccagccac 12000
acccatgccc gtgccaacag ccgcatccaa gcccgtgcca gaaggacgag ctgtaac 12057

<210> SEQ ID NO 73
<211> LENGTH: 12210
<212> TYPE: DNA
<213> ORGANISM: Artificial Sequence
<220> FEATURE:
<223> OTHER INFORMATION: Synthetic construct, pAG4311

<400> SEQUENCE: 73
ctaggtcccc gaatttcccc gatcgttcaa acatttggca ataaagtttc ttaagattga 60
atcctgttgc cggtcttgcg atgattatca tataatttct gttgaattac gttaagcatg 120
taataattaa catgtaatgc atgacgttat ttatgagatg ggtttttatg attagagtcc 180
cgcaattata catttaatac gcgatagaaa acaaaatata gcgcgcaaac taggataaat 240
tatcgcgcgc ggtgtcatct atgttactag atcgggaatt ggaattcctg cagtgcagcg 300
tgacccggtc gtgcccctct ctagagataa tgagcattgc atgtctaagt tataaaaaat 360
taccacatat ttttttgtc acacttgttt gaagtgcagt ttatctatct ttatacatat 420
atttaaactt tactctacga ataatataat ctatagtact acaataatat cagtgtttta 480
gagaatcata taaatgaaca gttagacatg gtctaaagga caattgagta ttttgacaac 540
aggactctac agttttatct ttttagtgtg catgtgttct cctttttttt tgcaaatagc 600
ttcacctata taatacttca tccattttat tagtacatcc atttagggtt tagggttaat 660
ggtttttata gactaatttt tttagtacat ctattttatt ctattttagc ctctaaatta 720
agaaaactaa aactctattt tagttttttt atttaataat ttagatataa aatagaataa 780
aataaagtga ctaaaaatta aacaaatacc ctttaagaaa ttaaaaaaac taaggaaaca 840
tttttcttgt ttcgagtaga taatgccagc ctgttaaacg ccgtcgacga gtctaacgga 900
caccaaccag cgaaccagca gcgtcgcgtc gggccaagcg aagcagacgg cacggcatct 960
ctgtcgctgc ctctggaccc ctctcgagag ttccgctcca ccgttggact tgctccgctg 1020
tcggcatcca gaaattgcgt ggcggagcgg cagacgtgag ccggcacggc aggcggcctc 1080
ctcctcctct cacggcacgg cagctacggg ggattccttt cccaccgctc cttcgctttc 1140
ccttcctcgc ccgccgtaat aaatagacac cccctccaca ccctctttcc ccaacctcgt 1200
gttgttcgga gcgcacacac acacaaccag atctccccca aatccacccg tcggcacctc 1260
cgcttcaagg tacgccgctc gtcctccccc ccccccctc tctaccttct ctagatcggc 1320
gttccggtcc atggttaggg cccggtagtt ctacttctgt tcatgtttgt gttagatccg 1380
tgtttgtgtt agatccgtgc tgctagcgtt cgtacacgga tgcgacctgt acgtcagaca 1440

-continued

```
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
ttttttgtct tggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
tttcactgcg tgatgtgatt gagagtgata aatcgactct gctcggagag gccgttgcca   2520
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
gtatcccgat ggatgccgcc gagcgtaact ataaagatcc taaccacaag ccggagctgg   2700
tttttgcgct gacgcctttc cttgcgatga acgcgtttcg tgaattttcc gagattgtct   2760
ccctactcca gccggtcgca ggtgcacatc cggcgattgc tcacttttta caacagcctg   2820
atgccgaacg tttaagcgaa ctgttcgcca gcctgttgaa tatgcagggt gaagaaaaat   2880
cccgcgcgct ggcgatttta aaatcggccc tcgatagcca gcagggtgaa ccgtggcaaa   2940
cgattcgttt aatttctgaa ttttacccgg aagacagcgg tctgttctcc ccgctattgc   3000
tgaatgtggt gaaattgaac cctggcgaag cgatgttcct gttcgctgaa acaccgcacg   3060
cttacctgca aggcgtggcg ctggaagtga tggcaaactc cgataacgtg ctgcgtgcgg   3120
gtctgacgcc taaatacatt gatattccgg aactggttgc caatgtgaaa ttcgaagcca   3180
aaccggctaa ccagttgttg acccagccgg tgaaacaagg tgcagaactg gacttcccga   3240
ttccagtgga tgattttgcc ttctcgctgc atgaccttag tgataaagaa accaccatta   3300
gccagcagag tgccgccatt ttgttctgcg tcgaaggcga tgcaacgttg tggaaaggtt   3360
ctcagcagtt acagcttaaa ccgggtgaat cagcgtttat tgccgccaac gaatcaccgg   3420
tgactgtcaa aggccacggc cgtttagcgc gtgtttacaa caagctgtaa gagcttactg   3480
aaaaaattaa catctcttgc taagctggga gctctagatc cccgaatttc cccgatcgtt   3540
caaacatttg gcaataaagt ttcttaagat tgaatcctgt tgccggtctt gcgatgatta   3600
tcatataatt tctgttgaat tacgttaagc atgtaataat taacatgtaa tgcatgacgt   3660
tatttatgag atgggttttt atgattagag tcccgcaatt atacatttaa tacgcgatag   3720
aaaacaaaat atagcgcgca aactaggata aattatcgcg cgcggtgtca tctatgttac   3780
tagatcggga attggcgagc tcgaattaat tcagtacatt aaaaacgtcc gcaatgtgtt   3840
```

```
attaagttgt ctaagcgtca atttgtttac accacaatat atcctgccac cagccagcca   3900
acagctcccc gaccggcagc tcggcacaaa atcaccactc gatacaggca gcccatcagt   3960
ccgggacggc gtcagcggga gagccgttgt aaggcggcag actttgctca tgttaccgat   4020
gctattcgga agaacggcaa ctaagctgcc gggtttgaaa cacggatgat ctcgcggagg   4080
gtagcatgtt gattgtaacg atgacagagc gttgctgcct gtgatcaaat atcatctccc   4140
tcgcagagat ccgaattatc agccttctta ttcatttctc gcttaaccgt gacaggctgt   4200
cgatcttgag aactatgccg acataatagg aaatcgctgg ataaagccgc tgaggaagct   4260
gagtggcgct atttctttag aagtgaacgt tgacgatcgt cgaccgtacc ccgatgaatt   4320
aattcggacg tacgttctga acacagctgg atacttactt gggcgattgt catacatgac   4380
atcaacaatg tacccgtttg tgtaaccgtc tcttggaggt tcgtatgaca ctagtggttc   4440
ccctcagctt gcgactagat gttgaggcct aacattttat tagagagcag gctagttgct   4500
tagatacatg atcttcaggc cgttatctgt cagggcaagc gaaaattggc catttatgac   4560
gaccaatgcc ccgcagaagc tcccatcttt gccgccatag acgccgcgcc cccttttgg    4620
ggtgtagaac atccttttgc cagatgtgga aaagaagttc gttgtcccat tgttggcaat   4680
gacgtagtag ccggcgaaag tgcgagaccc atttgcgcta tatataagcc tacgatttcc   4740
gttgcgacta ttgtcgtaat tggatgaact attatcgtag ttgctctcag agttgtcgta   4800
atttgatgga ctattgtcgt aattgcttat ggagttgtcg tagttgcttg gagaaatgtc   4860
gtagttggat ggggagtagt catagggaag acgagcttca tccactaaaa caattggcag   4920
gtcagcaagt gcctgccccg atgccatcgc aagtacgagg cttagaacca ccttcaacag   4980
atcgcgcata gtcttcccca gctctctaac gcttgagtta agccgcgccg cgaagcggcg   5040
tcggcttgaa cgaattgtta gacattattt gccgactacc ttggtgatct cgcctttcac   5100
gtagtgaaca aattcttcca actgatctgc gcgcgaggcc aagcgatctt cttgtccaag   5160
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
agtcgatact tcggcgatca ccgcttccct catgatgttt aactcctgaa ttaagccgcg   5880
ccgcgaagcg gtgtcggctt gaatgaattg ttaggcgtca tcctgtgctc ccgagaacca   5940
gtaccagtac atcgctgttt cgttcgagac ttgaggtcta gttttatacg tgaacaggtc   6000
aatgccgccg agagtaaagc cacattttgc gtacaaattg caggcaggta cattgttcgt   6060
ttgtgtctct aatcgtatgc caaggagctg tctgcttagt gcccactttt tcgcaaattc   6120
gatgagactg tgcgcgactc ctttgcctcg gtgcgtgtgc gacacaacaa tgtgttcgat   6180
```

-continued agaggctaga tcgttccatg ttgagttgag ttcaatcttc ccgacaagct cttggtcgat 6240
gaatgcgcca tagcaagcag agtcttcatc agagtcatca tccgagatgt aatccttccg 6300
gtaggggctc acacttctgg tagatagttc aaagccttgg tcggataggt gcacatcgaa 6360
cacttcacga acaatgaaat ggttctcagc atccaatgtt tccgccacct gctcagggat 6420
caccgaaatc ttcatatgac gcctaacgcc tggcacagcg gatcgcaaac ctggcgcggc 6480
ttttggcaca aaaggcgtga caggtttgcg aatccgttgc tgccacttgt taaccctttt 6540
gccagatttg gtaactataa tttatgttag aggcgaagtc ttgggtaaaa actggcctaa 6600
aattgctggg gatttcagga aagtaaacat caccttccgg ctcgatgtct attgtagata 6660
tatgtagtgt atctacttga tcgggggatc tgctgcctcg cgcgtttcgg tgatgacggt 6720
gaaaacctct gacacatgca gctcccggag acggtcacag cttgtctgta agcggatgcc 6780
gggagcagac aagcccgtca gggcgcgtca gcgggtgttg gcgggtgtcg gggcgcagcc 6840
atgacccagt cacgtagcga tagcggagtg tatactggct taactatgcg gcatcagagc 6900
agattgtact gagagtgcac catatgcggt gtgaaatacc gcacagatgc gtaaggagaa 6960
aataccgcat caggcgctct tccgcttcct cgctcactga ctcgctgcgc tcggtcgttc 7020
ggctgcggcg agcggtatca gctcactcaa aggcggtaat acggttatcc acagaatcag 7080
gggataacgc aggaaagaac atgtgagcaa aaggccagca aaaggccagg aaccgtaaaa 7140
aggccgcgtt gctggcgttt ttccataggc tccgcccccc tgacgagcat cacaaaaatc 7200
gacgctcaag tcagaggtgg cgaaacccga caggactata aagataccag gcgtttcccc 7260
ctggaagctc cctcgtgcgc tctcctgttc cgaccctgcc gcttaccgga tacctgtccg 7320
cctttctccc ttcgggaagc gtggcgcttt ctcatagctc acgctgtagg tatctcagtt 7380
cggtgtaggt cgttcgctcc aagctgggct gtgtgcacga accccccgtt cagcccgacc 7440
gctgcgcctt atccggtaac tatcgtcttg agtccaaccc ggtaagacac gacttatcgc 7500
cactggcagc agccactggt aacaggatta gcagagcgag gtatgtaggc ggtgctacag 7560
agttcttgaa gtggtggcct aactacggct acactagaag gacagtattt ggtatctgcg 7620
ctctgctgaa gccagttacc ttcggaaaaa gagttggtag ctcttgatcc ggcaaacaaa 7680
ccaccgctgg tagcggtggt ttttttgttt gcaagcagca gattacgcgc agaaaaaaag 7740
gatctcaaga agatcctttg atcttttcta cggggtctga cgctcagtgg aacgaaaact 7800
cacgttaagg gattttggtc atgagattat caaaaaggat cttcacctag atccttttaa 7860
attaaaaatg aagttttaaa tcaatctaaa gtatatatga gtaaacttgg tctgacagtt 7920
accaatgctt aatcagtgag gcacctatct cagcgatctg tctatttcgt tcatccatag 7980
ttgcctgact ccccgtcgtg tagataacta cgatacggga gggcttacca tctggcccca 8040
gtgctgcaat gataccgcga gacccacgct caccggctcc agatttatca gcaataaacc 8100
agccagccgg aagggccgag cgcagaagtg gtcctgcaac tttatccgcc tccatccagt 8160
ctattaattg ttgccgggaa gctagagtaa gtagttcgcc agttaatagt ttgcgcaacg 8220
ttgttgccat tgctgcaggg gggggggggg gggggttcca ttgttcattc cacggacaaa 8280
aacagagaaa ggaaacgaca gaggccaaaa agctcgcttt cagcacctgt cgtttccttt 8340
cttttcagag ggtattttaa ataaaaacat taagttatga cgaagaagaa cggaaacgcc 8400
ttaaaccgga aaattttcat aaatagcgaa aacccgcgag gtcgccgccc cgtaacctgt 8460
cggatcaccg gaaaggaccc gtaaagtgat aatgattatc atctacatat cacaacgtgc 8520
gtggaggcca tcaaaccacg tcaaataatc aattatgacg caggtatcgt attaattgat 8580

```
ctgcatcaac ttaacgtaaa aacaacttca gacaatacaa atcagcgaca ctgaatacgg   8640
ggcaacctca tgtccccccc cccccccccc tgcaggcatc gtggtgtcac gctcgtcgtt   8700
tggtatggct tcattcagct ccggttccca acgatcaagg cgagttacat gatcccccat   8760
gttgtgcaaa aaagcggtta gctccttcgg tcctccgatc gttgtcagaa gtaagttggc   8820
cgcagtgtta tcactcatgg ttatggcagc actgcataat tctcttactg tcatgccatc   8880
cgtaagatgc ttttctgtga ctggtgagta ctcaaccaag tcattctgag aatagtgtat   8940
gcggcgaccg agttgctctt gcccggcgtc aacacgggat aataccgcgc cacatagcag   9000
aactttaaaa gtgctcatca ttggaaaacg ttcttcgggg cgaaaactct caaggatctt   9060
accgctgttg agatccagtt cgatgtaacc cactcgtgca cccaactgat cttcagcatc   9120
ttttactttc accagcgttt ctgggtgagc aaaaacagga aggcaaaatg ccgcaaaaaa   9180
gggaataagg gcgacacgga aatgttgaat actcatactc ttcctttttc aatattattg   9240
aagcatttat cagggttatt gtctcatgag cggatacata tttgaatgta tttagaaaaa   9300
taaacaaata ggggttccgc gcacatttcc ccgaaaagtg ccacctgacg tctaagaaac   9360
cattattatc atgacattaa cctataaaaa taggcgtatc acgaggccct ttcgtcttca   9420
agaattggtc gacgatcttg ctgcgttcgg atattttcgt ggagttcccg ccacagaccc   9480
ggattgaagg cgagatccag caactcgcgc cagatcatcc tgtgacggaa ctttggcgcg   9540
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc tttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
```

```
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac ctttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ccggccaggc tgagggagct gagggccggc ccggccccgg  11700
ccaggctgag ggagctgagg gccggcccgg ccccggccag gctgagggag ctgaggggca  11760
gcggcggcag cggcgtgccg ggcgtgggcg tgccgggcgt gggcgtgccg ggcgtgggcg  11820
tgccgggcgt gggcgtgccg ggcgtgggcg tgccgggcgt gggcgtgccg ggcgtgggcg  11880
tgccgggcgt gggcgtgccg ggcgtgggcg tgccgggcgt gggcgtgccg ggcgtgggcg  11940
tgccgggcgt gggcgtgccg ggcgtgggcg tgccgggcgt gggcgtgccg ggcgtgggcg  12000
tgccgggcgt gggcgtgccg ggcgtgggcg tgccgggcgt gggcgtgccg ggcgtgggcg  12060
tgccgggcgt gggcgtgccg ggcgtgggcg tgccgggcgt gggcgtgccg ggcgtgggcg  12120
tgccgggcgt gggcgtgccg ggcgtgggcg tgccgggcgt gggcgtgccg ggcgtgggcg  12180
tgccgggcgt gggcaaggac gagctgtaac                                    12210
```

```
<210> SEQ ID NO 74
<211> LENGTH: 12015
<212> TYPE: DNA
<213> ORGANISM: Artificial Sequence
<220> FEATURE:
<223> OTHER INFORMATION: Synthetic construct, pAG4312

<400> SEQUENCE: 74
```

```
ctaggtcccc gaatttcccc gatcgttcaa acatttggca ataaagtttc ttaagattga     60
atcctgttgc cggtcttgcg atgattatca tataatttct gttgaattac gttaagcatg    120
taataattaa catgtaatgc atgacgttat ttatgagatg ggtttttatg attagagtcc    180
cgcaattata catttaatac gcgatagaaa acaaaatata gcgcgcaaac taggataaat    240
tatcgcgcgc ggtgtcatct atgttactag atcgggaatt ggaattcctg cagtgcagcg    300
tgacccggtc gtgcccctct ctagagataa tgagcattgc atgtctaagt tataaaaaat    360
taccacatat ttttttgtc acacttgttt gaagtgcagt ttatctatct ttatacatat    420
atttaaactt tactctacga ataatataat ctatagtact acaataatat cagtgtttta    480
gagaatcata taaatgaaca gttagacatg gtctaaagga caattgagta ttttgacaac    540
aggactctac agttttatct ttttagtgtg catgtgttct cctttttttt tgcaaatagc    600
ttcacctata taatacttca tccattttat tagtacatcc atttagggtt tagggttaat    660
ggtttttata gactaatttt tttagtacat ctattttatt ctattttagc ctctaaatta    720
agaaaactaa aactctattt tagttttttt atttaataat ttagatataa aatagaataa    780
```

-continued

```
aataaagtga ctaaaaatta aacaaatacc ctttaagaaa ttaaaaaaac taaggaaaca    840
tttttcttgt ttcgagtaga taatgccagc ctgttaaacg ccgtcgacga gtctaacgga    900
caccaaccag cgaaccagca gcgtcgcgtc gggccaagcg aagcagacgg cacggcatct    960
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc ccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
ttttttgtct tggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
tttcactgcg tgatgtgatt gagagtgata aatcgactct gctcggagag gccgttgcca   2520
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
gtatcccgat ggatgccgcc gagcgtaact ataaagatcc taaccacaag ccggagctgg   2700
tttttgcgct gacgcctttc cttgcgatga acgcgtttcg tgaattttcc gagattgtct   2760
ccctactcca gccggtcgca ggtgcacatc cggcgattgc tcacttttta caacagcctg   2820
atgccgaacg tttaagcgaa ctgttcgcca gcctgttgaa tatgcagggt gaagaaaaat   2880
cccgcgcgct ggcgatttta aaatcggccc tcgatagcca gcagggtgaa ccgtggcaaa   2940
cgattcgttt aatttctgaa ttttacccgg aagacagcgg tctgttctcc ccgctattgc   3000
tgaatgtggt gaaattgaac cctggcgaag cgatgttcct gttcgctgaa acaccgcacg   3060
cttacctgca aggcgtggcg ctggaagtga tggcaaactc cgataacgtg ctgcgtgcgg   3120
```

-continued gtctgacgcc taaatacatt gatattccgg aactggttgc caatgtgaaa ttcgaagcca 3180
aaccggctaa ccagttgttg acccagccgg tgaaacaagg tgcagaactg gacttcccga 3240
ttccagtgga tgattttgcc ttctcgctgc atgaccttag tgataaagaa accaccatta 3300
gccagcagag tgccgccatt ttgttctgcg tcgaaggcga tgcaacgttg tggaaaggtt 3360
ctcagcagtt acagcttaaa ccgggtgaat cagcgtttat tgccgccaac gaatcaccgg 3420
tgactgtcaa aggccacggc cgtttagcgc gtgtttacaa caagctgtaa gagcttactg 3480
aaaaaattaa catctcttgc taagctggga gctctagatc cccgaatttc cccgatcgtt 3540
caaacatttg gcaataaagt ttcttaagat tgaatcctgt tgccggtctt gcgatgatta 3600
tcatataatt tctgttgaat tacgttaagc atgtaataat taacatgtaa tgcatgacgt 3660
tatttatgag atgggttttt atgattagag tcccgcaatt atacatttaa tacgcgatag 3720
aaaacaaaat atagcgcgca aactaggata aattatcgcg cgcggtgtca tctatgttac 3780
tagatcggga attggcgagc tcgaattaat tcagtacatt aaaaacgtcc gcaatgtgtt 3840
attaagttgt ctaagcgtca atttgtttac accacaatat atcctgccac cagccagcca 3900
acagctcccc gaccggcagc tcggcacaaa atcaccactc gatacaggca gcccatcagt 3960
ccgggacggc gtcagcggga gagccgttgt aaggcggcag actttgctca tgttaccgat 4020
gctattcgga agaacggcaa ctaagctgcc gggtttgaaa cacggatgat ctcgcggagg 4080
gtagcatgtt gattgtaacg atgacagagc gttgctgcct gtgatcaaat atcatctccc 4140
tcgcagagat ccgaattatc agccttctta ttcatttctc gcttaaccgt gacaggctgt 4200
cgatcttgag aactatgccg acataatagg aaatcgctgg ataaagccgc tgaggaagct 4260
gagtggcgct atttctttag aagtgaacgt tgacgatcgt cgaccgtacc ccgatgaatt 4320
aattcggacg tacgttctga acacagctgg atacttactt gggcgattgt catacatgac 4380
atcaacaatg tacccgtttg tgtaaccgtc tcttggaggt tcgtatgaca ctagtggttc 4440
ccctcagctt gcgactagat gttgaggcct aacattttat tagagagcag gctagttgct 4500
tagatacatg atcttcaggc cgttatctgt cagggcaagc gaaaattggc catttatgac 4560
gaccaatgcc ccgcagaagc tcccatcttt gccgccatag acgccgcgcc ccccttttgg 4620
ggtgtagaac atccttttgc cagatgtgga aaagaagttc gttgtcccat tgttggcaat 4680
gacgtagtag ccggcgaaag tgcgagaccc atttgcgcta tatataagcc tacgatttcc 4740
gttgcgacta ttgtcgtaat tggatgaact attatcgtag ttgctctcag agttgtcgta 4800
atttgatgga ctattgtcgt aattgcttat ggagttgtcg tagttgcttg gagaaatgtc 4860
gtagttggat ggggagtagt catagggaag acgagcttca tccactaaaa caattggcag 4920
gtcagcaagt gcctgccccg atgccatcgc aagtacgagg cttagaacca ccttcaacag 4980
atcgcgcata gtcttcccca gctctctaac gcttgagtta agccgcgccg cgaagcggcg 5040
tcggcttgaa cgaattgtta gacattattt gccgactacc ttggtgatct cgcctttcac 5100
gtagtgaaca aattcttcca actgatctgc gcgcgaggcc aagcgatctt cttgtccaag 5160
ataagcctgc ctagcttcaa gtatgacggg ctgatactgg gccggcaggc gctccattgc 5220
ccagtcggca gcgacatcct tcggcgcgat tttgccggtt actgcgctgt accaaatgcg 5280
ggacaacgta agcactacat ttcgctcatc gccagcccag tcgggcggcg agttccatag 5340
cgttaaggtt tcatttagcg cctcaaatag atcctgttca ggaaccggat caaagagttc 5400
ctccgccgct ggacctacca aggcaacgct atgttctctt gcttttgtca gcaagatagc 5460
cagatcaatg tcgatcgtgg ctggctcgaa gatacctgca agaatgtcat tgcgctgcca 5520
ttctccaaat tgcagttcgc gcttagctgg ataacgccac ggaatgatgt cgtcgtgcac 5580
aacaatggtg acttctacag cgcggagaat ctcgctctct ccaggggaag ccgaagtttc 5640
caaaaggtcg ttgatcaaag ctcgccgcgt tgtttcatca agccttacgg tcaccgtaac 5700
cagcaaatca atatcactgt gtggcttcag gccgccatcc actgcggagc cgtacaaatg 5760
tacggccagc aacgtcggtt cgagatggcg ctcgatgacg ccaactacct ctgatagttg 5820
agtcgatact tcggcgatca ccgcttccct catgatgttt aactcctgaa ttaagccgcg 5880
ccgcgaagcg gtgtcggctt gaatgaattg ttaggcgtca tcctgtgctc ccgagaacca 5940
gtaccagtac atcgctgttt cgttcgagac ttgaggtcta gttttatacg tgaacaggtc 6000
aatgccgccg agagtaaagc cacattttgc gtacaaattg caggcaggta cattgttcgt 6060
ttgtgtctct aatcgtatgc caaggagctg tctgcttagt gcccactttt tcgcaaattc 6120
gatgagactg tgcgcgactc ctttgcctcg gtgcgtgtgc gacacaacaa tgtgttcgat 6180
agaggctaga tcgttccatg ttgagttgag ttcaatcttc ccgacaagct cttggtcgat 6240
gaatgcgcca tagcaagcag agtcttcatc agagtcatca tccgagatgt aatccttccg 6300
gtaggggctc acacttctgg tagatagttc aaagccttgg tcggataggt gcacatcgaa 6360
cacttcacga acaatgaaat ggttctcagc atccaatgtt tccgccacct gctcagggat 6420
caccgaaatc ttcatatgac gcctaacgcc tggcacagcg gatcgcaaac ctggcgcggc 6480
ttttggcaca aaaggcgtga caggtttgcg aatccgttgc tgccacttgt taaccctttt 6540
gccagatttg gtaactataa tttatgttag aggcgaagtc ttgggtaaaa actggcctaa 6600
aattgctggg gatttcagga aagtaaacat caccttccgg ctcgatgtct attgtagata 6660
tatgtagtgt atctacttga tcgggggatc tgctgcctcg cgcgtttcgg tgatgacggt 6720
gaaaacctct gacacatgca gctcccggag acggtcacag cttgtctgta agcggatgcc 6780
gggagcagac aagcccgtca gggcgcgtca gcgggtgttg gcgggtgtcg gggcgcagcc 6840
atgacccagt cacgtagcga tagcggagtg tatactggct taactatgcg gcatcagagc 6900
agattgtact gagagtgcac catatgcggt gtgaaatacc gcacagatgc gtaaggagaa 6960
aataccgcat caggcgctct tccgcttcct cgctcactga ctcgctgcgc tcggtcgttc 7020
ggctgcggcg agcggtatca gctcactcaa aggcggtaat acggttatcc acagaatcag 7080
gggataacgc aggaaagaac atgtgagcaa aaggccagca aaaggccagg aaccgtaaaa 7140
aggccgcgtt gctggcgttt ttccataggc tccgcccccc tgacgagcat cacaaaaatc 7200
gacgctcaag tcagaggtgg cgaaacccga caggactata aagataccag gcgtttcccc 7260
ctggaagctc cctcgtgcgc tctcctgttc cgaccctgcc gcttaccgga tacctgtccg 7320
cctttctccc ttcgggaagc gtggcgcttt ctcatagctc acgctgtagg tatctcagtt 7380
cggtgtaggt cgttcgctcc aagctgggct gtgtgcacga accccccgtt cagcccgacc 7440
gctgcgcctt atccggtaac tatcgtcttg agtccaaccc ggtaagacac gacttatcgc 7500
cactggcagc agccactggt aacaggatta gcagagcgag gtatgtaggc ggtgctacag 7560
agttcttgaa gtggtggcct aactacggct acactagaag gacagtattt ggtatctgcg 7620
ctctgctgaa gccagttacc ttcggaaaaa gagttggtag ctcttgatcc ggcaaacaaa 7680
ccaccgctgg tagcggtggt ttttttgttt gcaagcagca gattacgcgc agaaaaaaag 7740
gatctcaaga agatcctttg atcttttcta cggggtctga cgctcagtgg aacgaaaact 7800
cacgttaagg gattttggtc atgagattat caaaaaggat cttcacctag atccttttaa 7860

-continued

```
attaaaaatg aagttttaaa tcaatctaaa gtatatatga gtaaacttgg tctgacagtt   7920
accaatgctt aatcagtgag gcacctatct cagcgatctg tctatttcgt tcatccatag   7980
ttgcctgact ccccgtcgtg tagataacta cgatacggga gggcttacca tctggcccca   8040
gtgctgcaat gataccgcga gacccacgct caccggctcc agatttatca gcaataaacc   8100
agccagccgg aagggccgag cgcagaagtg gtcctgcaac tttatccgcc tccatccagt   8160
ctattaattg ttgccgggaa gctagagtaa gtagttcgcc agttaatagt ttgcgcaacg   8220
ttgttgccat tgctgcaggg gggggggggg gggggttcca ttgttcattc cacggacaaa   8280
aacagagaaa ggaaacgaca gaggccaaaa agctcgcttt cagcacctgt cgtttccttt   8340
cttttcagag ggtattttaa ataaaaacat taagttatga cgaagaagaa cggaaacgcc   8400
ttaaaccgga aattttcat aaatagcgaa aacccgcgag gtcgccgccc cgtaacctgt   8460
cggatcaccg gaaaggaccc gtaaagtgat aatgattatc atctacatat cacaacgtgc   8520
gtggaggcca tcaaaccacg tcaaataatc aattatgacg caggtatcgt attaattgat   8580
ctgcatcaac ttaacgtaaa aacaacttca gacaatacaa atcagcgaca ctgaatacgg   8640
ggcaacctca tgtccccccc cccccccccc tgcaggcatc gtggtgtcac gctcgtcgtt   8700
tggtatggct tcattcagct ccggttccca acgatcaagg cgagttacat gatcccccat   8760
gttgtgcaaa aaagcggtta gctccttcgg tcctccgatc gttgtcagaa gtaagttggc   8820
cgcagtgtta tcactcatgg ttatggcagc actgcataat tctcttactg tcatgccatc   8880
cgtaagatgc ttttctgtga ctggtgagta ctcaaccaag tcattctgag aatagtgtat   8940
gcggcgaccg agttgctctt gcccggcgtc aacacgggat aataccgcgc cacatagcag   9000
aactttaaaa gtgctcatca ttggaaaacg ttcttcgggg cgaaaactct caaggatctt   9060
accgctgttg agatccagtt cgatgtaacc cactcgtgca cccaactgat cttcagcatc   9120
ttttactttc accagcgttt ctgggtgagc aaaaacagga aggcaaaatg ccgcaaaaaa   9180
gggaataagg gcgacacgga aatgttgaat actcatactc ttcctttttc aatattattg   9240
aagcatttat cagggttatt gtctcatgag cggatacata tttgaatgta tttagaaaaa   9300
taaacaaata ggggttccgc gcacatttcc ccgaaaagtg ccacctgacg tctaagaaac   9360
cattattatc atgacattaa cctataaaaa taggcgtatc acgaggccct ttcgtcttca   9420
agaattggtc gacgatcttg ctgcgttcgg atattttcgt ggagttcccg ccacagaccc   9480
ggattgaagg cgagatccag caactcgcgc cagatcatcc tgtgacggaa ctttggcgcg   9540
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
```

gatgccgatg gcacgtaact ggggcgccca atggcactca ctggcctacc tcaccggtca 10320
aggtctatcc tttagggtca ccaacacaga tgaccaaacg ctcgtcttca ccaacgtcgt 10380
gccaccagga tggaagtttg gccagacatt tgcaagcaag ctgcagttca agtgagagga 10440
gaagcctgaa ttgataccgg agcgtttctt ttgggagtaa catctctggt tgcctagcaa 10500
acatatgatt gtatataagt ttcgttgtgc gtttattctt tcggtgtgta aaataacata 10560
catgctttcc tgatattttc ttgtatatat gtacacacac acgacaaatc cttccatttc 10620
tattattatt gaacaattta attgcgaggg cgagtacttg tctgtttacc tttttttttt 10680
cagatggcat tttatagttt aacctttcat ggaccggcag tagttctaac catgaatgaa 10740
aagaaatcat agtccacacc acgcagggac attgtggtca ttttagacaa gacgatttga 10800
ttaatgtctt gtatgatatg gtcgacagtg aggactaaca aacatatggc atattttatt 10860
accggcgagt taaataaatt tatgtcacag taataaactg cctaataaat gcacgccaga 10920
aaatataatg ataaaaaaaa gaaaagatac ataagtccat tgcttctact tttttaaaaa 10980
ttaaatccaa cattttctat tttttggtat aaacttggaa gtactagttg gatatgcaaa 11040
atcatctaac ctccatatat ttcatcaatt tgtttacttt acatatggga gaggatagta 11100
tgtcaaagaa aatgacaaca agcttacaag tttcttattt taaaagttcc gctaacttat 11160
caagcatagt gtgccacgca aaactgacaa caaaccaaca aatttaagga gcgcctaact 11220
tatcatctat gacataccgc acaaaatgat aacatactag agaaacttta ttgcacaaaa 11280
ggaaatttat ccataaggca aaggaacatc ttaaggcttt ggatatacat ttaccaacaa 11340
gcattgtttg tattacccct aaagcgcaag acatgtcatc catgagtcat agtgtgtata 11400
tctcaacatt gcaaagctac ctttttttcta ttatactttt cgcattatag gctagatatt 11460
atctatacat gtcaacaaac tctatcccta cgtcatatct gaagattctt ttcttcacta 11520
tataagttgg cttccctgtc attgaactca catcaaccag cccaagtttc caataacatc 11580
ctcaaatagc tggatcctaa accatgaggg tgttgctcgt tgccctcgct ctcctggctc 11640
tcgctgcgag cgccacctcc ccggccaggc tgagggagct gagggccggc ccggccccgg 11700
ccaggctgag ggagctgagg gccggcccgg ccccggccag gctgagggag ctgaggggca 11760
gcggcggcag cggcagcaac ggcaacggca acgtgtgccc gccgggcctg ttcagcaacc 11820
cgcagtgctg cgccacccag gtgctgggcc tgatcggcct ggactgcaag gtgccgagcc 11880
agaacgtgta cgacggcacc gacttcagga acgtgtgcgc caagaccggc gcccagccgc 11940
tgtgctgcgt ggccccggtg gccggccagg ccctgctgtg ccagaccgcc gtgggcgcca 12000
aggacgagct gtaac 12015

<210> SEQ ID NO 75
<211> LENGTH: 12738
<212> TYPE: DNA
<213> ORGANISM: Artificial Sequence
<220> FEATURE:
<223> OTHER INFORMATION: Synthetic construct, pAG4313

<400> SEQUENCE: 75
ctaggtcccc gaatttcccc gatcgttcaa acatttggca ataaagtttc ttaagattga 60
atcctgttgc cggtcttgcg atgattatca tataatttct gttgaattac gttaagcatg 120
taataattaa catgtaatgc atgacgttat ttatgagatg ggtttttatg attagagtcc 180
cgcaattata catttaatac gcgatagaaa acaaaatata gcgcgcaaac taggataaat 240

-continued

```
tatcgcgcgc ggtgtcatct atgttactag atcgggaatt ggaattcctg cagtgcagcg    300
tgacccggtc gtgcccctct ctagagataa tgagcattgc atgtctaagt tataaaaaat    360
taccacatat ttttttgtc acacttgttt gaagtgcagt ttatctatct ttatacatat    420
atttaaactt tactctacga ataatataat ctatagtact acaataatat cagtgtttta    480
gagaatcata taaatgaaca gttagacatg gtctaaagga caattgagta ttttgacaac    540
aggactctac agttttatct ttttagtgtg catgtgttct cctttttttt tgcaaatagc    600
ttcacctata taatacttca tccattttat tagtacatcc atttagggtt tagggttaat    660
ggtttttata gactaatttt tttagtacat ctattttatt ctattttagc ctctaaatta    720
agaaaactaa aactctattt tagttttttt atttaataat ttagatataa aatagaataa    780
aataaagtga ctaaaaatta aacaaatacc ctttaagaaa ttaaaaaaac taaggaaaca    840
tttttcttgt ttcgagtaga taatgccagc ctgttaaacg ccgtcgacga gtctaacgga    900
caccaaccag cgaaccagca gcgtcgcgtc gggccaagcg aagcagacgg cacggcatct    960
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc cccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
tttttgtct tggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
tttcactgcg tgatgtgatt gagagtgata aatcgactct gctcggagag gccgttgcca   2520
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
```

gtatcccgat ggatgccgcc gagcgtaact ataaagatcc taaccacaag ccggagctgg 2700
tttttgcgct gacgcctttc cttgcgatga acgcgtttcg tgaattttcc gagattgtct 2760
ccctactcca gccggtcgca ggtgcacatc cggcgattgc tcacttttta caacagcctg 2820
atgccgaacg tttaagcgaa ctgttcgcca gcctgttgaa tatgcagggt gaagaaaaat 2880
cccgcgcgct ggcgatttta aaatcggccc tcgatagcca gcagggtgaa ccgtggcaaa 2940
cgattcgttt aatttctgaa ttttacccgg aagacagcgg tctgttctcc ccgctattgc 3000
tgaatgtggt gaaattgaac cctggcgaag cgatgttcct gttcgctgaa acaccgcacg 3060
cttacctgca aggcgtggcg ctggaagtga tggcaaactc cgataacgtg ctgcgtgcgg 3120
gtctgacgcc taaatacatt gatattccgg aactggttgc caatgtgaaa ttcgaagcca 3180
aaccggctaa ccagttgttg acccagccgg tgaaacaagg tgcagaactg gacttcccga 3240
ttccagtgga tgattttgcc ttctcgctgc atgaccttag tgataaagaa accaccatta 3300
gccagcagag tgccgccatt ttgttctgcg tcgaaggcga tgcaacgttg tggaaaggtt 3360
ctcagcagtt acagcttaaa ccgggtgaat cagcgtttat tgccgccaac gaatcaccgg 3420
tgactgtcaa aggccacggc cgtttagcgc gtgtttacaa caagctgtaa gagcttactg 3480
aaaaaattaa catctcttgc taagctggga gctctagatc cccgaatttc cccgatcgtt 3540
caaacatttg gcaataaagt ttcttaagat tgaatcctgt tgccggtctt gcgatgatta 3600
tcatataatt tctgttgaat tacgttaagc atgtaataat taacatgtaa tgcatgacgt 3660
tatttatgag atgggttttt atgattagag tcccgcaatt atacatttaa tacgcgatag 3720
aaaacaaaat atagcgcgca aactaggata aattatcgcg cgcggtgtca tctatgttac 3780
tagatcggga attggcgagc tcgaattaat tcagtacatt aaaaacgtcc gcaatgtgtt 3840
attaagttgt ctaagcgtca atttgtttac accacaatat atcctgccac cagccagcca 3900
acagctcccc gaccggcagc tcggcacaaa atcaccactc gatacaggca gcccatcagt 3960
ccgggacggc gtcagcggga gagccgttgt aaggcggcag actttgctca tgttaccgat 4020
gctattcgga agaacggcaa ctaagctgcc gggtttgaaa cacggatgat ctcgcggagg 4080
gtagcatgtt gattgtaacg atgacagagc gttgctgcct gtgatcaaat atcatctccc 4140
tcgcagagat ccgaattatc agccttctta ttcatttctc gcttaaccgt gacaggctgt 4200
cgatcttgag aactatgccg acataatagg aaatcgctgg ataaagccgc tgaggaagct 4260
gagtggcgct atttctttag aagtgaacgt tgacgatcgt cgaccgtacc ccgatgaatt 4320
aattcggacg tacgttctga acacagctgg atacttactt gggcgattgt catacatgac 4380
atcaacaatg tacccgtttg tgtaaccgtc tcttggaggt tcgtatgaca ctagtggttc 4440
ccctcagctt gcgactagat gttgaggcct aacattttat tagagagcag gctagttgct 4500
tagatacatg atcttcaggc cgttatctgt cagggcaagc gaaaattggc catttatgac 4560
gaccaatgcc ccgcagaagc tcccatcttt gccgccatag acgccgcgcc cccttttgg 4620
ggtgtagaac atccttttgc cagatgtgga aaagaagttc gttgtcccat tgttggcaat 4680
gacgtagtag ccggcgaaag tgcgagaccc atttgcgcta tatataagcc tacgatttcc 4740
gttgcgacta ttgtcgtaat tggatgaact attatcgtag ttgctctcag agttgtcgta 4800
atttgatgga ctattgtcgt aattgcttat ggagttgtcg tagttgcttg gagaaatgtc 4860
gtagttggat ggggagtagt catagggaag acgagcttca tccactaaaa caattggcag 4920
gtcagcaagt gcctgccccg atgccatcgc aagtacgagg cttagaacca ccttcaacag 4980

```
atcgcgcata gtcttcccca gctctctaac gcttgagtta agccgcgccg cgaagcggcg   5040
tcggcttgaa cgaattgtta gacattattt gccgactacc ttggtgatct cgcctttcac   5100
gtagtgaaca aattcttcca actgatctgc gcgcgaggcc aagcgatctt cttgtccaag   5160
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
agtcgatact tcggcgatca ccgcttccct catgatgttt aactcctgaa ttaagccgcg   5880
ccgcgaagcg gtgtcggctt gaatgaattg ttaggcgtca tcctgtgctc ccgagaacca   5940
gtaccagtac atcgctgttt cgttcgagac ttgaggtcta gttttatacg tgaacaggtc   6000
aatgccgccg agagtaaagc cacattttgc gtacaaattg caggcaggta cattgttcgt   6060
ttgtgtctct aatcgtatgc caaggagctg tctgcttagt gcccactttt tcgcaaattc   6120
gatgagactg tgcgcgactc ctttgcctcg gtgcgtgtgc gacacaacaa tgtgttcgat   6180
agaggctaga tcgttccatg ttgagttgag ttcaatcttc ccgacaagct cttggtcgat   6240
gaatgcgcca tagcaagcag agtcttcatc agagtcatca tccgagatgt aatccttccg   6300
gtaggggctc acacttctgg tagatagttc aaagccttgg tcggataggt gcacatcgaa   6360
cacttcacga acaatgaaat ggttctcagc atccaatgtt tccgccacct gctcagggat   6420
caccgaaatc ttcatatgac gcctaacgcc tggcacagcg gatcgcaaac ctggcgcggc   6480
ttttggcaca aaaggcgtga caggtttgcg aatccgttgc tgccacttgt taaccctttt   6540
gccagatttg gtaactataa tttatgttag aggcgaagtc ttgggtaaaa actggcctaa   6600
aattgctggg gatttcagga aagtaaacat caccttccgg ctcgatgtct attgtagata   6660
tatgtagtgt atctacttga tcgggggatc tgctgcctcg cgcgtttcgg tgatgacggt   6720
gaaaacctct gacacatgca gctcccggag acggtcacag cttgtctgta agcggatgcc   6780
gggagcagac aagcccgtca gggcgcgtca gcgggtgttg gcgggtgtcg gggcgcagcc   6840
atgacccagt cacgtagcga tagcggagtg tatactggct taactatgcg gcatcagagc   6900
agattgtact gagagtgcac catatgcggt gtgaaatacc gcacagatgc gtaaggagaa   6960
aataccgcat caggcgctct tccgcttcct cgctcactga ctcgctgcgc tcggtcgttc   7020
ggctgcggcg agcggtatca gctcactcaa aggcggtaat acggttatcc acagaatcag   7080
gggataacgc aggaaagaac atgtgagcaa aaggccagca aaaggccagg aaccgtaaaa   7140
aggccgcgtt gctggcgttt ttccataggc tccgcccccc tgacgagcat cacaaaaatc   7200
gacgctcaag tcagaggtgg cgaaacccga caggactata aagataccag gcgtttcccc   7260
ctggaagctc cctcgtgcgc tctcctgttc cgaccctgcc gcttaccgga tacctgtccg   7320
cctttctccc ttcgggaagc gtggcgcttt ctcatagctc acgctgtagg tatctcagtt   7380
```

cggtgtaggt cgttcgctcc aagctgggct gtgtgcacga accccccgtt cagcccgacc 7440
gctgcgcctt atccggtaac tatcgtcttg agtccaaccc ggtaagacac gacttatcgc 7500
cactggcagc agccactggt aacaggatta gcagagcgag gtatgtaggc ggtgctacag 7560
agttcttgaa gtggtggcct aactacggct acactagaag gacagtattt ggtatctgcg 7620
ctctgctgaa gccagttacc ttcggaaaaa gagttggtag ctcttgatcc ggcaaacaaa 7680
ccaccgctgg tagcggtggt ttttttgttt gcaagcagca gattacgcgc agaaaaaaag 7740
gatctcaaga agatcctttg atcttttcta cggggtctga cgctcagtgg aacgaaaact 7800
cacgttaagg gattttggtc atgagattat caaaaaggat cttcacctag atccttttaa 7860
attaaaaatg aagttttaaa tcaatctaaa gtatatatga gtaaacttgg tctgacagtt 7920
accaatgctt aatcagtgag gcacctatct cagcgatctg tctatttcgt tcatccatag 7980
ttgcctgact ccccgtcgtg tagataacta cgatacggga gggcttacca tctggcccca 8040
gtgctgcaat gataccgcga gacccacgct caccggctcc agatttatca gcaataaacc 8100
agccagccgg aagggccgag cgcagaagtg gtcctgcaac tttatccgcc tccatccagt 8160
ctattaattg ttgccgggaa gctagagtaa gtagttcgcc agttaatagt ttgcgcaacg 8220
ttgttgccat tgctgcaggg gggggggggg gggggttcca ttgttcattc cacggacaaa 8280
aacagagaaa ggaaacgaca gaggccaaaa agctcgcttt cagcacctgt cgtttccttt 8340
cttttcagag ggtattttaa ataaaaacat taagttatga cgaagaagaa cggaaacgcc 8400
ttaaaccgga aaattttcat aaatagcgaa aacccgcgag gtcgccgccc cgtaacctgt 8460
cggatcaccg gaaaggaccc gtaaagtgat aatgattatc atctacatat cacaacgtgc 8520
gtggaggcca tcaaaccacg tcaaataatc aattatgacg caggtatcgt attaattgat 8580
ctgcatcaac ttaacgtaaa aacaacttca gacaatacaa atcagcgaca ctgaatacgg 8640
ggcaacctca tgtccccccc cccccccccc tgcaggcatc gtggtgtcac gctcgtcgtt 8700
tggtatggct tcattcagct ccggttccca acgatcaagg cgagttacat gatcccccat 8760
gttgtgcaaa aaagcggtta gctccttcgg tcctccgatc gttgtcagaa gtaagttggc 8820
cgcagtgtta tcactcatgg ttatggcagc actgcataat tctcttactg tcatgccatc 8880
cgtaagatgc ttttctgtga ctggtgagta ctcaaccaag tcattctgag aatagtgtat 8940
gcggcgaccg agttgctctt gcccggcgtc aacacgggat aataccgcgc cacatagcag 9000
aactttaaaa gtgctcatca ttggaaaacg ttcttcgggg cgaaaactct caaggatctt 9060
accgctgttg agatccagtt cgatgtaacc cactcgtgca cccaactgat cttcagcatc 9120
ttttactttc accagcgttt ctgggtgagc aaaaacagga aggcaaaatg ccgcaaaaaa 9180
gggaataagg gcgacacgga aatgttgaat actcatactc ttcctttttc aatattattg 9240
aagcatttat cagggttatt gtctcatgag cggatacata tttgaatgta tttagaaaaa 9300
taaacaaata ggggttccgc gcacatttcc ccgaaaagtg ccacctgacg tctaagaaac 9360
cattattatc atgacattaa cctataaaaa taggcgtatc acgaggccct ttcgtcttca 9420
agaattggtc gacgatcttg ctgcgttcgg atattttcgt ggagttcccg ccacagaccc 9480
ggattgaagg cgagatccag caactcgcgc cagatcatcc tgtgacggaa ctttggcgcg 9540
tgatgactgg ccaggacgtc ggccgaaaga gcgacaagca gatcacgctt ttcgacagcg 9600
tcggatttgc gatcgaggat ttttcggcgc tgcgctacgt ccgcgaccgc gttgagggat 9660
caagccacag cagcccactc gaccttctag ccgacccaga cgagccaagg gatcttttg 9720

-continued

```
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc ttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac cttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ccggccaggc tgagggagct gagggccggc ccggccccgg  11700
ccaggctgag ggagctgagg gccggcccgg ccccggccag gctgagggag ctgaggggca  11760
gcggcggcag cggcggcgtg gacccgttcg agaggaacaa gatcctgggc aggggcatca  11820
acatcggcaa cgccctggag gccccgaacg agggcgactg ggggcgtggtg atcaaggacg  11880
agttcttcga catcatcaag gaggccggct tcagccacgt gagaatcccg atcaggtgga  11940
gcacccacgc ccaggccttc ccgccgtaca agatcgagcc gagcttcttc aagagggtgg  12000
acgaggtgat caacggcgcc ctgaagaggg gcctggccgt ggtgatcaac atccaccact  12060
acgaggagct gatgaacgac ccggaggagc acaaggagag gttcctggcc ctgtggaagc  12120
```

```
agatcgccga caggtacaag gactacccgg agaccctgtt cttcgagatc ctgaacgagc  12180

cgcacggcaa cctgaccccg gagaagtgga acgagctgct ggaggaggcc ctgaaggtga  12240

tcaggagcat cgacaagaag cacaccgtga tcatcggcac cgccgagtgg ggcggcatca  12300

gcgccctgga gaagctgagg gtgccgaagt gggagaagaa cgccatcgtg accatccact  12360

actacaaccc gttcgagttc acccaccagg gcgccgagtg ggtgccgggc agcgagaagt  12420

ggctgggcag gaagtggggc agcccggacg accagaagca cctgatcgag gagttcaact  12480

tcatcgagga gtggagcaag aagaacaaga ggccgatcta catcggcgag ttcggcgcct  12540

acaggaaggc cgacctggag agcaggatca agtggaccag cttcgtggtg agggaggccg  12600

agaagagggg ctggagctgg gcctactggg agttctgcag cggcttcggc gtgtacgacc  12660

cgctgaggaa gcagtggaac aaggacctgc tggaggccct gatcggcggc gacagcatcg  12720

agaaggacga gctgtaac                                                12738
```

<210> SEQ ID NO 76
<211> LENGTH: 11825
<212> TYPE: DNA
<213> ORGANISM: Artificial Sequence
<220> FEATURE:
<223> OTHER INFORMATION: Synthetic construct, pAG4981

<400> SEQUENCE: 76

```
ctaggtcccc gaatttcccc gatcgttcaa acatttggca ataaagtttc ttaagattga     60

atcctgttgc cggtcttgcg atgattatca tataatttct gttgaattac gttaagcatg    120

taataattaa catgtaatgc atgacgttat ttatgagatg ggtttttatg attagagtcc    180

cgcaattata catttaatac gcgatagaaa acaaaatata gcgcgcaaac taggataaat    240

tatcgcgcgc ggtgtcatct atgttactag atcgggaatt ggaattcctg cagtgcagcg    300

tgacccggtc gtgcccctct ctagagataa tgagcattgc atgtctaagt tataaaaaat    360

taccacatat ttttttgtc acacttgttt gaagtgcagt ttatctatct ttatacatat    420

atttaaactt tactctacga ataatataat ctatagtact acaataatat cagtgtttta    480

gagaatcata taaatgaaca gttagacatg gtctaaagga caattgagta ttttgacaac    540

aggactctac agttttatct ttttagtgtg catgtgttct cctttttttt tgcaaatagc    600

ttcacctata taatacttca tccattttat tagtacatcc atttagggtt tagggttaat    660

ggtttttata gactaatttt tttagtacat ctattttatt ctattttagc ctctaaatta    720

agaaaactaa aactctattt tagttttttt atttaataat ttagatataa aatagaataa    780

aataaagtga ctaaaaatta aacaaatacc ctttaagaaa ttaaaaaaac taaggaaaca    840

tttttcttgt ttcgagtaga taatgccagc ctgttaaacg ccgtcgacga gtctaacgga    900

caccaaccag cgaaccagca gcgtcgcgtc gggccaagcg aagcagacgg cacggcatct    960

ctgtcgctgc ctctggaccc ctctcgagag ttccgctcca ccgttggact tgctccgctg   1020

tcggcatcca gaaattgcgt ggcggagcgg cagacgtgag ccggcacggc aggcggcctc   1080

ctcctcctct cacggcacgg cagctacggg ggattccttt cccaccgctc cttcgctttc   1140

ccttcctcgc ccgccgtaat aaatagacac cccctccaca ccctctttcc ccaacctcgt   1200

gttgttcgga gcgcacacac acacaaccag atctccccca aatccacccg tcggcacctc   1260

cgcttcaagg tacgccgctc gtcctccccc cccccccctc tctaccttct ctagatcggc   1320

gttccggtcc atggttaggg cccggtagtt ctacttctgt tcatgtttgt gttagatccg   1380
```

-continued

```
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
ttttttgtct tggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
tttcactgcg tgatgtgatt gagagtgata aatcgactct gctcggagag gccgttgcca   2520
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
gtatcccgat ggatgccgcc gagcgtaact ataaagatcc taaccacaag ccggagctgg   2700
tttttgcgct gacgcctttc cttgcgatga acgcgtttcg tgaattttcc gagattgtct   2760
ccctactcca gccggtcgca ggtgcacatc cggcgattgc tcacttttta caacagcctg   2820
atgccgaacg tttaagcgaa ctgttcgcca gcctgttgaa tatgcagggt gaagaaaaat   2880
cccgcgcgct ggcgatttta aaatcggccc tcgatagcca gcagggtgaa ccgtggcaaa   2940
cgattcgttt aatttctgaa ttttacccgg aagacagcgg tctgttctcc ccgctattgc   3000
tgaatgtggt gaaattgaac cctggcgaag cgatgttcct gttcgctgaa acaccgcacg   3060
cttacctgca aggcgtggcg ctggaagtga tggcaaactc cgataacgtg ctgcgtgcgg   3120
gtctgacgcc taaatacatt gatattccgg aactggttgc caatgtgaaa ttcgaagcca   3180
aaccggctaa ccagttgttg acccagccgg tgaaacaagg tgcagaactg gacttcccga   3240
ttccagtgga tgattttgcc ttctcgctgc atgaccttag tgataaagaa accaccatta   3300
gccagcagag tgccgccatt ttgttctgcg tcgaaggcga tgcaacgttg tggaaaggtt   3360
ctcagcagtt acagcttaaa ccgggtgaat cagcgtttat tgccgccaac gaatcaccgg   3420
tgactgtcaa aggccacggc cgtttagcgc gtgtttacaa caagctgtaa gagcttactg   3480
aaaaaattaa catctcttgc taagctggga gctctagatc cccgaatttc cccgatcgtt   3540
caaacatttg gcaataaagt ttcttaagat tgaatcctgt tgccggtctt gcgatgatta   3600
tcatataatt tctgttgaat tacgttaagc atgtaataat taacatgtaa tgcatgacgt   3660
tatttatgag atgggttttt atgattagag tcccgcaatt atacatttaa tacgcgatag   3720
aaaacaaaat atagcgcgca aactaggata aattatcgcg cgcggtgtca tctatgttac   3780
```

-continued

```
tagatcggga attggcgagc tcgaattaat tcagtacatt aaaaacgtcc gcaatgtgtt   3840
attaagttgt ctaagcgtca atttgtttac accacaatat atcctgccac cagccagcca   3900
acagctcccc gaccggcagc tcggcacaaa atcaccactc gatacaggca gcccatcagt   3960
ccgggacggc gtcagcggga gagccgttgt aaggcggcag actttgctca tgttaccgat   4020
gctattcgga agaacggcaa ctaagctgcc gggtttgaaa cacggatgat ctcgcggagg   4080
gtagcatgtt gattgtaacg atgacagagc gttgctgcct gtgatcaaat atcatctccc   4140
tcgcagagat ccgaattatc agccttctta ttcatttctc gcttaaccgt gacaggctgt   4200
cgatcttgag aactatgccg acataatagg aaatcgctgg ataaagccgc tgaggaagct   4260
gagtggcgct atttctttag aagtgaacgt tgacgatcgt cgaccgtacc ccgatgaatt   4320
aattcggacg tacgttctga acacagctgg atacttactt gggcgattgt catacatgac   4380
atcaacaatg tacccgtttg tgtaaccgtc tcttggaggt tcgtatgaca ctagtggttc   4440
ccctcagctt gcgactagat gttgaggcct aacattttat tagagagcag gctagttgct   4500
tagatacatg atcttcaggc cgttatctgt cagggcaagc gaaaattggc catttatgac   4560
gaccaatgcc ccgcagaagc tcccatcttt gccgccatag acgccgcgcc cccttttgg    4620
ggtgtagaac atccttttgc cagatgtgga aaagaagttc gttgtcccat tgttggcaat   4680
gacgtagtag ccggcgaaag tgcgagaccc atttgcgcta tatataagcc tacgatttcc   4740
gttgcgacta ttgtcgtaat tggatgaact attatcgtag ttgctctcag agttgtcgta   4800
atttgatgga ctattgtcgt aattgcttat ggagttgtcg tagttgcttg gagaaatgtc   4860
gtagttggat ggggagtagt catagggaag acgagcttca tccactaaaa caattggcag   4920
gtcagcaagt gcctgccccg atgccatcgc aagtacgagg cttagaacca ccttcaacag   4980
atcgcgcata gtcttcccca gctctctaac gcttgagtta agccgcgccg cgaagcggcg   5040
tcggcttgaa cgaattgtta gacattattt gccgactacc ttggtgatct cgcctttcac   5100
gtagtgaaca aattcttcca actgatctgc gcgcgaggcc aagcgatctt cttgtccaag   5160
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
agtcgatact tcggcgatca ccgcttccct catgatgttt aactcctgaa ttaagccgcg   5880
ccgcgaagcg gtgtcggctt gaatgaattg ttaggcgtca tcctgtgctc ccgagaacca   5940
gtaccagtac atcgctgttt cgttcgagac ttgaggtcta gttttatacg tgaacaggtc   6000
aatgccgccg agagtaaagc cacattttgc gtacaaattg caggcaggta cattgttcgt   6060
ttgtgtctct aatcgtatgc caaggagctg tctgcttagt gcccactttt tcgcaaattc   6120
```

-continued gatgagactg tgcgcgactc ctttgcctcg gtgcgtgtgc gacacaacaa tgtgttcgat 6180
agaggctaga tcgttccatg ttgagttgag ttcaatcttc ccgacaagct cttggtcgat 6240
gaatgcgcca tagcaagcag agtcttcatc agagtcatca tccgagatgt aatccttccg 6300
gtaggggctc acacttctgg tagatagttc aaagccttgg tcggataggt gcacatcgaa 6360
cacttcacga acaatgaaat ggttctcagc atccaatgtt tccgccacct gctcagggat 6420
caccgaaatc ttcatatgac gcctaacgcc tggcacagcg gatcgcaaac ctggcgcggc 6480
ttttggcaca aaaggcgtga caggtttgcg aatccgttgc tgccacttgt taaccctttt 6540
gccagatttg gtaactataa tttatgttag aggcgaagtc ttgggtaaaa actggcctaa 6600
aattgctggg gatttcagga aagtaaacat caccttccgg ctcgatgtct attgtagata 6660
tatgtagtgt atctacttga tcgggggatc tgctgcctcg cgcgtttcgg tgatgacggt 6720
gaaaacctct gacacatgca gctcccggag acggtcacag cttgtctgta agcggatgcc 6780
gggagcagac aagcccgtca gggcgcgtca gcgggtgttg gcgggtgtcg gggcgcagcc 6840
atgacccagt cacgtagcga tagcggagtg tatactggct taactatgcg gcatcagagc 6900
agattgtact gagagtgcac catatgcggt gtgaaatacc gcacagatgc gtaaggagaa 6960
aataccgcat caggcgctct tccgcttcct cgctcactga ctcgctgcgc tcggtcgttc 7020
ggctgcggcg agcggtatca gctcactcaa aggcggtaat acggttatcc acagaatcag 7080
gggataacgc aggaaagaac atgtgagcaa aaggccagca aaaggccagg aaccgtaaaa 7140
aggccgcgtt gctggcgttt ttccataggc tccgcccccc tgacgagcat cacaaaaatc 7200
gacgctcaag tcagaggtgg cgaaacccga caggactata aagataccag gcgtttcccc 7260
ctggaagctc cctcgtgcgc tctcctgttc cgaccctgcc gcttaccgga tacctgtccg 7320
cctttctccc ttcgggaagc gtggcgcttt ctcatagctc acgctgtagg tatctcagtt 7380
cggtgtaggt cgttcgctcc aagctgggct gtgtgcacga accccccgtt cagcccgacc 7440
gctgcgcctt atccggtaac tatcgtcttg agtccaaccc ggtaagacac gacttatcgc 7500
cactggcagc agccactggt aacaggatta gcagagcgag gtatgtaggc ggtgctacag 7560
agttcttgaa gtggtggcct aactacggct acactagaag gacagtattt ggtatctgcg 7620
ctctgctgaa gccagttacc ttcggaaaaa gagttggtag ctcttgatcc ggcaaacaaa 7680
ccaccgctgg tagcggtggt ttttttgttt gcaagcagca gattacgcgc agaaaaaaag 7740
gatctcaaga agatcctttg atcttttcta cggggtctga cgctcagtgg aacgaaaact 7800
cacgttaagg gattttggtc atgagattat caaaaaggat cttcacctag atccttttaa 7860
attaaaaatg aagttttaaa tcaatctaaa gtatatatga gtaaacttgg tctgacagtt 7920
accaatgctt aatcagtgag gcacctatct cagcgatctg tctatttcgt tcatccatag 7980
ttgcctgact ccccgtcgtg tagataacta cgatacggga gggcttacca tctggcccca 8040
gtgctgcaat gataccgcga gacccacgct caccggctcc agatttatca gcaataaacc 8100
agccagccgg aagggccgag cgcagaagtg gtcctgcaac tttatccgcc tccatccagt 8160
ctattaattg ttgccgggaa gctagagtaa gtagttcgcc agttaatagt ttgcgcaacg 8220
ttgttgccat tgctgcaggg gggggggggg gggggttcca ttgttcattc cacggacaaa 8280
aacagagaaa ggaaacgaca gaggccaaaa agctcgcttt cagcacctgt cgtttccttt 8340
cttttcagag ggtattttaa ataaaaacat taagttatga cgaagaagaa cggaaacgcc 8400
ttaaaccgga aaattttcat aaatagcgaa aacccgcgag gtcgccgccc cgtaacctgt 8460
cggatcaccg gaaaggaccc gtaaagtgat aatgattatc atctacatat cacaacgtgc 8520

```
gtggaggcca tcaaaccacg tcaaataatc aattatgacg caggtatcgt attaattgat   8580
ctgcatcaac ttaacgtaaa aacaacttca gacaatacaa atcagcgaca ctgaatacgg   8640
ggcaacctca tgtccccccc cccccccccc tgcaggcatc gtggtgtcac gctcgtcgtt   8700
tggtatggct tcattcagct ccggttccca acgatcaagg cgagttacat gatcccccat   8760
gttgtgcaaa aaagcggtta gctccttcgg tcctccgatc gttgtcagaa gtaagttggc   8820
cgcagtgtta tcactcatgg ttatggcagc actgcataat tctcttactg tcatgccatc   8880
cgtaagatgc ttttctgtga ctggtgagta ctcaaccaag tcattctgag aatagtgtat   8940
gcggcgaccg agttgctctt gcccggcgtc aacacgggat aataccgcgc cacatagcag   9000
aactttaaaa gtgctcatca ttggaaaacg ttcttcgggg cgaaaactct caaggatctt   9060
accgctgttg agatccagtt cgatgtaacc cactcgtgca cccaactgat cttcagcatc   9120
ttttactttc accagcgttt ctgggtgagc aaaaacagga aggcaaaatg ccgcaaaaaa   9180
gggaataagg gcgacacgga aatgttgaat actcatactc ttcctttttc aatattattg   9240
aagcatttat cagggttatt gtctcatgag cggatacata tttgaatgta tttagaaaaa   9300
taaacaaata ggggttccgc gcacatttcc ccgaaaagtg ccacctgacg tctaagaaac   9360
cattattatc atgacattaa cctataaaaa taggcgtatc acgaggccct ttcgtcttca   9420
agaattggtc gacgatcttg ctgcgttcgg atattttcgt ggagttcccg ccacagaccc   9480
ggattgaagg cgagatccag caactcgcgc cagatcatcc tgtgacggaa ctttggcgcg   9540
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcctaagc ggccgcattg gacttaatta agtgaggccg gccaagcgtc gatttaaatg  10140
taccacatgg cgcgccaact atcatgcgat cgcttcatgt ctaactcgag ttactggtac  10200
gtaccaaatc catggaatca aggtaccaaa gtaatcatat tattttatgt gtgaatcttc  10260
tttacttttt catttgatta tgattatgaa ggtatgacct tcataacctt cgtccgaaat  10320
ccattatatc caaaggaaaa taatgcttcg aaggacgaag gattttgata tttaacattt  10380
tatgttgcct tgttcttaat tcatagcatt tgagaacaag tccccaacac caatctttat  10440
ctttactata ttaaagcacc agttcaacga tcgtctcgtg tcaatattat taaaaaactc  10500
ctacatttct ttataatcaa cccgcactct tataatctct tctcttacta ctataataag  10560
agagtttatg tacaaaataa ggtgaaatta tgtataagtg ttctggacct tggttgttgg  10620
ctcatattca cacaacctaa tcaatagaaa acatatgttt tattaaaaca aaatttatca  10680
tatatatata tatatatata tatatatata tatatatata taatataaac cgtagcaatg  10740
cacaggcata tgactagtgg caacttaata ccatgtgtgt attaagatga ataagaggta  10800
tccaaataaa taacttgttc gcttacgtct ggatcgaaag ggttggaaa cgattaaatc   10860
```

```
tcttcctagt caaaattaaa tagaaggaga tttaatcgat ttctcccaat ccccttcgat  10920
ccaggtgcaa ccgaataagt ccttaaatgt tgaggaacac gaaacaacca tgcattggca  10980
tgtaaagctc caagaattcg ttgtatcctt aacaactcac agaacatcaa ccaaaattgc  11040
acgtcaaggg tattgggtaa gaaacaatca aacaaatcct ctctgtgtgc aaagaaacac  11100
ggtgagtcat gccgagatca tactcatctg atatacatgc ttacagctca caagacatta  11160
caaacaactc atattgcatt acaaagatcg tttcatgaaa aataaaatag gccggaacag  11220
gacaaaaatc cttgacgtgt aaagtaaatt tacaacaaaa aaaaagccat atgtcaagct  11280
aaatctaatt cgttttacgt agatcaacaa cctgtagaag gcaacaaaac tgagccacgc  11340
agaagtacag aatgattcca gatgaaccat cgacgtgcta cgtaaagaga gtgacgagtc  11400
atatacattt ggcaagaaac catgaagctg cctacagccg tctcggtggc ataagaacac  11460
aagaaattgt gttaattaat caaagctata aataacgctc gcatgcctgt gcacttctcc  11520
atcaccacca ctgggtcttc agaccattag ctttatctac tccagagcgc agaagaaccc  11580
gatcgacacc ggatcctaaa ccatgagggt gttgctcgtt gccctcgctc tcctggctct  11640
cgctgcgagc gccacctccg gctgccagag cgtgagcgag atgctgaggt tctacaccga  11700
cgaggtgctg ccgagggcca tgcagggcgg cggcagcggc ggcggcagca aggccatggg  11760
cgagttcgac atcttcatca actacatcga ggagtacctg ctgatgagga aggacgagct  11820
gtaac                                                              11825
```

<210> SEQ ID NO 77
<211> LENGTH: 12533
<212> TYPE: DNA
<213> ORGANISM: Artificial Sequence
<220> FEATURE:
<223> OTHER INFORMATION: Synthetic construct, pAG4982

<400> SEQUENCE: 77

```
ctaggtcccc gaatttcccc gatcgttcaa acatttggca ataaagtttc ttaagattga     60
atcctgttgc cggtcttgcg atgattatca tataatttct gttgaattac gttaagcatg    120
taataattaa catgtaatgc atgacgttat ttatgagatg ggtttttatg attagagtcc    180
cgcaattata catttaatac gcgatagaaa acaaaatata gcgcgcaaac taggataaat    240
tatcgcgcgc ggtgtcatct atgttactag atcgggaatt ggaattcctg cagtgcagcg    300
tgacccggtc gtgcccctct ctagagataa tgagcattgc atgtctaagt tataaaaaat    360
taccacatat ttttttgtc acacttgttt gaagtgcagt ttatctatct ttatacatat    420
atttaaactt tactctacga ataatataat ctatagtact acaataatat cagtgtttta    480
gagaatcata taaatgaaca gttagacatg gtctaaagga caattgagta ttttgacaac    540
aggactctac agttttatct ttttagtgtg catgtgttct cctttttttt tgcaaatagc    600
ttcacctata taatacttca tccattttat tagtacatcc atttagggtt tagggttaat    660
ggtttttata gactaatttt tttagtacat ctattttatt ctattttagc ctctaaatta    720
agaaaactaa aactctattt tagttttttt atttaataat ttagatataa aatagaataa    780
aataaagtga ctaaaaatta aacaaatacc ctttaagaaa ttaaaaaaac taaggaaaca    840
tttttcttgt ttcgagtaga taatgccagc ctgttaaacg ccgtcgacga gtctaacgga    900
caccaaccag cgaaccagca gcgtcgcgtc gggccaagcg aagcagacgg cacggcatct    960
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
```

-continued

```
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc cccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
tttttgtctt ggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
tttcactgcg tgatgtgatt gagagtgata aatcgactct gctcggagag gccgttgcca   2520
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
gtatcccgat ggatgccgcc gagcgtaact ataaagatcc taaccacaag ccggagctgg   2700
tttttgcgct gacgcctttc cttgcgatga acgcgtttcg tgaattttcc gagattgtct   2760
ccctactcca gccggtcgca ggtgcacatc cggcgattgc tcacttttta caacagcctg   2820
atgccgaacg tttaagcgaa ctgttcgcca gcctgttgaa tatgcagggt gaagaaaaat   2880
cccgcgcgct ggcgatttta aaatcggccc tcgatagcca gcagggtgaa ccgtggcaaa   2940
cgattcgttt aatttctgaa ttttacccgg aagacagcgg tctgttctcc ccgctattgc   3000
tgaatgtggt gaaattgaac cctggcgaag cgatgttcct gttcgctgaa acaccgcacg   3060
cttacctgca aggcgtggcg ctggaagtga tggcaaactc cgataacgtg ctgcgtgcgg   3120
gtctgacgcc taaatacatt gatattccgg aactggttgc caatgtgaaa ttcgaagcca   3180
aaccggctaa ccagttgttg acccagccgg tgaaacaagg tgcagaactg gacttcccga   3240
ttccagtgga tgattttgcc ttctcgctgc atgaccttag tgataaagaa accaccatta   3300
gccagcagag tgccgccatt ttgttctgcg tcgaaggcga tgcaacgttg tggaaaggtt   3360
ctcagcagtt acagcttaaa ccgggtgaat cagcgtttat tgccgccaac gaatcaccgg   3420
```

-continued

```
tgactgtcaa aggccacggc cgtttagcgc gtgtttacaa caagctgtaa gagcttactg   3480
aaaaaattaa catctcttgc taagctggga gctctagatc cccgaatttc cccgatcgtt   3540
caaacatttg gcaataaagt ttcttaagat tgaatcctgt tgccggtctt gcgatgatta   3600
tcatataatt tctgttgaat tacgttaagc atgtaataat taacatgtaa tgcatgacgt   3660
tatttatgag atgggttttt atgattagag tcccgcaatt atacatttaa tacgcgatag   3720
aaaacaaaat atagcgcgca aactaggata aattatcgcg cgcggtgtca tctatgttac   3780
tagatcggga attggcgagc tcgaattaat tcagtacatt aaaaacgtcc gcaatgtgtt   3840
attaagttgt ctaagcgtca atttgtttac accacaatat atcctgccac cagccagcca   3900
acagctcccc gaccggcagc tcggcacaaa atcaccactc gatacaggca gcccatcagt   3960
ccgggacggc gtcagcggga gagccgttgt aaggcggcag actttgctca tgttaccgat   4020
gctattcgga agaacggcaa ctaagctgcc gggtttgaaa cacggatgat ctcgcggagg   4080
gtagcatgtt gattgtaacg atgacagagc gttgctgcct gtgatcaaat atcatctccc   4140
tcgcagagat ccgaattatc agccttctta ttcatttctc gcttaaccgt gacaggctgt   4200
cgatcttgag aactatgccg acataatagg aaatcgctgg ataaagccgc tgaggaagct   4260
gagtggcgct atttctttag aagtgaacgt tgacgatcgt cgaccgtacc ccgatgaatt   4320
aattcggacg tacgttctga acacagctgg atacttactt gggcgattgt catacatgac   4380
atcaacaatg tacccgtttg tgtaaccgtc tcttggaggt tcgtatgaca ctagtggttc   4440
ccctcagctt gcgactagat gttgaggcct aacattttat tagagagcag gctagttgct   4500
tagatacatg atcttcaggc cgttatctgt cagggcaagc gaaaattggc catttatgac   4560
gaccaatgcc ccgcagaagc tcccatcttt gccgccatag acgccgcgcc cccttttgg   4620
ggtgtagaac atccttttgc cagatgtgga aaagaagttc gttgtcccat tgttggcaat   4680
gacgtagtag ccggcgaaag tgcgagaccc atttgcgcta tatataagcc tacgatttcc   4740
gttgcgacta ttgtcgtaat tggatgaact attatcgtag ttgctctcag agttgtcgta   4800
atttgatgga ctattgtcgt aattgcttat ggagttgtcg tagttgcttg gagaaatgtc   4860
gtagttggat ggggagtagt catagggaag acgagcttca tccactaaaa caattggcag   4920
gtcagcaagt gcctgccccg atgccatcgc aagtacgagg cttagaacca ccttcaacag   4980
atcgcgcata gtcttcccca gctctctaac gcttgagtta agccgcgccg cgaagcggcg   5040
tcggcttgaa cgaattgtta gacattattt gccgactacc ttggtgatct cgcctttcac   5100
gtagtgaaca aattcttcca actgatctgc gcgcgaggcc aagcgatctt cttgtccaag   5160
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
```

agtcgatact tcggcgatca ccgcttccct catgatgttt aactcctgaa ttaagccgcg 5880
ccgcgaagcg gtgtcggctt gaatgaattg ttaggcgtca tcctgtgctc ccgagaacca 5940
gtaccagtac atcgctgttt cgttcgagac ttgaggtcta gttttatacg tgaacaggtc 6000
aatgccgccg agagtaaagc cacattttgc gtacaaattg caggcaggta cattgttcgt 6060
ttgtgtctct aatcgtatgc caaggagctg tctgcttagt gcccactttt tcgcaaattc 6120
gatgagactg tgcgcgactc ctttgcctcg gtgcgtgtgc gacacaacaa tgtgttcgat 6180
agaggctaga tcgttccatg ttgagttgag ttcaatcttc ccgacaagct cttggtcgat 6240
gaatgcgcca tagcaagcag agtcttcatc agagtcatca tccgagatgt aatccttccg 6300
gtaggggctc acacttctgg tagatagttc aaagccttgg tcggataggt gcacatcgaa 6360
cacttcacga acaatgaaat ggttctcagc atccaatgtt tccgccacct gctcagggat 6420
caccgaaatc ttcatatgac gcctaacgcc tggcacagcg gatcgcaaac ctggcgcggc 6480
ttttggcaca aaaggcgtga caggtttgcg aatccgttgc tgccacttgt taaccctttt 6540
gccagatttg gtaactataa tttatgttag aggcgaagtc ttgggtaaaa actggcctaa 6600
aattgctggg gatttcagga aagtaaacat caccttccgg ctcgatgtct attgtagata 6660
tatgtagtgt atctacttga tcgggggatc tgctgcctcg cgcgtttcgg tgatgacggt 6720
gaaaacctct gacacatgca gctcccggag acggtcacag cttgtctgta agcggatgcc 6780
gggagcagac aagcccgtca gggcgcgtca gcgggtgttg gcgggtgtcg gggcgcagcc 6840
atgacccagt cacgtagcga tagcggagtg tatactggct taactatgcg gcatcagagc 6900
agattgtact gagagtgcac catatgcggt gtgaaatacc gcacagatgc gtaaggagaa 6960
aataccgcat caggcgctct tccgcttcct cgctcactga ctcgctgcgc tcggtcgttc 7020
ggctgcggcg agcggtatca gctcactcaa aggcggtaat acggttatcc acagaatcag 7080
gggataacgc aggaaagaac atgtgagcaa aaggccagca aaaggccagg aaccgtaaaa 7140
aggccgcgtt gctggcgttt ttccataggc tccgcccccc tgacgagcat cacaaaaatc 7200
gacgctcaag tcagaggtgg cgaaacccga caggactata aagataccag gcgtttcccc 7260
ctggaagctc cctcgtgcgc tctcctgttc cgaccctgcc gcttaccgga tacctgtccg 7320
cctttctccc ttcgggaagc gtggcgcttt ctcatagctc acgctgtagg tatctcagtt 7380
cggtgtaggt cgttcgctcc aagctgggct gtgtgcacga accccccgtt cagcccgacc 7440
gctgcgcctt atccggtaac tatcgtcttg agtccaaccc ggtaagacac gacttatcgc 7500
cactggcagc agccactggt aacaggatta gcagagcgag gtatgtaggc ggtgctacag 7560
agttcttgaa gtggtggcct aactacggct acactagaag gacagtattt ggtatctgcg 7620
ctctgctgaa gccagttacc ttcggaaaaa gagttggtag ctcttgatcc ggcaaacaaa 7680
ccaccgctgg tagcggtggt ttttttgttt gcaagcagca gattacgcgc agaaaaaaag 7740
gatctcaaga agatcctttg atcttttcta cggggtctga cgctcagtgg aacgaaaact 7800
cacgttaagg gattttggtc atgagattat caaaaaggat cttcacctag atccttttaa 7860
attaaaaatg aagttttaaa tcaatctaaa gtatatatga gtaaacttgg tctgacagtt 7920
accaatgctt aatcagtgag gcacctatct cagcgatctg tctatttcgt tcatccatag 7980
ttgcctgact ccccgtcgtg tagataacta cgatacggga gggcttacca tctggcccca 8040
gtgctgcaat gataccgcga gacccacgct caccggctcc agatttatca gcaataaacc 8100
agccagccgg aagggccgag cgcagaagtg gtcctgcaac tttatccgcc tccatccagt 8160

```
ctattaattg ttgccgggaa gctagagtaa gtagttcgcc agttaatagt ttgcgcaacg   8220
ttgttgccat tgctgcaggg gggggggggg gggggttcca ttgttcattc cacggacaaa   8280
aacagagaaa ggaaacgaca gaggccaaaa agctcgcttt cagcacctgt cgtttccttt   8340
cttttcagag ggtattttaa ataaaaacat taagttatga cgaagaagaa cggaaacgcc   8400
ttaaaccgga aattttcat aaatagcgaa aacccgcgag gtcgccgccc cgtaacctgt   8460
cggatcaccg gaaaggaccc gtaaagtgat aatgattatc atctacatat cacaacgtgc   8520
gtggaggcca tcaaaccacg tcaaataatc aattatgacg caggtatcgt attaattgat   8580
ctgcatcaac ttaacgtaaa aacaacttca gacaatacaa atcagcgaca ctgaatacgg   8640
ggcaacctca tgtccccccc cccccccccc tgcaggcatc gtggtgtcac gctcgtcgtt   8700
tggtatggct tcattcagct ccggttccca acgatcaagg cgagttacat gatcccccat   8760
gttgtgcaaa aaagcggtta gctccttcgg tcctccgatc gttgtcagaa gtaagttggc   8820
cgcagtgtta tcactcatgg ttatggcagc actgcataat tctcttactg tcatgccatc   8880
cgtaagatgc ttttctgtga ctggtgagta ctcaaccaag tcattctgag aatagtgtat   8940
gcggcgaccg agttgctctt gcccggcgtc aacacgggat aataccgcgc cacatagcag   9000
aactttaaaa gtgctcatca ttggaaaacg ttcttcgggg cgaaaactct caaggatctt   9060
accgctgttg agatccagtt cgatgtaacc cactcgtgca cccaactgat cttcagcatc   9120
ttttactttc accagcgttt ctgggtgagc aaaaacagga aggcaaaatg ccgcaaaaaa   9180
gggaataagg gcgacacgga aatgttgaat actcatactc ttcctttttc aatattattg   9240
aagcatttat cagggttatt gtctcatgag cggatacata tttgaatgta tttagaaaaa   9300
taaacaaata ggggttccgc gcacatttcc ccgaaaagtg ccacctgacg tctaagaaac   9360
cattattatc atgacattaa cctataaaaa taggcgtatc acgaggccct ttcgtcttca   9420
agaattggtc gacgatcttg ctgcgttcgg atattttcgt ggagttcccg ccacagaccc   9480
ggattgaagg cgagatccag caactcgcgc cagatcatcc tgtgacggaa ctttggcgcg   9540
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcctaagc ggccgcattg gacttaatta agtgaggccg gccaagcgtc gatttaaatg  10140
taccacatgg cgcgccaact atcatgcgat cgcttcatgt ctaactcgag ttactggtac  10200
gtaccaaatc catggaatca aggtacctcc atgctgtcct actacttgct tcatcccctt  10260
ctacattttg ttctggtttt tggcctgcat ttcggatcat gatgtatgtg atttccaatc  10320
tgctgcaata tgaatggaga ctctgtgcta accatcaaca acatgaaatg cttatgaggc  10380
ctttgctgag cagccaatct tgcctgtgtt tatgtcttca caggccgaat tcctctgttt  10440
tgtttttcac cctcaatatt tggaaacatt tatctaggtt gtttgtgtcc aggcctataa  10500
atcatacatg atgttgtcgt attggatgtg aatgtggtgg cgtgttcagt gccttggatt  10560
```

tgagtttgat gagagttgct tctgggtcac cactcaccat tatcgatgct cctcttcagc 10620
ataaggtaaa agtcttccct gtttacgtta ttttacccac tatggttgct tgggttggtt 10680
ttttcctgat tgcttatgcc atggaaagtc atttgatatg ttgaacttga attaactgta 10740
gaattgtata catgttccat ttgtgttgta cttccttctt ttctattagt agcctcagat 10800
gagtgtgaaa aaaacagatt atataacttg ccctataaat catttgaaaa aaatattgta 10860
cagtgagaaa ttgatatata gtgaattttt aagagcatgt tttcctaaag aagtatatat 10920
tttctatgta caaaggccat tgaagtaatt gtagatacag gataatgtag actttttgga 10980
cttacactgc tacctttaag taacaatcat gagcaatagt gttgcaatga tatttaggct 11040
gcattcgttt actctcttga tttccatgag cacgcttccc aaactgttaa actctgtgtt 11100
ttttgccaaa aaaaaatgca taggaaagtt gcttttaaaa aatcatatca atccattttt 11160
taagttatag ctaatactta attaatcatg cgctaataag tcactctgtt tttcgtacta 11220
gagagattgt tttgaaccag cactcaagaa cacagcctta acccagccaa ataatgctac 11280
aacctaccag tccacacctc ttgtaaagca tttgttgcat ggaaaagcta agatgacagc 11340
aacctgttca ggaaaacaac tgacaaggtc atagggagag ggagcttttg gaaaggtgcc 11400
gtgcagttca aacaattagt tagcagtagg gtgttggttt ttgctcacag caataagaag 11460
ttaatcatgg tgtaggcaac ccaaataaaa caccaaaata tgcacaaggc agtttgttgt 11520
attctgtagt acagacaaaa ctaaaagtaa tgaaagaaga tgtggtgtta gaaaaggaaa 11580
caatatcatg agtaatgtgt gggcattatg ggaccacgaa ataaaaagaa cattttgatg 11640
agtcgtgtat cctcgatgag cctcaaaagt tctctcaccc cggataagaa acccttaagc 11700
aatgtgcaaa gtttgcattc tccactgaca taatgcaaaa taagatatca tcgatgacat 11760
agcaactcat gcatcatatc atgcctctct caacctattc attcctactc atctacataa 11820
gtatcttcag ctaaatgtta gaacataaac ccataagtca cgtttgatga gtattaggcg 11880
tgacacatga caaatcacag actcaagcaa gataaagcaa aatgatgtgt acataaaact 11940
ccagagctat atgtcatatt gcaaaaagag gagagcttat aagacaaggc atgactcaca 12000
aaaattcatt tgcctttcgt gtcaaaaaga ggagggcttt acattatcca tgtcatattg 12060
caaaagaaag agagaaagaa caacacaatg ctgcgtcaat tatacatatc tgtatgtcca 12120
tcattattca tccacctttc gtgtaccaca cttcatatat catgagtcac ttcatgtctg 12180
gacattaaca aactctatct taacatttag atgcaagagc ctttatctca ctataaatgc 12240
acgatgattt ctcattgttt ctcacaaaaa gcattcagtt cattagtcct acaacaacgg 12300
atcctaaacc atgagggtgt tgctcgttgc cctcgctctc ctggctctcg ctgcgagcgc 12360
cacctccggc tgccagagcg tgagcgagat gctgaggttc tacaccgacg aggtgctgcc 12420
gagggccatg cagggcggcg gcagcggcgg cggcagcaag gccatgggcg agttcgacat 12480
cttcatcaac tacatcgagg agtacctgct gatgaggaag gacgagctgt aac 12533

<210> SEQ ID NO 78
<211> LENGTH: 13466
<212> TYPE: DNA
<213> ORGANISM: Artificial Sequence
<220> FEATURE:
<223> OTHER INFORMATION: Synthetic construct, pAG4983

<400> SEQUENCE: 78
ctaggtcccc gaatttcccc gatcgttcaa acatttggca ataaagtttc ttaagattga 60

-continued

```
atcctgttgc cggtcttgcg atgattatca tataatttct gttgaattac gttaagcatg    120
taataattaa catgtaatgc atgacgttat ttatgagatg ggtttttatg attagagtcc    180
cgcaattata catttaatac gcgatagaaa acaaaatata gcgcgcaaac taggataaat    240
tatcgcgcgc ggtgtcatct atgttactag atcgggaatt ggaattcctg cagtgcagcg    300
tgacccggtc gtgcccctct ctagagataa tgagcattgc atgtctaagt tataaaaaat    360
taccacatat ttttttgtc acacttgttt gaagtgcagt ttatctatct ttatacatat    420
atttaaactt tactctacga ataatataat ctatagtact acaataatat cagtgtttta    480
gagaatcata taaatgaaca gttagacatg gtctaaagga caattgagta ttttgacaac    540
aggactctac agttttatct ttttagtgtg catgtgttct cctttttttt tgcaaatagc    600
ttcacctata taatacttca tccattttat tagtacatcc atttagggtt tagggttaat    660
ggtttttata gactaatttt tttagtacat ctattttatt ctattttagc ctctaaatta    720
agaaaactaa aactctattt tagttttttt atttaataat ttagatataa aatagaataa    780
aataaagtga ctaaaaatta aacaaatacc ctttaagaaa ttaaaaaaac taaggaaaca    840
tttttcttgt ttcgagtaga taatgccagc ctgttaaacg ccgtcgacga gtctaacgga    900
caccaaccag cgaaccagca gcgtcgcgtc gggccaagcg aagcagacgg cacggcatct    960
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc cccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
ttttttgtct tggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
```

```
tttcactgcg tgatgtgatt gagagtgata aatcgactct gctcggagag gccgttgcca   2520
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
gtatcccgat ggatgccgcc gagcgtaact ataaagatcc taaccacaag ccggagctgg   2700
tttttgcgct gacgcctttc cttgcgatga acgcgtttcg tgaattttcc gagattgtct   2760
ccctactcca gccggtcgca ggtgcacatc cggcgattgc tcactttta caacagcctg   2820
atgccgaacg tttaagcgaa ctgttcgcca gcctgttgaa tatgcagggt gaagaaaaat   2880
cccgcgcgct ggcgatttta aaatcggccc tcgatagcca gcagggtgaa ccgtggcaaa   2940
cgattcgttt aatttctgaa ttttacccgg aagacagcgg tctgttctcc ccgctattgc   3000
tgaatgtggt gaaattgaac cctggcgaag cgatgttcct gttcgctgaa acaccgcacg   3060
cttacctgca aggcgtggcg ctggaagtga tggcaaactc cgataacgtg ctgcgtgcgg   3120
gtctgacgcc taaatacatt gatattccgg aactggttgc caatgtgaaa ttcgaagcca   3180
aaccggctaa ccagttgttg acccagccgg tgaaacaagg tgcagaactg gacttcccga   3240
ttccagtgga tgattttgcc ttctcgctgc atgaccttag tgataaagaa accaccatta   3300
gccagcagag tgccgccatt ttgttctgcg tcgaaggcga tgcaacgttg tggaaaggtt   3360
ctcagcagtt acagcttaaa ccgggtgaat cagcgtttat tgccgccaac gaatcaccgg   3420
tgactgtcaa aggccacggc cgtttagcgc gtgtttacaa caagctgtaa gagcttactg   3480
aaaaaattaa catctcttgc taagctggga gctctagatc cccgaatttc cccgatcgtt   3540
caaacatttg gcaataaagt ttcttaagat tgaatcctgt tgccggtctt gcgatgatta   3600
tcatataatt tctgttgaat tacgttaagc atgtaataat taacatgtaa tgcatgacgt   3660
tatttatgag atgggttttt atgattagag tcccgcaatt atacatttaa tacgcgatag   3720
aaaacaaaat atagcgcgca aactaggata aattatcgcg cgcggtgtca tctatgttac   3780
tagatcggga attggcgagc tcgaattaat tcagtacatt aaaaacgtcc gcaatgtgtt   3840
attaagttgt ctaagcgtca atttgtttac accacaatat atcctgccac cagccagcca   3900
acagctcccc gaccggcagc tcggcacaaa atcaccactc gatacaggca gcccatcagt   3960
ccgggacggc gtcagcggga gagccgttgt aaggcggcag actttgctca tgttaccgat   4020
gctattcgga agaacggcaa ctaagctgcc gggtttgaaa cacggatgat ctcgcggagg   4080
gtagcatgtt gattgtaacg atgacagagc gttgctgcct gtgatcaaat atcatctccc   4140
tcgcagagat ccgaattatc agccttctta ttcatttctc gcttaaccgt gacaggctgt   4200
cgatcttgag aactatgccg acataatagg aaatcgctgg ataaagccgc tgaggaagct   4260
gagtggcgct atttctttag aagtgaacgt tgacgatcgt cgaccgtacc ccgatgaatt   4320
aattcggacg tacgttctga acacagctgg atacttactt gggcgattgt catacatgac   4380
atcaacaatg tacccgtttg tgtaaccgtc tcttggaggt tcgtatgaca ctagtggttc   4440
ccctcagctt gcgactagat gttgaggcct aacattttat tagagagcag gctagttgct   4500
tagatacatg atcttcaggc cgttatctgt cagggcaagc gaaaattggc catttatgac   4560
gaccaatgcc ccgcagaagc tcccatcttt gccgccatag acgccgcgcc cccttttgg   4620
ggtgtagaac atccttttgc cagatgtgga aaagaagttc gttgtcccat tgttggcaat   4680
gacgtagtag ccggcgaaag tgcgagaccc atttgcgcta tatataagcc tacgatttcc   4740
gttgcgacta ttgtcgtaat tggatgaact attatcgtag ttgctctcag agttgtcgta   4800
```

-continued

```
atttgatgga ctattgtcgt aattgcttat ggagttgtcg tagttgcttg gagaaatgtc   4860
gtagttggat ggggagtagt catagggaag acgagcttca tccactaaaa caattggcag   4920
gtcagcaagt gcctgccccg atgccatcgc aagtacgagg cttagaacca ccttcaacag   4980
atcgcgcata gtcttcccca gctctctaac gcttgagtta agccgcgccg cgaagcggcg   5040
tcggcttgaa cgaattgtta gacattattt gccgactacc ttggtgatct cgcctttcac   5100
gtagtgaaca aattcttcca actgatctgc gcgcgaggcc aagcgatctt cttgtccaag   5160
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
agtcgatact tcggcgatca ccgcttccct catgatgttt aactcctgaa ttaagccgcg   5880
ccgcgaagcg gtgtcggctt gaatgaattg ttaggcgtca tcctgtgctc ccgagaacca   5940
gtaccagtac atcgctgttt cgttcgagac ttgaggtcta gttttatacg tgaacaggtc   6000
aatgccgccg agagtaaagc cacattttgc gtacaaattg caggcaggta cattgttcgt   6060
ttgtgtctct aatcgtatgc caaggagctg tctgcttagt gcccactttt tcgcaaattc   6120
gatgagactg tgcgcgactc ctttgcctcg gtgcgtgtgc gacacaacaa tgtgttcgat   6180
agaggctaga tcgttccatg ttgagttgag ttcaatcttc ccgacaagct cttggtcgat   6240
gaatgcgcca tagcaagcag agtcttcatc agagtcatca tccgagatgt aatccttccg   6300
gtaggggctc acacttctgg tagatagttc aaagccttgg tcggataggt gcacatcgaa   6360
cacttcacga acaatgaaat ggttctcagc atccaatgtt tccgccacct gctcagggat   6420
caccgaaatc ttcatatgac gcctaacgcc tggcacagcg gatcgcaaac ctggcgcggc   6480
ttttggcaca aaaggcgtga caggtttgcg aatccgttgc tgccacttgt taaccctttt   6540
gccagatttg gtaactataa tttatgttag aggcgaagtc ttgggtaaaa actggcctaa   6600
aattgctggg gatttcagga aagtaaacat caccttccgg ctcgatgtct attgtagata   6660
tatgtagtgt atctacttga tcgggggatc tgctgcctcg cgcgtttcgg tgatgacggt   6720
gaaaacctct gacacatgca gctcccggag acggtcacag cttgtctgta agcggatgcc   6780
gggagcagac aagcccgtca gggcgcgtca gcgggtgttg gcgggtgtcg gggcgcagcc   6840
atgacccagt cacgtagcga tagcggagtg tatactggct taactatgcg gcatcagagc   6900
agattgtact gagagtgcac catatgcggt gtgaaatacc gcacagatgc gtaaggagaa   6960
aataccgcat caggcgctct tccgcttcct cgctcactga ctcgctgcgc tcggtcgttc   7020
ggctgcggcg agcggtatca gctcactcaa aggcggtaat acggttatcc acagaatcag   7080
gggataacgc aggaaagaac atgtgagcaa aaggccagca aaaggccagg aaccgtaaaa   7140
aggccgcgtt gctggcgttt ttccataggc tccgcccccc tgacgagcat cacaaaaatc   7200
```

gacgctcaag tcagaggtgg cgaaacccga caggactata aagataccag gcgtttcccc 7260
ctggaagctc cctcgtgcgc tctcctgttc cgaccctgcc gcttaccgga tacctgtccg 7320
cctttctccc ttcgggaagc gtggcgcttt ctcatagctc acgctgtagg tatctcagtt 7380
cggtgtaggt cgttcgctcc aagctgggct gtgtgcacga accccccgtt cagcccgacc 7440
gctgcgcctt atccggtaac tatcgtcttg agtccaaccc ggtaagacac gacttatcgc 7500
cactggcagc agccactggt aacaggatta gcagagcgag gtatgtaggc ggtgctacag 7560
agttcttgaa gtggtggcct aactacggct acactagaag gacagtattt ggtatctgcg 7620
ctctgctgaa gccagttacc ttcggaaaaa gagttggtag ctcttgatcc ggcaaacaaa 7680
ccaccgctgg tagcggtggt ttttttgttt gcaagcagca gattacgcgc agaaaaaaag 7740
gatctcaaga agatcctttg atcttttcta cggggtctga cgctcagtgg aacgaaaact 7800
cacgttaagg gattttggtc atgagattat caaaaaggat cttcacctag atccttttaa 7860
attaaaaatg aagttttaaa tcaatctaaa gtatatatga gtaaacttgg tctgacagtt 7920
accaatgctt aatcagtgag gcacctatct cagcgatctg tctatttcgt tcatccatag 7980
ttgcctgact ccccgtcgtg tagataacta cgatacggga gggcttacca tctggcccca 8040
gtgctgcaat gataccgcga gacccacgct caccggctcc agatttatca gcaataaacc 8100
agccagccgg aagggccgag cgcagaagtg gtcctgcaac tttatccgcc tccatccagt 8160
ctattaattg ttgccgggaa gctagagtaa gtagttcgcc agttaatagt ttgcgcaacg 8220
ttgttgccat tgctgcaggg gggggggggg gggggttcca ttgttcattc cacggacaaa 8280
aacagagaaa ggaaacgaca gaggccaaaa agctcgcttt cagcacctgt cgtttccttt 8340
cttttcagag ggtattttaa ataaaaacat taagttatga cgaagaagaa cggaaacgcc 8400
ttaaaccgga aaattttcat aaatagcgaa aacccgcgag gtcgccgccc cgtaacctgt 8460
cggatcaccg gaaaggaccc gtaaagtgat aatgattatc atctacatat cacaacgtgc 8520
gtggaggcca tcaaaccacg tcaaataatc aattatgacg caggtatcgt attaattgat 8580
ctgcatcaac ttaacgtaaa aacaacttca gacaatacaa atcagcgaca ctgaatacgg 8640
ggcaacctca tgtccccccc cccccccccc tgcaggcatc gtggtgtcac gctcgtcgtt 8700
tggtatggct tcattcagct ccggttccca acgatcaagg cgagttacat gatcccccat 8760
gttgtgcaaa aaagcggtta gctccttcgg tcctccgatc gttgtcagaa gtaagttggc 8820
cgcagtgtta tcactcatgg ttatggcagc actgcataat tctcttactg tcatgccatc 8880
cgtaagatgc ttttctgtga ctggtgagta ctcaaccaag tcattctgag aatagtgtat 8940
gcggcgaccg agttgctctt gcccggcgtc aacacgggat aataccgcgc cacatagcag 9000
aactttaaaa gtgctcatca ttggaaaacg ttcttcgggg cgaaaactct caaggatctt 9060
accgctgttg agatccagtt cgatgtaacc cactcgtgca cccaactgat cttcagcatc 9120
ttttactttc accagcgttt ctgggtgagc aaaaacagga aggcaaaatg ccgcaaaaaa 9180
gggaataagg gcgacacgga aatgttgaat actcatactc ttcctttttc aatattattg 9240
aagcatttat cagggttatt gtctcatgag cggatacata tttgaatgta tttagaaaaa 9300
taaacaaata ggggttccgc gcacatttcc ccgaaaagtg ccacctgacg tctaagaaac 9360
cattattatc atgacattaa cctataaaaa taggcgtatc acgaggccct ttcgtcttca 9420
agaattggtc gacgatcttg ctgcgttcgg atattttcgt ggagttcccg ccacagaccc 9480
ggattgaagg cgagatccag caactcgcgc cagatcatcc tgtgacggaa ctttggcgcg 9540

-continued

```
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcctaagc ggccgcattg gacttaatta agtgaggccg gccaagcgtc gatttaaatg  10140
taccacatgg cgcgccaact atcatgcgat cgcttcatgt ctaactcgag ttactggtac  10200
gtaccaaatc catggaatca aggtacccgg tatgaatttg gaaacaaatt cagtactttt  10260
aaaaaaattt gttgtaggga gcaaataata cataaaataa tttatgcatt attttatttt  10320
ttatttgtaa taatatgctt gaaacgataa ttcagtatgc atgttgtgcc agtgtactac  10380
acgggcgggg ggaggggatt gagtgggcca gcgcggtgcg tagggtagat gggctgaaat  10440
tgataactca agtccgacta ggttctcttt ttatttccct tccttttcta ttttcctttc  10500
ttttaatttt catgctttca aactaaattc aaattcgagt tttgaatttc agcttctaaa  10560
ttgtacacta aaattatatg ataaggtaac ccctactatt acttttaatt tttttattct  10620
accccatatt gtttacttag ggagaataa ttgacttaat cacattcttc cttaggtttc  10680
aattctcaat ctttcaaatc cacattttta gatttctatt ttgaatttaa ataccagttt  10740
ggatttagag ttcaatttca aaatacacaa ccaaaatacc agcatgaatg caaatatatt  10800
ttatgtttat gtatttactt ttcttttata ctttgctcaa aatagttatt ttcatgtatg  10860
aaactcaata agcaaggaac tcacgttatt atataaccta ataggaataa tttaggtaac  10920
ataatttatc atcctcttga tttaaaagag atatgcctcc agaataagac acatactaaa  10980
aataactcta atattgaata actaaagtcg tacaaatctc tactattatt cctataaaat  11040
aataaagaac tagctacaac ttctttaagg cattattcag ggtttacagc ttgagaggca  11100
tgaacccatc ctgtatactc ctggacttgg aagacaaaat gtcaaccaaa gtgaaaggtt  11160
ttcttatggt tgctgctaag agatagattg aacactagat ctctcctaag acgtcagggc  11220
atgcgtttag actcctacac atgcgaaaac tgcatcttac agttggaaga aactatatct  11280
caccacttcc tgcggtgtaa ctttgcccaa agatgttggc tcactgttgg aatcactccg  11340
ccccgaactt tggatctaac gcttgcagtg ctacatatta gagcaagact aacaatgccg  11400
tggagaatgg aaggtattat aaccatgtca tggtgcatat ggaaatgtcg aaataactgg  11460
atattcgaaa acataccgcc aacggtggcg gcctgcaagg aaatgttcaa gactgaaatg  11520
aactacatct gctaccaagt taagctcgag acaggagcta aaagtagaaa ctggatacaa  11580
cactttgtaa catagtgaca ctcccctttt cctttctttt accttagaac tatacataca  11640
atccacattc aataaaaatt tgtaggtacg ccatacacac taccggaatc cggctctttg  11700
ccgagtgtga ggcgctttgt cgagtgcttt ttgtccagca ctcggcaaaa aagtctttgc  11760
catgtgccgc actcggcaaa gtcctgctct cggtaacgac cgcgtttacc gagagcagga  11820
ctctcgacac agaaatacac tcgacaaaga aatctttgcc gagagccaaa cactcggcga  11880
acggcagcgc tcggcaaagg gtcgtcagcc gccgtctaaa gctgacggtc gttatctttg  11940
```

tcgagtgccc cctcgtccga cactcagtag agcaagcttg ccgagtgcca tccttggaca 12000
ctcgataaag tatattttat ttttttttat tttgccaacc aaactttttg tggtatgttc 12060
ctacactatg tagatctaca tgtaccattt tggcacaatt acaaaaatgt tttctataac 12120
tattagattt agttcgttta tttgaatttc ttcggaaaat tcacatatga actgcaagtc 12180
actcgaaaca tgaaaaaccg tgcatgcaaa ataaatgata tgcatgttat ctagcacaag 12240
ttacgaccga attcagaagc agaccagaat cttcaagcac catgctcact aaacatgacc 12300
gtgaacttgt tatccagttg tttaaaaatt gtataaaaca caaataaagt cagaaattaa 12360
tgaaacttgt ccacatgtca tgatatcata tatagaggtt gtgataaaaa tttgataatg 12420
tttcggtaaa gttgtgacgt actatgtgta gaaacctaag tgacctacac ataaaatcat 12480
agagtttcaa tgtagttcac tcgacaaaga ctttgtcaag tgtccgataa aaagtattca 12540
gcaaagaagc cgttgtcgat ttactgttcg tcgagatctc tttgccgagt gtcacactag 12600
gcaaagtctt tacggagtgt ttttcaggct ttgacactcg gcaaagcgct cgattccagt 12660
agtgacagta atttgcatca aaaatagccg agagatttaa aatgagtcaa ctaatagacc 12720
aactaattat tagctattag tcgttagctt ctttaatcta agctaaaacc aactaatagc 12780
ttatttgttg aattacaatt agctcaacgg aattctctgt tttttctata aaaaaaaggg 12840
aaactgcccc tcatttacag caaactgtcc gctgcctgtc gtccagatac aatgaacgta 12900
cctagtagga actcttttac acgctcggtc gctcgccgcg gatcggagtc ccaggaacac 12960
gacaccactg tggaacacga caaagtctgc tcagaggcgg ccacaccctg gcgtgcaccg 13020
agccggagcc cggataagca cggtaaggag agtacggcgg gacgtggcga cccgtgtgtc 13080
tgctgccacg cagccttcct ccacgtagcc gcgcggccgc gccacgtacc agggcccggc 13140
gctggtataa atgcgcgcca cctccgcttt agttctgcat acagccaacc caacacacac 13200
ccgagcatat cacagtgaca gacactacac gggatcctaa accatgaggg tgttgctcgt 13260
tgccctcgct ctcctggctc tcgctgcgag cgccacctcc ggctgccaga gcgtgagcga 13320
gatgctgagg ttctacaccg acgaggtgct gccgagggcc atgcagggcg gcggcagcgg 13380
cggcggcagc aaggccatgg gcgagttcga catcttcatc aactacatcg aggagtacct 13440
gctgatgagg aaggacgagc tgtaac 13466

<210> SEQ ID NO 79
<211> LENGTH: 12474
<212> TYPE: DNA
<213> ORGANISM: Artificial Sequence
<220> FEATURE:
<223> OTHER INFORMATION: Synthetic construct, pAG4984

<400> SEQUENCE: 79
ctaggtcccc gaatttcccc gatcgttcaa acatttggca ataaagtttc ttaagattga 60
atcctgttgc cggtcttgcg atgattatca tataatttct gttgaattac gttaagcatg 120
taataattaa catgtaatgc atgacgttat ttatgagatg ggtttttatg attagagtcc 180
cgcaattata catttaatac gcgatagaaa acaaaatata gcgcgcaaac taggataaat 240
tatcgcgcgc ggtgtcatct atgttactag atcgggaatt ggaattcctg cagtgcagcg 300
tgacccggtc gtgcccctct ctagagataa tgagcattgc atgtctaagt tataaaaaat 360
taccacatat ttttttgtc acacttgttt gaagtgcagt ttatctatct ttatacatat 420
atttaaactt tactctacga ataatataat ctatagtact acaataatat cagtgtttta 480

-continued

```
gagaatcata taaatgaaca gttagacatg gtctaaagga caattgagta ttttgacaac    540
aggactctac agttttatct ttttagtgtg catgtgttct ccttttttt tgcaaatagc    600
ttcacctata taatacttca tccattttat tagtacatcc atttagggtt tagggttaat    660
ggtttttata gactaatttt tttagtacat ctattttatt ctattttagc ctctaaatta    720
agaaaactaa aactctattt tagttttttt atttaataat ttagatataa aatagaataa    780
aataaagtga ctaaaaatta aacaaatacc ctttaagaaa ttaaaaaaac taaggaaaca    840
tttttcttgt ttcgagtaga taatgccagc ctgttaaacg ccgtcgacga gtctaacgga    900
caccaaccag cgaaccagca gcgtcgcgtc gggccaagcg aagcagacgg cacggcatct    960
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc cccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
tttttgtctt ggttgtgatg atgtggtctg gttgggcggt cgttctagat cggagtagaa   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tccagatcta aaccatgcag aaactcatta actcagtgca aaactatgcc tggggcagca   2340
aaacggcgtt gactgaactt tatggtatgg aaaatccgtc cagccagccg atggccgagc   2400
tgtggatggg cgcacatccg aaaagcagtt cacgagtgca gaatgccgcc ggagatatcg   2460
tttcactgcg tgatgtgatt gagagtgata aatcgactct gctcggagag gccgttgcca   2520
aacgctttgg cgaactgcct ttcctgttca aagtattatg cgcagcacag ccactctcca   2580
ttcaggttca tccaaacaaa cacaattctg aaatcggttt tgccaaagaa aatgccgcag   2640
gtatcccgat ggatgccgcc gagcgtaact ataaagatcc taaccacaag ccggagctgg   2700
tttttgcgct gacgcctttc cttgcgatga acgcgtttcg tgaattttcc gagattgtct   2760
ccctactcca gccggtcgca ggtgcacatc cggcgattgc tcacttttta caacagcctg   2820
atgccgaacg tttaagcgaa ctgttcgcca gcctgttgaa tatgcagggt gaagaaaaat   2880
```

cccgcgcgct ggcgatttta aaatcggccc tcgatagcca gcagggtgaa ccgtggcaaa 2940
cgattcgttt aatttctgaa ttttacccgg aagacagcgg tctgttctcc ccgctattgc 3000
tgaatgtggt gaaattgaac cctggcgaag cgatgttcct gttcgctgaa acaccgcacg 3060
cttacctgca aggcgtggcg ctggaagtga tggcaaactc cgataacgtg ctgcgtgcgg 3120
gtctgacgcc taaatacatt gatattccgg aactggttgc caatgtgaaa ttcgaagcca 3180
aaccggctaa ccagttgttg acccagccgg tgaaacaagg tgcagaactg gacttcccga 3240
ttccagtgga tgattttgcc ttctcgctgc atgaccttag tgataaagaa accaccatta 3300
gccagcagag tgccgccatt ttgttctgcg tcgaaggcga tgcaacgttg tggaaaggtt 3360
ctcagcagtt acagcttaaa ccgggtgaat cagcgtttat tgccgccaac gaatcaccgg 3420
tgactgtcaa aggccacggc cgtttagcgc gtgtttacaa caagctgtaa gagcttactg 3480
aaaaaattaa catctcttgc taagctggga gctctagatc cccgaatttc cccgatcgtt 3540
caaacatttg gcaataaagt ttcttaagat tgaatcctgt tgccggtctt gcgatgatta 3600
tcatataatt tctgttgaat tacgttaagc atgtaataat taacatgtaa tgcatgacgt 3660
tatttatgag atgggttttt atgattagag tcccgcaatt atacatttaa tacgcgatag 3720
aaaacaaaat atagcgcgca aactaggata aattatcgcg cgcggtgtca tctatgttac 3780
tagatcggga attggcgagc tcgaattaat tcagtacatt aaaaacgtcc gcaatgtgtt 3840
attaagttgt ctaagcgtca atttgtttac accacaatat atcctgccac cagccagcca 3900
acagctcccc gaccggcagc tcggcacaaa atcaccactc gatacaggca gcccatcagt 3960
ccgggacggc gtcagcggga gagccgttgt aaggcggcag actttgctca tgttaccgat 4020
gctattcgga agaacggcaa ctaagctgcc gggtttgaaa cacggatgat ctcgcggagg 4080
gtagcatgtt gattgtaacg atgacagagc gttgctgcct gtgatcaaat atcatctccc 4140
tcgcagagat ccgaattatc agccttctta ttcatttctc gcttaaccgt gacaggctgt 4200
cgatcttgag aactatgccg acataatagg aaatcgctgg ataaagccgc tgaggaagct 4260
gagtggcgct atttctttag aagtgaacgt tgacgatcgt cgaccgtacc ccgatgaatt 4320
aattcggacg tacgttctga acacagctgg atacttactt gggcgattgt catacatgac 4380
atcaacaatg tacccgtttg tgtaaccgtc tcttggaggt tcgtatgaca ctagtggttc 4440
ccctcagctt gcgactagat gttgaggcct aacattttat tagagagcag gctagttgct 4500
tagatacatg atcttcaggc cgttatctgt cagggcaagc gaaaattggc catttatgac 4560
gaccaatgcc ccgcagaagc tcccatcttt gccgccatag acgccgcgcc cccttttgg 4620
ggtgtagaac atccttttgc cagatgtgga aaagaagttc gttgtcccat tgttggcaat 4680
gacgtagtag ccggcgaaag tgcgagaccc atttgcgcta tatataagcc tacgatttcc 4740
gttgcgacta ttgtcgtaat tggatgaact attatcgtag ttgctctcag agttgtcgta 4800
atttgatgga ctattgtcgt aattgcttat ggagttgtcg tagttgcttg gagaaatgtc 4860
gtagttggat ggggagtagt catagggaag acgagcttca tccactaaaa caattggcag 4920
gtcagcaagt gcctgccccg atgccatcgc aagtacgagg cttagaacca ccttcaacag 4980
atcgcgcata gtcttcccca gctctctaac gcttgagtta agccgcgccg cgaagcggcg 5040
tcggcttgaa cgaattgtta gacattattt gccgactacc ttggtgatct cgcctttcac 5100
gtagtgaaca aattcttcca actgatctgc gcgcgaggcc aagcgatctt cttgtccaag 5160
ataagcctgc ctagcttcaa gtatgacggg ctgatactgg gccggcaggc gctccattgc 5220
ccagtcggca gcgacatcct tcggcgcgat tttgccggtt actgcgctgt accaaatgcg 5280
ggacaacgta agcactacat ttcgctcatc gccagcccag tcgggcggcg agttccatag 5340
cgttaaggtt tcatttagcg cctcaaatag atcctgttca ggaaccggat caaagagttc 5400
ctccgccgct ggacctacca aggcaacgct atgttctctt gcttttgtca gcaagatagc 5460
cagatcaatg tcgatcgtgg ctggctcgaa gatacctgca agaatgtcat tgcgctgcca 5520
ttctccaaat tgcagttcgc gcttagctgg ataacgccac ggaatgatgt cgtcgtgcac 5580
aacaatggtg acttctacag cgcggagaat ctcgctctct ccaggggaag ccgaagtttc 5640
caaaaggtcg ttgatcaaag ctcgccgcgt tgtttcatca agccttacgg tcaccgtaac 5700
cagcaaatca atatcactgt gtggcttcag gccgccatcc actgcggagc cgtacaaatg 5760
tacggccagc aacgtcggtt cgagatggcg ctcgatgacg ccaactacct ctgatagttg 5820
agtcgatact tcggcgatca ccgcttccct catgatgttt aactcctgaa ttaagccgcg 5880
ccgcgaagcg gtgtcggctt gaatgaattg ttaggcgtca tcctgtgctc ccgagaacca 5940
gtaccagtac atcgctgttt cgttcgagac ttgaggtcta gttttatacg tgaacaggtc 6000
aatgccgccg agagtaaagc cacattttgc gtacaaattg caggcaggta cattgttcgt 6060
ttgtgtctct aatcgtatgc caaggagctg tctgcttagt gcccactttt tcgcaaattc 6120
gatgagactg tgcgcgactc ctttgcctcg gtgcgtgtgc gacacaacaa tgtgttcgat 6180
agaggctaga tcgttccatg ttgagttgag ttcaatcttc ccgacaagct cttggtcgat 6240
gaatgcgcca tagcaagcag agtcttcatc agagtcatca tccgagatgt aatccttccg 6300
gtaggggctc acacttctgg tagatagttc aaagccttgg tcggataggt gcacatcgaa 6360
cacttcacga acaatgaaat ggttctcagc atccaatgtt tccgccacct gctcagggat 6420
caccgaaatc ttcatatgac gcctaacgcc tggcacagcg gatcgcaaac ctggcgcggc 6480
ttttggcaca aaaggcgtga caggtttgcg aatccgttgc tgccacttgt taaccctttt 6540
gccagatttg gtaactataa tttatgttag aggcgaagtc ttgggtaaaa actggcctaa 6600
aattgctggg gatttcagga aagtaaacat caccttccgg ctcgatgtct attgtagata 6660
tatgtagtgt atctacttga tcgggggatc tgctgcctcg cgcgtttcgg tgatgacggt 6720
gaaaacctct gacacatgca gctcccggag acggtcacag cttgtctgta agcggatgcc 6780
gggagcagac aagcccgtca gggcgcgtca gcgggtgttg gcgggtgtcg gggcgcagcc 6840
atgacccagt cacgtagcga tagcggagtg tatactggct taactatgcg gcatcagagc 6900
agattgtact gagagtgcac catatgcggt gtgaaatacc gcacagatgc gtaaggagaa 6960
aataccgcat caggcgctct tccgcttcct cgctcactga ctcgctgcgc tcggtcgttc 7020
ggctgcggcg agcggtatca gctcactcaa aggcggtaat acggttatcc acagaatcag 7080
gggataacgc aggaaagaac atgtgagcaa aaggccagca aaaggccagg aaccgtaaaa 7140
aggccgcgtt gctggcgttt ttccataggc tccgcccccc tgacgagcat cacaaaaatc 7200
gacgctcaag tcagaggtgg cgaaacccga caggactata aagataccag gcgtttcccc 7260
ctggaagctc cctcgtgcgc tctcctgttc cgaccctgcc gcttaccgga tacctgtccg 7320
cctttctccc ttcgggaagc gtggcgcttt ctcatagctc acgctgtagg tatctcagtt 7380
cggtgtaggt cgttcgctcc aagctgggct gtgtgcacga accccccgtt cagcccgacc 7440
gctgcgcctt atccggtaac tatcgtcttg agtccaaccc ggtaagacac gacttatcgc 7500
cactggcagc agccactggt aacaggatta gcagagcgag gtatgtaggc ggtgctacag 7560
agttcttgaa gtggtggcct aactacggct acactagaag gacagtattt ggtatctgcg 7620

-continued

```
ctctgctgaa gccagttacc ttcggaaaaa gagttggtag ctcttgatcc ggcaaacaaa   7680
ccaccgctgg tagcggtggt ttttttgttt gcaagcagca gattacgcgc agaaaaaaag   7740
gatctcaaga agatcctttg atcttttcta cggggtctga cgctcagtgg aacgaaaact   7800
cacgttaagg gattttggtc atgagattat caaaaaggat cttcacctag atccttttaa   7860
attaaaaatg aagttttaaa tcaatctaaa gtatatatga gtaaacttgg tctgacagtt   7920
accaatgctt aatcagtgag gcacctatct cagcgatctg tctatttcgt tcatccatag   7980
ttgcctgact ccccgtcgtg tagataacta cgatacggga gggcttacca tctggcccca   8040
gtgctgcaat gataccgcga gacccacgct caccggctcc agatttatca gcaataaacc   8100
agccagccgg aagggccgag cgcagaagtg gtcctgcaac tttatccgcc tccatccagt   8160
ctattaattg ttgccgggaa gctagagtaa gtagttcgcc agttaatagt ttgcgcaacg   8220
ttgttgccat tgctgcaggg gggggggggg gggggttcca ttgttcattc cacggacaaa   8280
aacagagaaa ggaaacgaca gaggccaaaa agctcgcttt cagcacctgt cgtttccttt   8340
cttttcagag ggtattttaa ataaaaacat taagttatga cgaagaagaa cggaaacgcc   8400
ttaaaccgga aattttcat  aaatagcgaa aacccgcgag gtcgccgccc cgtaacctgt   8460
cggatcaccg gaaaggaccc gtaaagtgat aatgattatc atctacatat cacaacgtgc   8520
gtggaggcca tcaaaccacg tcaaataatc aattatgacg caggtatcgt attaattgat   8580
ctgcatcaac ttaacgtaaa aacaacttca gacaatacaa atcagcgaca ctgaatacgg   8640
ggcaacctca tgtccccccc cccccccccc tgcaggcatc gtggtgtcac gctcgtcgtt   8700
tggtatggct tcattcagct ccggttccca acgatcaagg cgagttacat gatcccccat   8760
gttgtgcaaa aaagcggtta gctccttcgg tcctccgatc gttgtcagaa gtaagttggc   8820
cgcagtgtta tcactcatgg ttatggcagc actgcataat tctcttactg tcatgccatc   8880
cgtaagatgc ttttctgtga ctggtgagta ctcaaccaag tcattctgag aatagtgtat   8940
gcggcgaccg agttgctctt gcccggcgtc aacacgggat aataccgcgc cacatagcag   9000
aactttaaaa gtgctcatca ttggaaaacg ttcttcgggg cgaaaactct caaggatctt   9060
accgctgttg agatccagtt cgatgtaacc cactcgtgca cccaactgat cttcagcatc   9120
ttttactttc accagcgttt ctgggtgagc aaaaacagga aggcaaaatg ccgcaaaaaa   9180
gggaataagg gcgacacgga aatgttgaat actcatactc ttcctttttc aatattattg   9240
aagcatttat cagggttatt gtctcatgag cggatacata tttgaatgta tttagaaaaa   9300
taaacaaata ggggttccgc gcacatttcc ccgaaaagtg ccacctgacg tctaagaaac   9360
cattattatc atgacattaa cctataaaaa taggcgtatc acgaggccct ttcgtcttca   9420
agaattggtc gacgatcttg ctgcgttcgg atattttcgt ggagttcccg ccacagaccc   9480
ggattgaagg cgagatccag caactcgcgc cagatcatcc tgtgacggaa ctttggcgcg   9540
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
```

-continued

```
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcctaagc ggccgcattg gacttaatta agtgaggccg gccaagcgtc gatttaaatg  10140
taccacatgg cgcgccaact atcatgcgat cgcttcatgt ctaactcgag ttactggtac  10200
gtaccaaatc catggaatca aggtaccatc aatcccggga taaaatttta gtgaagctaa  10260
agcggtgaaa gattatagaa tttgatgtgc cagattaata aatcgattaa ctcctaaagt  10320
tcaagccgag actacagaca catgagctac ataaatgagc caaggactcg agcaaagaca  10380
aatcgacaca gacattataa ttcaagtcat tctagaagat tcatgagaag agtatcattt  10440
atttaaatca atgacttgat caaataagac ctaggagcta ctattgataa tatatatcat  10500
gggtatctag atcaagcatt atgaagaaga gcctaagtag aaggccccat gggctcgacc  10560
acaaacccaa ggactcgaca ataaagtcta ggagggatcc catagctaaa aggactctag  10620
aagtgtatgt atggtaaaga ttttatcgag acaagaaata cgataaagat cttaacagaa  10680
tcggagtcat acttgtaaaa atagagttgg actcgtgtac aacttggtct tcgacttagt  10740
tcggtcatga attcagtaac cgactagata tgtaccatgg aacccctagg gcatgaggct  10800
atgagccata ggatcatcag atccaaacat acaccaacaa atccatcaca caccgaagat  10860
ccatattaac aagggattag ctactttaca atttcagagt aacaaataga gccaaactca  10920
tagcacaggg gaacttcata tcacaaatgg aggcattgaa ttgatataaa aagctaaagt  10980
tctaaaaagt ttgaagtgct gaaacttcaa agccgctaac tagtgaagca ccgaagcctt  11040
ccggggagag aagacataca cgacacgtta gggacgtaaa atgacgaaat tatacaacta  11100
cctctatatg taacacttat gtaatagaaa agacagaatc catatgaaga tgtataatgg  11160
atcaaccata taaatagata aacaatatat ctgctatggg gattggcatt cttgtatccc  11220
tacgcctgta tatcccctgt ttagagaacc tccgaaggta tatgatgctg aagattattg  11280
ttgtcttgtc tttcatcata tatcgagtct ttccctagga tattattatt cgcaatgtgc  11340
attacatggt taatcgattg agagaacatg catctcacct ttagctgata aacgataatc  11400
catgttttac acttcgtagc tactcatgag tttcgatata caaatttgtt ttctggacta  11460
cgtaccattc catcctctta ggagaggaga ggaagtgtcc tcgatttaat tatgttgtca  11520
ttttgtagtt cttcacaaaa tctcaacagg taccaaacac attgtttcca caagacatat  11580
tttagtcaca acaaatctat attattatta atcactaaaa ctatactgag gctcagatgc  11640
ttttactagc tcttgctagt atgtgatgta ggtctctttc gacatcattc catcaaaatc  11700
atatgattag cccataccaa acatttctat accattcaga gaccagaata gtcttttcta  11760
atagaaaaaa ggaaaataga gtgggccgac gacgacacaa attactgcgt ggaccagaaa  11820
atagtgagac acggaagaca aaagaagtaa aagaggcaag gactacggcc cacatgagat  11880
tcggccccgc cacctccggc aaccagcggc cgatccaacg gcagtgcatc ctcaacggcg  11940
cgcgcgcgcg cgcgcgcgca caacctcgta tatatcgccg cgcggaagcg gcgcgaccga  12000
ggaagccttg tcctcgacac cccctacaca ggtgtcgcgc tgcccccgac acgagtcccg  12060
catgcgtccc acgcggccgc gccagatccc gcctccgcgc gttgccacgc cctctataaa  12120
cacccagctc tctccctcgc cctcatctat cgcactcgta gtcgtagctc aagcatcagc  12180
ggcaggagct ctgggcagcg tgcgcacgtg gggtacctag ctcgctctgc tagcctaccg  12240
gatcctaaac catgagggtg ttgctcgttg ccctcgctct cctggctctc gctgcgagcg  12300
ccacctccgg ctgccagagc gtgagcgaga tgctgaggtt ctacaccgac gaggtgctgc  12360
```

cgagggccat gcagggcggc ggcagcggcg gcggcagcaa ggccatgggc gagttcgaca 12420
tcttcatcaa ctacatcgag gagtacctgc tgatgaggaa ggacgagctg taac 12474

<210> SEQ ID NO 80
<211> LENGTH: 153
<212> TYPE: PRT
<213> ORGANISM: Gallus gallus
<220> FEATURE:
<221> NAME/KEY: MISC_FEATURE
<222> LOCATION: (1)..(153)
<223> OTHER INFORMATION: chicken IL-10

<400> SEQUENCE: 80

```
Leu Glu Pro Thr Cys Leu His Phe Ser Glu Leu Leu Pro Ala Arg Leu
1               5                   10                  15

Arg Glu Leu Arg Val Lys Phe Glu Glu Ile Lys Asp Tyr Phe Gln Ser
            20                  25                  30

Arg Asp Asp Glu Leu Asn Ile Gln Leu Leu Ser Ser Glu Leu Leu Asp
        35                  40                  45

Glu Phe Lys Gly Thr Phe Gly Cys Gln Ser Val Ser Glu Met Leu Arg
    50                  55                  60

Phe Tyr Thr Asp Glu Val Leu Pro Arg Ala Met Gln Thr Ser Thr Ser
65                  70                  75                  80

His Gln Gln Ser Met Gly Asp Leu Gly Asn Met Leu Leu Gly Leu Lys
                85                  90                  95

Ala Thr Met Arg Arg Cys His Arg Phe Phe Thr Cys Glu Lys Arg Ser
            100                 105                 110

Lys Ala Ile Lys Gln Ile Lys Glu Thr Phe Glu Lys Met Asp Glu Asn
        115                 120                 125

Gly Ile Tyr Lys Ala Met Gly Glu Phe Asp Ile Phe Ile Asn Tyr Ile
    130                 135                 140

Glu Glu Tyr Leu Leu Met Arg Arg Arg
145                 150
```

<210> SEQ ID NO 81
<211> LENGTH: 160
<212> TYPE: PRT
<213> ORGANISM: Homo sapiens
<220> FEATURE:
<221> NAME/KEY: MISC_FEATURE
<222> LOCATION: (1)..(160)
<223> OTHER INFORMATION: IL-10

<400> SEQUENCE: 81

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110
```

```
Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160


<210> SEQ ID NO 82
<211> LENGTH: 233
<212> TYPE: PRT
<213> ORGANISM: Homo sapiens
<220> FEATURE:
<221> NAME/KEY: MISC_FEATURE
<222> LOCATION: (1)..(233)
<223> OTHER INFORMATION: IL-10R1
<220> FEATURE:
<221> NAME/KEY: MISC_FEATURE
<222> LOCATION: (1)..(233)
<223> OTHER INFORMATION: human IL-10R1

<400> SEQUENCE: 82

His Gly Thr Glu Leu Pro Ser Pro Pro Ser Val Trp Phe Glu Ala Glu
1               5                   10                  15

Phe Phe His His Ile Leu His Trp Thr Pro Ile Pro Asn Gln Ser Glu
            20                  25                  30

Ser Thr Cys Tyr Glu Val Ala Leu Leu Arg Tyr Gly Ile Glu Ser Trp
        35                  40                  45

Asn Ser Ile Ser Asn Cys Ser Gln Thr Leu Ser Tyr Asp Leu Thr Ala
    50                  55                  60

Val Thr Leu Asp Leu Tyr His Ser Asn Gly Tyr Arg Ala Arg Val Arg
65                  70                  75                  80

Ala Val Asp Gly Ser Arg His Ser Asn Trp Thr Val Thr Asn Thr Arg
                85                  90                  95

Phe Ser Val Asp Glu Val Thr Leu Thr Val Gly Ser Val Asn Leu Glu
            100                 105                 110

Ile His Asn Gly Phe Ile Leu Gly Lys Ile Gln Leu Pro Arg Pro Lys
        115                 120                 125

Met Ala Pro Ala Asn Asp Thr Tyr Glu Ser Ile Phe Ser His Phe Arg
    130                 135                 140

Glu Tyr Glu Ile Ala Ile Arg Lys Val Pro Gly Asn Phe Thr Phe Thr
145                 150                 155                 160

His Lys Lys Val Lys His Glu Asn Phe Ser Leu Leu Thr Ser Gly Glu
                165                 170                 175

Val Gly Glu Phe Cys Val Gln Val Lys Pro Ser Val Ala Ser Arg Ser
            180                 185                 190

Asn Lys Gly Met Trp Ser Lys Glu Glu Cys Ile Ser Leu Thr Arg Gln
        195                 200                 205

Tyr Phe Thr Val Thr Asn Val Ile Ile Phe Phe Ala Phe Val Leu Leu
    210                 215                 220

Leu Ser Gly Ala Leu Ala Tyr Cys Leu
225                 230


<210> SEQ ID NO 83
<211> LENGTH: 210
<212> TYPE: PRT
<213> ORGANISM: Gallus gallus
<220> FEATURE:
<221> NAME/KEY: MISC_FEATURE
<222> LOCATION: (1)..(210)
```

```
<223> OTHER INFORMATION: huan IL-10R1
<220> FEATURE:
<221> NAME/KEY: MISC_FEATURE
<222> LOCATION: (1)..(210)
<223> OTHER INFORMATION: chicken  IL-10R1

<400> SEQUENCE: 83

Glu Leu Arg Leu Lys Pro Thr Arg Val Arg Phe Val Ala Glu Met Val
1               5                   10                  15

Tyr His Leu Leu Gln Trp Glu Pro Gly Arg Asp Ala Pro Ser Asp Thr
            20                  25                  30

Arg Tyr Asp Val Glu His Lys Ile Tyr Gly Thr Asn Ser Pro Trp Thr
        35                  40                  45

Ala Ile Pro Asn Cys Met Lys Ile His Gly His Ser Cys Asp Leu Thr
    50                  55                  60

Tyr Tyr Thr Leu Asp Pro Ser Leu Arg Tyr Tyr Ala Arg Val Arg Ala
65                  70                  75                  80

Val Val Gly Asn His Thr Ser Asp Trp Lys Arg Thr Asn Ala Phe Ser
                85                  90                  95

Pro Gln Glu Ala Ser Leu Arg Leu Ser Gly His Ser Leu Ala Val Thr
            100                 105                 110

Asp Asn Ser Ile His Val Gln Leu Gln Leu Leu Leu Arg Ala Gly Asn
        115                 120                 125

Arg Thr Val Lys Tyr Asp Asp Ile Gln Lys His Ala Arg Arg Tyr Arg
    130                 135                 140

Val Tyr Ile Arg Arg Ala Arg Asp Asn Gln Thr Tyr Glu Val Trp Glu
145                 150                 155                 160

Thr Ala Ser Glu Phe Tyr Ile Arg Asn Leu Phe Trp Asn Thr Glu Tyr
                165                 170                 175

Cys Ile Ser Val Glu Pro Asp Val Ala Ser Arg His Ile Pro Ala Met
            180                 185                 190

Arg Thr Ala Glu Gln Cys Val Thr Ile Gly His Arg Asp Glu Ser Ala
        195                 200                 205

Glu Leu
    210


<210> SEQ ID NO 84
<211> LENGTH: 147
<212> TYPE: PRT
<213> ORGANISM: Artificial Sequence
<220> FEATURE:
<223> OTHER INFORMATION: Synthetic construct,
      xGZein27ss:chIL10sdAb1A11:KDEL

<400> SEQUENCE: 84

Met Arg Val Leu Leu Val Ala Leu Ala Leu Leu Ala Leu Ala Ala Ser
1               5                   10                  15

Ala Thr Ser Gln Val Gln Leu Gln Glu Ser Gly Gly Gly Leu Val Gln
            20                  25                  30

Pro Gly Gly Ser Leu Arg Leu Ser Cys Ala Ala Ser Gly Asn Ile Phe
        35                  40                  45

Ser Ile Asn Thr Met Gly Trp Tyr Arg Gln Ala Pro Gly Lys Gln Arg
    50                  55                  60

Glu Leu Val Ala Ser Ile Thr Thr Gly Gly Thr Thr Asn Tyr Glu Asp
65                  70                  75                  80

Ser Val Lys Gly Arg Phe Thr Ile Ser Arg Asp Asn Ala Lys Lys Thr
                85                  90                  95
```

```
Val Tyr Leu Gln Met Asn Arg Leu Lys Pro Glu Asp Thr Ala Val Tyr
            100                 105                 110

Tyr Cys Asn His Arg Arg Ser Tyr Ser Gly Arg Asp Tyr Pro Val Tyr
        115                 120                 125

Gly Met Asp Tyr Trp Gly Lys Gly Thr Leu Val Thr Val Ser Ser Lys
    130                 135                 140

Asp Glu Leu
145
```

<210> SEQ ID NO 85
<211> LENGTH: 147
<212> TYPE: PRT
<213> ORGANISM: Artificial Sequence
<220> FEATURE:
<223> OTHER INFORMATION: Synthetic construct,
xGZein27ss:chIL10sdAb1B9:KDEL

<400> SEQUENCE: 85

```
Met Arg Val Leu Leu Val Ala Leu Ala Leu Leu Ala Leu Ala Ala Ser
1               5                   10                  15

Ala Thr Ser Gln Val Gln Leu Gln Glu Ser Gly Gly Gly Leu Val Gln
            20                  25                  30

Ala Gly Gly Ser Leu Arg Leu Ser Cys Ala Ala Ser Gly Arg Thr Phe
        35                  40                  45

Ser Ser Tyr Ala Trp Gly Trp Phe Arg Gln Ala Pro Gly Lys Glu Arg
    50                  55                  60

Glu Phe Val Ala Arg Ile Ser Phe Ser Gly Gly His Thr Tyr Tyr Ser
65                  70                  75                  80

Asp Ser Val Lys Gly Arg Phe Thr Ile Ser Arg Asp Asn Ala Lys Asn
                85                  90                  95

Thr Val Tyr Leu Gln Met Asn Ser Leu Lys Pro Glu Asp Thr Ala Val
            100                 105                 110

Tyr Tyr Cys Ala Ala Asp Pro Thr Pro Tyr Gly Leu Arg Asn Glu Arg
        115                 120                 125

Asn Tyr Pro Tyr Trp Gly Gln Gly Thr Gln Val Thr Val Ser Ser Lys
    130                 135                 140

Asp Glu Leu
145
```

<210> SEQ ID NO 86
<211> LENGTH: 148
<212> TYPE: PRT
<213> ORGANISM: Artificial Sequence
<220> FEATURE:
<223> OTHER INFORMATION: Synthetic construct,
xGZein27ss:chIL10sdAb1F11:KDEL

<400> SEQUENCE: 86

```
Met Arg Val Leu Leu Val Ala Leu Ala Leu Leu Ala Leu Ala Ala Ser
1               5                   10                  15

Ala Thr Ser Gln Val Gln Leu Gln Glu Phe Gly Gly Gly Leu Val Gln
            20                  25                  30

Pro Gly Gly Ser Leu Arg Leu Ser Cys Ala Ala Ser Gly Arg Thr Gly
        35                  40                  45

Ser Ser Tyr Ala Met Gly Trp Phe Arg Gln Ala Pro Gly Lys Glu Arg
    50                  55                  60

Glu Phe Val Ala Ala Ile Ser Trp Ser Gly Gly Ser Thr Asp Tyr Ala
65                  70                  75                  80
```

```
Asp Ser Val Lys Gly Arg Phe Thr Ile Ser Arg Asp Asn Ala Lys Asn
                85                  90                  95

Thr Met Tyr Leu Gln Met Asn Ser Leu Lys Pro Glu Asp Thr Ala Val
            100                 105                 110

Tyr Tyr Cys Ala Val Asp Arg Asn Leu Phe Lys Leu Arg Val Ala Val
        115                 120                 125

Gln Glu Tyr Thr Asn Leu Gly Gln Gly Thr Gln Val Thr Val Ser Ser
    130                 135                 140

Lys Asp Glu Leu
145


<210> SEQ ID NO 87
<211> LENGTH: 125
<212> TYPE: PRT
<213> ORGANISM: Artificial Sequence
<220> FEATURE:
<223> OTHER INFORMATION: Synthetic construct,  chIL10sdAB1H5

<400> SEQUENCE: 87

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125


<210> SEQ ID NO 88
<211> LENGTH: 125
<212> TYPE: PRT
<213> ORGANISM: Artificial Sequence
<220> FEATURE:
<223> OTHER INFORMATION: Synthetic construct, chIL10sdAB1E9

<400> SEQUENCE: 88

Met Gln Val Gln Leu Gln Ala Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Thr Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110
```

```
His Tyr Trp Gly Gln Gly Thr Gln Val Thr Val Ser Ser
        115                 120                 125


<210> SEQ ID NO 89
<211> LENGTH: 125
<212> TYPE: PRT
<213> ORGANISM: Artificial Sequence
<220> FEATURE:
<223> OTHER INFORMATION: Synthetic construct, chIL10sdAB1H1

<400> SEQUENCE: 89

Met Gln Val Gln Leu Gln Ala Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125


<210> SEQ ID NO 90
<211> LENGTH: 125
<212> TYPE: PRT
<213> ORGANISM: Artificial Sequence
<220> FEATURE:
<223> OTHER INFORMATION: Synthetic construct,  chIL10sdAB1G6

<400> SEQUENCE: 90

Met Gln Val Gln Leu Gln Ala Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125


<210> SEQ ID NO 91
<211> LENGTH: 125
<212> TYPE: PRT
<213> ORGANISM: Artificial Sequence
<220> FEATURE:
<223> OTHER INFORMATION: Synthetic construct, chIL10sdAB1C10
```

<400> SEQUENCE: 91

Met Gln Val Gln Leu Gln Glu Phe Gly Gly Gly Leu Val Leu Pro Gly
1 5 10 15

Gly Ser Leu Arg Leu Ser Cys Ala Ala Ser Gly Arg Thr Phe Asn Ser
20 25 30

Tyr Ala Trp Gly Trp Phe Arg Gln Ala Pro Gly Lys Glu Arg Gly Phe
35 40 45

Val Ala Arg Ile Ser Phe Ser Gly Gly His Thr Tyr Tyr Ser Asp Ser
50 55 60

Val Lys Gly Arg Phe Thr Ile Ser Arg Asp Asn Ala Lys Asn Ser Val
65 70 75 80

Tyr Leu Gln Met Asn Ser Leu Lys Pro Glu Asp Thr Ala Val Tyr Tyr
85 90 95

Cys Ala Ala Asp Pro Thr Pro Tyr Gly Leu Arg Asn Glu Arg Asn Tyr
100 105 110

His Tyr Trp Gly Gln Gly Thr Gln Val Thr Val Ser Ser
115 120 125

<210> SEQ ID NO 92
<211> LENGTH: 125
<212> TYPE: PRT
<213> ORGANISM: Artificial Sequence
<220> FEATURE:
<223> OTHER INFORMATION: Synthetic construct, chIL10sdAB1B6

<400> SEQUENCE: 92

Met Gln Val Gln Leu Gln Gln Ser Gly Gly Gly Leu Val Gln Ala Gly
1 5 10 15

Gly Ser Leu Arg Leu Ser Cys Ala Ala Ser Gly Arg Thr Phe Asn Ser
20 25 30

Tyr Ala Trp Gly Trp Phe Arg Gln Ala Pro Gly Lys Glu Arg Gly Phe
35 40 45

Val Ala Arg Ile Ser Phe Ser Gly Gly His Thr Tyr Tyr Ser Asp Ser
50 55 60

Val Lys Gly Arg Phe Thr Ile Ser Arg Asp Asn Ala Lys Asn Ser Val
65 70 75 80

Tyr Leu Gln Met Asn Ser Leu Lys Pro Glu Asp Thr Ala Val Tyr Tyr
85 90 95

Cys Ala Ala Asp Pro Thr Pro Tyr Gly Leu Arg Asn Glu Arg Asn Tyr
100 105 110

His Tyr Trp Gly Gln Gly Thr Gln Val Thr Val Ser Ser
115 120 125

<210> SEQ ID NO 93
<211> LENGTH: 125
<212> TYPE: PRT
<213> ORGANISM: Artificial Sequence
<220> FEATURE:
<223> OTHER INFORMATION: Synthetic construct, chIL10sdAB1D12

<400> SEQUENCE: 93

Met Gln Val Gln Leu Gln Gln Ser Gly Gly Gly Leu Val Gln Ala Gly
1 5 10 15

Gly Ser Leu Arg Leu Ser Cys Ala Ala Ser Gly Arg Thr Phe Asn Ser
20 25 30

Tyr Ala Trp Gly Trp Phe Arg Gln Ala Pro Gly Lys Glu Arg Gly Phe
35 40 45

```
Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125


<210> SEQ ID NO 94
<211> LENGTH: 125
<212> TYPE: PRT
<213> ORGANISM: Artificial Sequence
<220> FEATURE:
<223> OTHER INFORMATION: Synthetic construct, chIL10sdAB1C2

<400> SEQUENCE: 94

Met Gln Val Gln Leu Gln Glu Phe Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125


<210> SEQ ID NO 95
<211> LENGTH: 125
<212> TYPE: PRT
<213> ORGANISM: Artificial Sequence
<220> FEATURE:
<223> OTHER INFORMATION: Synthetic construct, chIL10sdAB1B5

<400> SEQUENCE: 95

Met Gln Val Gln Leu Gln Glu Phe Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
```

```
            100                 105                 110

His Tyr Trp Gly Gln Gly Thr Gln Val Thr Val Ser Ser
        115                 120                 125


<210> SEQ ID NO 96
<211> LENGTH: 125
<212> TYPE: PRT
<213> ORGANISM: Artificial Sequence
<220> FEATURE:
<223> OTHER INFORMATION: Synthetic construct,  chIL10sdAB1E2

<400> SEQUENCE: 96

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125


<210> SEQ ID NO 97
<211> LENGTH: 125
<212> TYPE: PRT
<213> ORGANISM: Artificial Sequence
<220> FEATURE:
<223> OTHER INFORMATION: Synthetic construct, chIL10sdAB1G7

<400> SEQUENCE: 97

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125


<210> SEQ ID NO 98
<211> LENGTH: 125
<212> TYPE: PRT
<213> ORGANISM: Artificial Sequence
<220> FEATURE:
```

<223> OTHER INFORMATION: Synthetic construct, chIL10sdAB1G9

<400> SEQUENCE: 98

```
Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125
```

<210> SEQ ID NO 99
<211> LENGTH: 125
<212> TYPE: PRT
<213> ORGANISM: Artificial Sequence
<220> FEATURE:
<223> OTHER INFORMATION: Synthetic construct, chIL10sdAB1H12

<400> SEQUENCE: 99

```
Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125
```

<210> SEQ ID NO 100
<211> LENGTH: 125
<212> TYPE: PRT
<213> ORGANISM: Artificial Sequence
<220> FEATURE:
<223> OTHER INFORMATION: Synthetic construct, chIL10sdAB2A9

<400> SEQUENCE: 100

```
Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
```

35 40 45

Val Ala Arg Ile Ser Phe Ser Gly Gly His Thr Tyr Tyr Ser Asp Ser
50 55 60

Val Lys Gly Arg Phe Thr Ile Ser Arg Asp Asn Ala Lys Asn Ser Val
65 70 75 80

Tyr Leu Gln Met Asn Ser Leu Lys Pro Glu Asp Thr Ala Val Tyr Tyr
85 90 95

Cys Ala Ala Asp Pro Thr Pro Tyr Gly Leu Arg Asn Glu Arg Asn Tyr
100 105 110

His Tyr Trp Gly Gln Gly Thr Gln Val Thr Val Ser Ser
115 120 125

<210> SEQ ID NO 101
<211> LENGTH: 125
<212> TYPE: PRT
<213> ORGANISM: Artificial Sequence
<220> FEATURE:
<223> OTHER INFORMATION: Synthetic construct, chIL10sdAB1E12

<400> SEQUENCE: 101

Met Gln Val Gln Leu Gln Glu Ser Gly Gly Gly Leu Val Gln Ala Gly
1 5 10 15

Gly Ser Leu Arg Leu Ser Cys Ala Ala Ser Gly Arg Thr Phe Asn Ser
20 25 30

Tyr Ala Trp Gly Trp Phe Arg Gln Ala Pro Gly Lys Glu Arg Gly Phe
35 40 45

Val Ala Arg Ile Ser Phe Ser Gly Gly His Thr Tyr Tyr Ser Asp Ser
50 55 60

Val Lys Gly Arg Phe Thr Ile Ser Arg Asp Asn Ala Lys Asn Ser Val
65 70 75 80

Tyr Leu Gln Met Asn Ser Leu Lys Pro Glu Asp Thr Ala Val Tyr Tyr
85 90 95

Cys Ala Ala Asp Pro Thr Pro Tyr Gly Leu Arg Asn Glu Arg Asn Tyr
100 105 110

His Tyr Trp Gly Gln Gly Thr Gln Val Thr Val Ser Ser
115 120 125

<210> SEQ ID NO 102
<211> LENGTH: 125
<212> TYPE: PRT
<213> ORGANISM: Artificial Sequence
<220> FEATURE:
<223> OTHER INFORMATION: Synthetic construct, chIL10sdAB1E10

<400> SEQUENCE: 102

Met Gln Val Gln Leu Gln Glu Phe Gly Gly Gly Leu Val Gln Ala Gly
1 5 10 15

Gly Ser Leu Arg Leu Ser Cys Ala Ala Ser Gly Arg Thr Phe Asn Ser
20 25 30

Tyr Ala Trp Gly Trp Phe Arg Gln Ala Pro Gly Lys Glu Arg Gly Phe
35 40 45

Val Ala Arg Ile Ser Phe Ser Gly Gly His Thr Tyr Tyr Ser Asp Ser
50 55 60

Val Lys Gly Arg Phe Thr Ile Ser Arg Asp Asn Ala Lys Asn Ser Val
65 70 75 80

Tyr Leu Gln Met Asn Ser Leu Lys Pro Glu Asp Thr Ala Val Tyr Tyr
85 90 95

```
Cys Ala Ala Asp Pro Thr Pro Tyr Gly Leu Arg Asn Glu Arg Asn Tyr
            100                 105                 110

His Tyr Trp Gly Gln Gly Thr Leu Val Thr Val Ser Ser
        115                 120                 125


<210> SEQ ID NO 103
<211> LENGTH: 125
<212> TYPE: PRT
<213> ORGANISM: Artificial Sequence
<220> FEATURE:
<223> OTHER INFORMATION: Synthetic construct, chIL10sdAB1F12

<400> SEQUENCE: 103

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Leu Val Thr Val Ser Ser
        115                 120                 125


<210> SEQ ID NO 104
<211> LENGTH: 125
<212> TYPE: PRT
<213> ORGANISM: Artificial Sequence
<220> FEATURE:
<223> OTHER INFORMATION: Synthetic construct, chIL10sdAB1A8

<400> SEQUENCE: 104

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Leu Val Thr Val Ser Ser
        115                 120                 125


<210> SEQ ID NO 105
<211> LENGTH: 125
<212> TYPE: PRT
<213> ORGANISM: Artificial Sequence
```

<220> FEATURE:
<223> OTHER INFORMATION: Synthetic construct, chIL10sdAB1C8

<400> SEQUENCE: 105

Met Gln Val Gln Leu Gln Glu Ser Gly Gly Gly Leu Val Gln Pro Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Leu Val Thr Val Ser Ser
        115                 120                 125

<210> SEQ ID NO 106
<211> LENGTH: 125
<212> TYPE: PRT
<213> ORGANISM: Artificial Sequence
<220> FEATURE:
<223> OTHER INFORMATION: Synthetic construct,  chIL10sdAB1C12

<400> SEQUENCE: 106

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Leu Val Thr Val Ser Ser
        115                 120                 125

<210> SEQ ID NO 107
<211> LENGTH: 125
<212> TYPE: PRT
<213> ORGANISM: Artificial Sequence
<220> FEATURE:
<223> OTHER INFORMATION: Synthetic construct, chIL10sdAB1B1

<400> SEQUENCE: 107

Met Gln Val Gln Leu Gln Ala Ser Gly Gly Gly Leu Val Gln Ala Gly
1               5                   10                  15

Gly Ser Leu Arg Leu Ser Cys Ala Ala Ser Gly Arg Asn Phe Asn Ser
            20                  25                  30

```
Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Leu Val Thr Val Ser Ser
        115                 120                 125


<210> SEQ ID NO 108
<211> LENGTH: 125
<212> TYPE: PRT
<213> ORGANISM: Artificial Sequence
<220> FEATURE:
<223> OTHER INFORMATION: Synthetic construct,  chIL10sdAB1F1

<400> SEQUENCE: 108

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Arg
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly Asn Thr Tyr Tyr Ala Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

His Tyr Trp Gly Gln Gly Thr Gln Val Thr Val Ser Ser
        115                 120                 125


<210> SEQ ID NO 109
<211> LENGTH: 125
<212> TYPE: PRT
<213> ORGANISM: Artificial Sequence
<220> FEATURE:
<223> OTHER INFORMATION: Synthetic construct, chIL10sdAB1D11

<400> SEQUENCE: 109

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Ile Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95
```

```
Cys Ala Ala Asp Pro Thr Pro Tyr Gly Leu Arg Asn Glu Arg Asn Tyr
            100                 105                 110

His Tyr Trp Gly Gln Gly Thr Leu Val Thr Val Ser Ser
        115                 120                 125


<210> SEQ ID NO 110
<211> LENGTH: 125
<212> TYPE: PRT
<213> ORGANISM: Artificial Sequence
<220> FEATURE:
<223> OTHER INFORMATION: Synthetic construct, chIL10sdAB1E6

<400> SEQUENCE: 110

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Asn Ser
            20                  25                  30

Tyr Ala Trp Gly Trp Phe Arg Gln Ala Pro Gly Lys Glu Arg Gly Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Ser Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Leu Val Thr Val Ser Ser
        115                 120                 125


<210> SEQ ID NO 111
<211> LENGTH: 125
<212> TYPE: PRT
<213> ORGANISM: Artificial Sequence
<220> FEATURE:
<223> OTHER INFORMATION: Synthetic construct, chIL10sdAB1B9

<400> SEQUENCE: 111

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125


<210> SEQ ID NO 112
<211> LENGTH: 125
<212> TYPE: PRT
```

<213> ORGANISM: Artificial Sequence
<220> FEATURE:
<223> OTHER INFORMATION: Synthetic construct, chIL10sdAB1B10

<400> SEQUENCE: 112

```
Met Gln Val Gln Leu Gln Glu Phe Gly Gly Gly Leu Val Gln Pro Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125
```

<210> SEQ ID NO 113
<211> LENGTH: 125
<212> TYPE: PRT
<213> ORGANISM: Artificial Sequence
<220> FEATURE:
<223> OTHER INFORMATION: Synthetic construct, chIL10sdAB1F5

<400> SEQUENCE: 113

```
Met Gln Val Gln Leu Gln Glu Ser Gly Gly Gly Leu Val Gln Pro Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125
```

<210> SEQ ID NO 114
<211> LENGTH: 125
<212> TYPE: PRT
<213> ORGANISM: Artificial Sequence
<220> FEATURE:
<223> OTHER INFORMATION: Synthetic construct, chIL10sdAB1A6

<400> SEQUENCE: 114

```
Met Gln Val Gln Leu Gln Glu Phe Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30
```

```
Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125


<210> SEQ ID NO 115
<211> LENGTH: 125
<212> TYPE: PRT
<213> ORGANISM: Artificial Sequence
<220> FEATURE:
<223> OTHER INFORMATION: Synthetic construct, chIL10sdAB1D5

<400> SEQUENCE: 115

Met Gln Val Gln Leu Gln Gln Phe Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125


<210> SEQ ID NO 116
<211> LENGTH: 125
<212> TYPE: PRT
<213> ORGANISM: Artificial Sequence
<220> FEATURE:
<223> OTHER INFORMATION: Synthetic construct, chIL10sdAB1D8

<400> SEQUENCE: 116

Met Gln Val Gln Leu Gln Gln Phe Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
```

```
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125


<210> SEQ ID NO 117
<211> LENGTH: 125
<212> TYPE: PRT
<213> ORGANISM: Artificial Sequence
<220> FEATURE:
<223> OTHER INFORMATION: Synthetic construct, chIL10sdAB1B4

<400> SEQUENCE: 117

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125


<210> SEQ ID NO 118
<211> LENGTH: 125
<212> TYPE: PRT
<213> ORGANISM: Artificial Sequence
<220> FEATURE:
<223> OTHER INFORMATION: Synthetic construct, chIL10sdAB1C7

<400> SEQUENCE: 118

Met Gln Val Gln Leu Gln Ala Phe Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125


<210> SEQ ID NO 119
<211> LENGTH: 125
```

<212> TYPE: PRT
<213> ORGANISM: Artificial Sequence
<220> FEATURE:
<223> OTHER INFORMATION: Synthetic construct, chIL10sdAB1B3

<400> SEQUENCE: 119

```
Met Gln Val Gln Leu Gln Ala Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125
```

<210> SEQ ID NO 120
<211> LENGTH: 125
<212> TYPE: PRT
<213> ORGANISM: Artificial Sequence
<220> FEATURE:
<223> OTHER INFORMATION: Synthetic construct, chIL10sdAB1D7

<400> SEQUENCE: 120

```
Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Gln Val Thr Val Ser Ser
        115                 120                 125
```

<210> SEQ ID NO 121
<211> LENGTH: 125
<212> TYPE: PRT
<213> ORGANISM: Artificial Sequence
<220> FEATURE:
<223> OTHER INFORMATION: Synthetic construct, chIL10sdAB1F7

<400> SEQUENCE: 121

```
Met Gln Val Gln Leu Gln Glu Phe Gly Gly Gly Leu Val Gln Ala Gly
1               5                   10                  15

Gly Ser Leu Arg Leu Ser Cys Ala Ala Ser Gly Arg Thr Phe Ser Ser
```

```
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Leu Val Thr Val Ser Ser
        115                 120                 125


<210> SEQ ID NO 122
<211> LENGTH: 125
<212> TYPE: PRT
<213> ORGANISM: Artificial Sequence
<220> FEATURE:
<223> OTHER INFORMATION: Synthetic construct, chIL10sdAB1F10

<400> SEQUENCE: 122

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Leu Val Thr Val Ser Ser
        115                 120                 125


<210> SEQ ID NO 123
<211> LENGTH: 125
<212> TYPE: PRT
<213> ORGANISM: Artificial Sequence
<220> FEATURE:
<223> OTHER INFORMATION: Synthetic construct, chIL10sdAB1F2

<400> SEQUENCE: 123

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80
```

-continued

```
Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Leu Val Thr Val Ser Ser
        115                 120                 125


<210> SEQ ID NO 124
<211> LENGTH: 125
<212> TYPE: PRT
<213> ORGANISM: Artificial Sequence
<220> FEATURE:
<223> OTHER INFORMATION: Synthetic construct,  chIL10sdAB1F3

<400> SEQUENCE: 124

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Leu Val Thr Val Ser Ser
        115                 120                 125


<210> SEQ ID NO 125
<211> LENGTH: 125
<212> TYPE: PRT
<213> ORGANISM: Artificial Sequence
<220> FEATURE:
<223> OTHER INFORMATION: Synthetic construct, chIL10sdAB1F8

<400> SEQUENCE: 125

Met Gln Val Gln Leu Gln Ala Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Leu Val Thr Val Ser Ser
        115                 120                 125


<210> SEQ ID NO 126
```

<211> LENGTH: 125
<212> TYPE: PRT
<213> ORGANISM: Artificial Sequence
<220> FEATURE:
<223> OTHER INFORMATION: Synthetic construct, chIL10sdAB1C9

<400> SEQUENCE: 126

```
Met Gln Val Gln Leu Gln Glu Phe Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Leu Val Thr Val Ser Ser
        115                 120                 125
```

<210> SEQ ID NO 127
<211> LENGTH: 125
<212> TYPE: PRT
<213> ORGANISM: Artificial Sequence
<220> FEATURE:
<223> OTHER INFORMATION: Synthetic construct, chIL10sdAB1A12

<400> SEQUENCE: 127

```
Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Leu Val Thr Val Ser Ser
        115                 120                 125
```

<210> SEQ ID NO 128
<211> LENGTH: 125
<212> TYPE: PRT
<213> ORGANISM: Artificial Sequence
<220> FEATURE:
<223> OTHER INFORMATION: Synthetic construct, chIL10sdAB1C3

<400> SEQUENCE: 128

```
Met Gln Val Gln Leu Gln Glu Ser Gly Gly Gly Leu Val Gln Ala Gly
1               5                   10                  15
```

```
Gly Ser Leu Arg Leu Ser Cys Ala Ala Ser Gly Arg Thr Phe Ser Ser
            20                  25                  30

Tyr Ala Trp Gly Trp Phe Arg Gln Ala Pro Gly Lys Glu Arg Glu Phe
        35                  40                  45

Val Ser Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Asn Tyr
            100                 105                 110

Pro Tyr Trp Gly Gln Gly Thr Leu Val Thr Val Ser Ser
        115                 120                 125


<210> SEQ ID NO 129
<211> LENGTH: 125
<212> TYPE: PRT
<213> ORGANISM: Artificial Sequence
<220> FEATURE:
<223> OTHER INFORMATION: Synthetic construct,  chIL10sdAB1E7

<400> SEQUENCE: 129

Met Gln Val Gln Leu Gln Glu Phe Gly Gly Gly Leu Val Gln Ala Gly
1               5                   10                  15

Gly Ser Leu Arg Leu Ser Cys Ala Ala Ser Gly Arg Thr Phe Ser Thr
            20                  25                  30

Tyr Ala Trp Gly Trp Phe Arg Gln Ala Pro Gly Lys Glu Arg Glu Phe
        35                  40                  45

Val Ala Arg Ile Ser Phe Ser Gly Gly His Thr Tyr Tyr Ser Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Arg Asn Glu Arg Ser Tyr
            100                 105                 110

Pro Tyr Trp Gly Gln Gly Thr Leu Val Thr Val Ser Ser
        115                 120                 125


<210> SEQ ID NO 130
<211> LENGTH: 124
<212> TYPE: PRT
<213> ORGANISM: Artificial Sequence
<220> FEATURE:
<223> OTHER INFORMATION: Synthetic construct, chIL10sdAB1D9

<400> SEQUENCE: 130

Met Gln Val Gln Leu Gln Ala Ser Gly Gly Gly Leu Val Gln Ala Gly
1               5                   10                  15

Gly Ser Leu Arg Leu Ser Cys Ala Ala Ser Gly Arg Arg Leu Ser Ile
            20                  25                  30

Asn Val Met Gly Trp Tyr Arg Gln Ala Pro Gly Lys Gln Arg Glu Leu
        35                  40                  45

Val Ala Thr Ile Gly Thr Ser Gly Lys Thr Asn Tyr Ala Asp Ser Val
    50                  55                  60

Arg Gly Arg Phe Thr Ile Ser Arg Asp Asn Ala Gln Asn Thr Val Tyr
65                  70                  75                  80
```

```
Leu Gln Met Asn Ser Leu Lys Pro Glu Asp Thr Ala Val Tyr Tyr Cys
                85                  90                  95

Ala Ala Asp Pro Thr Pro Tyr Gly Leu Arg Asn Glu Arg Asn Tyr His
            100                 105                 110

Tyr Trp Gly Gln Gly Thr Gln Val Thr Val Ser Ser
        115                 120


<210> SEQ ID NO 131
<211> LENGTH: 125
<212> TYPE: PRT
<213> ORGANISM: Artificial Sequence
<220> FEATURE:
<223> OTHER INFORMATION: Synthetic construct, chIL10sdAB1A9

<400> SEQUENCE: 131

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Arg
            20                  25                  30

Tyr Ala Trp Gly Trp Phe Arg Gln Ala Pro Gly Lys Glu Arg Glu Phe
        35                  40                  45

Val Ala Arg Ile Ser Trp Ser Gly Gly His Thr Tyr Phe Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Lys Asn Glu Arg Asn Tyr
            100                 105                 110

His Tyr Trp Gly Gln Gly Thr Gln Val Thr Val Ser Ser
        115                 120                 125


<210> SEQ ID NO 132
<211> LENGTH: 125
<212> TYPE: PRT
<213> ORGANISM: Artificial Sequence
<220> FEATURE:
<223> OTHER INFORMATION: Synthetic construct,   chIL10sdAB1H10

<400> SEQUENCE: 132

Met Gln Val Gln Leu Gln Glu Phe Gly Gly Gly Leu Val Gln Ala Gly
1               5                   10                  15

Gly Ser Leu Arg Leu Ser Cys Ala Ala Ser Gly Arg Thr Phe Ser Arg
            20                  25                  30

Tyr Ala Trp Gly Trp Phe Arg Gln Ala Pro Gly Lys Glu Arg Glu Phe
        35                  40                  45

Val Ala Arg Ile Ser Phe Asn Ser Arg Ser Thr Tyr Tyr Ala Asp Ser
    50                  55                  60

Val Gln Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Pro Thr Pro Tyr Gly Leu Lys Asn Glu Arg Asn Tyr
            100                 105                 110

Asp Tyr Trp Gly Gln Gly Thr Gln Val Thr Val Ser Ser
        115                 120                 125
```

<210> SEQ ID NO 133
<211> LENGTH: 125
<212> TYPE: PRT
<213> ORGANISM: Artificial Sequence
<220> FEATURE:
<223> OTHER INFORMATION: Synthetic construct, chIL10sdAB1C1

<400> SEQUENCE: 133

```
Met Gln Val Gln Leu Gln Ala Ser Gly Gly Gly Leu Val Gln Pro Gly
1               5                   10                  15

Gly Ser Leu Arg Leu Ser Cys Ala Ala Ser Gly Asn Ile Phe Ser Ile
            20                  25                  30

Asn Thr Met Gly Trp Tyr Arg Gln Ala Pro Gly Lys Gln Arg Glu Leu
        35                  40                  45

Val Ala Ser Ile Thr Thr Gly Gly Thr Thr Asn Tyr Glu Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Arg Leu Lys Pro Glu Asp Thr Ala Val Tyr Tyr Cys
                85                  90                  95

Asn His Arg Arg Ser Tyr Ser Gly Arg Asp Tyr Pro Val Tyr Gly Met
            100                 105                 110

Asp Tyr Trp Gly Lys Gly Thr Gln Val Thr Val Ser Ser
        115                 120                 125
```

<210> SEQ ID NO 134
<211> LENGTH: 125
<212> TYPE: PRT
<213> ORGANISM: Artificial Sequence
<220> FEATURE:
<223> OTHER INFORMATION: Synthetic construct, chIL10sdAB1D1

<400> SEQUENCE: 134

```
Met Gln Val Gln Leu Gln Glu Ser Gly Gly Gly Leu Val Gln Pro Gly
1               5                   10                  15

Gly Ser Leu Arg Leu Ser Cys Ala Ala Ser Gly Asn Ile Phe Ser Ile
            20                  25                  30

Asn Thr Met Gly Trp Tyr Arg Gln Ala Pro Gly Lys Gln Arg Glu Leu
        35                  40                  45

Val Ala Ser Ile Thr Thr Gly Gly Thr Thr Asn Tyr Glu Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Arg Leu Lys Pro Glu Asp Thr Ala Val Tyr Tyr Cys
                85                  90                  95

Asn His Arg Arg Ser Tyr Ser Gly Arg Asp Tyr Pro Val Tyr Gly Met
            100                 105                 110

Asp Tyr Trp Gly Lys Gly Thr Leu Val Thr Val Ser Ser
        115                 120                 125
```

<210> SEQ ID NO 135
<211> LENGTH: 125
<212> TYPE: PRT
<213> ORGANISM: Artificial Sequence
<220> FEATURE:
<223> OTHER INFORMATION: Synthetic construct,  chIL10sdAB1A11

<400> SEQUENCE: 135

```
Met Gln Val Gln Leu Gln Glu Ser Gly Gly Gly Leu Val Gln Pro Gly
1               5                   10                  15
```

```
Gly Ser Leu Arg Leu Ser Cys Ala Ala Ser Gly Asn Ile Phe Ser Ile
            20                  25                  30

Asn Thr Met Gly Trp Tyr Arg Gln Ala Pro Gly Lys Gln Arg Glu Leu
        35                  40                  45

Val Ala Ser Ile Thr Thr Gly Gly Thr Thr Asn Tyr Glu Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Arg Leu Lys Pro Glu Asp Thr Ala Val Tyr Tyr Cys
                85                  90                  95

Asn His Arg Arg Ser Tyr Ser Gly Arg Asp Tyr Pro Val Tyr Gly Met
            100                 105                 110

Asp Tyr Trp Gly Lys Gly Thr Leu Val Thr Val Ser Ser
        115                 120                 125


<210> SEQ ID NO 136
<211> LENGTH: 125
<212> TYPE: PRT
<213> ORGANISM: Artificial Sequence
<220> FEATURE:
<223> OTHER INFORMATION: Synthetic construct,  chIL10sdAB1G8

<400> SEQUENCE: 136

Met Gln Val Gln Leu Gln Glu Ser Gly Gly Gly Leu Val Gln Pro Gly
1               5                   10                  15

Gly Ser Leu Arg Leu Ser Cys Ala Ala Ser Gly Asn Ile Phe Ser Ile
            20                  25                  30

Asn Thr Met Gly Trp Tyr Arg Gln Ala Pro Gly Lys Gln Arg Glu Leu
        35                  40                  45

Val Ala Ser Ile Thr Thr Gly Gly Thr Thr Asn Tyr Glu Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Arg Leu Lys Pro Glu Asp Thr Ala Val Tyr Tyr Cys
                85                  90                  95

Asn His Arg Arg Ser Tyr Ser Gly Arg Asp Tyr Pro Val Tyr Gly Met
            100                 105                 110

Asp Tyr Trp Gly Lys Gly Thr Leu Val Thr Val Ser Ser
        115                 120                 125


<210> SEQ ID NO 137
<211> LENGTH: 125
<212> TYPE: PRT
<213> ORGANISM: Artificial Sequence
<220> FEATURE:
<223> OTHER INFORMATION: Synthetic construct, chIL10sdAB1A5

<400> SEQUENCE: 137

Met Gln Val Gln Leu Gln Glu Ser Gly Gly Gly Leu Val Gln Pro Gly
1               5                   10                  15

Gly Ser Leu Arg Leu Ser Cys Ala Ala Ser Gly Asn Ile Phe Ser Ile
            20                  25                  30

Asn Thr Met Gly Trp Tyr Arg Gln Ala Pro Gly Lys Gln Arg Glu Leu
        35                  40                  45

Val Ala Ser Ile Thr Thr Gly Gly Thr Thr Asn Tyr Glu Asp Ser Val
    50                  55                  60

Lys Gly Arg Phe Thr Ile Ser Arg Asp Asn Ala Lys Lys Thr Val Tyr
```

```
65                  70                  75                  80

Leu Gln Met Asn Arg Leu Lys Pro Glu Asp Thr Ala Val Tyr Tyr Cys
                85                  90                  95

Asn His Arg Arg Ser Tyr Ser Gly Arg Asp Tyr Pro Val Tyr Gly Met
            100                 105                 110

Asp Tyr Trp Gly Lys Gly Thr Gln Val Thr Val Ser Ser
        115                 120                 125


<210> SEQ ID NO 138
<211> LENGTH: 125
<212> TYPE: PRT
<213> ORGANISM: Artificial Sequence
<220> FEATURE:
<223> OTHER INFORMATION: Synthetic construct,  chIL10sdAB1C5

<400> SEQUENCE: 138

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Gly Ile
            20                  25                  30

Asn Val Met Gly Trp Tyr Arg Gln Ala Pro Gly Glu Glu Arg Glu Leu
        35                  40                  45

Val Ala Thr Val Thr Thr Gly Gly Thr Thr Asn Tyr Glu Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Arg Leu Lys Pro Glu Asp Thr Ala Val Tyr Tyr Cys
                85                  90                  95

Asn His Arg Arg Ser Tyr Ser Gly Arg Asp Tyr Pro Val Tyr Gly Met
            100                 105                 110

Asp Tyr Trp Gly Lys Gly Thr Gln Val Thr Val Ser Ser
        115                 120                 125


<210> SEQ ID NO 139
<211> LENGTH: 125
<212> TYPE: PRT
<213> ORGANISM: Artificial Sequence
<220> FEATURE:
<223> OTHER INFORMATION: Synthetic construct,  chIL10sdAB1H6

<400> SEQUENCE: 139

Met Gln Val Gln Leu Gln Glu Ser Gly Gly Gly Leu Val Gln Ala Gly
1               5                   10                  15

Gly Ser Leu Arg Leu Ser Cys Thr Val Ser Gly Ser Ile Ser Ser Ile
            20                  25                  30

Asp Gly Met Gly Trp Tyr Arg Gln Ala Pro Gly Asn Gln Arg Glu Leu
        35                  40                  45

Val Ala Thr Ile Ala Arg Thr Gly Ser Thr Ser Tyr Val Pro Ser Val
    50                  55                  60

Lys Gly Arg Phe Thr Ile Ser Arg Asp Asn Asp Gln Thr Thr Leu Tyr
65                  70                  75                  80

Leu Gln Met Asn Asp Leu Thr Pro Glu Asp Thr Ala Val Tyr Tyr Cys
                85                  90                  95

Ala Ala Asp Pro Arg Lys Arg Gly Val Pro Asp Trp Tyr Tyr Gly Met
            100                 105                 110

Asp Tyr Trp Gly Lys Gly Thr Leu Val Thr Val Ser Ser
        115                 120                 125
```

<210> SEQ ID NO 140
<211> LENGTH: 125
<212> TYPE: PRT
<213> ORGANISM: Artificial Sequence
<220> FEATURE:
<223> OTHER INFORMATION: Synthetic construct, chIL10sdAB2A8

<400> SEQUENCE: 140

```
Met Gln Val Gln Leu Gln Ala Ser Gly Gly Gly Leu Val Gln Ala Gly
1               5                   10                  15

Gly Ser Leu Arg Leu Ser Cys Thr Val Ser Gly Ser Ile Ser Ser Ile
            20                  25                  30

Asp Gly Met Gly Trp Tyr Arg Gln Ala Pro Gly Asn Gln Arg Glu Leu
        35                  40                  45

Val Ala Thr Ile Ala Arg Thr Gly Ser Thr Ser Tyr Val Pro Ser Val
    50                  55                  60

Lys Gly Arg Phe Thr Ile Ser Arg Asp Asn Ala Gln Thr Thr Leu Tyr
65                  70                  75                  80

Leu Gln Met Asn Asp Leu Thr Pro Glu Asp Thr Ala Val Tyr Tyr Cys
                85                  90                  95

Ala Ala Asp Pro Arg Lys Arg Gly Val Pro Asp Trp Tyr Tyr Gly Met
            100                 105                 110

Asp Tyr Trp Gly Lys Gly Thr Gln Val Thr Val Ser Ser
        115                 120                 125
```

<210> SEQ ID NO 141
<211> LENGTH: 125
<212> TYPE: PRT
<213> ORGANISM: Artificial Sequence
<220> FEATURE:
<223> OTHER INFORMATION: Synthetic construct, chIL10sdAB1F9

<400> SEQUENCE: 141

```
Met Gln Val Gln Leu Gln Ala Ser Gly Gly Gly Leu Val Gln Ala Gly
1               5                   10                  15

Gly Ser Leu Arg Leu Ser Cys Thr Val Ser Gly Ser Ile Ser Ser Ile
            20                  25                  30

Asp Gly Met Gly Trp Tyr Arg Gln Ala Pro Gly Asn Gln Arg Glu Leu
        35                  40                  45

Val Ala Thr Ile Ala Arg Thr Gly Ser Thr Ser Tyr Val Pro Ser Val
    50                  55                  60

Lys Gly Arg Phe Thr Ile Ser Arg Asp Asn Ala Gln Thr Thr Leu Tyr
65                  70                  75                  80

Leu Gln Met Asn Asp Leu Thr Pro Glu Asp Thr Ala Val Tyr Tyr Cys
                85                  90                  95

Ala Ala Asp Pro Arg Lys Arg Gly Val Pro Asp Trp Tyr Tyr Gly Met
            100                 105                 110

Asp Tyr Trp Gly Lys Gly Thr Leu Val Thr Val Ser Ser
        115                 120                 125
```

<210> SEQ ID NO 142
<211> LENGTH: 124
<212> TYPE: PRT
<213> ORGANISM: Artificial Sequence
<220> FEATURE:
<223> OTHER INFORMATION: Synthetic construct, chIL10sdAB1E11

<400> SEQUENCE: 142

```
Met Gln Val Gln Leu Gln Ala Ser Gly Gly Gly Val Val Gln Ala Gly
```

```
1               5                   10                  15

Gly Ser Leu Arg Leu Thr Cys Ala Ala Ser Gly Arg Thr Tyr Ala Met
            20                  25                  30

Gly Trp Phe Arg Gln Ala Pro Gly Lys Glu Arg Asp Phe Ala Ala Ala
        35                  40                  45

Ile Asn Trp Ile Gly Ser Thr Thr Asp Tyr Ala Asp Ser Val Lys Gly
    50                  55                  60

Arg Phe Thr Ile Ser Arg Asp Ile Ala Lys Asn Thr Met Tyr Leu Gln
65                  70                  75                  80

Met Asn Ser Leu Lys Pro Glu Asp Thr Ala Val Tyr Tyr Cys Ala Ala
                85                  90                  95

Glu Lys Thr Ala Ser Leu Ser Ile Tyr Arg Arg Ala Tyr Asp Tyr Gly
            100                 105                 110

Tyr Trp Gly Gln Gly Thr Leu Val Thr Val Ser Ser
        115                 120


<210> SEQ ID NO 143
<211> LENGTH: 125
<212> TYPE: PRT
<213> ORGANISM: Artificial Sequence
<220> FEATURE:
<223> OTHER INFORMATION: Synthetic construct, chIL10sdAB1D6

<400> SEQUENCE: 143

Met Gln Val Gln Leu Gln Ala Ser Gly Gly Gly Leu Val Gln Ala Gly
1               5                   10                  15

Gly Ser Leu Arg Leu Ser Cys Gln Ala Ser Glu Ser Ile Ser Ser Ile
            20                  25                  30

Asn Thr Met Gly Trp Phe Arg Gln Ala Ser Gly Glu Glu Arg Glu Phe
        35                  40                  45

Val Ala Ala Ile Glu Ser Gly Gly Ala Thr Ala Tyr Ala Glu Ser Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Val Pro Thr Tyr Asp Asp Asp Ala Met Pro Ile Ser Trp
            100                 105                 110

Arg Phe Trp Gly Arg Gly Thr Leu Val Thr Val Ser Ser
        115                 120                 125


<210> SEQ ID NO 144
<211> LENGTH: 126
<212> TYPE: PRT
<213> ORGANISM: Artificial Sequence
<220> FEATURE:
<223> OTHER INFORMATION: Synthetic construct, chIL10sdAB1C4

<400> SEQUENCE: 144

Met Gln Val Gln Leu Gln Ala Ser Gly Gly Gly Leu Val Gln Pro Gly
1               5                   10                  15

Gly Ser Leu Arg Leu Ser Cys Ala Ala Ser Gly Phe Ser Leu Glu Asn
            20                  25                  30

Tyr Val Ile Gly Trp Phe Arg Gln Ala Pro Gly Lys Gly Arg Glu Gly
        35                  40                  45

Leu Ser Cys Ile Ser Ser Thr Asp Asp Ser Ile Phe Ser Val Asp Ser
    50                  55                  60
```

```
Val Lys Gly Arg Phe Thr Val Ser Arg Asp Asn Ala Lys Asn Met Val
65                  70                  75                  80

Tyr Leu Gln Met Asn Ser Leu Lys Ser Glu Asp Thr Ala Val Tyr Tyr
                85                  90                  95

Cys Ala Thr Ser Arg Gly Leu Gly Ser Cys Arg Val Asp Glu Phe Tyr
            100                 105                 110

Tyr Asp Met Trp Gly Gln Gly Thr Gln Val Thr Val Ser Ser
        115                 120                 125


<210> SEQ ID NO 145
<211> LENGTH: 125
<212> TYPE: PRT
<213> ORGANISM: Artificial Sequence
<220> FEATURE:
<223> OTHER INFORMATION: Synthetic construct, chIL10sdAB1H4

<400> SEQUENCE: 145

Met Gln Val Gln Leu Gln Ala Phe Gly Gly Ala Leu Val Gln Ala Gly
1               5                   10                  15

Gly Ser Leu Arg Leu Ser Cys Ala Thr Ser Gly Phe Thr Phe Gly Tyr
            20                  25                  30

Tyr Ala Ile Gly Trp Leu Arg Gln Ala Pro Gly Lys Glu Arg Glu Gly
        35                  40                  45

Val Leu Cys Ile Thr Asn Ala Asp Arg Ile Thr Tyr Tyr Thr Asn Ser
    50                  55                  60

Val Lys Asp Arg Phe Thr Ile Ser Arg Asp Asn Thr Ala Asn Thr Val
65                  70                  75                  80

Tyr Leu Gln Met Asn Asn Leu Lys Pro Glu Asp Thr Ala Thr Tyr Tyr
                85                  90                  95

Cys Ala Thr Asn Phe Tyr Ser Tyr Cys Ser Asp Asn Gly Gly Lys Tyr
            100                 105                 110

Gln Glu Trp Gly Gln Gly Thr Leu Val Thr Val Ser Ser
        115                 120                 125


<210> SEQ ID NO 146
<211> LENGTH: 126
<212> TYPE: PRT
<213> ORGANISM: Artificial Sequence
<220> FEATURE:
<223> OTHER INFORMATION: Synthetic construct, chIL10sdAB1F11

<400> SEQUENCE: 146

Met Gln Val Gln Leu Gln Glu Phe Gly Gly Gly Leu Val Gln Pro Gly
1               5                   10                  15

Gly Ser Leu Arg Leu Ser Cys Ala Ala Ser Gly Arg Thr Gly Ser Ser
            20                  25                  30

Tyr Ala Met Gly Trp Phe Arg Gln Ala Pro Gly Lys Glu Arg Glu Phe
        35                  40                  45

Val Ala Ala Ile Ser Trp Ser Gly Gly Ser Thr Asp Tyr Ala Asp Ser
    50                  55                  60

Val Lys Gly Arg Phe Thr Ile Ser Arg Asp Asn Ala Lys Asn Thr Met
65                  70                  75                  80

Tyr Leu Gln Met Asn Ser Leu Lys Pro Glu Asp Thr Ala Val Tyr Tyr
                85                  90                  95

Cys Ala Val Asp Arg Asn Leu Phe Lys Leu Arg Val Ala Val Gln Glu
            100                 105                 110

Tyr Thr Asn Leu Gly Gln Gly Thr Gln Val Thr Val Ser Ser
        115                 120                 125
```

<210> SEQ ID NO 147
<211> LENGTH: 123
<212> TYPE: PRT
<213> ORGANISM: Artificial Sequence
<220> FEATURE:
<223> OTHER INFORMATION: Synthetic construct, chIL10sdAB1D3

<400> SEQUENCE: 147

```
Met Gln Val Gln Leu Gln Ala Ser Gly Gly Gly Leu Val Gln Pro Gly
1               5                   10                  15

Gly Ser Leu Arg Leu Ser Cys Ala Ala Ser Gly Phe Thr Phe Asp Asp
            20                  25                  30

Tyr Ala Met Ser Trp Val Arg Gln Ala Pro Gly Lys Gly Leu Glu Trp
        35                  40                  45

Val Ser Ala Ile Thr Trp Asn Val Gly Thr Ile Tyr Tyr Ala Glu Ser
    50                  55                  60

Met Lys Gly Arg Phe Thr Ile Ser Arg Asp Asn Ala Lys Asn Thr Leu
65                  70                  75                  80

Tyr Leu Gln Met Asn Ser Leu Lys Ser Glu Asp Thr Ala Met Tyr Tyr
                85                  90                  95

Cys Ala Arg Asp Gly Ile Ala Pro Arg Arg Tyr Tyr Glu Met Ala Asp
            100                 105                 110

Trp Gly Lys Gly Thr Leu Val Thr Val Ser Ser
        115                 120
```

<210> SEQ ID NO 148
<211> LENGTH: 120
<212> TYPE: PRT
<213> ORGANISM: Artificial Sequence
<220> FEATURE:
<223> OTHER INFORMATION: Synthetic construct, chIL10sdAB1A7

<400> SEQUENCE: 148

```
Met Gln Val Gln Leu Gln Ala Ser Gly Gly Gly Ser Val Gln Ala Gly
1               5                   10                  15

Glu Ser Leu Thr Val Ser Cys Ser Val Ser Gly Asn Ile Tyr Asp Ile
            20                  25                  30

Asn Thr Met Ala Trp Tyr Arg Glu Ala Pro Gly Lys Gln Arg Glu Leu
        35                  40                  45

Val Ala Ser Ile Gly Pro Asn Gly Asn Ser Asp Tyr Ala Asn Gly Val
    50                  55                  60

Arg Gly Arg Phe Thr Val Ser Arg Asp Ser Val Lys Asn Thr Val Asp
65                  70                  75                  80

Leu Gln Met Thr Asn Leu Lys Val Asp Asp Thr Ala Ser Tyr Tyr Cys
                85                  90                  95

Asn Val Lys Thr Gly Arg Gly Arg Asn Leu Tyr Ser Asp Trp Gly Asp
            100                 105                 110

Gly Thr Gln Val Thr Val Ser Ser
        115                 120
```

<210> SEQ ID NO 149
<211> LENGTH: 122
<212> TYPE: PRT
<213> ORGANISM: Artificial Sequence
<220> FEATURE:
<223> OTHER INFORMATION: Synthetic construct, chIL10sdAB1H8

<400> SEQUENCE: 149

```
Met Gln Val Gln Leu Gln Glu Ser Gly Gly Gly Leu Val Gln Pro Gly
1               5                   10                  15

Gly Ser Leu Arg Leu Ser Cys Ala Ala Ser Gly Phe Thr Phe Asp Asp
            20                  25                  30

Tyr Ala Met Ser Trp Val Arg Gln Ala Pro Gly Lys Gly Leu Glu Trp
        35                  40                  45

Val Ser Ala Ile Thr Trp Ala Gly Gly Ser Thr Tyr Tyr Ala Glu Ser
    50                  55                  60

Met Lys Gly Arg Phe Thr Ile Ser Arg Asp Asn Ala Lys Asn Thr Leu
65                  70                  75                  80

Tyr Leu Gln Met Asn Ser Leu Lys Ser Glu Asp Thr Ala Val Tyr Tyr
                85                  90                  95

Cys Ala Arg Asn Thr Gly Leu Ala Tyr Glu Val Gly Tyr Asp Tyr Trp
            100                 105                 110

Gly Gln Gly Thr Gln Val Thr Val Ser Ser
        115                 120
```

<210> SEQ ID NO 150
<211> LENGTH: 119
<212> TYPE: PRT
<213> ORGANISM: Artificial Sequence
<220> FEATURE:
<223> OTHER INFORMATION: Synthetic construct, chIL10sdAB1H3

<400> SEQUENCE: 150

```
Met Gln Val Gln Leu Gln Ala Ser Gly Gly Gly Leu Val Gln Pro Gly
1               5                   10                  15

Gly Ser Leu Arg Leu Ser Cys Ala Ala Ser Gly Ser Ile Ser Ser Ile
            20                  25                  30

Asp Thr Met Gly Trp Tyr Arg Arg Ala Pro Gly Lys Gln Arg Glu Leu
        35                  40                  45

Val Ala Thr Ile Ser Ser Gly Gly Arg Thr Thr Tyr Lys Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Asp Asp Thr Ala Val Tyr Tyr Cys
                85                  90                  95

Ala Val Val Val Ser Pro Thr Leu Ile Ala Gly Ser Trp Gly Gln Gly
            100                 105                 110

Thr Gln Val Thr Val Ser Ser
        115
```

<210> SEQ ID NO 151
<211> LENGTH: 119
<212> TYPE: PRT
<213> ORGANISM: Artificial Sequence
<220> FEATURE:
<223> OTHER INFORMATION: Synthetic construct, chIL10sdAB1B8

<400> SEQUENCE: 151

```
Met Gln Val Gln Leu Gln Ala Ser Gly Gly Ala Leu Val Gln Pro Gly
1               5                   10                  15

Gly Ser Leu Arg Leu Ser Cys Ser Ala Ser Glu Ser Ile Asp Thr Phe
            20                  25                  30

Asp Ile Ile Asp Trp Tyr Arg Gln Ala Pro Gly Lys Gln Arg Asp Gln
        35                  40                  45

Arg Glu Leu Val Ala Gln Met Leu Pro Val Gly Ala Thr Thr Tyr Ala
    50                  55                  60
```

```
Asp Ser Val Lys Gly Arg Phe Thr Phe Ser Arg Asp Asn Ala Asn Asn
65                  70                  75                  80

Met Val Tyr Leu Gln Met Asp Asn Leu Gln Pro Asp Asp Thr Ala Val
                85                  90                  95

Tyr Tyr Cys His Ser Ile Asn Arg Asp His Asn Ile Trp Cys Gln Gly
            100                 105                 110

Thr Gln Val Thr Val Ser Ser
        115


<210> SEQ ID NO 152
<211> LENGTH: 116
<212> TYPE: PRT
<213> ORGANISM: Artificial Sequence
<220> FEATURE:
<223> OTHER INFORMATION: Synthetic construct, chIL10sdAB1B2

<400> SEQUENCE: 152

Met Gln Val Gln Leu Gln Ala Phe Gly Gly Gly Thr Val Gln Pro Gly
1               5                   10                  15

Glu Ser Leu Thr Ile His Cys Ala Ala Ser Gly Val Ile Pro Asp Ala
            20                  25                  30

Ser Ala Met Ala Trp Tyr Arg Gln Ala Pro Gly Lys Gln Arg Glu Leu
        35                  40                  45

Val Ala Arg Ile Val Gly Pro Thr Asn Ile Leu Tyr Gly Ala Ser Val
    50                  55                  60

Lys Gly Arg Phe Thr Ile Ser Arg Gly Asn Gly Gly Asp Thr Ile Ser
65                  70                  75                  80

Leu Gln Met Thr Asn Leu Lys Pro Asp Asp Thr Ala Leu Tyr Ile Cys
                85                  90                  95

Asn Leu Leu Gln Ser Gly Thr Asn Tyr Phe Gly Lys Gly Thr Leu Val
            100                 105                 110

Thr Val Ser Ser
        115


<210> SEQ ID NO 153
<211> LENGTH: 116
<212> TYPE: PRT
<213> ORGANISM: Artificial Sequence
<220> FEATURE:
<223> OTHER INFORMATION: Synthetic construct,  chIL10sdAB1D2

<400> SEQUENCE: 153

Met Gln Val Gln Leu Gln Gln Ser Gly Gly Gly Leu Val Gln Thr Gly
1               5                   10                  15

Gly Ser Leu Arg Leu Ser Cys Ala Ala Ser Thr Asn Ile Phe Ser Arg
            20                  25                  30

Asn Thr Met Gly Trp Tyr Arg Gln Ala Pro Ala Lys Gln Arg Glu Phe
        35                  40                  45

Val Ala Ser Ile Thr Arg Ser Asp Ile Thr Asn Tyr Ala Asp Ser Val
    50                  55                  60

Lys Gly Arg Phe Thr Ile Ser Arg Asp Asn Ala Lys Ser Thr Val Tyr
65                  70                  75                  80

Leu Gln Met Asp Ser Leu Lys Ala Glu Asp Thr Ala Val Tyr Tyr Cys
                85                  90                  95

Tyr Ala Arg Gly Arg Pro Gly Ile Tyr Trp Gly Gln Gly Thr Gln Val
            100                 105                 110

Thr Val Ser Ser
```

115

<210> SEQ ID NO 154
<211> LENGTH: 115
<212> TYPE: PRT
<213> ORGANISM: Artificial Sequence
<220> FEATURE:
<223> OTHER INFORMATION: Synthetic construct, chIL10sdAB1D10

<400> SEQUENCE: 154

Met Gln Val Gln Leu Gln Glu Ser Gly Gly Gly Leu Val Gln Ala Gly
1 5 10 15

Gly Ser Leu Arg Leu Ser Cys Val Ala Ser Gly Ile Thr Phe Asn Thr
20 25 30

Tyr Ala Met Gly Trp Tyr Arg Gln Ala Pro Gly Lys Gln Arg Glu Arg
35 40 45

Val Ala Val Ile Ser Asn Phe Gly Val Thr Val Tyr Glu Asn Ser Val
50 55 60

Lys Gly Arg Phe Thr Ile Ser Arg Asp Asn Ala Lys Asn Ala Val Tyr
65 70 75 80

Leu Gln Met Asn Asn Leu Arg Ser Glu Asp Thr Ala Val Tyr Phe Cys
85 90 95

Ser Ala Ile Arg Gly Val Asn Tyr Trp Gly Gln Gly Thr Leu Val Thr
100 105 110

Val Ser Ser
115

<210> SEQ ID NO 155
<211> LENGTH: 6030
<212> TYPE: DNA
<213> ORGANISM: Artificial Sequence
<220> FEATURE:
<223> OTHER INFORMATION: Synthetic construct, pAG4314

<400> SEQUENCE: 155
gtttacccgc caatatatcc tgtcaaacac tgatagttta aactgaaggc gggaaacgac 60
aacctgatca tgagcggaga attaagggag tcacgttatg acccccgccg atgacgcggg 120
acaagccgtt ttacgtttgg aactgacaga accgcaacgt tgaaggagcc actcagctta 180
attaagtcta actcgagtta ctggtacgta tacagggttc cttgcgtgaa gaagggtggc 240
ctgcggttca ccattaacgg tcacgactac ttccagctag tactggtgac caacgtcgcg 300
gcggcagggt caatcaagtc catggaggtt atgggttcca acacagcgga ttggatgccg 360
atggcacgta actggggcgc ccaatggcac tcactggcct acctcaccgg tcaaggtcta 420
tcctttaggg tcaccaacac agatgaccaa acgctcgtct tcaccaacgt cgtgccacca 480
ggatggaagt ttggccagac atttgcaagc aagctgcagt tcaagtgaga ggagaagcct 540
gaattgatac cggagcgttt cttttgggag taacatctct ggttgcctag caaacatatg 600
attgtatata agtttcgttg tgcgtttatt ctttcggtgt gtaaaataac atacatgctt 660
tcctgatatt ttcttgtata tatgtacaca cacacgacaa atccttccat ttctattatt 720
attgaacaat ttaattgcga gggcgagtac ttgtctgttt accttttttt tttcagatgg 780
cattttatag tttaaccttt catggaccgg cagtagttct aaccatgaat gaaaagaaat 840
catagtccac accacgcagg gacattgtgg tcattttaga caagacgatt tgattaatgt 900
cttgtatgat atggtcgaca gtgaggacta acaaacatat ggcatatttt attaccggcg 960
agttaaataa atttatgtca cagtaataaa ctgcctaata aatgcacgcc agaaaatata 1020

```
atgataaaaa aaagaaaaga tacataagtc cattgcttct actttttttaa aaattaaatc   1080
caacattttc tattttttgg tataaacttg gaagtactag ttggatatgc aaaatcatct   1140
aacctccata tatttcatca atttgtttac tttacatatg ggagaggata gtatgtcaaa   1200
gaaaatgaca acaagcttac aagtttctta ttttaaaagt tccgctaact tatcaagcat   1260
agtgtgccac gcaaaactga caacaaacca acaaatttaa ggagcgccta acttatcatc   1320
tatgacatac cgcacaaaat gataacatac tagagaaact ttattgcaca aaaggaaatt   1380
tatccataag gcaaaggaac atcttaaggc tttggatata catttaccaa caagcattgt   1440
ttgtattacc cctaaagcgc aagacatgtc atccatgagt catagtgtgt atatctcaac   1500
attgcaaagc taccttttt ctattatact tttcgcatta taggctagat attatctata   1560
catgtcaaca aactctatcc ctacgtcata tctgaagatt cttttcttca ctatataagt   1620
tggcttccct gtcattgaac tcacatcaac cagcccaagt ttccaataac atcctcaaat   1680
agctggatcc taaaccatga gggtgttgct cgttgccctc gctctcctgg ctctcgctgc   1740
gagcgccacc tcccaggttc agctgcagga aagcggtggc ggactggtgc agccaggtgg   1800
cagcctcagg ctgagctgcg ctgctagcgg caatattttt agcattaaca caatgggttg   1860
gtatagacag gctcctggca agcagcgtga gctcgttgcc agcattacca cgggtggtac   1920
aaccaattat gaagatagcg tgaagggtcg ttttaccatt agcagggaca atgctaagaa   1980
gaccgtttac ctccagatga acaggctgaa gccagaagat accgccgtgt attactgcaa   2040
ccacaggaga agctatagcg gaagagatta tcctgtttac ggtatggact actggggcaa   2100
gggaaccctg gttaccgtga gcagcaagga cgagctgtaa cctaggtccc cgaatttccc   2160
cgatcgttca aacatttggc aataaagttt cttaagattg aatcctgttg ccggtcttgc   2220
gatgattatc atataatttc tgttgaatta cgttaagcat gtaataatta acatgtaatg   2280
catgacgtta tttatgagat gggtttttat gattagagtc ccgcaattat acatttaata   2340
cgcgatagaa aacaaaatat agcgcgcaaa ctaggataaa ttatcgcgcg cggtgtcatc   2400
tatgttacta gatcgggaat tggaattcct gcagtgcagc gtgacccggt cgtgcccctc   2460
tctagagata atgagcattg catgtctaag ttataaaaaa ttaccacata tttttttgt   2520
cacacttgtt tgaagtgcag tttatctatc tttatacata tatttaaact ttactctacg   2580
aataatataa tctatagtac tacaataata tcagtgtttt agagaatcat ataaatgaac   2640
agttagacat ggtctaaagg acaattgagt attttgacaa caggactcta cagttttatc   2700
tttttagtgt gcatgtgttc tcctttttt ttgcaaatag cttcacctat ataatacttc   2760
atccatttta ttagtacatc catttagggt ttagggttaa tggtttttat agactaattt   2820
ttttagtaca tctattttat tctattttag cctctaaatt aagaaaacta aaactctatt   2880
ttagtttttt tatttaataa tttagatata aaatagaata aaataaagtg actaaaaatt   2940
aaacaaatac cctttaagaa attaaaaaaa ctaaggaaac atttttcttg tttcgagtag   3000
ataatgccag cctgttaaac gccgtcgacg agtctaacgg acaccaacca gcgaaccagc   3060
agcgtcgcgt cgggccaagc gaagcagacg gcacggcatc tctgtcgctg cctctggacc   3120
cctctcgaga gttccgctcc accgttggac ttgctccgct gtcggcatcc agaaattgcg   3180
tggcggagcg gcagacgtga gccggcacgg caggcggcct cctcctcctc tcacggcacg   3240
gcagctacgg gggattcctt tcccaccgct ccttcgcttt cccttcctcg cccgccgtaa   3300
taaatagaca ccccctccac accctctttc cccaacctcg tgttgttcgg agcgcacaca   3360
```

```
cacacaacca gatctccccc aaatccaccc gtcggcacct ccgcttcaag gtacgccgct   3420
cgtcctcccc ccccccccct ctctaccttc tctagatcgg cgttccggtc catggttagg   3480
gcccggtagt tctacttctg ttcatgtttg tgttagatcc gtgtttgtgt tagatccgtg   3540
ctgctagcgt tcgtacacgg atgcgacctg tacgtcagac acgttctgat tgctaacttg   3600
ccagtgtttc tctttgggga atcctgggat ggctctagcc gttccgcaga cgggatcgat   3660
ttcatgattt tttttgtttc gttgcatagg gtttggtttg cccttttcct ttatttcaat   3720
atatgccgtg cacttgtttg tcgggtcatc ttttcatgct ttttttgtc ttggttgtga   3780
tgatgtggtc tggttgggcg gtcgttctag atcggagtag aattctgttt caaactacct   3840
ggtggattta ttaattttgg atctgtatgt gtgtgccata catattcata gttacgaatt   3900
gaagatgatg gatggaaata tcgatctagg ataggtatac atgttgatgc gggttttact   3960
gatgcatata cagagatgct tttgttcgc ttggttgtga tgatgtggtg tggttgggcg   4020
gtcgttcatt cgttctagat cggagtagaa tactgtttca aactacctgg tgtatttatt   4080
aattttggaa ctgtatgtgt gtgtcataca tcttcatagt tacgagttta agatggatgg   4140
aaatatcgat ctaggatagg tatacatgtt gatgtgggtt ttactgatgc atatacatga   4200
tggcatatgc agcatctatt catatgctct aaccttgagt acctatctat tataataaac   4260
aagtatgttt tataattatt ttgatcttga tatacttgga tgatggcata tgcagcagct   4320
atatgtggat ttttttagcc ctgccttcat acgctattta tttgcttggt actgtttctt   4380
ttgtcgatgc tcaccctgtt gtttggtgtt acttctgcag atccagatct aaaccatgca   4440
gaaactcatt aactcagtgc aaaactatgc ctggggcagc aaaacggcgt tgactgaact   4500
ttatggtatg gaaaatccgt ccagccagcc gatggccgag ctgtggatgg gcgcacatcc   4560
gaaaagcagt tcacgagtgc agaatgccgc cggagatatc gtttcactgc gtgatgtgat   4620
tgagagtgat aaatcgactc tgctcggaga ggccgttgcc aaacgctttg gcgaactgcc   4680
tttcctgttc aaagtattat gcgcagcaca gccactctcc attcaggttc atccaaacaa   4740
acacaattct gaaatcggtt ttgccaaaga aaatgccgca ggtatcccga tggatgccgc   4800
cgagcgtaac tataaagatc ctaaccacaa gccggagctg gtttttgcgc tgacgccttt   4860
ccttgcgatg aacgcgtttc gtgaattttc cgagattgtc tccctactcc agccggtcgc   4920
aggtgcacat ccggcgattg ctcacttttt acaacagcct gatgccgaac gtttaagcga   4980
actgttcgcc agcctgttga atatgcaggg tgaagaaaaa tcccgcgcgc tggcgatttt   5040
aaaatcggcc ctcgatagcc agcagggtga accgtggcaa acgattcgtt taatttctga   5100
attttacccg gaagacagcg gtctgttctc cccgctattg ctgaatgtgg tgaaattgaa   5160
ccctggcgaa gcgatgttcc tgttcgctga aacaccgcac gcttacctgc aaggcgtggc   5220
gctggaagtg atggcaaact ccgataacgt gctgcgtgcg ggtctgacgc ctaaatacat   5280
tgatattccg gaactggttg ccaatgtgaa attcgaagcc aaaccggcta accagttgtt   5340
gacccagccg gtgaaacaag gtgcagaact ggacttcccg attccagtgg atgattttgc   5400
cttctcgctg catgacctta gtgataaaga aaccaccatt agccagcaga gtgccgccat   5460
tttgttctgc gtcgaaggcg atgcaacgtt gtggaaaggt tctcagcagt tacagcttaa   5520
accgggtgaa tcagcgttta ttgccgccaa cgaatcaccg gtgactgtca aaggccacgg   5580
ccgtttagcg cgtgtttaca acaagctgta agagcttact gaaaaaatta acatctcttg   5640
ctaagctggg agctctagat ccccgaattt ccccgatcgt tcaaacattt ggcaataaag   5700
tttcttaaga ttgaatcctg ttgccggtct tgcgatgatt atcatataat ttctgttgaa   5760
```

```
ttacgttaag catgtaataa ttaacatgta atgcatgacg ttatttatga gatgggtttt   5820

tatgattaga gtcccgcaat tatacattta atacgcgata gaaaacaaaa tatagcgcgc   5880

aaactaggat aaattatcgc gcgcggtgtc atctatgtta ctagatcggg aattggcgag   5940

ctcgaattaa ttcagtacat taaaaacgtc cgcaatgtgt tattaagttg tctaagcgtc   6000

aatttgttta caccacaata tatcctgcca                                    6030
```

```
<210> SEQ ID NO 156
<211> LENGTH: 6030
<212> TYPE: DNA
<213> ORGANISM: Artificial Sequence
<220> FEATURE:
<223> OTHER INFORMATION: Synthetic construct, pAG4315

<400> SEQUENCE: 156
```

```
gtttacccgc caatatatcc tgtcaaacac tgatagttta aactgaaggc gggaaacgac     60

aacctgatca tgagcggaga attaagggag tcacgttatg acccccgccg atgacgcggg    120

acaagccgtt ttacgtttgg aactgacaga accgcaacgt tgaaggagcc actcagctta    180

attaagtcta actcgagtta ctggtacgta tacagggttc cttgcgtgaa gaagggtggc    240

ctgcggttca ccattaacgg tcacgactac ttccagctag tactggtgac caacgtcgcg    300

gcggcagggt caatcaagtc catggaggtt atgggttcca acacagcgga ttggatgccg    360

atggcacgta actggggcgc ccaatggcac tcactggcct acctcaccgg tcaaggtcta    420

tcctttaggg tcaccaacac agatgaccaa acgctcgtct tcaccaacgt cgtgccacca    480

ggatggaagt ttggccagac atttgcaagc aagctgcagt tcaagtgaga ggagaagcct    540

gaattgatac cggagcgttt cttttgggag taacatctct ggttgcctag caaacatatg    600

attgtatata agtttcgttg tgcgtttatt ctttcggtgt gtaaaataac atacatgctt    660

tcctgatatt ttcttgtata tatgtacaca cacacgacaa atccttccat ttctattatt    720

attgaacaat ttaattgcga gggcgagtac ttgtctgttt accttttttt tttcagatgg    780

cattttatag tttaaccttt catggaccgg cagtagttct aaccatgaat gaaaagaaat    840

catagtccac accacgcagg gacattgtgg tcattttaga caagacgatt tgattaatgt    900

cttgtatgat atggtcgaca gtgaggacta acaaacatat ggcatatttt attaccggcg    960

agttaaataa atttatgtca cagtaataaa ctgcctaata aatgcacgcc agaaaatata   1020

atgataaaaa aaagaaaaga tacataagtc cattgcttct actttttaa aaattaaatc   1080

caacattttc tattttttgg tataaacttg gaagtactag ttggatatgc aaaatcatct   1140

aacctccata tatttcatca atttgtttac tttacatatg ggagaggata gtatgtcaaa   1200

gaaaatgaca acaagcttac aagtttctta ttttaaaagt tccgctaact tatcaagcat   1260

agtgtgccac gcaaaactga caacaaacca acaaatttaa ggagcgccta acttatcatc   1320

tatgacatac cgcacaaaat gataacatac tagagaaact ttattgcaca aaaggaaatt   1380

tatccataag gcaaaggaac atcttaaggc tttggatata catttaccaa caagcattgt   1440

ttgtattacc cctaaagcgc aagacatgtc atccatgagt catagtgtgt atatctcaac   1500

attgcaaagc tacctttttt ctattatact tttcgcatta taggctagat attatctata   1560

catgtcaaca aactctatcc ctacgtcata tctgaagatt cttttcttca ctatataagt   1620

tggcttccct gtcattgaac tcacatcaac cagcccaagt ttccaataac atcctcaaat   1680

agctggatcc taaaccatga gggtgttgct cgttgccctc gctctcctgg ctctcgctgc   1740
```

-continued

```
gagcgccacc tcccaggttc agctgcagga aagcggtggc ggactggtgc aggctggtgg   1800
cagcctcagg ctgagctgcg ctgctagcgg cagaaccttt agcagctatg cttggggttg   1860
gtttaggcag gccccaggca aggagcgtga atttgttgcc aggattagct ttagcggagg   1920
tcacacctat tacagcgata gcgtgaaggg aaggtttacc attagccgtg acaatgctaa   1980
gaacaccgtt tatctccaga tgaatagcct gaagccagag gataccgccg tgtattactg   2040
cgctgccgac ccaacccctt acggtctcag gaatgagaga aactatcctt actggggcca   2100
gggaacccag gttaccgtga gcagcaagga cgagctgtaa cctaggtccc cgaatttccc   2160
cgatcgttca aacatttggc aataaagttt cttaagattg aatcctgttg ccggtcttgc   2220
gatgattatc atataatttc tgttgaatta cgttaagcat gtaataatta acatgtaatg   2280
catgacgtta tttatgagat gggtttttat gattagagtc ccgcaattat acatttaata   2340
cgcgatagaa aacaaaatat agcgcgcaaa ctaggataaa ttatcgcgcg cggtgtcatc   2400
tatgttacta gatcgggaat tggaattcct gcagtgcagc gtgacccggt cgtgcccctc   2460
tctagagata atgagcattg catgtctaag ttataaaaaa ttaccacata tttttttgt    2520
cacacttgtt tgaagtgcag tttatctatc tttatacata tatttaaact ttactctacg   2580
aataatataa tctatagtac tacaataata tcagtgtttt agagaatcat ataaatgaac   2640
agttagacat ggtctaaagg acaattgagt attttgacaa caggactcta cagttttatc   2700
tttttagtgt gcatgtgttc tcctttttt ttgcaaatag cttcacctat ataatacttc    2760
atccatttta ttagtacatc catttagggt ttagggttaa tggtttttat agactaattt   2820
ttttagtaca tctattttat tctattttag cctctaaatt aagaaaacta aaactctatt   2880
ttagtttttt tatttaataa tttagatata aaatagaata aaataaagtg actaaaaatt   2940
aaacaaatac cctttaagaa attaaaaaaa ctaaggaaac atttttcttg tttcgagtag   3000
ataatgccag cctgttaaac gccgtcgacg agtctaacgg acaccaacca gcgaaccagc   3060
agcgtcgcgt cgggccaagc gaagcagacg gcacggcatc tctgtcgctg cctctggacc   3120
cctctcgaga gttccgctcc accgttggac ttgctccgct gtcggcatcc agaaattgcg   3180
tggcggagcg gcagacgtga gccggcacgg caggcggcct cctcctcctc tcacggcacg   3240
gcagctacgg gggattcctt tcccaccgct ccttcgcttt cccttcctcg cccgccgtaa   3300
taaatagaca ccccctccac accctctttc cccaacctcg tgttgttcgg agcgcacaca   3360
cacacaacca gatctccccc aaatccaccc gtcggcacct ccgcttcaag gtacgccgct   3420
cgtcctcccc ccccccccct ctctaccttc tctagatcgg cgttccggtc catggttagg   3480
gcccggtagt tctacttctg ttcatgtttg tgttagatcc gtgtttgtgt tagatccgtg   3540
ctgctagcgt tcgtacacgg atgcgacctg tacgtcagac acgttctgat tgctaacttg   3600
ccagtgtttc tctttgggga atcctgggat ggctctagcc gttccgcaga cgggatcgat   3660
ttcatgattt tttttgtttc gttgcatagg gtttggtttg cccttttcct ttatttcaat   3720
atatgccgtg cacttgtttg tcgggtcatc ttttcatgct ttttttgtc ttggttgtga    3780
tgatgtggtc tggttgggcg gtcgttctag atcggagtag aattctgttt caaactacct   3840
ggtggattta ttaattttgg atctgtatgt gtgtgccata catattcata gttacgaatt   3900
gaagatgatg gatggaaata tcgatctagg ataggtatac atgttgatgc gggttttact   3960
gatgcatata cagagatgct tttgttcgc ttggttgtga tgatgtggtg tggttgggcg    4020
gtcgttcatt cgttctagat cggagtagaa tactgtttca aactacctgg tgtatttatt   4080
aattttggaa ctgtatgtgt gtgtcataca tcttcatagt tacgagttta agatggatgg   4140
```

```
aaatatcgat ctaggatagg tatacatgtt gatgtgggtt ttactgatgc atatacatga   4200

tggcatatgc agcatctatt catatgctct aaccttgagt acctatctat tataataaac   4260

aagtatgttt tataattatt ttgatcttga tatacttgga tgatggcata tgcagcagct   4320

atatgtggat ttttttagcc ctgccttcat acgctattta tttgcttggt actgtttctt   4380

ttgtcgatgc tcaccctgtt gtttggtgtt acttctgcag atccagatct aaaccatgca   4440

gaaactcatt aactcagtgc aaaactatgc ctggggcagc aaaacggcgt tgactgaact   4500

ttatggtatg gaaaatccgt ccagccagcc gatggccgag ctgtggatgg gcgcacatcc   4560

gaaaagcagt tcacgagtgc agaatgccgc cggagatatc gtttcactgc gtgatgtgat   4620

tgagagtgat aaatcgactc tgctcggaga ggccgttgcc aaacgctttg gcgaactgcc   4680

tttcctgttc aaagtattat gcgcagcaca gccactctcc attcaggttc atccaaacaa   4740

acacaattct gaaatcggtt ttgccaaaga aaatgccgca ggtatcccga tggatgccgc   4800

cgagcgtaac tataaagatc ctaaccacaa gccggagctg gtttttgcgc tgacgccttt   4860

ccttgcgatg aacgcgtttc gtgaattttc cgagattgtc tccctactcc agccggtcgc   4920

aggtgcacat ccggcgattg ctcacttttt acaacagcct gatgccgaac gtttaagcga   4980

actgttcgcc agcctgttga atatgcaggg tgaagaaaaa tcccgcgcgc tggcgatttt   5040

aaaatcggcc ctcgatagcc agcagggtga accgtggcaa acgattcgtt taatttctga   5100

attttacccg gaagacagcg gtctgttctc cccgctattg ctgaatgtgg tgaaattgaa   5160

ccctggcgaa gcgatgttcc tgttcgctga aacaccgcac gcttacctgc aaggcgtggc   5220

gctggaagtg atggcaaact ccgataacgt gctgcgtgcg ggtctgacgc ctaaatacat   5280

tgatattccg gaactggttg ccaatgtgaa attcgaagcc aaaccggcta accagttgtt   5340

gacccagccg gtgaaacaag gtgcagaact ggacttcccg attccagtgg atgattttgc   5400

cttctcgctg catgacctta gtgataaaga aaccaccatt agccagcaga gtgccgccat   5460

tttgttctgc gtcgaaggcg atgcaacgtt gtggaaaggt tctcagcagt tacagcttaa   5520

accgggtgaa tcagcgttta ttgccgccaa cgaatcaccg gtgactgtca aaggccacgg   5580

ccgtttagcg cgtgtttaca acaagctgta agagcttact gaaaaaatta acatctcttg   5640

ctaagctggg agctctagat ccccgaattt ccccgatcgt tcaaacattt ggcaataaag   5700

tttcttaaga ttgaatcctg ttgccggtct tgcgatgatt atcatataat ttctgttgaa   5760

ttacgttaag catgtaataa ttaacatgta atgcatgacg ttatttatga gatgggtttt   5820

tatgattaga gtcccgcaat tatacattta atacgcgata gaaaacaaaa tatagcgcgc   5880

aaactaggat aaattatcgc gcgcggtgtc atctatgtta ctagatcggg aattggcgag   5940

ctcgaattaa ttcagtacat taaaaacgtc cgcaatgtgt tattaagttg tctaagcgtc   6000

aatttgttta caccacaata tatcctgcca                                    6030
```

<210> SEQ ID NO 157
<211> LENGTH: 6033
<212> TYPE: DNA
<213> ORGANISM: Artificial Sequence
<220> FEATURE:
<223> OTHER INFORMATION: Synthetic construct, pAG4316

<400> SEQUENCE: 157

```
gtttacccgc caatatatcc tgtcaaacac tgatagttta aactgaaggc gggaaacgac     60

aacctgatca tgagcggaga attaagggag tcacgttatg acccccgccg atgacgcggg    120
```

-continued

```
acaagccgtt ttacgtttgg aactgacaga accgcaacgt tgaaggagcc actcagctta    180
attaagtcta actcgagtta ctggtacgta tacagggttc cttgcgtgaa gaagggtggc    240
ctgcggttca ccattaacgg tcacgactac ttccagctag tactggtgac caacgtcgcg    300
gcggcagggt caatcaagtc catggaggtt atgggttcca acacagcgga ttggatgccg    360
atggcacgta actggggcgc ccaatggcac tcactggcct acctcaccgg tcaaggtcta    420
tcctttaggg tcaccaacac agatgaccaa acgctcgtct tcaccaacgt cgtgccacca    480
ggatggaagt ttggccagac atttgcaagc aagctgcagt tcaagtgaga ggagaagcct    540
gaattgatac cggagcgttt cttttgggag taacatctct ggttgcctag caaacatatg    600
attgtatata agtttcgttg tgcgtttatt ctttcggtgt gtaaaataac atacatgctt    660
tcctgatatt ttcttgtata tatgtacaca cacacgacaa atccttccat ttctattatt    720
attgaacaat ttaattgcga gggcgagtac ttgtctgttt accttttttt tttcagatgg    780
cattttatag tttaaccttt catggaccgg cagtagttct aaccatgaat gaaaagaaat    840
catagtccac accacgcagg gacattgtgg tcattttaga caagacgatt tgattaatgt    900
cttgtatgat atggtcgaca gtgaggacta acaaacatat ggcatatttt attaccggcg    960
agttaaataa atttatgtca cagtaataaa ctgcctaata aatgcacgcc agaaaatata   1020
atgataaaaa aaagaaaaga tacataagtc cattgcttct actttttaa aaattaaatc   1080
caacattttc tattttttgg tataaacttg gaagtactag ttggatatgc aaaatcatct   1140
aacctccata tatttcatca atttgtttac tttacatatg ggagaggata gtatgtcaaa   1200
gaaaatgaca acaagcttac aagtttctta ttttaaaagt tccgctaact tatcaagcat   1260
agtgtgccac gcaaaactga caacaaacca acaaatttaa ggagcgccta acttatcatc   1320
tatgacatac cgcacaaaat gataacatac tagagaaact ttattgcaca aaaggaaatt   1380
tatccataag gcaaaggaac atcttaaggc tttggatata catttaccaa caagcattgt   1440
ttgtattacc cctaaagcgc aagacatgtc atccatgagt catagtgtgt atatctcaac   1500
attgcaaagc taccttttt ctattatact tttcgcatta taggctagat attatctata   1560
catgtcaaca aactctatcc ctacgtcata tctgaagatt cttttcttca ctatataagt   1620
tggcttccct gtcattgaac tcacatcaac cagcccaagt ttccaataac atcctcaaat   1680
agctggatcc taaaccatga gggtgttgct cgttgccctc gctctcctgg ctctcgctgc   1740
gagcgccacc tcccaggttc agctccagga gtttggtggc ggactggtgc agccaggtgg   1800
cagcctcagg ctgagctgcg ctgctagcgg tagaaccggc agcagctatg ctatgggatg   1860
gtttagacag gctccaggca aggagcgtga atttgttgct gccattagct ggagcggagg   1920
tagcaccgat tatgctgaca gcgtgaaggg caggtttacc attagcagag ataatgccaa   1980
gaacaccatg tacctccaga tgaatagcct gaagccagag gataccgctg tttattactg   2040
cgccgtggac cgtaatctct ttaagctgag ggttgctgtg caggaataca ccaacctcgg   2100
ccagggaacc caggttaccg tgagcagcaa ggacgagctg taacctaggt ccccgaattt   2160
ccccgatcgt tcaaacattt ggcaataaag tttcttaaga ttgaatcctg ttgccggtct   2220
tgcgatgatt atcatataat ttctgttgaa ttacgttaag catgtaataa ttaacatgta   2280
atgcatgacg ttatttatga gatgggtttt tatgattaga gtcccgcaat tatacattta   2340
atacgcgata gaaaacaaaa tatagcgcgc aaactaggat aaattatcgc gcgcggtgtc   2400
atctatgtta ctagatcggg aattggaatt cctgcagtgc agcgtgaccc ggtcgtgccc   2460
ctctctagag ataatgagca ttgcatgtct aagttataaa aaattaccac atattttttt   2520
```

-continued tgtcacactt gtttgaagtg cagtttatct atctttatac atatatttaa actttactct 2580
acgaataata taatctatag tactacaata atatcagtgt tttagagaat catataaatg 2640
aacagttaga catggtctaa aggacaattg agtattttga caacaggact ctacagtttt 2700
atctttttag tgtgcatgtg ttctcctttt tttttgcaaa tagcttcacc tatataatac 2760
ttcatccatt ttattagtac atccatttag ggtttagggt taatggtttt tatagactaa 2820 ttttttttagt acatctattt tattctattt tagcctctaa attaagaaaa ctaaaactct 2880
attttagttt ttttatttaa taatttagat ataaaataga ataaaataaa gtgactaaaa 2940
attaaacaaa taccctttaa gaaattaaaa aaactaagga aacatttttc ttgtttcgag 3000
tagataatgc cagcctgtta aacgccgtcg acgagtctaa cggacaccaa ccagcgaacc 3060
agcagcgtcg cgtcgggcca agcgaagcag acggcacggc atctctgtcg ctgcctctgg 3120
acccctctcg agagttccgc tccaccgttg gacttgctcc gctgtcggca tccagaaatt 3180
gcgtggcgga gcggcagacg tgagccggca cggcaggcgg cctcctcctc ctctcacggc 3240
acggcagcta cgggggattc ctttcccacc gctccttcgc tttcccttcc tcgcccgccg 3300
taataaatag acaccccctc cacaccctct ttccccaacc tcgtgttgtt cggagcgcac 3360
acacacacaa ccagatctcc cccaaatcca cccgtcggca cctccgcttc aaggtacgcc 3420
gctcgtcctc cccccccccc cctctctacc ttctctagat cggcgttccg gtccatggtt 3480
agggcccggt agttctactt ctgttcatgt ttgtgttaga tccgtgtttg tgttagatcc 3540
gtgctgctag cgttcgtaca cggatgcgac ctgtacgtca gacacgttct gattgctaac 3600
ttgccagtgt ttctctttgg ggaatcctgg gatggctcta gccgttccgc agacgggatc 3660
gatttcatga ttttttttgt ttcgttgcat agggtttggt ttgccctttt cctttatttc 3720
aatatatgcc gtgcacttgt ttgtcgggtc atcttttcat gctttttttt gtcttggttg 3780
tgatgatgtg gtctggttgg gcggtcgttc tagatcggag tagaattctg tttcaaacta 3840
cctggtggat ttattaattt tggatctgta tgtgtgtgcc atacatattc atagttacga 3900
attgaagatg atggatggaa atatcgatct aggataggta tacatgttga tgcgggtttt 3960
actgatgcat atacagagat gctttttgtt cgcttggttg tgatgatgtg gtgtggttgg 4020
gcggtcgttc attcgttcta gatcggagta gaatactgtt tcaaactacc tggtgtattt 4080
attaattttg gaactgtatg tgtgtgtcat acatcttcat agttacgagt ttaagatgga 4140
tggaaatatc gatctaggat aggtatacat gttgatgtgg gttttactga tgcatataca 4200
tgatggcata tgcagcatct attcatatgc tctaaccttg agtacctatc tattataata 4260
aacaagtatg ttttataatt attttgatct tgatatactt ggatgatggc atatgcagca 4320
gctatatgtg gattttttta gccctgcctt catacgctat ttatttgctt ggtactgttt 4380
cttttgtcga tgctcaccct gttgtttggt gttacttctg cagatccaga tctaaaccat 4440
gcagaaactc attaactcag tgcaaaacta tgcctggggc agcaaaacgg cgttgactga 4500
actttatggt atggaaaatc cgtccagcca gccgatggcc gagctgtgga tgggcgcaca 4560
tccgaaaagc agttcacgag tgcagaatgc cgccggagat atcgtttcac tgcgtgatgt 4620
gattgagagt gataaatcga ctctgctcgg agaggccgtt gccaaacgct ttggcgaact 4680
gcctttcctg ttcaaagtat tatgcgcagc acagccactc tccattcagg ttcatccaaa 4740
caaacacaat tctgaaatcg gttttgccaa agaaaatgcc gcaggtatcc cgatggatgc 4800
cgccgagcgt aactataaag atcctaacca caagccggag ctggtttttg cgctgacgcc 4860

-continued

```
tttccttgcg atgaacgcgt ttcgtgaatt ttccgagatt gtctccctac tccagccggt   4920

cgcaggtgca catccggcga ttgctcactt tttacaacag cctgatgccg aacgtttaag   4980

cgaactgttc gccagcctgt tgaatatgca gggtgaagaa aaatcccgcg cgctggcgat   5040

tttaaaatcg gccctcgata gccagcaggg tgaaccgtgg caaacgattc gtttaatttc   5100

tgaattttac ccggaagaca gcggtctgtt ctccccgcta ttgctgaatg tggtgaaatt   5160

gaaccctggc gaagcgatgt tcctgttcgc tgaaacaccg cacgcttacc tgcaaggcgt   5220

ggcgctggaa gtgatggcaa actccgataa cgtgctgcgt gcgggtctga cgcctaaata   5280

cattgatatt ccggaactgg ttgccaatgt gaaattcgaa gccaaaccgg ctaaccagtt   5340

gttgacccag ccggtgaaac aaggtgcaga actggacttc ccgattccag tggatgattt   5400

tgccttctcg ctgcatgacc ttagtgataa agaaaccacc attagccagc agagtgccgc   5460

cattttgttc tgcgtcgaag gcgatgcaac gttgtggaaa ggttctcagc agttacagct   5520

taaaccgggt gaatcagcgt ttattgccgc caacgaatca ccggtgactg tcaaaggcca   5580

cggccgttta gcgcgtgttt acaacaagct gtaagagctt actgaaaaaa ttaacatctc   5640

ttgctaagct gggagctcta gatccccgaa tttccccgat cgttcaaaca tttggcaata   5700

aagtttctta agattgaatc ctgttgccgg tcttgcgatg attatcatat aatttctgtt   5760

gaattacgtt aagcatgtaa taattaacat gtaatgcatg acgttattta tgagatgggt   5820

ttttatgatt agagtcccgc aattatacat ttaatacgcg atagaaaaca aaatatagcg   5880

cgcaaactag gataaattat cgcgcgcggt gtcatctatg ttactagatc gggaattggc   5940

gagctcgaat taattcagta cattaaaaac gtccgcaatg tgttattaag ttgtctaagc   6000

gtcaatttgt ttacaccaca atatatcctg cca                                6033
```

<210> SEQ ID NO 158
<211> LENGTH: 6030
<212> TYPE: DNA
<213> ORGANISM: Artificial Sequence
<220> FEATURE:
<223> OTHER INFORMATION: Synthetic construct, pAG4317

<400> SEQUENCE: 158

```
gtttacccgc caatatatcc tgtcaaacac tgatagttta aactgaaggc gggaaacgac     60

aacctgatca tgagcggaga attaagggag tcacgttatg acccccgccg atgacgcggg    120

acaagccgtt ttacgtttgg aactgacaga accgcaacgt tgaaggagcc actcagctta    180

attaagtcta actcgagtta ctggtacgta tacagggttc cttgcgtgaa gaagggtggc    240

ctgcggttca ccattaacgg tcacgactac ttccagctag tactggtgac caacgtcgcg    300

gcggcagggt caatcaagtc catggaggtt atgggttcca acacagcgga ttggatgccg    360

atggcacgta actggggcgc ccaatggcac tcactggcct acctcaccgg tcaaggtcta    420

tcctttaggg tcaccaacac agatgaccaa acgctcgtct tcaccaacgt cgtgccacca    480

ggatggaagt ttggccagac atttgcaagc aagctgcagt tcaagtgaga ggagaagcct    540

gaattgatac cggagcgttt cttttgggag taacatctct ggttgcctag caaacatatg    600

attgtatata agtttcgttg tgcgtttatt ctttcggtgt gtaaaataac atacatgctt    660

tcctgatatt ttcttgtata tatgtacaca cacacgacaa atccttccat ttctattatt    720

attgaacaat ttaattgcga gggcgagtac ttgtctgttt accttttttt tttcagatgg    780

cattttatag tttaaccttt catggaccgg cagtagttct aaccatgaat gaaaagaaat    840

catagtccac accacgcagg gacattgtgg tcattttaga caagacgatt tgattaatgt    900
```

```
cttgtatgat atggtcgaca gtgaggacta acaaacatat ggcatatttt attaccggcg    960
agttaaataa atttatgtca cagtaataaa ctgcctaata aatgcacgcc agaaaatata   1020
atgataaaaa aaagaaaaga tacataagtc cattgcttct actttttaa aaattaaatc   1080
caacattttc tattttttgg tataaacttg gaagtactag ttggatatgc aaaatcatct   1140
aacctccata tatttcatca atttgtttac tttacatatg ggagaggata gtatgtcaaa   1200
gaaaatgaca acaagcttac aagtttctta ttttaaaagt tccgctaact tatcaagcat   1260
agtgtgccac gcaaaactga caacaaacca acaaatttaa ggagcgccta acttatcatc   1320
tatgacatac cgcacaaaat gataacatac tagagaaact ttattgcaca aaaggaaatt   1380
tatccataag gcaaaggaac atcttaaggc tttggatata catttaccaa caagcattgt   1440
ttgtattacc cctaaagcgc aagacatgtc atccatgagt catagtgtgt atatctcaac   1500
attgcaaagc taccttttt ctattatact tttcgcatta taggctagat attatctata   1560
catgtcaaca aactctatcc ctacgtcata tctgaagatt cttttcttca ctatataagt   1620
tggcttccct gtcattgaac tcacatcaac cagcccaagt ttccaataac atcctcaaat   1680
agctggatcc taaaccatga gggtgttgct cgttgccctc gctctcctgg ctctcgctgc   1740
gagcgccacc tcccaggttc agctccaggc ttcgggcggc gggctcgtcc aggcgggcgg   1800
ctcgctcagg ctctcgtgcg cggcgtcggg gcggactttc aacagctacg cttggggctg   1860
gttcaggcag gcgccgggca aggagcgcgg cttcgtggcc aggatctcct tcagcggcgg   1920
ccacacctac tactccgaca gcgtcaaggg ccgcttcacg atctccaggg acaacgccaa   1980
gaacagcgtg tacctccaga tgaactccct gaagcccgag gacacggccg tctactactg   2040
cgcggcggac ccgacgccct acggcctcag gaacgagcgg aactaccatt actgggggca   2100
gggcacgcag gtcactgtct cttcgaagga cgagctgtaa cctaggtccc cgaatttccc   2160
cgatcgttca aacatttggc aataaagttt cttaagattg aatcctgttg ccggtcttgc   2220
gatgattatc atataatttc tgttgaatta cgttaagcat gtaataatta acatgtaatg   2280
catgacgtta tttatgagat gggtttttat gattagagtc ccgcaattat acatttaata   2340
cgcgatagaa aacaaaatat agcgcgcaaa ctaggataaa ttatcgcgcg cggtgtcatc   2400
tatgttacta gatcgggaat tggaattcct gcagtgcagc gtgacccggt cgtgcccctc   2460
tctagagata atgagcattg catgtctaag ttataaaaaa ttaccacata ttttttttgt   2520
cacacttgtt tgaagtgcag tttatctatc tttatacata tatttaaact ttactctacg   2580
aataatataa tctatagtac tacaataata tcagtgtttt agagaatcat ataaatgaac   2640
agttagacat ggtctaaagg acaattgagt attttgacaa caggactcta cagttttatc   2700
tttttagtgt gcatgtgttc tcctttttt ttgcaaatag cttcacctat ataatacttc   2760
atccatttta ttagtacatc catttagggt ttagggttaa tggtttttat agactaattt   2820
ttttagtaca tctattttat tctattttag cctctaaatt aagaaaacta aaactctatt   2880
ttagtttttt tatttaataa tttagatata aaatagaata aaataaagtg actaaaaatt   2940
aaacaaatac cctttaagaa attaaaaaaa ctaaggaaac atttttcttg tttcgagtag   3000
ataatgccag cctgttaaac gccgtcgacg agtctaacgg acaccaacca gcgaaccagc   3060
agcgtcgcgt cgggccaagc gaagcagacg gcacggcatc tctgtcgctg cctctggacc   3120
cctctcgaga gttccgctcc accgttggac ttgctccgct gtcggcatcc agaaattgcg   3180
tggcggagcg gcagacgtga gccggcacgg caggcggcct cctcctcctc tcacggcacg   3240
```

```
gcagctacgg gggattcctt tcccaccgct ccttcgcttt cccttcctcg cccgccgtaa   3300
taaatagaca ccccctccac accctctttc cccaacctcg tgttgttcgg agcgcacaca   3360
cacacaacca gatctccccc aaatccaccc gtcggcacct ccgcttcaag gtacgccgct   3420
cgtcctcccc ccccccccct ctctaccttc tctagatcgg cgttccggtc catggttagg   3480
gcccggtagt tctacttctg ttcatgtttg tgttagatcc gtgtttgtgt tagatccgtg   3540
ctgctagcgt tcgtacacgg atgcgacctg tacgtcagac acgttctgat tgctaacttg   3600
ccagtgtttc tctttgggga atcctgggat ggctctagcc gttccgcaga cgggatcgat   3660
ttcatgattt tttttgtttc gttgcatagg gtttggtttg ccctttttcct ttatttcaat   3720
atatgccgtg cacttgtttg tcgggtcatc ttttcatgct ttttttttgtc ttggttgtga   3780
tgatgtggtc tggttgggcg gtcgttctag atcggagtag aattctgttt caaactacct   3840
ggtggattta ttaattttgg atctgtatgt gtgtgccata catattcata gttacgaatt   3900
gaagatgatg gatggaaata tcgatctagg ataggtatac atgttgatgc gggttttact   3960
gatgcatata cagagatgct tttgttcgc ttggttgtga tgatgtggtg tggttgggcg   4020
gtcgttcatt cgttctagat cggagtagaa tactgtttca aactacctgg tgtatttatt   4080
aattttggaa ctgtatgtgt gtgtcataca tcttcatagt tacgagttta agatggatgg   4140
aaatatcgat ctaggatagg tatacatgtt gatgtgggtt ttactgatgc atatacatga   4200
tggcatatgc agcatctatt catatgctct aaccttgagt acctatctat tataataaac   4260
aagtatgttt tataattatt ttgatcttga tatacttgga tgatggcata tgcagcagct   4320
atatgtggat ttttttagcc ctgccttcat acgctattta tttgcttggt actgtttctt   4380
ttgtcgatgc tcaccctgtt gtttggtgtt acttctgcag atccagatct aaaccatgca   4440
gaaactcatt aactcagtgc aaaactatgc ctggggcagc aaaacggcgt tgactgaact   4500
ttatggtatg gaaaatccgt ccagccagcc gatggccgag ctgtggatgg gcgcacatcc   4560
gaaaagcagt tcacgagtgc agaatgccgc cggagatatc gtttcactgc gtgatgtgat   4620
tgagagtgat aaatcgactc tgctcggaga ggccgttgcc aaacgctttg gcgaactgcc   4680
tttcctgttc aaagtattat gcgcagcaca gccactctcc attcaggttc atccaaacaa   4740
acacaattct gaaatcggtt ttgccaaaga aaatgccgca ggtatcccga tggatgccgc   4800
cgagcgtaac tataaagatc ctaaccacaa gccggagctg gtttttgcgc tgacgccttt   4860
ccttgcgatg aacgcgtttc gtgaattttc cgagattgtc tccctactcc agccggtcgc   4920
aggtgcacat ccggcgattg ctcacttttt acaacagcct gatgccgaac gtttaagcga   4980
actgttcgcc agcctgttga atatgcaggg tgaagaaaaa tcccgcgcgc tggcgatttt   5040
aaaatcggcc ctcgatagcc agcagggtga accgtggcaa acgattcgtt taatttctga   5100
attttacccg gaagacagcg gtctgttctc cccgctattg ctgaatgtgg tgaaattgaa   5160
ccctggcgaa gcgatgttcc tgttcgctga aacaccgcac gcttacctgc aaggcgtggc   5220
gctggaagtg atggcaaact ccgataacgt gctgcgtgcg ggtctgacgc ctaaatacat   5280
tgatattccg gaactggttg ccaatgtgaa attcgaagcc aaaccggcta accagttgtt   5340
gacccagccg gtgaaacaag gtgcagaact ggacttcccg attccagtgg atgattttgc   5400
cttctcgctg catgacctta gtgataaaga aaccaccatt agccagcaga gtgccgccat   5460
tttgttctgc gtcgaaggcg atgcaacgtt gtggaaaggt tctcagcagt tacagcttaa   5520
accgggtgaa tcagcgttta ttgccgccaa cgaatcaccg gtgactgtca aaggccacgg   5580
ccgtttagcg cgtgtttaca acaagctgta agagcttact gaaaaaatta acatctcttg   5640
```

```
ctaagctggg agctctagat ccccgaattt ccccgatcgt tcaaacattt ggcaataaag   5700

tttcttaaga ttgaatcctg ttgccggtct tgcgatgatt atcatataat ttctgttgaa   5760

ttacgttaag catgtaataa ttaacatgta atgcatgacg ttatttatga gatgggtttt   5820

tatgattaga gtcccgcaat tatacattta atacgcgata gaaaacaaaa tatagcgcgc   5880

aaactaggat aaattatcgc gcgcggtgtc atctatgtta ctagatcggg aattggcgag   5940

ctcgaattaa ttcagtacat taaaaacgtc cgcaatgtgt tattaagttg tctaagcgtc   6000

aatttgttta caccacaata tatcctgcca                                    6030
```

<210> SEQ ID NO 159
<211> LENGTH: 6029
<212> TYPE: DNA
<213> ORGANISM: Artificial Sequence
<220> FEATURE:
<223> OTHER INFORMATION: Synthetic construct, pAG4985

<400> SEQUENCE: 159

```
gtttacccgc caatatatcc tgtcaaacac tgatagttta aactgaaggc gggaaacgac     60

aacctgatca tgagcggaga attaagggag tcacgttatg acccccgccg atgacgcggg    120

acaagccgtt ttacgtttgg aactgacaga accgcaacgt tgaaggagcc actcagccta    180

agcggccgca ttggacttaa ttaagtgagg ccggccaagc gtcgatttaa atgtaccaca    240

tggcgcgcca actatcatgc gatcgcttca tgtctaactc gagttactgg tacgtaccaa    300

atccatggaa tcaaggtacc aaagtaatca tattatttta tgtgtgaatc ttctttactt    360

tttcatttga ttatgattat gaaggtatga ccttcataac cttcgtccga aatccattat    420

atccaaagga aaataatgct tcgaaggacg aaggattttg atatttaaca ttttatgttg    480

ccttgttctt aattcatagc atttgagaac aagtccccaa caccaatctt tatctttact    540

atattaaagc accagttcaa cgatcgtctc gtgtcaatat tattaaaaaa ctcctacatt    600

tctttataat caacccgcac tcttataatc tcttctctta ctactataat aagagagttt    660

atgtacaaaa taaggtgaaa ttatgtataa gtgttctgga ccttggttgt tggctcatat    720

tcacacaacc taatcaatag aaaacatatg ttttattaaa acaaaattta tcatatatat    780

atatatatat atatatatat atatatatat atataatata aaccgtagca atgcacaggc    840

atatgactag tggcaactta ataccatgtg tgtattaaga tgaataagag gtatccaaat    900

aaataacttg ttcgcttacg tctggatcga aaggggttgg aaacgattaa atctcttcct    960

agtcaaaatt aaatagaagg agatttaatc gatttctccc aatccccttc gatccaggtg   1020

caaccgaata agtccttaaa tgttgaggaa cacgaaacaa ccatgcattg gcatgtaaag   1080

ctccaagaat tcgttgtatc cttaacaact cacagaacat caaccaaaat tgcacgtcaa   1140

gggtattggg taagaaacaa tcaaacaaat cctctctgtg tgcaaagaaa cacggtgagt   1200

catgccgaga tcatactcat ctgatataca tgcttacagc tcacaagaca ttacaaacaa   1260

ctcatattgc attacaaaga tcgtttcatg aaaaataaaa taggccggaa caggacaaaa   1320

atccttgacg tgtaaagtaa atttacaaca aaaaaaaagc catatgtcaa gctaaatcta   1380

attcgtttta cgtagatcaa caacctgtag aaggcaacaa aactgagcca cgcagaagta   1440

cagaatgatt ccagatgaac catcgacgtg ctacgtaaag agagtgacga gtcatataca   1500

tttggcaaga aaccatgaag ctgcctacag ccgtctcggt ggcataagaa cacaagaaat   1560

tgtgttaatt aatcaaagct ataaataacg ctcgcatgcc tgtgcacttc tccatcacca   1620
```

-continued

```
ccactgggtc ttcagaccat tagctttatc tactccagag cgcagaagaa cccgatcgac   1680
accggatcct aaaccatgag ggtgttgctc gttgccctcg ctctcctggc tctcgctgcg   1740
agcgccacct cccaggttca gctgcaggaa agcggtggcg gactggtgca gccaggtggc   1800
agcctcaggc tgagctgcgc tgctagcggc aatattttta gcattaacac aatgggttgg   1860
tatagacagg ctcctggcaa gcagcgtgag ctcgttgcca gcattaccac gggtggtaca   1920
accaattatg aagatagcgt gaagggtcgt tttaccatta gcagggacaa tgctaagaag   1980
accgtttacc tccagatgaa caggctgaag ccagaagata ccgccgtgta ttactgcaac   2040
cacaggagaa gctatagcgg aagagattat cctgtttacg gtatggacta ctggggcaag   2100
ggaaccctgg ttaccgtgag cagcaaggac gagctgtaac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
atgttactag atcgggaatt ggaattcctg cagtgcagcg tgacccggtc gtgcccctct   2460
ctagagataa tgagcattgc atgtctaagt tataaaaaat taccacatat ttttttgtc   2520
acacttgttt gaagtgcagt ttatctatct ttatacatat atttaaactt tactctacga   2580
ataatataat ctatagtact acaataatat cagtgtttta gagaatcata taaatgaaca   2640
gttagacatg gtctaaagga caattgagta ttttgacaac aggactctac agttttatct   2700
ttttagtgtg catgtgttct cctttttttt tgcaaatagc ttcacctata taatacttca   2760
tccattttat tagtacatcc atttagggtt tagggttaat ggtttttata gactaatttt   2820
tttagtacat ctattttatt ctattttagc ctctaaatta agaaaactaa aactctattt   2880
tagttttttt atttaataat ttagatataa aatagaataa aataaagtga ctaaaaatta   2940
aacaaatacc ctttaagaaa ttaaaaaaac taaggaaaca tttttcttgt ttcgagtaga   3000
taatgccagc ctgttaaacg ccgtcgacga gtctaacgga caccaaccag cgaaccagca   3060
gcgtcgcgtc gggccaagcg aagcagacgg cacggcatct ctgtcgctgc ctctggaccc   3120
ctctcgagag ttccgctcca ccgttggact tgctccgctg tcggcatcca gaaattgcgt   3180
ggcggagcgg cagacgtgag ccggcacggc aggcggcctc ctcctcctct cacggcacgg   3240
cagctacggg ggattccttt cccaccgctc cttcgctttc ccttcctcgc ccgccgtaat   3300
aaatagacac cccctccaca ccctctttcc ccaacctcgt gttgttcgga gcgcacacac   3360
acacaaccag atctccccca aatccacccg tcggcacctc cgcttcaagg tacgccgctc   3420
gtcctccccc cccccccctc tctaccttct ctagatcggc gttccggtcc atggttaggg   3480
cccggtagtt ctacttctgt tcatgtttgt gttagatccg tgtttgtgtt agatccgtgc   3540
tgctagcgtt cgtacacgga tgcgacctgt acgtcagaca cgttctgatt gctaacttgc   3600
cagtgtttct ctttggggaa tcctgggatg gctctagccg ttccgcagac gggatcgatt   3660
tcatgatttt ttttgtttcg ttgcataggg tttggtttgc ccttttcctt tatttcaata   3720
tatgccgtgc acttgtttgt cgggtcatct tttcatgctt ttttttgtct tggttgtgat   3780
gatgtggtct ggttgggcgg tcgttctaga tcggagtaga attctgtttc aaactacctg   3840
gtggatttat taattttgga tctgtatgtg tgtgccatac atattcatag ttacgaattg   3900
aagatgatgg atggaaatat cgatctagga taggtataca tgttgatgcg ggttttactg   3960
atgcatatac agagatgctt tttgttcgct tggttgtgat gatgtggtgt ggttgggcgg   4020
```

```
tcgttcattc gttctagatc ggagtagaat actgtttcaa actacctggt gtatttatta   4080

attttggaac tgtatgtgtg tgtcatacat cttcatagtt acgagtttaa gatggatgga   4140

aatatcgatc taggataggt atacatgttg atgtgggttt tactgatgca tatacatgat   4200

ggcatatgca gcatctattc atatgctcta accttgagta cctatctatt ataataaaca   4260

agtatgtttt ataattattt tgatcttgat atacttggat gatggcatat gcagcagcta   4320

tatgtggatt tttttagccc tgccttcata cgctatttat ttgcttggta ctgtttcttt   4380

tgtcgatgct caccctgttg tttggtgtta cttctgcaga tccagatcta aaccatgcag   4440

aaactcatta actcagtgca aaactatgcc tggggcagca aaacggcgtt gactgaactt   4500

tatggtatgg aaaatccgtc cagccagccg atggccgagc tgtggatggg cgcacatccg   4560

aaaagcagtt cacgagtgca gaatgccgcc ggagatatcg tttcactgcg tgatgtgatt   4620

gagagtgata aatcgactct gctcggagag gccgttgcca aacgctttgg cgaactgcct   4680

ttcctgttca aagtattatg cgcagcacag ccactctcca ttcaggttca tccaaacaaa   4740

cacaattctg aaatcggttt tgccaaagaa aatgccgcag gtatcccgat ggatgccgcc   4800

gagcgtaact ataaagatcc taaccacaag ccggagctgg tttttgcgct gacgcctttc   4860

cttgcgatga acgcgtttcg tgaattttcc gagattgtct ccctactcca gccggtcgca   4920

ggtgcacatc cggcgattgc tcacttttta caacagcctg atgccgaacg tttaagcgaa   4980

ctgttcgcca gcctgttgaa tatgcagggt gaagaaaaat cccgcgcgct ggcgatttta   5040

aaatcggccc tcgatagcca gcagggtgaa ccgtggcaaa cgattcgttt aatttctgaa   5100

ttttacccgg aagacagcgg tctgttctcc ccgctattgc tgaatgtggt gaaattgaac   5160

cctggcgaag cgatgttcct gttcgctgaa acaccgcacg cttacctgca aggcgtggcg   5220

ctggaagtga tggcaaactc cgataacgtg ctgcgtgcgg gtctgacgcc taaatacatt   5280

gatattccgg aactggttgc caatgtgaaa ttcgaagcca aaccggctaa ccagttgttg   5340

acccagccgg tgaaacaagg tgcagaactg gacttcccga ttccagtgga tgattttgcc   5400

ttctcgctgc atgaccttag tgataaagaa accaccatta gccagcagag tgccgccatt   5460

ttgttctgcg tcgaaggcga tgcaacgttg tggaaaggtt ctcagcagtt acagcttaaa   5520

ccgggtgaat cagcgtttat tgccgccaac gaatcaccgg tgactgtcaa aggccacggc   5580

cgtttagcgc gtgtttacaa caagctgtaa gagcttactg aaaaaattaa catctcttgc   5640

taagctggga gctctagatc cccgaatttc cccgatcgtt caaacatttg gcaataaagt   5700

ttcttaagat tgaatcctgt tgccggtctt gcgatgatta tcatataatt tctgttgaat   5760

tacgttaagc atgtaataat taacatgtaa tgcatgacgt tatttatgag atgggttttt   5820

atgattagag tcccgcaatt atacatttaa tacgcgatag aaaacaaaat atagcgcgca   5880

aactaggata aattatcgcg cgcggtgtca tctatgttac tagatcggga attggcgagc   5940

tcgaattaat tcagtacatt aaaaacgtcc gcaatgtgtt attaagttgt ctaagcgtca   6000

atttgtttac accacaatat atcctgcca                                     6029
```

<210> SEQ ID NO 160
<211> LENGTH: 6029
<212> TYPE: DNA
<213> ORGANISM: Artificial Sequence
<220> FEATURE:
<223> OTHER INFORMATION: Synthetic construct, pAG4986

<400> SEQUENCE: 160

```
gtttacccgc caatatatcc tgtcaaacac tgatagttta aactgaaggc gggaaacgac     60
aacctgatca tgagcggaga attaagggag tcacgttatg acccccgccg atgacgcggg    120
acaagccgtt ttacgtttgg aactgacaga accgcaacgt tgaaggagcc actcagccta    180
agcggccgca ttggacttaa ttaagtgagg ccggccaagc gtcgatttaa atgtaccaca    240
tggcgcgcca actatcatgc gatcgcttca tgtctaactc gagttactgg tacgtaccaa    300
atccatggaa tcaaggtacc aaagtaatca tattatttta tgtgtgaatc ttctttactt    360
tttcatttga ttatgattat gaaggtatga ccttcataac cttcgtccga aatccattat    420
atccaaagga aaataatgct tcgaaggacg aaggattttg atatttaaca ttttatgttg    480
ccttgttctt aattcatagc atttgagaac aagtccccaa caccaatctt tatctttact    540
atattaaagc accagttcaa cgatcgtctc gtgtcaatat tattaaaaaa ctcctacatt    600
tctttataat caacccgcac tcttataatc tcttctctta ctactataat aagagagttt    660
atgtacaaaa taaggtgaaa ttatgtataa gtgttctgga ccttggttgt tggctcatat    720
tcacacaacc taatcaatag aaaacatatg ttttattaaa acaaaattta tcatatatat    780
atatatatat atatatatat atatatatat atataatata aaccgtagca atgcacaggc    840
atatgactag tggcaactta ataccatgtg tgtattaaga tgaataagag gtatccaaat    900
aaataacttg ttcgcttacg tctggatcga aaggggttgg aaacgattaa atctcttcct    960
agtcaaaatt aaatagaagg agatttaatc gatttctccc aatccccttc gatccaggtg   1020
caaccgaata agtccttaaa tgttgaggaa cacgaaacaa ccatgcattg gcatgtaaag   1080
ctccaagaat tcgttgtatc cttaacaact cacagaacat caaccaaaat tgcacgtcaa   1140
gggtattggg taagaaacaa tcaaacaaat cctctctgtg tgcaaagaaa cacggtgagt   1200
catgccgaga tcatactcat ctgatataca tgcttacagc tcacaagaca ttacaaacaa   1260
ctcatattgc attacaaaga tcgtttcatg aaaaataaaa taggccggaa caggacaaaa   1320
atccttgacg tgtaaagtaa atttacaaca aaaaaaaagc catatgtcaa gctaaatcta   1380
attcgtttta cgtagatcaa caacctgtag aaggcaacaa aactgagcca cgcagaagta   1440
cagaatgatt ccagatgaac catcgacgtg ctacgtaaag agagtgacga gtcatataca   1500
tttggcaaga aaccatgaag ctgcctacag ccgtctcggt ggcataagaa cacaagaaat   1560
tgtgttaatt aatcaaagct ataaataacg ctcgcatgcc tgtgcacttc tccatcacca   1620
ccactgggtc ttcagaccat tagctttatc tactccagag cgcagaagaa cccgatcgac   1680
accggatcct aaaccatgag ggtgttgctc gttgccctcg ctctcctggc tctcgctgcg   1740
agcgccacct cccaggttca gctgcaggaa agcggtggcg gactggtgca ggctggtggc   1800
agcctcaggc tgagctgcgc tgctagcggc agaaccttta gcagctatgc ttggggttgg   1860
tttaggcagg ccccaggcaa ggagcgtgaa tttgttgcca ggattagctt tagcggaggt   1920
cacacctatt acagcgatag cgtgaaggga aggtttacca ttagccgtga caatgctaag   1980
aacaccgttt atctccagat gaatagcctg aagccagagg ataccgccgt gtattactgc   2040
gctgccgacc caacccctta cggtctcagg aatgagagaa actatcctta ctggggccag   2100
ggaacccagg ttaccgtgag cagcaaggac gagctgtaac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
```

atgttactag atcgggaatt ggaattcctg cagtgcagcg tgacccggtc gtgcccctct 2460
ctagagataa tgagcattgc atgtctaagt tataaaaaat taccacatat ttttttgtc 2520
acacttgttt gaagtgcagt ttatctatct ttatacatat atttaaactt tactctacga 2580
ataatataat ctatagtact acaataatat cagtgtttta gagaatcata taaatgaaca 2640
gttagacatg gtctaaagga caattgagta ttttgacaac aggactctac agttttatct 2700
ttttagtgtg catgtgttct cctttttttt tgcaaatagc ttcacctata taatacttca 2760
tccattttat tagtacatcc atttagggtt tagggttaat ggtttttata gactaatttt 2820
tttagtacat ctattttatt ctattttagc ctctaaatta agaaaactaa aactctattt 2880
tagtttttt atttaataat ttagatataa aatagaataa aataaagtga ctaaaaatta 2940
aacaaatacc ctttaagaaa ttaaaaaaac taaggaaaca tttttcttgt ttcgagtaga 3000
taatgccagc ctgttaaacg ccgtcgacga gtctaacgga caccaaccag cgaaccagca 3060
gcgtcgcgtc gggccaagcg aagcagacgg cacggcatct ctgtcgctgc ctctggaccc 3120
ctctcgagag ttccgctcca ccgttggact tgctccgctg tcggcatcca gaaattgcgt 3180
ggcggagcgg cagacgtgag ccggcacggc aggcggcctc ctcctcctct cacggcacgg 3240
cagctacggg ggattccttt cccaccgctc cttcgctttc ccttcctcgc ccgccgtaat 3300
aaatagacac cccctccaca ccctctttcc ccaacctcgt gttgttcgga gcgcacacac 3360
acacaaccag atctccccca aatccacccg tcggcacctc cgcttcaagg tacgccgctc 3420
gtcctccccc cccccccctc tctaccttct ctagatcggc gttccggtcc atggttaggg 3480
cccggtagtt ctacttctgt tcatgtttgt gttagatccg tgtttgtgtt agatccgtgc 3540
tgctagcgtt cgtacacgga tgcgacctgt acgtcagaca cgttctgatt gctaacttgc 3600
cagtgtttct ctttggggaa tcctgggatg gctctagccg ttccgcagac gggatcgatt 3660
tcatgatttt ttttgtttcg ttgcataggg tttggtttgc cctttttcctt tatttcaata 3720
tatgccgtgc acttgtttgt cgggtcatct tttcatgctt ttttttgtct tggttgtgat 3780
gatgtggtct ggttgggcgg tcgttctaga tcggagtaga attctgtttc aaactacctg 3840
gtggatttat taattttgga tctgtatgtg tgtgccatac atattcatag ttacgaattg 3900
aagatgatgg atggaaatat cgatctagga taggtataca tgttgatgcg ggttttactg 3960
atgcatatac agagatgctt tttgttcgct tggttgtgat gatgtggtgt ggttgggcgg 4020
tcgttcattc gttctagatc ggagtagaat actgtttcaa actacctggt gtatttatta 4080
attttggaac tgtatgtgtg tgtcatacat cttcatagtt acgagtttaa gatggatgga 4140
aatatcgatc taggataggt atacatgttg atgtgggttt tactgatgca tatacatgat 4200
ggcatatgca gcatctattc atatgctcta accttgagta cctatctatt ataataaaca 4260
agtatgtttt ataattattt tgatcttgat atacttggat gatggcatat gcagcagcta 4320
tatgtggatt tttttagccc tgccttcata cgctatttat ttgcttggta ctgtttcttt 4380
tgtcgatgct caccctgttg tttggtgtta cttctgcaga tccagatcta aaccatgcag 4440
aaactcatta actcagtgca aaactatgcc tggggcagca aaacggcgtt gactgaactt 4500
tatggtatgg aaaatccgtc cagccagccg atggccgagc tgtggatggg cgcacatccg 4560
aaaagcagtt cacgagtgca gaatgccgcc ggagatatcg tttcactgcg tgatgtgatt 4620
gagagtgata aatcgactct gctcggagag gccgttgcca aacgctttgg cgaactgcct 4680
ttcctgttca aagtattatg cgcagcacag ccactctcca ttcaggttca tccaaacaaa 4740

```
cacaattctg aaatcggttt tgccaaagaa aatgccgcag gtatcccgat ggatgccgcc   4800
gagcgtaact ataaagatcc taaccacaag ccggagctgg tttttgcgct gacgcctttc   4860
cttgcgatga acgcgtttcg tgaattttcc gagattgtct ccctactcca gccggtcgca   4920
ggtgcacatc cggcgattgc tcacttttta caacagcctg atgccgaacg tttaagcgaa   4980
ctgttcgcca gcctgttgaa tatgcagggt gaagaaaaat cccgcgcgct ggcgatttta   5040
aaatcggccc tcgatagcca gcagggtgaa ccgtggcaaa cgattcgttt aatttctgaa   5100
ttttacccgg aagacagcgg tctgttctcc ccgctattgc tgaatgtggt gaaattgaac   5160
cctggcgaag cgatgttcct gttcgctgaa acaccgcacg cttacctgca aggcgtggcg   5220
ctggaagtga tggcaaactc cgataacgtg ctgcgtgcgg gtctgacgcc taaatacatt   5280
gatattccgg aactggttgc caatgtgaaa ttcgaagcca aaccggctaa ccagttgttg   5340
acccagccgg tgaaacaagg tgcagaactg gacttcccga ttccagtgga tgattttgcc   5400
ttctcgctgc atgaccttag tgataaagaa accaccatta gccagcagag tgccgccatt   5460
ttgttctgcg tcgaaggcga tgcaacgttg tggaaaggtt ctcagcagtt acagcttaaa   5520
ccgggtgaat cagcgtttat tgccgccaac gaatcaccgg tgactgtcaa aggccacggc   5580
cgtttagcgc gtgtttacaa caagctgtaa gagcttactg aaaaaattaa catctcttgc   5640
taagctggga gctctagatc cccgaatttc cccgatcgtt caaacatttg gcaataaagt   5700
ttcttaagat tgaatcctgt tgccggtctt gcgatgatta tcatataatt tctgttgaat   5760
tacgttaagc atgtaataat taacatgtaa tgcatgacgt tatttatgag atgggttttt   5820
atgattagag tcccgcaatt atacatttaa tacgcgatag aaaacaaaat atagcgcgca   5880
aactaggata aattatcgcg cgcggtgtca tctatgttac tagatcggga attggcgagc   5940
tcgaattaat tcagtacatt aaaaacgtcc gcaatgtgtt attaagttgt ctaagcgtca   6000
atttgtttac accacaatat atcctgcca                                      6029
```

<210> SEQ ID NO 161
<211> LENGTH: 6032
<212> TYPE: DNA
<213> ORGANISM: Artificial Sequence
<220> FEATURE:
<223> OTHER INFORMATION: Synthetic construct, pAG4987

<400> SEQUENCE: 161

```
gtttacccgc caatatatcc tgtcaaacac tgatagttta aactgaaggc gggaaacgac     60
aacctgatca tgagcggaga attaagggag tcacgttatg acccccgccg atgacgcggg    120
acaagccgtt ttacgtttgg aactgacaga accgcaacgt tgaaggagcc actcagccta    180
agcggccgca ttggacttaa ttaagtgagg ccggccaagc gtcgatttaa atgtaccaca    240
tggcgcgcca actatcatgc gatcgcttca tgtctaactc gagttactgg tacgtaccaa    300
atccatggaa tcaaggtacc aaagtaatca tattatttta tgtgtgaatc ttctttactt    360
tttcatttga ttatgattat gaaggtatga ccttcataac cttcgtccga aatccattat    420
atccaaagga aaataatgct tcgaaggacg aaggattttg atatttaaca ttttatgttg    480
ccttgttctt aattcatagc atttgagaac aagtccccaa caccaatctt tatctttact    540
atattaaagc accagttcaa cgatcgtctc gtgtcaatat tattaaaaaa ctcctacatt    600
tctttataat caacccgcac tcttataatc tcttctctta ctactataat aagagagttt    660
atgtacaaaa taaggtgaaa ttatgtataa gtgttctgga ccttggttgt tggctcatat    720
tcacacaacc taatcaatag aaaacatatg ttttattaaa acaaaattta tcatatatat    780
```

-continued atatatatat atatatatat atatatatat atataatata aaccgtagca atgcacaggc 840
atatgactag tggcaactta ataccatgtg tgtattaaga tgaataagag gtatccaaat 900
aaataacttg ttcgcttacg tctggatcga aaggggttgg aaacgattaa atctcttcct 960
agtcaaaatt aaatagaagg agatttaatc gatttctccc aatccccttc gatccaggtg 1020
caaccgaata agtccttaaa tgttgaggaa cacgaaacaa ccatgcattg gcatgtaaag 1080
ctccaagaat tcgttgtatc cttaacaact cacagaacat caaccaaaat tgcacgtcaa 1140
gggtattggg taagaaacaa tcaaacaaat cctctctgtg tgcaaagaaa cacggtgagt 1200
catgccgaga tcatactcat ctgatataca tgcttacagc tcacaagaca ttacaaacaa 1260
ctcatattgc attacaaaga tcgtttcatg aaaaataaaa taggccggaa caggacaaaa 1320
atccttgacg tgtaaagtaa atttacaaca aaaaaaaagc catatgtcaa gctaaatcta 1380
attcgtttta cgtagatcaa caacctgtag aaggcaacaa aactgagcca cgcagaagta 1440
cagaatgatt ccagatgaac catcgacgtg ctacgtaaag agagtgacga gtcatataca 1500
tttggcaaga aaccatgaag ctgcctacag ccgtctcggt ggcataagaa cacaagaaat 1560
tgtgttaatt aatcaaagct ataaataacg ctcgcatgcc tgtgcacttc tccatcacca 1620
ccactgggtc ttcagaccat tagctttatc tactccagag cgcagaagaa cccgatcgac 1680
accggatcct aaaccatgag ggtgttgctc gttgccctcg ctctcctggc tctcgctgcg 1740
agcgccacct cccaggttca gctccaggag tttggtggcg gactggtgca gccaggtggc 1800
agcctcaggc tgagctgcgc tgctagcggt agaaccggca gcagctatgc tatgggatgg 1860
tttagacagg ctccaggcaa ggagcgtgaa tttgttgctg ccattagctg gagcggaggt 1920
agcaccgatt atgctgacag cgtgaagggc aggtttacca ttagcagaga taatgccaag 1980
aacaccatgt acctccagat gaatagcctg aagccagagg ataccgctgt ttattactgc 2040
gccgtggacc gtaatctctt taagctgagg gttgctgtgc aggaatacac caacctcggc 2100
cagggaaccc aggttaccgt gagcagcaag gacgagctgt aacctaggtc cccgaatttc 2160
cccgatcgtt caaacatttg gcaataaagt ttcttaagat tgaatcctgt tgccggtctt 2220
gcgatgatta tcatataatt tctgttgaat tacgttaagc atgtaataat taacatgtaa 2280
tgcatgacgt tatttatgag atgggttttt atgattagag tcccgcaatt atacatttaa 2340
tacgcgatag aaaacaaaat atagcgcgca aactaggata aattatcgcg cgcggtgtca 2400
tctatgttac tagatcggga attggaattc ctgcagtgca gcgtgacccg gtcgtgcccc 2460
tctctagaga taatgagcat tgcatgtcta agttataaaa aattaccaca tatttttttt 2520
gtcacacttg tttgaagtgc agtttatcta tctttataca tatatttaaa ctttactcta 2580
cgaataatat aatctatagt actacaataa tatcagtgtt ttagagaatc atataaatga 2640
acagttagac atggtctaaa ggacaattga gtattttgac aacaggactc tacagtttta 2700
tctttttagt gtgcatgtgt tctccttttt ttttgcaaat agcttcacct atataatact 2760
tcatccattt tattagtaca tccatttagg gtttagggtt aatggttttt atagactaat 2820
ttttttagta catctatttt attctatttt agcctctaaa ttaagaaaac taaaactcta 2880
ttttagtttt tttatttaat aatttagata taaaatagaa taaaataaag tgactaaaaa 2940
ttaaacaaat accctttaag aaattaaaaa aactaaggaa acatttttct tgtttcgagt 3000
agataatgcc agcctgttaa acgccgtcga cgagtctaac ggacaccaac cagcgaacca 3060
gcagcgtcgc gtcgggccaa gcgaagcaga cggcacggca tctctgtcgc tgcctctgga 3120

-continued

```
ccccctctcga gagttccgct ccaccgttgg acttgctccg ctgtcggcat ccagaaattg   3180

cgtggcggag cggcagacgt gagccggcac ggcaggcggc ctcctcctcc tctcacggca   3240

cggcagctac gggggattcc tttcccaccg ctccttcgct ttcccttcct cgcccgccgt   3300

aataaataga cacccccctcc acaccctctt tccccaacct cgtgttgttc ggagcgcaca   3360

cacacacaac cagatctccc ccaaatccac ccgtcggcac ctccgcttca aggtacgccg   3420

ctcgtcctcc cccccccccc ctctctacct tctctagatc ggcgttccgg tccatggtta   3480

gggcccggta gttctacttc tgttcatgtt tgtgttagat ccgtgtttgt gttagatccg   3540

tgctgctagc gttcgtacac ggatgcgacc tgtacgtcag acacgttctg attgctaact   3600

tgccagtgtt tctctttggg gaatcctggg atggctctag ccgttccgca gacgggatcg   3660

atttcatgat ttttttgtt tcgttgcata gggtttggtt tgccctttc ctttatttca   3720

atatatgccg tgcacttgtt tgtcgggtca tcttttcatg cttttttttg tcttggttgt   3780

gatgatgtgg tctggttggg cggtcgttct agatcggagt agaattctgt ttcaaactac   3840

ctggtggatt tattaatttt ggatctgtat gtgtgtgcca tacatattca tagttacgaa   3900

ttgaagatga tggatggaaa tatcgatcta ggataggtat acatgttgat gcgggtttta   3960

ctgatgcata tacagagatg ctttttgttc gcttggttgt gatgatgtgg tgtggttggg   4020

cggtcgttca ttcgttctag atcggagtag aatactgttt caaactacct ggtgtattta   4080

ttaattttgg aactgtatgt gtgtgtcata catcttcata gttacgagtt taagatggat   4140

ggaaatatcg atctaggata ggtatacatg ttgatgtggg ttttactgat gcatatacat   4200

gatggcatat gcagcatcta ttcatatgct ctaaccttga gtacctatct attataataa   4260

acaagtatgt tttataatta ttttgatctt gatatacttg gatgatggca tatgcagcag   4320

ctatatgtgg attttttag ccctgccttc atacgctatt tatttgcttg gtactgtttc   4380

ttttgtcgat gctcaccctg ttgtttggtg ttacttctgc agatccagat ctaaaccatg   4440

cagaaactca ttaactcagt gcaaaactat gcctggggca gcaaaacggc gttgactgaa   4500

ctttatggta tggaaaatcc gtccagccag ccgatggccg agctgtggat gggcgcacat   4560

ccgaaaagca gttcacgagt gcagaatgcc gccggagata tcgtttcact gcgtgatgtg   4620

attgagagtg ataaatcgac tctgctcgga gaggccgttg ccaaacgctt tggcgaactg   4680

cctttcctgt tcaaagtatt atgcgcagca cagccactct ccattcaggt tcatccaaac   4740

aaacacaatt ctgaaatcgg ttttgccaaa gaaaatgccg caggtatccc gatggatgcc   4800

gccgagcgta actataaaga tcctaaccac aagccggagc tggtttttgc gctgacgcct   4860

ttccttgcga tgaacgcgtt tcgtgaattt tccgagattg tctccctact ccagccggtc   4920

gcaggtgcac atccggcgat tgctcacttt ttacaacagc ctgatgccga acgtttaagc   4980

gaactgttcg ccagcctgtt gaatatgcag ggtgaagaaa aatcccgcgc gctggcgatt   5040

ttaaaatcgg ccctcgatag ccagcagggt gaaccgtggc aaacgattcg tttaatttct   5100

gaattttacc cggaagacag cggtctgttc tccccgctat tgctgaatgt ggtgaaattg   5160

aaccctggcg aagcgatgtt cctgttcgct gaaacaccgc acgcttacct gcaaggcgtg   5220

gcgctggaag tgatggcaaa ctccgataac gtgctgcgtg cgggtctgac gcctaaatac   5280

attgatattc cggaactggt tgccaatgtg aaattcgaag ccaaaccggc taaccagttg   5340

ttgacccagc cggtgaaaca aggtgcagaa ctggacttcc cgattccagt ggatgatttt   5400

gccttctcgc tgcatgacct tagtgataaa gaaaccacca ttagccagca gagtgccgcc   5460

attttgttct gcgtcgaagg cgatgcaacg ttgtggaaag gttctcagca gttacagctt   5520
```

aaaccgggtg aatcagcgtt tattgccgcc aacgaatcac cggtgactgt caaaggccac 5580
ggccgtttag cgcgtgttta caacaagctg taagagctta ctgaaaaaat taacatctct 5640
tgctaagctg ggagctctag atccccgaat ttccccgatc gttcaaacat ttggcaataa 5700
agtttcttaa gattgaatcc tgttgccggt cttgcgatga ttatcatata atttctgttg 5760
aattacgtta agcatgtaat aattaacatg taatgcatga cgttatttat gagatgggtt 5820
tttatgatta gagtcccgca attatacatt taatacgcga tagaaaacaa aatatagcgc 5880
gcaaactagg ataaattatc gcgcgcggtg tcatctatgt tactagatcg ggaattggcg 5940
agctcgaatt aattcagtac attaaaaacg tccgcaatgt gttattaagt tgtctaagcg 6000
tcaatttgtt tacaccacaa tatatcctgc ca 6032

<210> SEQ ID NO 162
<211> LENGTH: 8274
<212> TYPE: DNA
<213> ORGANISM: Artificial Sequence
<220> FEATURE:
<223> OTHER INFORMATION: Synthetic construct, pAG4988

<400> SEQUENCE: 162
gtttacccgc caatatatcc tgtcaaacac tgatagttta aactgaaggc gggaaacgac 60
aacctgatca tgagcggaga attaagggag tcacgttatg acccccgccg atgacgcggg 120
acaagccgtt ttacgtttgg aactgacaga accgcaacgt tgaaggagcc actcagccta 180
agcggccgca ttggacttaa ttaagtgagg ccggccaagc gtcgatttaa atgtaccaca 240
tggcgcgcca actatcatgc gatcgcttca tgtctaactc gagttactgg tacgtaccaa 300
atccatggaa tcaaggtacc aaagtaatca tattatttta tgtgtgaatc ttctttactt 360
tttcatttga ttatgattat gaaggtatga ccttcataac cttcgtccga aatccattat 420
atccaaagga aaataatgct tcgaaggacg aaggattttg atatttaaca ttttatgttg 480
ccttgttctt aattcatagc atttgagaac aagtccccaa caccaatctt tatctttact 540
atattaaagc accagttcaa cgatcgtctc gtgtcaatat tattaaaaaa ctcctacatt 600
tctttataat caacccgcac tcttataatc tcttctctta ctactataat aagagagttt 660
atgtacaaaa taaggtgaaa ttatgtataa gtgttctgga ccttggttgt tggctcatat 720
tcacacaacc taatcaatag aaaacatatg ttttattaaa acaaaattta tcatatatat 780
atatatatat atatatatat atatatatat atataatata aaccgtagca atgcacaggc 840
atatgactag tggcaactta ataccatgtg tgtattaaga tgaataagag gtatccaaat 900
aaataacttg ttcgcttacg tctggatcga aaggggttgg aaacgattaa atctcttcct 960
agtcaaaatt aaatagaagg agatttaatc gatttctccc aatccccttc gatccaggtg 1020
caaccgaata agtccttaaa tgttgaggaa cacgaaacaa ccatgcattg gcatgtaaag 1080
ctccaagaat tcgttgtatc cttaacaact cacagaacat caaccaaaat tgcacgtcaa 1140
gggtattggg taagaaacaa tcaaacaaat cctctctgtg tgcaaagaaa cacggtgagt 1200
catgccgaga tcatactcat ctgatataca tgcttacagc tcacaagaca ttacaaacaa 1260
ctcatattgc attacaaaga tcgtttcatg aaaaataaaa taggccggaa caggacaaaa 1320
atccttgacg tgtaaagtaa atttacaaca aaaaaaaagc catatgtcaa gctaaatcta 1380
attcgtttta cgtagatcaa caacctgtag aaggcaacaa aactgagcca cgcagaagta 1440
cagaatgatt ccagatgaac catcgacgtg ctacgtaaag agagtgacga gtcatataca 1500

-continued

```
tttggcaaga aaccatgaag ctgcctacag ccgtctcggt ggcataagaa cacaagaaat   1560
tgtgttaatt aatcaaagct ataaataacg ctcgcatgcc tgtgcacttc tccatcacca   1620
ccactgggtc ttcagaccat tagctttatc tactccagag cgcagaagaa cccgatcgac   1680
accggatcct aaaccatgag ggtgttgctc gttgccctcg ctctcctggc tctcgctgcg   1740
agcgccacct cccaggttca gctgcaggaa agcggtggcg gactggtgca gccaggtggc   1800
agcctcaggc tgagctgcgc tgctagcggc aatattttta gcattaacac aatgggttgg   1860
tatagacagg ctcctggcaa gcagcgtgag ctcgttgcca gcattaccac gggtggtaca   1920
accaattatg aagatagcgt gaagggtcgt tttaccatta gcagggacaa tgctaagaag   1980
accgtttacc tccagatgaa caggctgaag ccagaagata ccgccgtgta ttactgcaac   2040
cacaggagaa gctatagcgg aagagattat cctgtttacg gtatggacta ctggggcaag   2100
ggaaccctgg ttaccgtgag cagcaaggac gagctgtaac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
atgttactag atcgggaatt gttaattaag tctaactcga gttactggta cgtatacagg   2460
gttccttgcg tgaagaaggg tggcctgcgg ttcaccatta acggtcacga ctacttccag   2520
ctagtactgg tgaccaacgt cgcggcggca gggtcaatca agtccatgga ggttatgggt   2580
tccaacacag cggattggat gccgatggca cgtaactggg gcgcccaatg gcactcactg   2640
gcctacctca ccggtcaagg tctatccttt agggtcacca acacagatga ccaaacgctc   2700
gtcttcacca acgtcgtgcc accaggatgg aagtttggcc agacatttgc aagcaagctg   2760
cagttcaagt gagaggagaa gcctgaattg ataccggagc gtttcttttg ggagtaacat   2820
ctctggttgc ctagcaaaca tatgattgta tataagtttc gttgtgcgtt tattctttcg   2880
gtgtgtaaaa taacatacat gctttcctga tattttcttg tatatatgta cacacacacg   2940
acaaatcctt ccatttctat tattattgaa caatttaatt gcgagggcga gtacttgtct   3000
gtttaccttt tttttttcag atggcatttt atagtttaac ctttcatgga ccggcagtag   3060
ttctaaccat gaatgaaaag aaatcatagt ccacaccacg cagggacatt gtggtcattt   3120
tagacaagac gatttgatta atgtcttgta tgatatggtc gacagtgagg actaacaaac   3180
atatggcata ttttattacc ggcgagttaa ataaatttat gtcacagtaa taaactgcct   3240
aataaatgca cgccagaaaa tataatgata aaaaaaagaa aagatacata agtccattgc   3300
ttctactttt ttaaaaatta aatccaacat tttctatttt ttggtataaa cttggaagta   3360
ctagttggat atgcaaaatc atctaacctc catatatttc atcaatttgt ttactttaca   3420
tatgggagag gatagtatgt caaagaaaat gacaacaagc ttacaagttt cttattttaa   3480
aagttccgct aacttatcaa gcatagtgtg ccacgcaaaa ctgacaacaa accaacaaat   3540
ttaaggagcg cctaacttat catctatgac ataccgcaca aaatgataac atactagaga   3600
aactttattg cacaaaagga aatttatcca taaggcaaag gaacatctta aggctttgga   3660
tatacattta ccaacaagca ttgtttgtat taccccctaaa gcgcaagaca tgtcatccat   3720
gagtcatagt gtgtatatct caacattgca aagctacctt ttttctatta tacttttcgc   3780
attataggct agatattatc tatacatgtc aacaaactct atccctacgt catatctgaa   3840
gattcttttc ttcactatat aagttggctt ccctgtcatt gaactcacat caaccagccc   3900
```

-continued aagtttccaa taacatcctc aaatagctgg atcctaaacc atgagggtgt tgctcgttgc 3960
cctcgctctc ctggctctcg ctgcgagcgc cacctcccag gttcagctgc aggaaagcgg 4020
tggcggactg gtgcagccag gtggcagcct caggctgagc tgcgctgcta gcggcaatat 4080
ttttagcatt aacacaatgg gttggtatag acaggctcct ggcaagcagc gtgagctcgt 4140
tgccagcatt accacgggtg gtacaaccaa ttatgaagat agcgtgaagg gtcgttttac 4200
cattagcagg gacaatgcta agaagaccgt ttacctccag atgaacaggc tgaagccaga 4260
agataccgcc gtgtattact gcaaccacag gagaagctat agcggaagag attatcctgt 4320
ttacggtatg gactactggg gcaagggaac cctggttacc gtgagcagca aggacgagct 4380
gtaacctagg tccccgaatt tccccgatcg ttcaaacatt tggcaataaa gtttcttaag 4440
attgaatcct gttgccggtc ttgcgatgat tatcatataa tttctgttga attacgttaa 4500
gcatgtaata attaacatgt aatgcatgac gttatttatg agatgggttt ttatgattag 4560
agtcccgcaa ttatacattt aatacgcgat agaaaacaaa atatagcgcg caaactagga 4620
taaattatcg cgcgcggtgt catctatgtt actagatcgg gaattggaat tcctgcagtg 4680
cagcgtgacc cggtcgtgcc cctctctaga gataatgagc attgcatgtc taagttataa 4740
aaaattacca catatttttt ttgtcacact tgtttgaagt gcagtttatc tatctttata 4800
catatattta aactttactc tacgaataat ataatctata gtactacaat aatatcagtg 4860
ttttagagaa tcatataaat gaacagttag acatggtcta aaggacaatt gagtattttg 4920
acaacaggac tctacagttt tatcttttta gtgtgcatgt gttctccttt ttttttgcaa 4980
atagcttcac ctatataata cttcatccat tttattagta catccattta gggtttaggg 5040
ttaatggttt ttatagacta atttttttag tacatctatt ttattctatt ttagcctcta 5100
aattaagaaa actaaaactc tattttagtt tttttattta ataatttaga tataaaatag 5160
aataaaataa agtgactaaa aattaaacaa ataccettta agaaattaaa aaaactaagg 5220
aaacattttt cttgtttcga gtagataatg ccagcctgtt aaacgccgtc gacgagtcta 5280
acggacacca accagcgaac cagcagcgtc gcgtcgggcc aagcgaagca gacggcacgg 5340
catctctgtc gctgcctctg gacccctctc gagagttccg ctccaccgtt ggacttgctc 5400
cgctgtcggc atccagaaat tgcgtggcgg agcggcagac gtgagccggc acggcaggcg 5460
gcctcctcct cctctcacgg cacggcagct acgggggatt cctttcccac cgctccttcg 5520
ctttcccttc ctcgcccgcc gtaataaata gacacccct ccacaccctc tttccccaac 5580
ctcgtgttgt tcggagcgca cacacacaca accagatctc ccccaaatcc acccgtcggc 5640
acctccgctt caaggtacgc cgctcgtcct cccccccccc ccctctctac cttctctaga 5700
tcggcgttcc ggtccatggt tagggcccgg tagttctact tctgttcatg tttgtgttag 5760
atccgtgttt gtgttagatc cgtgctgcta gcgttcgtac acggatgcga cctgtacgtc 5820
agacacgttc tgattgctaa cttgccagtg tttctctttg gggaatcctg ggatggctct 5880
agccgttccg cagacgggat cgatttcatg attttttttg tttcgttgca tagggtttgg 5940
tttgcccttt tcctttattt caatatatgc cgtgcacttg tttgtcgggt catcttttca 6000
tgcttttttt tgtcttggtt gtgatgatgt ggtctggttg ggcggtcgtt ctagatcgga 6060
gtagaattct gtttcaaact acctggtgga tttattaatt ttggatctgt atgtgtgtgc 6120
catacatatt catagttacg aattgaagat gatggatgga aatatcgatc taggataggt 6180
atacatgttg atgcgggttt tactgatgca tatacagaga tgctttttgt tcgcttggtt 6240
gtgatgatgt ggtgtggttg ggcggtcgtt cattcgttct agatcggagt agaatactgt 6300
ttcaaactac ctggtgtatt tattaatttt ggaactgtat gtgtgtgtca tacatcttca 6360
tagttacgag tttaagatgg atggaaatat cgatctagga taggtataca tgttgatgtg 6420
ggttttactg atgcatatac atgatggcat atgcagcatc tattcatatg ctctaacctt 6480
gagtacctat ctattataat aaacaagtat gttttataat tattttgatc ttgatatact 6540
tggatgatgg catatgcagc agctatatgt ggattttttt agccctgcct tcatacgcta 6600
tttatttgct tggtactgtt tcttttgtcg atgctcaccc tgttgtttgg tgttacttct 6660
gcagatccag atctaaacca tgcagaaact cattaactca gtgcaaaact atgcctgggg 6720
cagcaaaacg gcgttgactg aactttatgg tatggaaaat ccgtccagcc agccgatggc 6780
cgagctgtgg atgggcgcac atccgaaaag cagttcacga gtgcagaatg ccgccggaga 6840
tatcgtttca ctgcgtgatg tgattgagag tgataaatcg actctgctcg gagaggccgt 6900
tgccaaacgc tttggcgaac tgcctttcct gttcaaagta ttatgcgcag cacagccact 6960
ctccattcag gttcatccaa acaaacacaa ttctgaaatc ggttttgcca aagaaaatgc 7020
cgcaggtatc ccgatggatg ccgccgagcg taactataaa gatcctaacc acaagccgga 7080
gctggttttt gcgctgacgc ctttccttgc gatgaacgcg tttcgtgaat tttccgagat 7140
tgtctcccta ctccagccgg tcgcaggtgc acatccggcg attgctcact tttacaaca 7200 gcctgatgcc gaacgtttaa gcgaactgtt cgccagcctg ttgaatatgc agggtgaaga 7260
aaaatcccgc gcgctggcga ttttaaaatc ggccctcgat agccagcagg gtgaaccgtg 7320
gcaaacgatt cgtttaattt ctgaatttta cccggaagac agcggtctgt tctccccgct 7380
attgctgaat gtggtgaaat tgaaccctgg cgaagcgatg ttcctgttcg ctgaaacacc 7440
gcacgcttac ctgcaaggcg tggcgctgga agtgatggca aactccgata acgtgctgcg 7500
tgcgggtctg acgcctaaat acattgatat tccggaactg gttgccaatg tgaaattcga 7560
agccaaaccg gctaaccagt tgttgaccca gccggtgaaa caaggtgcag aactggactt 7620
cccgattcca gtggatgatt ttgccttctc gctgcatgac cttagtgata aagaaaccac 7680
cattagccag cagagtgccg ccattttgtt ctgcgtcgaa ggcgatgcaa cgttgtggaa 7740
aggttctcag cagttacagc ttaaaccggg tgaatcagcg tttattgccg ccaacgaatc 7800
accggtgact gtcaaaggcc acggccgttt agcgcgtgtt tacaacaagc tgtaagagct 7860
tactgaaaaa attaacatct cttgctaagc tgggagctct agatccccga atttccccga 7920
tcgttcaaac atttggcaat aaagtttctt aagattgaat cctgttgccg gtcttgcgat 7980
gattatcata taatttctgt tgaattacgt taagcatgta ataattaaca tgtaatgcat 8040
gacgttattt atgagatggg tttttatgat tagagtcccg caattataca tttaatacgc 8100
gatagaaaac aaaatatagc gcgcaaacta ggataaatta tcgcgcgcgg tgtcatctat 8160
gttactagat cgggaattgg cgagctcgaa ttaattcagt acattaaaaa cgtccgcaat 8220
gtgttattaa gttgtctaag cgtcaatttg tttacaccac aatatatcct gcca 8274

<210> SEQ ID NO 163
<211> LENGTH: 8274
<212> TYPE: DNA
<213> ORGANISM: Artificial Sequence
<220> FEATURE:
<223> OTHER INFORMATION: Synthetic construct, pAG4989

<400> SEQUENCE: 163
gtttacccgc caatatatcc tgtcaaacac tgatagttta aactgaaggc gggaaacgac 60

```
aacctgatca tgagcggaga attaagggag tcacgttatg acccccgccg atgacgcggg    120
acaagccgtt ttacgtttgg aactgacaga accgcaacgt tgaaggagcc actcagccta    180
agcggccgca ttggacttaa ttaagtgagg ccggccaagc gtcgatttaa atgtaccaca    240
tggcgcgcca actatcatgc gatcgcttca tgtctaactc gagttactgg tacgtaccaa    300
atccatggaa tcaaggtacc aaagtaatca tattatttta tgtgtgaatc ttctttactt    360
tttcatttga ttatgattat gaaggtatga ccttcataac cttcgtccga aatccattat    420
atccaaagga aaataatgct tcgaaggacg aaggattttg atatttaaca ttttatgttg    480
ccttgttctt aattcatagc atttgagaac aagtccccaa caccaatctt tatctttact    540
atattaaagc accagttcaa cgatcgtctc gtgtcaatat tattaaaaaa ctcctacatt    600
tctttataat caacccgcac tcttataatc tcttctctta ctactataat aagagagttt    660
atgtacaaaa taaggtgaaa ttatgtataa gtgttctgga ccttggttgt tggctcatat    720
tcacacaacc taatcaatag aaaacatatg ttttattaaa acaaaattta tcatatatat    780
atatatatat atatatatat atatatatat atataatata aaccgtagca atgcacaggc    840
atatgactag tggcaactta ataccatgtg tgtattaaga tgaataagag gtatccaaat    900
aaataacttg ttcgcttacg tctggatcga aaggggttgg aaacgattaa atctcttcct    960
agtcaaaatt aaatagaagg agatttaatc gatttctccc aatccccttc gatccaggtg   1020
caaccgaata agtccttaaa tgttgaggaa cacgaaacaa ccatgcattg gcatgtaaag   1080
ctccaagaat tcgttgtatc cttaacaact cacagaacat caaccaaaat tgcacgtcaa   1140
gggtattggg taagaaacaa tcaaacaaat cctctctgtg tgcaaagaaa cacggtgagt   1200
catgccgaga tcatactcat ctgatataca tgcttacagc tcacaagaca ttacaaacaa   1260
ctcatattgc attacaaaga tcgtttcatg aaaaataaaa taggccggaa caggacaaaa   1320
atccttgacg tgtaaagtaa atttacaaca aaaaaaaagc catatgtcaa gctaaatcta   1380
attcgtttta cgtagatcaa caacctgtag aaggcaacaa aactgagcca cgcagaagta   1440
cagaatgatt ccagatgaac catcgacgtg ctacgtaaag agagtgacga gtcatataca   1500
tttggcaaga aaccatgaag ctgcctacag ccgtctcggt ggcataagaa cacaagaaat   1560
tgtgttaatt aatcaaagct ataaataacg ctcgcatgcc tgtgcacttc tccatcacca   1620
ccactgggtc ttcagaccat tagctttatc tactccagag cgcagaagaa cccgatcgac   1680
accggatcct aaaccatgag ggtgttgctc gttgccctcg ctctcctggc tctcgctgcg   1740
agcgccacct cccaggttca gctgcaggaa agcggtggcg gactggtgca ggctggtggc   1800
agcctcaggc tgagctgcgc tgctagcggc agaaccttta gcagctatgc ttggggttgg   1860
tttaggcagg ccccaggcaa ggagcgtgaa tttgttgcca ggattagctt tagcggaggt   1920
cacacctatt acagcgatag cgtgaaggga aggtttacca ttagccgtga caatgctaag   1980
aacaccgttt atctccagat gaatagcctg aagccagagg ataccgccgt gtattactgc   2040
gctgccgacc caaccccta cggtctcagg aatgagagaa actatcctta ctggggccag    2100
ggaacccagg ttaccgtgag cagcaaggac gagctgtaac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
```

-continued atgttactag atcgggaatt gttaattaag tctaactcga gttactggta cgtatacagg 2460
gttccttgcg tgaagaaggg tggcctgcgg ttcaccatta acggtcacga ctacttccag 2520
ctagtactgg tgaccaacgt cgcggcggca gggtcaatca agtccatgga ggttatgggt 2580
tccaacacag cggattggat gccgatggca cgtaactggg gcgcccaatg gcactcactg 2640
gcctacctca ccggtcaagg tctatccttt agggtcacca acacagatga ccaaacgctc 2700
gtcttcacca acgtcgtgcc accaggatgg aagtttggcc agacatttgc aagcaagctg 2760
cagttcaagt gagaggagaa gcctgaattg ataccggagc gtttcttttg ggagtaacat 2820
ctctggttgc ctagcaaaca tatgattgta tataagtttc gttgtgcgtt tattctttcg 2880
gtgtgtaaaa taacatacat gctttcctga tattttcttg tatatatgta cacacacacg 2940
acaaatcctt ccatttctat tattattgaa caatttaatt gcgagggcga gtacttgtct 3000
gtttaccttt ttttttcag atggcatttt atagtttaac ctttcatgga ccggcagtag 3060
ttctaaccat gaatgaaaag aaatcatagt ccacaccacg cagggacatt gtggtcattt 3120
tagacaagac gatttgatta atgtcttgta tgatatggtc gacagtgagg actaacaaac 3180
atatggcata ttttattacc ggcgagttaa ataaatttat gtcacagtaa taaactgcct 3240
aataaatgca cgccagaaaa tataatgata aaaaaaagaa aagatacata agtccattgc 3300
ttctactttt ttaaaaatta aatccaacat tttctatttt ttggtataaa cttggaagta 3360
ctagttggat atgcaaaatc atctaacctc catatatttc atcaatttgt ttactttaca 3420
tatgggagag gatagtatgt caaagaaaat gacaacaagc ttacaagttt cttattttaa 3480
aagttccgct aacttatcaa gcatagtgtg ccacgcaaaa ctgacaacaa accaacaaat 3540
ttaaggagcg cctaacttat catctatgac ataccgcaca aaatgataac atactagaga 3600
aactttattg cacaaaagga aatttatcca taaggcaaag gaacatctta aggctttgga 3660
tatacattta ccaacaagca ttgtttgtat taccccctaaa gcgcaagaca tgtcatccat 3720
gagtcatagt gtgtatatct caacattgca aagctacctt ttttctatta tacttttcgc 3780
attataggct agatattatc tatacatgtc aacaaactct atccctacgt catatctgaa 3840
gattcttttc ttcactatat aagttggctt ccctgtcatt gaactcacat caaccagccc 3900
aagtttccaa taacatcctc aaatagctgg atcctaaacc atgagggtgt tgctcgttgc 3960
cctcgctctc ctggctctcg ctgcgagcgc cacctcccag gttcagctgc aggaaagcgg 4020
tggcggactg gtgcaggctg gtggcagcct caggctgagc tgcgctgcta gcggcagaac 4080
ctttagcagc tatgcttggg gttggtttag gcaggcccca ggcaaggagc gtgaatttgt 4140
tgccaggatt agctttagcg gaggtcacac ctattacagc gatagcgtga agggaaggtt 4200
taccattagc cgtgacaatg ctaagaacac cgtttatctc cagatgaata gcctgaagcc 4260
agaggatacc gccgtgtatt actgcgctgc cgacccaacc ccttacggtc tcaggaatga 4320
gagaaactat ccttactggg gccagggaac ccaggttacc gtgagcagca aggacgagct 4380
gtaacctagg tccccgaatt tccccgatcg ttcaaacatt tggcaataaa gtttcttaag 4440
attgaatcct gttgccggtc ttgcgatgat tatcatataa tttctgttga attacgttaa 4500
gcatgtaata attaacatgt aatgcatgac gttatttatg agatgggttt ttatgattag 4560
agtcccgcaa ttatacattt aatacgcgat agaaaacaaa atatagcgcg caaactagga 4620
taaattatcg cgcgcggtgt catctatgtt actagatcgg gaattggaat tcctgcagtg 4680
cagcgtgacc cggtcgtgcc cctctctaga gataatgagc attgcatgtc taagttataa 4740
aaaattacca catatttttt ttgtcacact tgtttgaagt gcagtttatc tatctttata 4800

```
catatattta aactttactc tacgaataat ataatctata gtactacaat aatatcagtg   4860
ttttagagaa tcatataaat gaacagttag acatggtcta aaggacaatt gagtattttg   4920
acaacaggac tctacagttt tatcttttta gtgtgcatgt gttctccttt ttttttgcaa   4980
atagcttcac ctatataata cttcatccat tttattagta catccattta gggtttaggg   5040
ttaatggttt ttatagacta attttttag tacatctatt ttattctatt ttagcctcta    5100
aattaagaaa actaaaactc tattttagtt tttttattta ataatttaga tataaaatag   5160
aataaaataa agtgactaaa aattaaacaa ataccctta agaaattaaa aaaactaagg    5220
aaacattttt cttgtttcga gtagataatg ccagcctgtt aaacgccgtc gacgagtcta   5280
acggacacca accagcgaac cagcagcgtc gcgtcgggcc aagcgaagca gacggcacgg   5340
catctctgtc gctgcctctg gacccctctc gagagttccg ctccaccgtt ggacttgctc   5400
cgctgtcggc atccagaaat tgcgtggcgg agcggcagac gtgagccggc acggcaggcg   5460
gcctcctcct cctctcacgg cacggcagct acgggggatt cctttcccac cgctccttcg   5520
ctttcccttc ctcgcccgcc gtaataaata gacacccct ccacaccctc tttccccaac    5580
ctcgtgttgt tcggagcgca cacacacaca accagatctc ccccaaatcc acccgtcggc   5640
acctccgctt caaggtacgc cgctcgtcct cccccccccc ccctctctac cttctctaga   5700
tcggcgttcc ggtccatggt tagggcccgg tagttctact tctgttcatg tttgtgttag   5760
atccgtgttt gtgttagatc cgtgctgcta gcgttcgtac acggatgcga cctgtacgtc   5820
agacacgttc tgattgctaa cttgccagtg tttctctttg gggaatcctg ggatggctct   5880
agccgttccg cagacgggat cgatttcatg atttttttg tttcgttgca tagggtttgg    5940
tttgcccttt tcctttattt caatatatgc cgtgcacttg tttgtcgggt catcttttca   6000
tgcttttttt tgtcttggtt gtgatgatgt ggtctggttg ggcggtcgtt ctagatcgga   6060
gtagaattct gtttcaaact acctggtgga tttattaatt ttggatctgt atgtgtgtgc   6120
catacatatt catagttacg aattgaagat gatggatgga aatatcgatc taggataggt   6180
atacatgttg atgcgggttt tactgatgca tatacagaga tgctttttgt tcgcttggtt   6240
gtgatgatgt ggtgtggttg ggcggtcgtt cattcgttct agatcggagt agaatactgt   6300
ttcaaactac ctggtgtatt tattaatttt ggaactgtat gtgtgtgtca tacatcttca   6360
tagttacgag tttaagatgg atggaaatat cgatctagga taggtataca tgttgatgtg   6420
ggttttactg atgcatatac atgatggcat atgcagcatc tattcatatg ctctaacctt   6480
gagtacctat ctattataat aaacaagtat gttttataat tattttgatc ttgatatact   6540
tggatgatgg catatgcagc agctatatgt ggattttttt agccctgcct tcatacgcta   6600
tttatttgct tggtactgtt tcttttgtcg atgctcaccc tgttgtttgg tgttacttct   6660
gcagatccag atctaaacca tgcagaaact cattaactca gtgcaaaact atgcctgggg   6720
cagcaaaacg gcgttgactg aactttatgg tatggaaaat ccgtccagcc agccgatggc   6780
cgagctgtgg atgggcgcac atccgaaaag cagttcacga gtgcagaatg ccgccggaga   6840
tatcgtttca ctgcgtgatg tgattgagag tgataaatcg actctgctcg gagaggccgt   6900
tgccaaacgc tttggcgaac tgcctttcct gttcaaagta ttatgcgcag cacagccact   6960
ctccattcag gttcatccaa acaaacacaa ttctgaaatc ggttttgcca aagaaaatgc   7020
cgcaggtatc ccgatggatg ccgccgagcg taactataaa gatcctaacc acaagccgga   7080
gctggttttt gcgctgacgc ctttccttgc gatgaacgcg tttcgtgaat tttccgagat   7140
```

```
tgtctcccta ctccagccgg tcgcaggtgc acatccggcg attgctcact ttttacaaca   7200
gcctgatgcc gaacgtttaa gcgaactgtt cgccagcctg ttgaatatgc agggtgaaga   7260
aaaatcccgc gcgctggcga ttttaaaatc ggccctcgat agccagcagg gtgaaccgtg   7320
gcaaacgatt cgtttaattt ctgaatttta cccggaagac agcggtctgt tctccccgct   7380
attgctgaat gtggtgaaat tgaaccctgg cgaagcgatg ttcctgttcg ctgaaacacc   7440
gcacgcttac ctgcaaggcg tggcgctgga agtgatggca aactccgata acgtgctgcg   7500
tgcgggtctg acgcctaaat acattgatat tccggaactg gttgccaatg tgaaattcga   7560
agccaaaccg gctaaccagt tgttgaccca gccggtgaaa caaggtgcag aactggactt   7620
cccgattcca gtggatgatt ttgccttctc gctgcatgac cttagtgata aagaaaccac   7680
cattagccag cagagtgccg ccattttgtt ctgcgtcgaa ggcgatgcaa cgttgtggaa   7740
aggttctcag cagttacagc ttaaaccggg tgaatcagcg tttattgccg ccaacgaatc   7800
accggtgact gtcaaaggcc acggccgttt agcgcgtgtt tacaacaagc tgtaagagct   7860
tactgaaaaa attaacatct cttgctaagc tgggagctct agatccccga atttccccga   7920
tcgttcaaac atttggcaat aaagtttctt aagattgaat cctgttgccg gtcttgcgat   7980
gattatcata taatttctgt tgaattacgt taagcatgta ataattaaca tgtaatgcat   8040
gacgttattt atgagatggg tttttatgat tagagtcccg caattataca tttaatacgc   8100
gatagaaaac aaaatatagc gcgcaaacta ggataaatta tcgcgcgcgg tgtcatctat   8160
gttactagat cgggaattgg cgagctcgaa ttaattcagt acattaaaaa cgtccgcaat   8220
gtgttattaa gttgtctaag cgtcaatttg tttacaccac aatatatcct gcca         8274
```

```
<210> SEQ ID NO 164
<211> LENGTH: 8280
<212> TYPE: DNA
<213> ORGANISM: Artificial Sequence
<220> FEATURE:
<223> OTHER INFORMATION: Synthetic construct, pAG4990

<400> SEQUENCE: 164
```

```
gtttacccgc caatatatcc tgtcaaacac tgatagttta aactgaaggc gggaaacgac     60
aacctgatca tgagcggaga attaagggag tcacgttatg acccccgccg atgacgcggg    120
acaagccgtt ttacgtttgg aactgacaga accgcaacgt tgaaggagcc actcagccta    180
agcggccgca ttggacttaa ttaagtgagg ccggccaagc gtcgatttaa atgtaccaca    240
tggcgcgcca actatcatgc gatcgcttca tgtctaactc gagttactgg tacgtaccaa    300
atccatggaa tcaaggtacc aaagtaatca tattatttta tgtgtgaatc ttctttactt    360
tttcatttga ttatgattat gaaggtatga ccttcataac cttcgtccga aatccattat    420
atccaaagga aaataatgct tcgaaggacg aaggattttg atatttaaca ttttatgttg    480
ccttgttctt aattcatagc atttgagaac aagtccccaa caccaatctt tatctttact    540
atattaaagc accagttcaa cgatcgtctc gtgtcaatat tattaaaaaa ctcctacatt    600
tctttataat caacccgcac tcttataatc tcttctctta ctactataat aagagagttt    660
atgtacaaaa taaggtgaaa ttatgtataa gtgttctgga ccttggttgt tggctcatat    720
tcacacaacc taatcaatag aaaacatatg ttttattaaa acaaaattta tcatatatat    780
atatatatat atatatatat atatatatat atataatata aaccgtagca atgcacaggc    840
atatgactag tggcaactta ataccatgtg tgtattaaga tgaataagag gtatccaaat    900
aaataacttg ttcgcttacg tctggatcga aaggggttgg aaacgattaa atctcttcct    960
```

-continued agtcaaaatt aaatagaagg agatttaatc gatttctccc aatccccttc gatccaggtg 1020
caaccgaata agtccttaaa tgttgaggaa cacgaaacaa ccatgcattg gcatgtaaag 1080
ctccaagaat tcgttgtatc cttaacaact cacagaacat caaccaaaat tgcacgtcaa 1140
gggtattggg taagaaacaa tcaaacaaat cctctctgtg tgcaaagaaa cacggtgagt 1200
catgccgaga tcatactcat ctgatataca tgcttacagc tcacaagaca ttacaaacaa 1260
ctcatattgc attacaaaga tcgtttcatg aaaaataaaa taggccggaa caggacaaaa 1320
atccttgacg tgtaaagtaa atttacaaca aaaaaaaagc catatgtcaa gctaaatcta 1380
attcgtttta cgtagatcaa caacctgtag aaggcaacaa aactgagcca cgcagaagta 1440
cagaatgatt ccagatgaac catcgacgtg ctacgtaaag agagtgacga gtcatataca 1500
tttggcaaga aaccatgaag ctgcctacag ccgtctcggt ggcataagaa cacaagaaat 1560
tgtgttaatt aatcaaagct ataaataacg ctcgcatgcc tgtgcacttc tccatcacca 1620
ccactgggtc ttcagaccat tagctttatc tactccagag cgcagaagaa cccgatcgac 1680
accggatcct aaaccatgag ggtgttgctc gttgccctcg ctctcctggc tctcgctgcg 1740
agcgccacct cccaggttca gctccaggag tttggtggcg gactggtgca gccaggtggc 1800
agcctcaggc tgagctgcgc tgctagcggt agaaccggca gcagctatgc tatgggatgg 1860
tttagacagg ctccaggcaa ggagcgtgaa tttgttgctg ccattagctg gagcggaggt 1920
agcaccgatt atgctgacag cgtgaagggc aggtttacca ttagcagaga taatgccaag 1980
aacaccatgt acctccagat gaatagcctg aagccagagg ataccgctgt ttattactgc 2040
gccgtggacc gtaatctctt taagctgagg gttgctgtgc aggaatacac caacctcggc 2100
cagggaaccc aggttaccgt gagcagcaag gacgagctgt aacctaggtc cccgaatttc 2160
cccgatcgtt caaacatttg gcaataaagt ttcttaagat tgaatcctgt tgccggtctt 2220
gcgatgatta tcatataatt tctgttgaat tacgttaagc atgtaataat taacatgtaa 2280
tgcatgacgt tatttatgag atgggttttt atgattagag tcccgcaatt atacatttaa 2340
tacgcgatag aaaacaaaat atagcgcgca aactaggata aattatcgcg cgcggtgtca 2400
tctatgttac tagatcggga attgttaatt aagtctaact cgagttactg gtacgtatac 2460
agggttcctt gcgtgaagaa gggtggcctg cggttcacca ttaacggtca cgactacttc 2520
cagctagtac tggtgaccaa cgtcgcggcg gcagggtcaa tcaagtccat ggaggttatg 2580
ggttccaaca cagcggattg gatgccgatg gcacgtaact ggggcgccca atggcactca 2640
ctggcctacc tcaccggtca aggtctatcc tttagggtca ccaacacaga tgaccaaacg 2700
ctcgtcttca ccaacgtcgt gccaccagga tggaagtttg gccagacatt tgcaagcaag 2760
ctgcagttca agtgagagga gaagcctgaa ttgataccgg agcgtttctt ttgggagtaa 2820
catctctggt tgcctagcaa acatatgatt gtatataagt ttcgttgtgc gtttattctt 2880
tcggtgtgta aaataacata catgctttcc tgatattttc ttgtatatat gtacacacac 2940
acgacaaatc cttccatttc tattattatt gaacaattta attgcgaggg cgagtacttg 3000
tctgtttacc ttttttttt cagatggcat tttatagttt aacctttcat ggaccggcag 3060
tagttctaac catgaatgaa aagaaatcat agtccacacc acgcagggac attgtggtca 3120
ttttagacaa gacgatttga ttaatgtctt gtatgatatg gtcgacagtg aggactaaca 3180
aacatatggc atattttatt accggcgagt taaataaatt tatgtcacag taataaactg 3240
cctaataaat gcacgccaga aaatataatg ataaaaaaaa gaaaagatac ataagtccat 3300

-continued

```
tgcttctact tttttaaaaa ttaaatccaa cattttctat tttttggtat aaacttggaa   3360
gtactagttg gatatgcaaa atcatctaac ctccatatat ttcatcaatt tgtttacttt   3420
acatatggga gaggatagta tgtcaaagaa aatgacaaca agcttacaag tttcttattt   3480
taaaagttcc gctaacttat caagcatagt gtgccacgca aaactgacaa caaaccaaca   3540
aatttaagga gcgcctaact tatcatctat gacataccgc acaaaatgat aacatactag   3600
agaaacttta ttgcacaaaa ggaaatttat ccataaggca aaggaacatc ttaaggcttt   3660
ggatatacat ttaccaacaa gcattgtttg tattacccct aaagcgcaag acatgtcatc   3720
catgagtcat agtgtgtata tctcaacatt gcaaagctac ctttttttcta ttatactttt   3780
cgcattatag gctagatatt atctatacat gtcaacaaac tctatcccta cgtcatatct   3840
gaagattctt ttcttcacta tataagttgg cttccctgtc attgaactca catcaaccag   3900
cccaagtttc caataacatc ctcaaatagc tggatcctaa accatgaggg tgttgctcgt   3960
tgccctcgct ctcctggctc tcgctgcgag cgccacctcc caggttcagc tccaggagtt   4020
tggtggcgga ctggtgcagc caggtggcag cctcaggctg agctgcgctg ctagcggtag   4080
aaccggcagc agctatgcta tgggatggtt tagacaggct ccaggcaagg agcgtgaatt   4140
tgttgctgcc attagctgga gcggaggtag caccgattat gctgacagcg tgaagggcag   4200
gtttaccatt agcagagata atgccaagaa caccatgtac ctccagatga atagcctgaa   4260
gccagaggat accgctgttt attactgcgc cgtggaccgt aatctcttta agctgagggt   4320
tgctgtgcag gaatacacca acctcggcca gggaacccag gttaccgtga gcagcaagga   4380
cgagctgtaa cctaggtccc cgaatttccc cgatcgttca aacatttggc aataaagttt   4440
cttaagattg aatcctgttg ccggtcttgc gatgattatc atataatttc tgttgaatta   4500
cgttaagcat gtaataatta acatgtaatg catgacgtta tttatgagat gggtttttat   4560
gattagagtc ccgcaattat acatttaata cgcgatagaa aacaaaatat agcgcgcaaa   4620
ctaggataaa ttatcgcgcg cggtgtcatc tatgttacta gatcgggaat tggaattcct   4680
gcagtgcagc gtgacccggt cgtgcccctc tctagagata atgagcattg catgtctaag   4740
ttataaaaaa ttaccacata tttttttgt cacacttgtt tgaagtgcag tttatctatc   4800
tttatacata tatttaaact ttactctacg aataatataa tctatagtac tacaataata   4860
tcagtgtttt agagaatcat ataaatgaac agttagacat ggtctaaagg acaattgagt   4920
attttgacaa caggactcta cagttttatc tttttagtgt gcatgtgttc tcctttttt   4980
ttgcaaatag cttcacctat ataatacttc atccatttta ttagtacatc catttagggt   5040
ttagggttaa tggtttttat agactaattt ttttagtaca tctattttat tctattttag   5100
cctctaaatt aagaaaacta aaactctatt ttagtttttt tatttaataa tttagatata   5160
aaatagaata aaataaagtg actaaaaatt aaacaaatac cctttaagaa attaaaaaaa   5220
ctaaggaaac atttttcttg tttcgagtag ataatgccag cctgttaaac gccgtcgacg   5280
agtctaacgg acaccaacca gcgaaccagc agcgtcgcgt cgggccaagc gaagcagacg   5340
gcacggcatc tctgtcgctg cctctggacc cctctcgaga gttccgctcc accgttggac   5400
ttgctccgct gtcggcatcc agaaattgcg tggcggagcg gcagacgtga gccggcacgg   5460
caggcggcct cctcctcctc tcacggcacg gcagctacgg gggattcctt tcccaccgct   5520
ccttcgcttt cccttcctcg cccgccgtaa taaatagaca ccccctccac accctctttc   5580
cccaacctcg tgttgttcgg agcgcacaca cacacaacca gatctccccc aaatccaccc   5640
gtcggcacct ccgcttcaag gtacgccgct cgtcctcccc cccccccct ctctaccttc   5700
```

```
tctagatcgg cgttccggtc catggttagg gcccggtagt tctacttctg ttcatgtttg   5760
tgttagatcc gtgtttgtgt tagatccgtg ctgctagcgt tcgtacacgg atgcgacctg   5820
tacgtcagac acgttctgat tgctaacttg ccagtgtttc tctttgggga atcctgggat   5880
ggctctagcc gttccgcaga cgggatcgat ttcatgattt tttttgtttc gttgcatagg   5940
gtttggtttg cccttttcct ttatttcaat atatgccgtg cacttgtttg tcgggtcatc   6000
ttttcatgct ttttttgtc ttggttgtga tgatgtggtc tggttgggcg gtcgttctag   6060
atcggagtag aattctgttt caaactacct ggtggattta ttaattttgg atctgtatgt   6120
gtgtgccata catattcata gttacgaatt gaagatgatg gatggaaata tcgatctagg   6180
ataggtatac atgttgatgc gggttttact gatgcatata cagagatgct tttgttcgc   6240
ttggttgtga tgatgtggtg tggttgggcg gtcgttcatt cgttctagat cggagtagaa   6300
tactgtttca aactacctgg tgtatttatt aattttggaa ctgtatgtgt gtgtcataca   6360
tcttcatagt tacgagttta agatggatgg aaatatcgat ctaggatagg tatacatgtt   6420
gatgtgggtt ttactgatgc atatacatga tggcatatgc agcatctatt catatgctct   6480
aaccttgagt acctatctat tataataaac aagtatgttt tataattatt ttgatcttga   6540
tatacttgga tgatggcata tgcagcagct atatgtggat ttttttagcc ctgccttcat   6600
acgctattta tttgcttggt actgtttctt ttgtcgatgc tcaccctgtt gtttggtgtt   6660
acttctgcag atccagatct aaaccatgca gaaactcatt aactcagtgc aaaactatgc   6720
ctggggcagc aaaacggcgt tgactgaact ttatggtatg gaaaatccgt ccagccagcc   6780
gatggccgag ctgtggatgg gcgcacatcc gaaaagcagt tcacgagtgc agaatgccgc   6840
cggagatatc gtttcactgc gtgatgtgat tgagagtgat aaatcgactc tgctcggaga   6900
ggccgttgcc aaacgctttg gcgaactgcc tttcctgttc aaagtattat gcgcagcaca   6960
gccactctcc attcaggttc atccaaacaa acacaattct gaaatcggtt ttgccaaaga   7020
aaatgccgca ggtatcccga tggatgccgc cgagcgtaac tataaagatc ctaaccacaa   7080
gccggagctg gtttttgcgc tgacgccttt ccttgcgatg aacgcgtttc gtgaattttc   7140
cgagattgtc tccctactcc agccggtcgc aggtgcacat ccggcgattg ctcacttttt   7200
acaacagcct gatgccgaac gtttaagcga actgttcgcc agcctgttga atatgcaggg   7260
tgaagaaaaa tcccgcgcgc tggcgatttt aaaatcggcc ctcgatagcc agcagggtga   7320
accgtggcaa acgattcgtt taatttctga attttacccg gaagacagcg gtctgttctc   7380
cccgctattg ctgaatgtgg tgaaattgaa ccctggcgaa gcgatgttcc tgttcgctga   7440
aacaccgcac gcttacctgc aaggcgtggc gctggaagtg atggcaaact ccgataacgt   7500
gctgcgtgcg ggtctgacgc ctaaatacat tgatattccg gaactggttg ccaatgtgaa   7560
attcgaagcc aaaccggcta accagttgtt gacccagccg gtgaaacaag gtgcagaact   7620
ggacttcccg attccagtgg atgattttgc cttctcgctg catgacctta gtgataaaga   7680
aaccaccatt agccagcaga gtgccgccat tttgttctgc gtcgaaggcg atgcaacgtt   7740
gtggaaaggt tctcagcagt tacagcttaa accgggtgaa tcagcgttta ttgccgccaa   7800
cgaatcaccg gtgactgtca aaggccacgg ccgtttagcg cgtgtttaca acaagctgta   7860
agagcttact gaaaaaatta acatctcttg ctaagctggg agctctagat ccccgaattt   7920
ccccgatcgt tcaaacattt ggcaataaag tttcttaaga ttgaatcctg ttgccggtct   7980
tgcgatgatt atcatataat ttctgttgaa ttacgttaag catgtaataa ttaacatgta   8040
```

atgcatgacg ttatttatga gatgggtttt tatgattaga gtcccgcaat tatacattta 8100
atacgcgata gaaaacaaaa tatagcgcgc aaactaggat aaattatcgc gcgcggtgtc 8160
atctatgtta ctagatcggg aattggcgag ctcgaattaa ttcagtacat taaaaacgtc 8220
cgcaatgtgt tattaagttg tctaagcgtc aatttgttta caccacaata tatcctgcca 8280

<210> SEQ ID NO 165
<211> LENGTH: 6029
<212> TYPE: DNA
<213> ORGANISM: Artificial Sequence
<220> FEATURE:
<223> OTHER INFORMATION: Synthetic construct, pAG4991

<400> SEQUENCE: 165
gtttacccgc caatatatcc tgtcaaacac tgatagttta aactgaaggc gggaaacgac 60
aacctgatca tgagcggaga attaagggag tcacgttatg acccccgccg atgacgcggg 120
acaagccgtt ttacgtttgg aactgacaga accgcaacgt tgaaggagcc actcagccta 180
agcggccgca ttggacttaa ttaagtgagg ccggccaagc gtcgatttaa atgtaccaca 240
tggcgcgcca actatcatgc gatcgcttca tgtctaactc gagttactgg tacgtaccaa 300
atccatggaa tcaaggtacc aaagtaatca tattatttta tgtgtgaatc ttctttactt 360
tttcatttga ttatgattat gaaggtatga ccttcataac cttcgtccga aatccattat 420
atccaaagga aaataatgct tcgaaggacg aaggattttg atatttaaca ttttatgttg 480
ccttgttctt aattcatagc atttgagaac aagtccccaa caccaatctt tatctttact 540
atattaaagc accagttcaa cgatcgtctc gtgtcaatat tattaaaaaa ctcctacatt 600
tctttataat caacccgcac tcttataatc tcttctctta ctactataat aagagagttt 660
atgtacaaaa taaggtgaaa ttatgtataa gtgttctgga ccttggttgt tggctcatat 720
tcacacaacc taatcaatag aaaacatatg ttttattaaa acaaaattta tcatatatat 780
atatatatat atatatatat atatatatat atataatata aaccgtagca atgcacaggc 840
atatgactag tggcaactta ataccatgtg tgtattaaga tgaataagag gtatccaaat 900
aaataacttg ttcgcttacg tctggatcga aaggggttgg aaacgattaa atctcttcct 960
agtcaaaatt aaatagaagg agatttaatc gatttctccc aatccccttc gatccaggtg 1020
caaccgaata agtccttaaa tgttgaggaa cacgaaacaa ccatgcattg gcatgtaaag 1080
ctccaagaat tcgttgtatc cttaacaact cacagaacat caaccaaaat tgcacgtcaa 1140
gggtattggg taagaaacaa tcaaacaaat cctctctgtg tgcaaagaaa cacggtgagt 1200
catgccgaga tcatactcat ctgatataca tgcttacagc tcacaagaca ttacaaacaa 1260
ctcatattgc attacaaaga tcgtttcatg aaaaataaaa taggccggaa caggacaaaa 1320
atccttgacg tgtaaagtaa atttacaaca aaaaaaaagc catatgtcaa gctaaatcta 1380
attcgtttta cgtagatcaa caacctgtag aaggcaacaa aactgagcca cgcagaagta 1440
cagaatgatt ccagatgaac catcgacgtg ctacgtaaag agagtgacga gtcatataca 1500
tttggcaaga aaccatgaag ctgcctacag ccgtctcggt ggcataagaa cacaagaaat 1560
tgtgttaatt aatcaaagct ataaataacg ctcgcatgcc tgtgcacttc tccatcacca 1620
ccactgggtc ttcagaccat tagctttatc tactccagag cgcagaagaa cccgatcgac 1680
accggatcct aaaccatgag ggtgttgctc gttgccctcg ctctcctggc tctcgctgcg 1740
agcgccacct cccaggttca gctccaggct tcgggcggcg ggctcgtcca ggcgggcggc 1800
tcgctcaggc tctcgtgcgc ggcgtcgggg cggactttca acagctacgc ttggggctgg 1860

```
ttcaggcagg cgccgggcaa ggagcgcggc ttcgtggcca ggatctcctt cagcggcggc   1920
cacacctact actccgacag cgtcaagggc cgcttcacga tctccaggga caacgccaag   1980
aacagcgtgt acctccagat gaactccctg aagcccgagg acacggccgt ctactactgc   2040
gcggcggacc cgacgcccta cggcctcagg aacgagcgga actaccatta ctgggggcag   2100
ggcacgcagg tcactgtctc ttcgaaggac gagctgtaac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
atgttactag atcgggaatt ggaattcctg cagtgcagcg tgacccggtc gtgcccctct   2460
ctagagataa tgagcattgc atgtctaagt tataaaaaat taccacatat ttttttgtc    2520
acacttgttt gaagtgcagt ttatctatct ttatacatat atttaaactt tactctacga   2580
ataatataat ctatagtact acaataatat cagtgtttta gagaatcata taaatgaaca   2640
gttagacatg gtctaaagga caattgagta ttttgacaac aggactctac agttttatct   2700
ttttagtgtg catgtgttct cctttttttt tgcaaatagc ttcacctata taatacttca   2760
tccattttat tagtacatcc atttagggtt tagggttaat ggtttttata gactaatttt   2820
tttagtacat ctattttatt ctattttagc ctctaaatta agaaaactaa aactctattt   2880
tagtttttt atttaataat ttagatataa aatagaataa aataaagtga ctaaaaatta    2940
aacaaatacc ctttaagaaa ttaaaaaaac taaggaaaca tttttcttgt ttcgagtaga   3000
taatgccagc ctgttaaacg ccgtcgacga gtctaacgga caccaaccag cgaaccagca   3060
gcgtcgcgtc gggccaagcg aagcagacgg cacggcatct ctgtcgctgc ctctggaccc   3120
ctctcgagag ttccgctcca ccgttggact tgctccgctg tcggcatcca gaaattgcgt   3180
ggcggagcgg cagacgtgag ccggcacggc aggcggcctc ctcctcctct cacggcacgg   3240
cagctacggg ggattccttt cccaccgctc cttcgctttc ccttcctcgc ccgccgtaat   3300
aaatagacac cccctccaca ccctctttcc ccaacctcgt gttgttcgga gcgcacacac   3360
acacaaccag atctccccca aatccacccg tcggcacctc cgcttcaagg tacgccgctc   3420
gtcctccccc cccccccctc tctaccttct ctagatcggc gttccggtcc atggttaggg   3480
cccggtagtt ctacttctgt tcatgtttgt gttagatccg tgtttgtgtt agatccgtgc   3540
tgctagcgtt cgtacacgga tgcgacctgt acgtcagaca cgttctgatt gctaacttgc   3600
cagtgtttct ctttggggaa tcctgggatg gctctagccg ttccgcagac gggatcgatt   3660
tcatgatttt ttttgtttcg ttgcataggg tttggtttgc ccttttcctt tatttcaata   3720
tatgccgtgc acttgtttgt cgggtcatct tttcatgctt ttttttgtct tggttgtgat   3780
gatgtggtct ggttgggcgg tcgttctaga tcggagtaga attctgtttc aaactacctg   3840
gtggatttat taattttgga tctgtatgtg tgtgccatac atattcatag ttacgaattg   3900
aagatgatgg atggaaatat cgatctagga taggtataca tgttgatgcg ggttttactg   3960
atgcatatac agagatgctt tttgttcgct tggttgtgat gatgtggtgt ggttgggcgg   4020
tcgttcattc gttctagatc ggagtagaat actgtttcaa actacctggt gtatttatta   4080
attttggaac tgtatgtgtg tgtcatacat cttcatagtt acgagtttaa gatggatgga   4140
aatatcgatc taggataggt atacatgttg atgtgggttt tactgatgca tatacatgat   4200
```

```
ggcatatgca gcatctattc atatgctcta accttgagta cctatctatt ataataaaca   4260
agtatgtttt ataattattt tgatcttgat atacttggat gatggcatat gcagcagcta   4320
tatgtggatt tttttagccc tgccttcata cgctatttat ttgcttggta ctgtttcttt   4380
tgtcgatgct caccctgttg tttggtgtta cttctgcaga tccagatcta aaccatgcag   4440
aaactcatta actcagtgca aaactatgcc tggggcagca aaacggcgtt gactgaactt   4500
tatggtatgg aaaatccgtc cagccagccg atggccgagc tgtggatggg cgcacatccg   4560
aaaagcagtt cacgagtgca gaatgccgcc ggagatatcg tttcactgcg tgatgtgatt   4620
gagagtgata aatcgactct gctcggagag gccgttgcca aacgctttgg cgaactgcct   4680
ttcctgttca aagtattatg cgcagcacag ccactctcca ttcaggttca tccaaacaaa   4740
cacaattctg aaatcggttt tgccaaagaa aatgccgcag gtatcccgat ggatgccgcc   4800
gagcgtaact ataaagatcc taaccacaag ccggagctgg tttttgcgct gacgcctttc   4860
cttgcgatga acgcgtttcg tgaattttcc gagattgtct ccctactcca gccggtcgca   4920
ggtgcacatc cggcgattgc tcacttttta caacagcctg atgccgaacg tttaagcgaa   4980
ctgttcgcca gcctgttgaa tatgcagggt gaagaaaaat cccgcgcgct ggcgatttta   5040
aaatcggccc tcgatagcca gcagggtgaa ccgtggcaaa cgattcgttt aatttctgaa   5100
ttttacccgg aagacagcgg tctgttctcc ccgctattgc tgaatgtggt gaaattgaac   5160
cctggcgaag cgatgttcct gttcgctgaa acaccgcacg cttacctgca aggcgtggcg   5220
ctggaagtga tggcaaactc cgataacgtg ctgcgtgcgg gtctgacgcc taaatacatt   5280
gatattccgg aactggttgc caatgtgaaa ttcgaagcca aaccggctaa ccagttgttg   5340
acccagccgg tgaaacaagg tgcagaactg gacttcccga ttccagtgga tgattttgcc   5400
ttctcgctgc atgaccttag tgataaagaa accaccatta gccagcagag tgccgccatt   5460
ttgttctgcg tcgaaggcga tgcaacgttg tggaaaggtt ctcagcagtt acagcttaaa   5520
ccgggtgaat cagcgtttat tgccgccaac gaatcaccgg tgactgtcaa aggccacggc   5580
cgtttagcgc gtgtttacaa caagctgtaa gagcttactg aaaaaattaa catctcttgc   5640
taagctggga gctctagatc cccgaatttc cccgatcgtt caaacatttg gcaataaagt   5700
ttcttaagat tgaatcctgt tgccggtctt gcgatgatta tcatataatt tctgttgaat   5760
tacgttaagc atgtaataat taacatgtaa tgcatgacgt tatttatgag atgggttttt   5820
atgattagag tcccgcaatt atacatttaa tacgcgatag aaaacaaaat atagcgcgca   5880
aactaggata aattatcgcg cgcggtgtca tctatgttac tagatcggga attggcgagc   5940
tcgaattaat tcagtacatt aaaaacgtcc gcaatgtgtt attaagttgt ctaagcgtca   6000
atttgtttac accacaatat atcctgcca                                    6029
```

<210> SEQ ID NO 166
<211> LENGTH: 8274
<212> TYPE: DNA
<213> ORGANISM: Artificial Sequence
<220> FEATURE:
<223> OTHER INFORMATION: Synthetic construct, pAG4992

<400> SEQUENCE: 166

```
gtttacccgc caatatatcc tgtcaaacac tgatagttta aactgaaggc gggaaacgac     60
aacctgatca tgagcggaga attaagggag tcacgttatg acccccgccg atgacgcggg    120
acaagccgtt ttacgtttgg aactgacaga accgcaacgt tgaaggagcc actcagccta    180
agcggccgca ttggacttaa ttaagtgagg ccggccaagc gtcgatttaa atgtaccaca    240
```

-continued

```
tggcgcgcca actatcatgc gatcgcttca tgtctaactc gagttactgg tacgtaccaa    300
atccatggaa tcaaggtacc aaagtaatca tattatttta tgtgtgaatc ttctttactt    360
tttcatttga ttatgattat gaaggtatga ccttcataac cttcgtccga aatccattat    420
atccaaagga aaataatgct tcgaaggacg aaggattttg atatttaaca ttttatgttg    480
ccttgttctt aattcatagc atttgagaac aagtccccaa caccaatctt tatctttact    540
atattaaagc accagttcaa cgatcgtctc gtgtcaatat tattaaaaaa ctcctacatt    600
tctttataat caacccgcac tcttataatc tcttctctta ctactataat aagagagttt    660
atgtacaaaa taaggtgaaa ttatgtataa gtgttctgga ccttggttgt tggctcatat    720
tcacacaacc taatcaatag aaaacatatg ttttattaaa acaaaattta tcatatatat    780
atatatatat atatatatat atatatatat atataatata aaccgtagca atgcacaggc    840
atatgactag tggcaactta ataccatgtg tgtattaaga tgaataagag gtatccaaat    900
aaataacttg ttcgcttacg tctggatcga aaggggttgg aaacgattaa atctcttcct    960
agtcaaaatt aaatagaagg agatttaatc gatttctccc aatccccttc gatccaggtg   1020
caaccgaata agtccttaaa tgttgaggaa cacgaaacaa ccatgcattg gcatgtaaag   1080
ctccaagaat tcgttgtatc cttaacaact cacagaacat caaccaaaat tgcacgtcaa   1140
gggtattggg taagaaacaa tcaaacaaat cctctctgtg tgcaaagaaa cacggtgagt   1200
catgccgaga tcatactcat ctgatataca tgcttacagc tcacaagaca ttacaaacaa   1260
ctcatattgc attacaaaga tcgtttcatg aaaaataaaa taggccggaa caggacaaaa   1320
atccttgacg tgtaaagtaa atttacaaca aaaaaaaagc catatgtcaa gctaaatcta   1380
attcgtttta cgtagatcaa caacctgtag aaggcaacaa aactgagcca cgcagaagta   1440
cagaatgatt ccagatgaac catcgacgtg ctacgtaaag agagtgacga gtcatataca   1500
tttggcaaga aaccatgaag ctgcctacag ccgtctcggt ggcataagaa cacaagaaat   1560
tgtgttaatt aatcaaagct ataaataacg ctcgcatgcc tgtgcacttc tccatcacca   1620
ccactgggtc ttcagaccat tagctttatc tactccagag cgcagaagaa cccgatcgac   1680
accggatcct aaaccatgag ggtgttgctc gttgccctcg ctctcctggc tctcgctgcg   1740
agcgccacct cccaggttca gctccaggct tcgggcggcg ggctcgtcca ggcgggcggc   1800
tcgctcaggc tctcgtgcgc ggcgtcgggg cggactttca acagctacgc ttggggctgg   1860
ttcaggcagg cgccgggcaa ggagcgcggc ttcgtggcca ggatctcctt cagcggcggc   1920
cacacctact actccgacag cgtcaagggc cgcttcacga tctccaggga caacgccaag   1980
aacagcgtgt acctccagat gaactccctg aagcccgagg acacggccgt ctactactgc   2040
gcggcggacc cgacgcccta cggcctcagg aacgagcgga actaccatta ctgggggcag   2100
ggcacgcagg tcactgtctc ttcgaaggac gagctgtaac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
atgttactag atcgggaatt gttaattaag tctaactcga gttactggta cgtatacagg   2460
gttccttgcg tgaagaaggg tggcctgcgg ttcaccatta acggtcacga ctacttccag   2520
ctagtactgg tgaccaacgt cgcggcggca gggtcaatca agtccatgga ggttatgggt   2580
```

tccaacacag cggattggat gccgatggca cgtaactggg gcgcccaatg gcactcactg 2640
gcctacctca ccggtcaagg tctatccttt agggtcacca acacagatga ccaaacgctc 2700
gtcttcacca acgtcgtgcc accaggatgg aagtttggcc agacatttgc aagcaagctg 2760
cagttcaagt gagaggagaa gcctgaattg ataccggagc gtttcttttg ggagtaacat 2820
ctctggttgc ctagcaaaca tatgattgta tataagtttc gttgtgcgtt tattctttcg 2880
gtgtgtaaaa taacatacat gctttcctga tattttcttg tatatatgta cacacacacg 2940
acaaatcctt ccatttctat tattattgaa caatttaatt gcgagggcga gtacttgtct 3000
gtttaccttt ttttttcag atggcatttt atagtttaac ctttcatgga ccggcagtag 3060
ttctaaccat gaatgaaaag aaatcatagt ccacaccacg cagggacatt gtggtcattt 3120
tagacaagac gatttgatta atgtcttgta tgatatggtc gacagtgagg actaacaaac 3180
atatggcata ttttattacc ggcgagttaa ataaatttat gtcacagtaa taaactgcct 3240
aataaatgca cgccagaaaa tataatgata aaaaaaagaa aagatacata agtccattgc 3300
ttctactttt ttaaaaatta aatccaacat tttctatttt ttggtataaa cttggaagta 3360
ctagttggat atgcaaaatc atctaacctc catatatttc atcaatttgt ttactttaca 3420
tatgggagag gatagtatgt caaagaaaat gacaacaagc ttacaagttt cttattttaa 3480
aagttccgct aacttatcaa gcatagtgtg ccacgcaaaa ctgacaacaa accaacaaat 3540
ttaaggagcg cctaacttat catctatgac ataccgcaca aaatgataac atactagaga 3600
aactttattg cacaaaagga aatttatcca taaggcaaag gaacatctta aggctttgga 3660
tatacattta ccaacaagca ttgtttgtat taccccctaaa gcgcaagaca tgtcatccat 3720
gagtcatagt gtgtatatct caacattgca aagctacctt ttttctatta tacttttcgc 3780
attataggct agatattatc tatacatgtc aacaaactct atccctacgt catatctgaa 3840
gattcttttc ttcactatat aagttggctt ccctgtcatt gaactcacat caaccagccc 3900
aagtttccaa taacatcctc aaatagctgg atcctaaacc atgagggtgt tgctcgttgc 3960
cctcgctctc ctggctctcg ctgcgagcgc cacctcccag gttcagctcc aggcttcggg 4020
cggcgggctc gtccaggcgg gcggctcgct caggctctcg tgcgcggcgt cggggcggac 4080
tttcaacagc tacgcttggg gctggttcag gcaggcgccg ggcaaggagc gcggcttcgt 4140
ggccaggatc tccttcagcg gcggccacac ctactactcc gacagcgtca agggccgctt 4200
cacgatctcc agggacaacg ccaagaacag cgtgtacctc cagatgaact ccctgaagcc 4260
cgaggacacg gccgtctact actgcgcggc ggacccgacg ccctacggcc tcaggaacga 4320
gcggaactac cattactggg ggcagggcac gcaggtcact gtctcttcga aggacgagct 4380
gtaacctagg tccccgaatt tccccgatcg ttcaaacatt tggcaataaa gtttcttaag 4440
attgaatcct gttgccggtc ttgcgatgat tatcatataa tttctgttga attacgttaa 4500
gcatgtaata attaacatgt aatgcatgac gttatttatg agatgggttt ttatgattag 4560
agtcccgcaa ttatacattt aatacgcgat agaaaacaaa atatagcgcg caaactagga 4620
taaattatcg cgcgcggtgt catctatgtt actagatcgg gaattggaat tcctgcagtg 4680
cagcgtgacc cggtcgtgcc cctctctaga gataatgagc attgcatgtc taagttataa 4740
aaaattacca catatttttt ttgtcacact tgtttgaagt gcagtttatc tatctttata 4800
catatattta aactttactc tacgaataat ataatctata gtactacaat aatatcagtg 4860
ttttagagaa tcatataaat gaacagttag acatggtcta aaggacaatt gagtattttg 4920
acaacaggac tctacagttt tatcttttta gtgtgcatgt gttctccttt ttttttgcaa 4980

-continued

```
atagcttcac ctatataata cttcatccat tttattagta catccattta gggtttaggg   5040
ttaatggttt ttatagacta attttttag tacatctatt ttattctatt ttagcctcta   5100
aattaagaaa actaaaactc tattttagtt tttttattta ataatttaga tataaaatag   5160
aataaaataa agtgactaaa aattaaacaa ataccottta agaaattaaa aaaactaagg   5220
aaacattttt cttgtttcga gtagataatg ccagcctgtt aaacgccgtc gacgagtcta   5280
acggacacca accagcgaac cagcagcgtc gcgtcgggcc aagcgaagca gacggcacgg   5340
catctctgtc gctgcctctg gacccctctc gagagttccg ctccaccgtt ggacttgctc   5400
cgctgtcggc atccagaaat tgcgtggcgg agcggcagac gtgagccggc acggcaggcg   5460
gcctcctcct cctctcacgg cacggcagct acgggggatt cctttcccac cgctccttcg   5520
ctttcccttc ctcgcccgcc gtaataaata gacacccct ccacaccctc tttccccaac   5580
ctcgtgttgt tcggagcgca cacacacaca accagatctc ccccaaatcc acccgtcggc   5640
acctccgctt caaggtacgc cgctcgtcct cccccccccc ccctctctac cttctctaga   5700
tcggcgttcc ggtccatggt tagggcccgg tagttctact tctgttcatg tttgtgttag   5760
atccgtgttt gtgttagatc cgtgctgcta gcgttcgtac acggatgcga cctgtacgtc   5820
agacacgttc tgattgctaa cttgccagtg tttctctttg gggaatcctg ggatggctct   5880
agccgttccg cagacgggat cgatttcatg atttttttg tttcgttgca tagggtttgg   5940
tttgcccttt tcctttattt caatatatgc cgtgcacttg tttgtcgggt catcttttca   6000
tgcttttttt tgtcttggtt gtgatgatgt ggtctggttg ggcggtcgtt ctagatcgga   6060
gtagaattct gtttcaaact acctggtgga tttattaatt ttggatctgt atgtgtgtgc   6120
catacatatt catagttacg aattgaagat gatggatgga aatatcgatc taggataggt   6180
atacatgttg atgcgggttt tactgatgca tatacagaga tgctttttgt tcgcttggtt   6240
gtgatgatgt ggtgtggttg ggcggtcgtt cattcgttct agatcggagt agaatactgt   6300
ttcaaactac ctggtgtatt tattaatttt ggaactgtat gtgtgtgtca tacatcttca   6360
tagttacgag tttaagatgg atggaaatat cgatctagga taggtataca tgttgatgtg   6420
ggttttactg atgcatatac atgatggcat atgcagcatc tattcatatg ctctaacctt   6480
gagtacctat ctattataat aaacaagtat gttttataat tattttgatc ttgatatact   6540
tggatgatgg catatgcagc agctatatgt ggattttttt agccctgcct tcatacgcta   6600
tttatttgct tggtactgtt tcttttgtcg atgctcaccc tgttgtttgg tgttacttct   6660
gcagatccag atctaaacca tgcagaaact cattaactca gtgcaaaact atgcctgggg   6720
cagcaaaacg gcgttgactg aactttatgg tatggaaaat ccgtccagcc agccgatggc   6780
cgagctgtgg atgggcgcac atccgaaaag cagttcacga gtgcagaatg ccgccggaga   6840
tatcgtttca ctgcgtgatg tgattgagag tgataaatcg actctgctcg gagaggccgt   6900
tgccaaacgc tttggcgaac tgcctttcct gttcaaagta ttatgcgcag cacagccact   6960
ctccattcag gttcatccaa acaaacacaa ttctgaaatc ggttttgcca aagaaaatgc   7020
cgcaggtatc ccgatggatg ccgccgagcg taactataaa gatcctaacc acaagccgga   7080
gctggttttt gcgctgacgc ctttccttgc gatgaacgcg tttcgtgaat tttccgagat   7140
tgtctcccta ctccagccgg tcgcaggtgc acatccggcg attgctcact tttacaaca    7200
gcctgatgcc gaacgtttaa gcgaactgtt cgccagcctg ttgaatatgc agggtgaaga   7260
aaaatcccgc gcgctggcga ttttaaaatc ggccctcgat agccagcagg gtgaaccgtg   7320
```

gcaaacgatt cgtttaattt ctgaatttta cccggaagac agcggtctgt tctccccgct 7380
attgctgaat gtggtgaaat tgaaccctgg cgaagcgatg ttcctgttcg ctgaaacacc 7440
gcacgcttac ctgcaaggcg tggcgctgga agtgatggca aactccgata acgtgctgcg 7500
tgcgggtctg acgcctaaat acattgatat tccggaactg gttgccaatg tgaaattcga 7560
agccaaaccg gctaaccagt tgttgaccca gccggtgaaa caaggtgcag aactggactt 7620
cccgattcca gtggatgatt ttgccttctc gctgcatgac cttagtgata aagaaaccac 7680
cattagccag cagagtgccg ccattttgtt ctgcgtcgaa ggcgatgcaa cgttgtggaa 7740
aggttctcag cagttacagc ttaaaccggg tgaatcagcg tttattgccg ccaacgaatc 7800
accggtgact gtcaaaggcc acggccgttt agcgcgtgtt tacaacaagc tgtaagagct 7860
tactgaaaaa attaacatct cttgctaagc tgggagctct agatccccga atttccccga 7920
tcgttcaaac atttggcaat aaagtttctt aagattgaat cctgttgccg gtcttgcgat 7980
gattatcata taatttctgt tgaattacgt taagcatgta ataattaaca tgtaatgcat 8040
gacgttattt atgagatggg tttttatgat tagagtcccg caattataca tttaatacgc 8100
gatagaaaac aaaatatagc gcgcaaacta ggataaatta tcgcgcgcgg tgtcatctat 8160
gttactagat cgggaattgg cgagctcgaa ttaattcagt acattaaaaa cgtccgcaat 8220
gtgttattaa gttgtctaag cgtcaatttg tttacaccac aatatatcct gcca 8274

<210> SEQ ID NO 167
<211> LENGTH: 6029
<212> TYPE: DNA
<213> ORGANISM: Artificial Sequence
<220> FEATURE:
<223> OTHER INFORMATION: Synthetic construct, pAG4993

<400> SEQUENCE: 167
gtttacccgc caatatatcc tgtcaaacac tgatagttta aactgaaggc gggaaacgac 60
aacctgatca tgagcggaga attaagggag tcacgttatg acccccgccg atgacgcggg 120
acaagccgtt ttacgtttgg aactgacaga accgcaacgt tgaaggagcc actcagccta 180
agcggccgca ttggacttaa ttaagtgagg ccggccaagc gtcgatttaa atgtaccaca 240
tggcgcgcca actatcatgc gatcgcttca tgtctaactc gagttactgg tacgtaccaa 300
atccatggaa tcaaggtacc aaagtaatca tattatttta tgtgtgaatc ttctttactt 360
tttcatttga ttatgattat gaaggtatga ccttcataac cttcgtccga aatccattat 420
atccaaagga aaataatgct tcgaaggacg aaggattttg atatttaaca ttttatgttg 480
ccttgttctt aattcatagc atttgagaac aagtccccaa caccaatctt tatctttact 540
atattaaagc accagttcaa cgatcgtctc gtgtcaatat tattaaaaaa ctcctacatt 600
tctttataat caacccgcac tcttataatc tcttctctta ctactataat aagagagttt 660
atgtacaaaa taaggtgaaa ttatgtataa gtgttctgga ccttggttgt tggctcatat 720
tcacacaacc taatcaatag aaaacatatg ttttattaaa acaaaattta tcatatatat 780
atatatatat atatatatat atatatatat atataatata aaccgtagca atgcacaggc 840
atatgactag tggcaactta ataccatgtg tgtattaaga tgaataagag gtatccaaat 900
aaataacttg ttcgcttacg tctggatcga aaggggttgg aaacgattaa atctcttcct 960
agtcaaaatt aaatagaagg agatttaatc gatttctccc aatccccttc gatccaggtg 1020
caaccgaata agtccttaaa tgttgaggaa cacgaaacaa ccatgcattg gcatgtaaag 1080
ctccaagaat tcgttgtatc cttaacaact cacagaacat caaccaaaat tgcacgtcaa 1140

-continued

```
gggtattggg taagaaacaa tcaaacaaat cctctctgtg tgcaaagaaa cacggtgagt   1200
catgccgaga tcatactcat ctgatataca tgcttacagc tcacaagaca ttacaaacaa   1260
ctcatattgc attacaaaga tcgtttcatg aaaaataaaa taggccggaa caggacaaaa   1320
atccttgacg tgtaaagtaa atttacaaca aaaaaaaagc catatgtcaa gctaaatcta   1380
attcgtttta cgtagatcaa caacctgtag aaggcaacaa aactgagcca cgcagaagta   1440
cagaatgatt ccagatgaac catcgacgtg ctacgtaaag agagtgacga gtcatataca   1500
tttggcaaga aaccatgaag ctgcctacag ccgtctcggt ggcataagaa cacaagaaat   1560
tgtgttaatt aatcaaagct ataaataacg ctcgcatgcc tgtgcacttc tccatcacca   1620
ccactgggtc ttcagaccat tagctttatc tactccagag cgcagaagaa cccgatcgac   1680
accggatcct aaaccatgag ggtgttgctc gttgccctcg ctctcctggc tctcgctgcg   1740
agcgccacct cccaggtgca gctccaggag tccggcggcg gcctcgtgca gccgggcggc   1800
tccctccgcc tgagctgcgc cgcgtccggc aacatcttca gcatcaacac gatgggctgg   1860
tacaggcagg cccccggcaa gcagcgggag ctcgtggcct ccatcaccac gggcggcacc   1920
acgaactacg aggacagcgt caagggccgc ttcaccatct ccagggacaa cgccaagaag   1980
acggtgtacc tccagatgaa ccgcctgaag ccggaggaca cggcggtcta ctactgcaac   2040
caccgcaggt cctacagcgg cagggactac cccgtgtacg gcatggacta ctggggcaag   2100
ggcaccctcg tgaccgtgtc ctccaaggac gagctgtgac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
atgttactag atcgggaatt ggaattcctg cagtgcagcg tgacccggtc gtgcccctct   2460
ctagagataa tgagcattgc atgtctaagt tataaaaaat taccacatat ttttttgtc    2520
acacttgttt gaagtgcagt ttatctatct ttatacatat atttaaactt tactctacga   2580
ataatataat ctatagtact acaataatat cagtgtttta gagaatcata taaatgaaca   2640
gttagacatg gtctaaagga caattgagta ttttgacaac aggactctac agttttatct   2700
ttttagtgtg catgtgttct cctttttttt tgcaaatagc ttcacctata taatacttca   2760
tccattttat tagtacatcc atttagggtt tagggttaat ggtttttata gactaatttt   2820
tttagtacat ctattttatt ctattttagc ctctaaatta agaaaactaa aactctattt   2880
tagttttttt atttaataat ttagatataa aatagaataa aataaagtga ctaaaaatta   2940
aacaaatacc ctttaagaaa ttaaaaaaac taaggaaaca tttttcttgt ttcgagtaga   3000
taatgccagc ctgttaaacg ccgtcgacga gtctaacgga caccaaccag cgaaccagca   3060
gcgtcgcgtc gggccaagcg aagcagacgg cacggcatct ctgtcgctgc ctctggaccc   3120
ctctcgagag ttccgctcca ccgttggact tgctccgctg tcggcatcca gaaattgcgt   3180
ggcggagcgg cagacgtgag ccggcacggc aggcggcctc ctcctcctct cacggcacgg   3240
cagctacggg ggattccttt cccaccgctc cttcgctttc ccttcctcgc ccgccgtaat   3300
aaatagacac cccctccaca ccctctttcc ccaacctcgt gttgttcgga gcgcacacac   3360
acacaaccag atctccccca aatccacccg tcggcacctc cgcttcaagg tacgccgctc   3420
gtcctccccc ccccccctc tctaccttct ctagatcggc gttccggtcc atggttaggg    3480
```

-continued

```
cccggtagtt ctacttctgt tcatgtttgt gttagatccg tgtttgtgtt agatccgtgc   3540
tgctagcgtt cgtacacgga tgcgacctgt acgtcagaca cgttctgatt gctaacttgc   3600
cagtgtttct ctttggggaa tcctgggatg gctctagccg ttccgcagac gggatcgatt   3660
tcatgatttt ttttgtttcg ttgcataggg tttggtttgc ccttttcctt tatttcaata   3720
tatgccgtgc acttgtttgt cgggtcatct tttcatgctt ttttttgtct tggttgtgat   3780
gatgtggtct ggttgggcgg tcgttctaga tcggagtaga attctgtttc aaactacctg   3840
gtggatttat taattttgga tctgtatgtg tgtgccatac atattcatag ttacgaattg   3900
aagatgatgg atggaaatat cgatctagga taggtataca tgttgatgcg ggttttactg   3960
atgcatatac agagatgctt tttgttcgct tggttgtgat gatgtggtgt ggttgggcgg   4020
tcgttcattc gttctagatc ggagtagaat actgtttcaa actacctggt gtatttatta   4080
attttggaac tgtatgtgtg tgtcatacat cttcatagtt acgagtttaa gatggatgga   4140
aatatcgatc taggataggt atacatgttg atgtgggttt tactgatgca tatacatgat   4200
ggcatatgca gcatctattc atatgctcta accttgagta cctatctatt ataataaaca   4260
agtatgtttt ataattattt tgatcttgat atacttggat gatggcatat gcagcagcta   4320
tatgtggatt tttttagccc tgccttcata cgctatttat ttgcttggta ctgtttcttt   4380
tgtcgatgct caccctgttg tttggtgtta cttctgcaga tccagatcta aaccatgcag   4440
aaactcatta actcagtgca aaactatgcc tggggcagca aaacggcgtt gactgaactt   4500
tatggtatgg aaaatccgtc cagccagccg atggccgagc tgtggatggg cgcacatccg   4560
aaaagcagtt cacgagtgca gaatgccgcc ggagatatcg tttcactgcg tgatgtgatt   4620
gagagtgata aatcgactct gctcggagag gccgttgcca aacgctttgg cgaactgcct   4680
ttcctgttca aagtattatg cgcagcacag ccactctcca ttcaggttca tccaaacaaa   4740
cacaattctg aaatcggttt tgccaaagaa aatgccgcag gtatcccgat ggatgccgcc   4800
gagcgtaact ataaagatcc taaccacaag ccggagctgg tttttgcgct gacgcctttc   4860
cttgcgatga acgcgtttcg tgaattttcc gagattgtct ccctactcca gccggtcgca   4920
ggtgcacatc cggcgattgc tcacttttta caacagcctg atgccgaacg tttaagcgaa   4980
ctgttcgcca gcctgttgaa tatgcagggt gaagaaaaat cccgcgcgct ggcgatttta   5040
aaatcggccc tcgatagcca gcagggtgaa ccgtggcaaa cgattcgttt aatttctgaa   5100
ttttacccgg aagacagcgg tctgttctcc ccgctattgc tgaatgtggt gaaattgaac   5160
cctggcgaag cgatgttcct gttcgctgaa acaccgcacg cttacctgca aggcgtggcg   5220
ctggaagtga tggcaaactc cgataacgtg ctgcgtgcgg gtctgacgcc taaatacatt   5280
gatattccgg aactggttgc caatgtgaaa ttcgaagcca aaccggctaa ccagttgttg   5340
acccagccgg tgaaacaagg tgcagaactg gacttcccga ttccagtgga tgattttgcc   5400
ttctcgctgc atgaccttag tgataaagaa accaccatta gccagcagag tgccgccatt   5460
ttgttctgcg tcgaaggcga tgcaacgttg tggaaaggtt ctcagcagtt acagcttaaa   5520
ccgggtgaat cagcgtttat tgccgccaac gaatcaccgg tgactgtcaa aggccacggc   5580
cgtttagcgc gtgtttacaa caagctgtaa gagcttactg aaaaaattaa catctcttgc   5640
taagctggga gctctagatc cccgaatttc cccgatcgtt caaacatttg gcaataaagt   5700
ttcttaagat tgaatcctgt tgccggtctt gcgatgatta tcatataatt tctgttgaat   5760
tacgttaagc atgtaataat taacatgtaa tgcatgacgt tatttatgag atgggttttt   5820
atgattagag tcccgcaatt atacatttaa tacgcgatag aaaacaaaat atagcgcgca   5880
```

```
aactaggata aattatcgcg cgcggtgtca tctatgttac tagatcggga attggcgagc   5940

tcgaattaat tcagtacatt aaaaacgtcc gcaatgtgtt attaagttgt ctaagcgtca   6000

atttgtttac accacaatat atcctgcca                                     6029
```

<210> SEQ ID NO 168
<211> LENGTH: 6032
<212> TYPE: DNA
<213> ORGANISM: Artificial Sequence
<220> FEATURE:
<223> OTHER INFORMATION: Synthetic construct, pAG4994

<400> SEQUENCE: 168

```
gtttacccgc caatatatcc tgtcaaacac tgatagttta aactgaaggc gggaaacgac     60

aacctgatca tgagcggaga attaagggag tcacgttatg acccccgccg atgacgcggg    120

acaagccgtt ttacgtttgg aactgacaga accgcaacgt tgaaggagcc actcagccta    180

agcggccgca ttggacttaa ttaagtgagg ccggccaagc gtcgatttaa atgtaccaca    240

tggcgcgcca actatcatgc gatcgcttca tgtctaactc gagttactgg tacgtaccaa    300

atccatggaa tcaaggtacc aaagtaatca tattatttta tgtgtgaatc ttctttactt    360

tttcatttga ttatgattat gaaggtatga ccttcataac cttcgtccga aatccattat    420

atccaaagga aaataatgct tcgaaggacg aaggattttg atatttaaca ttttatgttg    480

ccttgttctt aattcatagc atttgagaac aagtccccaa caccaatctt tatctttact    540

atattaaagc accagttcaa cgatcgtctc gtgtcaatat tattaaaaaa ctcctacatt    600

tctttataat caacccgcac tcttataatc tcttctctta ctactataat aagagagttt    660

atgtacaaaa taaggtgaaa ttatgtataa gtgttctgga ccttggttgt tggctcatat    720

tcacacaacc taatcaatag aaaacatatg ttttattaaa acaaaattta tcatatatat    780

atatatatat atatatatat atatatatat atataatata aaccgtagca atgcacaggc    840

atatgactag tggcaactta ataccatgtg tgtattaaga tgaataagag gtatccaaat    900

aaataacttg ttcgcttacg tctggatcga aaggggttgg aaacgattaa atctcttcct    960

agtcaaaatt aaatagaagg agatttaatc gatttctccc aatccccttc gatccaggtg   1020

caaccgaata agtccttaaa tgttgaggaa cacgaaacaa ccatgcattg gcatgtaaag   1080

ctccaagaat tcgttgtatc cttaacaact cacagaacat caaccaaaat tgcacgtcaa   1140

gggtattggg taagaaacaa tcaaacaaat cctctctgtg tgcaaagaaa cacggtgagt   1200

catgccgaga tcatactcat ctgatataca tgcttacagc tcacaagaca ttacaaacaa   1260

ctcatattgc attacaaaga tcgtttcatg aaaaataaaa taggccggaa caggacaaaa   1320

atccttgacg tgtaaagtaa atttacaaca aaaaaaaagc catatgtcaa gctaaatcta   1380

attcgtttta cgtagatcaa caacctgtag aaggcaacaa aactgagcca cgcagaagta   1440

cagaatgatt ccagatgaac catcgacgtg ctacgtaaag agagtgacga gtcatataca   1500

tttggcaaga aaccatgaag ctgcctacag ccgtctcggt ggcataagaa cacaagaaat   1560

tgtgttaatt aatcaaagct ataaataacg ctcgcatgcc tgtgcacttc tccatcacca   1620

ccactgggtc ttcagaccat tagctttatc tactccagag cgcagaagaa cccgatcgac   1680

accggatcct aaaccatgag ggtgttgctc gttgccctcg ctctcctggc tctcgctgcg   1740

agcgccacct cccaggtgca gctccaggag ttcggcggcg gcctcgtgca gccgggcggc   1800

tccctccgcc tgagctgcgc cgcgtccggc aggacgggct ccagctacgc gatgggctgg   1860
```

-continued

```
ttcaggcagg cgcccggcaa ggagagggag ttcgtggcgg ccatctcgtg gagcggcggc   1920
agcaccgact acgctgactc cgtcaagggc cgcttcacca tcagcaggga caacgcgaag   1980
aacacgatgt acctccagat gaactccctg aagccggagg acaccgccgt gtactactgc   2040
gcggtcgacc gcaacctctt caagctgagg gtggccgtcc aggagtacac caacctcggc   2100
cagggcaccc aggtgaccgt gtcctccaag gacgagctgt gacctaggtc cccgaatttc   2160
cccgatcgtt caaacatttg gcaataaagt ttcttaagat tgaatcctgt tgccggtctt   2220
gcgatgatta tcatataatt tctgttgaat tacgttaagc atgtaataat taacatgtaa   2280
tgcatgacgt tatttatgag atgggttttt atgattagag tcccgcaatt atacatttaa   2340
tacgcgatag aaaacaaaat atagcgcgca aactaggata aattatcgcg cgcggtgtca   2400
tctatgttac tagatcggga attggaattc ctgcagtgca gcgtgacccg gtcgtgcccc   2460
tctctagaga taatgagcat tgcatgtcta agttataaaa aattaccaca tatttttttt   2520
gtcacacttg tttgaagtgc agtttatcta tctttataca tatatttaaa ctttactcta   2580
cgaataatat aatctatagt actacaataa tatcagtgtt ttagagaatc atataaatga   2640
acagttagac atggtctaaa ggacaattga gtattttgac aacaggactc tacagtttta   2700
tctttttagt gtgcatgtgt tctccttttt ttttgcaaat agcttcacct atataatact   2760
tcatccattt tattagtaca tccatttagg gtttagggtt aatggttttt atagactaat   2820
tttttagta catctatttt attctatttt agcctctaaa ttaagaaaac taaaactcta   2880
ttttagtttt tttatttaat aatttagata taaaatagaa taaaataaag tgactaaaaa   2940
ttaaacaaat accctttaag aaattaaaaa aactaaggaa acatttttct tgtttcgagt   3000
agataatgcc agcctgttaa acgccgtcga cgagtctaac ggacaccaac cagcgaacca   3060
gcagcgtcgc gtcgggccaa gcgaagcaga cggcacggca tctctgtcgc tgcctctgga   3120
cccctctcga gagttccgct ccaccgttgg acttgctccg ctgtcggcat ccagaaattg   3180
cgtggcggag cggcagacgt gagccggcac ggcaggcggc ctcctcctcc tctcacggca   3240
cggcagctac gggggattcc tttcccaccg ctccttcgct ttcccttcct cgcccgccgt   3300
aataaataga caccccctcc acaccctctt tccccaacct cgtgttgttc ggagcgcaca   3360
cacacacaac cagatctccc ccaaatccac ccgtcggcac ctccgcttca aggtacgccg   3420
ctcgtcctcc cccccccccc ctctctacct tctctagatc ggcgttccgg tccatggtta   3480
gggcccggta gttctacttc tgttcatgtt tgtgttagat ccgtgtttgt gttagatccg   3540
tgctgctagc gttcgtacac ggatgcgacc tgtacgtcag acacgttctg attgctaact   3600
tgccagtgtt tctctttggg gaatcctggg atggctctag ccgttccgca gacgggatcg   3660
atttcatgat tttttttgtt tcgttgcata gggtttggtt tgcccttttc ctttatttca   3720
atatatgccg tgcacttgtt tgtcgggtca tcttttcatg cttttttttg tcttggttgt   3780
gatgatgtgg tctggttggg cggtcgttct agatcggagt agaattctgt ttcaaactac   3840
ctggtggatt tattaatttt ggatctgtat gtgtgtgcca tacatattca tagttacgaa   3900
ttgaagatga tggatggaaa tatcgatcta ggataggtat acatgttgat gcgggtttta   3960
ctgatgcata tacagagatg ctttttgttc gcttggttgt gatgatgtgg tgtggttggg   4020
cggtcgttca ttcgttctag atcggagtag aatactgttt caaactacct ggtgtattta   4080
ttaattttgg aactgtatgt gtgtgtcata catcttcata gttacgagtt taagatggat   4140
ggaaatatcg atctaggata ggtatacatg ttgatgtggg ttttactgat gcatatacat   4200
gatggcatat gcagcatcta ttcatatgct ctaaccttga gtacctatct attataataa   4260
```

acaagtatgt tttataatta ttttgatctt gatatacttg gatgatggca tatgcagcag 4320
ctatatgtgg attttttag ccctgccttc atacgctatt tatttgcttg gtactgtttc 4380
ttttgtcgat gctcaccctg ttgtttggtg ttacttctgc agatccagat ctaaaccatg 4440
cagaaactca ttaactcagt gcaaaactat gcctggggca gcaaaacggc gttgactgaa 4500
ctttatggta tggaaaatcc gtccagccag ccgatggccg agctgtggat gggcgcacat 4560
ccgaaaagca gttcacgagt gcagaatgcc gccggagata tcgtttcact gcgtgatgtg 4620
attgagagtg ataaatcgac tctgctcgga gaggccgttg ccaaacgctt tggcgaactg 4680
cctttcctgt tcaaagtatt atgcgcagca cagccactct ccattcaggt tcatccaaac 4740
aaacacaatt ctgaaatcgg ttttgccaaa gaaaatgccg caggtatccc gatggatgcc 4800
gccgagcgta actataaaga tcctaaccac aagccggagc tggtttttgc gctgacgcct 4860
ttccttgcga tgaacgcgtt tcgtgaattt tccgagattg tctccctact ccagccggtc 4920
gcaggtgcac atccggcgat tgctcacttt ttacaacagc ctgatgccga acgtttaagc 4980
gaactgttcg ccagcctgtt gaatatgcag ggtgaagaaa aatcccgcgc gctggcgatt 5040
ttaaaatcgg ccctcgatag ccagcagggt gaaccgtggc aaacgattcg tttaatttct 5100
gaattttacc cggaagacag cggtctgttc tccccgctat tgctgaatgt ggtgaaattg 5160
aaccctggcg aagcgatgtt cctgttcgct gaaacaccgc acgcttacct gcaaggcgtg 5220
gcgctggaag tgatggcaaa ctccgataac gtgctgcgtg cgggtctgac gcctaaatac 5280
attgatattc cggaactggt tgccaatgtg aaattcgaag ccaaaccggc taaccagttg 5340
ttgacccagc cggtgaaaca aggtgcagaa ctggacttcc cgattccagt ggatgatttt 5400
gccttctcgc tgcatgacct tagtgataaa gaaaccacca ttagccagca gagtgccgcc 5460
attttgttct gcgtcgaagg cgatgcaacg ttgtggaaag gttctcagca gttacagctt 5520
aaaccgggtg aatcagcgtt tattgccgcc aacgaatcac cggtgactgt caaaggccac 5580
ggccgtttag cgcgtgttta caacaagctg taagagctta ctgaaaaaat taacatctct 5640
tgctaagctg ggagctctag atccccgaat ttccccgatc gttcaaacat ttggcaataa 5700
agtttcttaa gattgaatcc tgttgccggt cttgcgatga ttatcatata atttctgttg 5760
aattacgtta agcatgtaat aattaacatg taatgcatga cgttatttat gagatgggtt 5820
tttatgatta gagtcccgca attatacatt taatacgcga tagaaaacaa aatatagcgc 5880
gcaaactagg ataaattatc gcgcgcggtg tcatctatgt tactagatcg ggaattggcg 5940
agctcgaatt aattcagtac attaaaaacg tccgcaatgt gttattaagt tgtctaagcg 6000
tcaatttgtt tacaccacaa tatatcctgc ca 6032

<210> SEQ ID NO 169
<211> LENGTH: 6029
<212> TYPE: DNA
<213> ORGANISM: Artificial Sequence
<220> FEATURE:
<223> OTHER INFORMATION: Synthetic construct, pAG4995

<400> SEQUENCE: 169
gtttacccgc caatatatcc tgtcaaacac tgatagttta aactgaaggc gggaaacgac 60
aacctgatca tgagcggaga attaagggag tcacgttatg acccccgccg atgacgcggg 120
acaagccgtt ttacgtttgg aactgacaga accgcaacgt tgaaggagcc actcagccta 180
agcggccgca ttggacttaa ttaagtgagg ccggccaagc gtcgatttaa atgtaccaca 240

-continued

```
tggcgcgcca actatcatgc gatcgcttca tgtctaactc gagttactgg tacgtaccaa    300
atccatggaa tcaaggtacc aaagtaatca tattatttta tgtgtgaatc ttctttactt    360
tttcatttga ttatgattat gaaggtatga ccttcataac cttcgtccga aatccattat    420
atccaaagga aaataatgct tcgaaggacg aaggattttg atatttaaca ttttatgttg    480
ccttgttctt aattcatagc atttgagaac aagtccccaa caccaatctt tatctttact    540
atattaaagc accagttcaa cgatcgtctc gtgtcaatat tattaaaaaa ctcctacatt    600
tctttataat caacccgcac tcttataatc tcttctctta ctactataat aagagagttt    660
atgtacaaaa taaggtgaaa ttatgtataa gtgttctgga ccttggttgt tggctcatat    720
tcacacaacc taatcaatag aaaacatatg ttttattaaa acaaaattta tcatatatat    780
atatatatat atatatatat atatatatat atataatata aaccgtagca atgcacaggc    840
atatgactag tggcaactta ataccatgtg tgtattaaga tgaataagag gtatccaaat    900
aaataacttg ttcgcttacg tctggatcga aaggggttgg aaacgattaa atctcttcct    960
agtcaaaatt aaatagaagg agatttaatc gatttctccc aatccccttc gatccaggtg   1020
caaccgaata agtccttaaa tgttgaggaa cacgaaacaa ccatgcattg gcatgtaaag   1080
ctccaagaat tcgttgtatc cttaacaact cacagaacat caaccaaaat tgcacgtcaa   1140
gggtattggg taagaaacaa tcaaacaaat cctctctgtg tgcaaagaaa cacggtgagt   1200
catgccgaga tcatactcat ctgatataca tgcttacagc tcacaagaca ttacaaacaa   1260
ctcatattgc attacaaaga tcgtttcatg aaaaataaaa taggccggaa caggacaaaa   1320
atccttgacg tgtaaagtaa atttacaaca aaaaaaaagc catatgtcaa gctaaatcta   1380
attcgtttta cgtagatcaa caacctgtag aaggcaacaa aactgagcca cgcagaagta   1440
cagaatgatt ccagatgaac catcgacgtg ctacgtaaag agagtgacga gtcatataca   1500
tttggcaaga aaccatgaag ctgcctacag ccgtctcggt ggcataagaa cacaagaaat   1560
tgtgttaatt aatcaaagct ataaataacg ctcgcatgcc tgtgcacttc tccatcacca   1620
ccactgggtc ttcagaccat tagctttatc tactccagag cgcagaagaa cccgatcgac   1680
accggatcct aaaccatgag ggtgttgctc gttgccctcg ctctcctggc tctcgctgcg   1740
agcgccacct cccaggtgca gctccaggcc tccggcggcg gcctcgtgca ggcgggcggc   1800
tccctccgcc tgagctgcgc cgcgtccggc aggaccttca acagctacgc ttggggctgg   1860
ttcaggcagg cgccgggcaa ggagcgcggc ttcgtggcca ggatctcctt cagcggcggc   1920
cacacctact actccgacag cgtcaagggc cgcttcacga tcagcaggga caacgccaag   1980
aactccgtgt acctccagat gaacagcctg aagcccgagg acacggccgt ctactactgc   2040
gcggcggacc cgaccccata cggcctccgc aacgagagga actaccacta ctggggccag   2100
ggcacccagg tgaccgtgtc ctccaaggac gagctgtgac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
atgttactag atcgggaatt ggaattcctg cagtgcagcg tgacccggtc gtgcccctct   2460
ctagagataa tgagcattgc atgtctaagt tataaaaaat taccacatat ttttttgtc    2520
acacttgttt gaagtgcagt ttatctatct ttatacatat atttaaactt tactctacga   2580
ataatataat ctatagtact acaataatat cagtgtttta gagaatcata taaatgaaca   2640
```

gttagacatg gtctaaagga caattgagta ttttgacaac aggactctac agttttatct 2700
ttttagtgtg catgtgttct cctttttttt tgcaaatagc ttcacctata taatacttca 2760
tccattttat tagtacatcc atttagggtt tagggttaat ggtttttata gactaatttt 2820
tttagtacat ctattttatt ctattttagc ctctaaatta agaaaactaa aactctattt 2880
tagttttttt atttaataat ttagatataa aatagaataa aataaagtga ctaaaaatta 2940
aacaaatacc ctttaagaaa ttaaaaaaac taaggaaaca tttttcttgt ttcgagtaga 3000
taatgccagc ctgttaaacg ccgtcgacga gtctaacgga caccaaccag cgaaccagca 3060
gcgtcgcgtc gggccaagcg aagcagacgg cacggcatct ctgtcgctgc ctctggaccc 3120
ctctcgagag ttccgctcca ccgttggact tgctccgctg tcggcatcca gaaattgcgt 3180
ggcggagcgg cagacgtgag ccggcacggc aggcggcctc ctcctcctct cacggcacgg 3240
cagctacggg ggattccttt cccaccgctc cttcgctttc ccttcctcgc ccgccgtaat 3300
aaatagacac cccctccaca ccctctttcc ccaacctcgt gttgttcgga gcgcacacac 3360
acacaaccag atctccccca aatccacccg tcggcacctc cgcttcaagg tacgccgctc 3420
gtcctccccc cccccccctc tctaccttct ctagatcggc gttccggtcc atggttaggg 3480
cccggtagtt ctacttctgt tcatgtttgt gttagatccg tgtttgtgtt agatccgtgc 3540
tgctagcgtt cgtacacgga tgcgacctgt acgtcagaca cgttctgatt gctaacttgc 3600
cagtgtttct ctttggggaa tcctgggatg gctctagccg ttccgcagac gggatcgatt 3660
tcatgatttt ttttgtttcg ttgcataggg tttggtttgc ccttttcctt tatttcaata 3720
tatgccgtgc acttgtttgt cgggtcatct tttcatgctt ttttttgtct tggttgtgat 3780
gatgtggtct ggttgggcgg tcgttctaga tcggagtaga attctgtttc aaactacctg 3840
gtggatttat taattttgga tctgtatgtg tgtgccatac atattcatag ttacgaattg 3900
aagatgatgg atggaaatat cgatctagga taggtataca tgttgatgcg ggttttactg 3960
atgcatatac agagatgctt tttgttcgct tggttgtgat gatgtggtgt ggttgggcgg 4020
tcgttcattc gttctagatc ggagtagaat actgtttcaa actacctggt gtatttatta 4080
attttggaac tgtatgtgtg tgtcatacat cttcatagtt acgagtttaa gatggatgga 4140
aatatcgatc taggataggt atacatgttg atgtgggttt tactgatgca tatacatgat 4200
ggcatatgca gcatctattc atatgctcta accttgagta cctatctatt ataataaaca 4260
agtatgtttt ataattattt tgatcttgat atacttggat gatggcatat gcagcagcta 4320
tatgtggatt tttttagccc tgccttcata cgctatttat ttgcttggta ctgtttcttt 4380
tgtcgatgct caccctgttg tttggtgtta cttctgcaga tccagatcta aaccatgcag 4440
aaactcatta actcagtgca aaactatgcc tggggcagca aaacggcgtt gactgaactt 4500
tatggtatgg aaaatccgtc cagccagccg atggccgagc tgtggatggg cgcacatccg 4560
aaaagcagtt cacgagtgca gaatgccgcc ggagatatcg tttcactgcg tgatgtgatt 4620
gagagtgata aatcgactct gctcggagag gccgttgcca aacgctttgg cgaactgcct 4680
ttcctgttca aagtattatg cgcagcacag ccactctcca ttcaggttca tccaaacaaa 4740
cacaattctg aaatcggttt tgccaaagaa aatgccgcag gtatcccgat ggatgccgcc 4800
gagcgtaact ataaagatcc taaccacaag ccggagctgg tttttgcgct gacgcctttc 4860
cttgcgatga acgcgtttcg tgaattttcc gagattgtct ccctactcca gccggtcgca 4920
ggtgcacatc cggcgattgc tcacttttta caacagcctg atgccgaacg tttaagcgaa 4980
ctgttcgcca gcctgttgaa tatgcagggt gaagaaaaat cccgcgcgct ggcgatttta 5040
aaatcggccc tcgatagcca gcagggtgaa ccgtggcaaa cgattcgttt aatttctgaa 5100
ttttacccgg aagacagcgg tctgttctcc ccgctattgc tgaatgtggt gaaattgaac 5160
cctggcgaag cgatgttcct gttcgctgaa acaccgcacg cttacctgca aggcgtggcg 5220
ctggaagtga tggcaaactc cgataacgtg ctgcgtgcgg gtctgacgcc taaatacatt 5280
gatattccgg aactggttgc caatgtgaaa ttcgaagcca aaccggctaa ccagttgttg 5340
acccagccgg tgaaacaagg tgcagaactg gacttcccga ttccagtgga tgattttgcc 5400
ttctcgctgc atgaccttag tgataaagaa accaccatta gccagcagag tgccgccatt 5460
ttgttctgcg tcgaaggcga tgcaacgttg tggaaaggtt ctcagcagtt acagcttaaa 5520
ccgggtgaat cagcgtttat tgccgccaac gaatcaccgg tgactgtcaa aggccacggc 5580
cgtttagcgc gtgtttacaa caagctgtaa gagcttactg aaaaaattaa catctcttgc 5640
taagctggga gctctagatc cccgaatttc cccgatcgtt caaacatttg gcaataaagt 5700
ttcttaagat tgaatcctgt tgccggtctt gcgatgatta tcatataatt tctgttgaat 5760
tacgttaagc atgtaataat taacatgtaa tgcatgacgt tatttatgag atgggttttt 5820
atgattagag tcccgcaatt atacatttaa tacgcgatag aaaacaaaat atagcgcgca 5880
aactaggata aattatcgcg cgcggtgtca tctatgttac tagatcggga attggcgagc 5940
tcgaattaat tcagtacatt aaaaacgtcc gcaatgtgtt attaagttgt ctaagcgtca 6000
atttgtttac accacaatat atcctgcca 6029

<210> SEQ ID NO 170
<211> LENGTH: 8274
<212> TYPE: DNA
<213> ORGANISM: Artificial Sequence
<220> FEATURE:
<223> OTHER INFORMATION: Synthetic construct, pAG4996

<400> SEQUENCE: 170
gtttacccgc caatatatcc tgtcaaacac tgatagttta aactgaaggc gggaaacgac 60
aacctgatca tgagcggaga attaagggag tcacgttatg acccccgccg atgacgcggg 120
acaagccgtt ttacgtttgg aactgacaga accgcaacgt tgaaggagcc actcagccta 180
agcggccgca ttggacttaa ttaagtgagg ccggccaagc gtcgatttaa atgtaccaca 240
tggcgcgcca actatcatgc gatcgcttca tgtctaactc gagttactgg tacgtaccaa 300
atccatggaa tcaaggtacc aaagtaatca tattatttta tgtgtgaatc ttctttactt 360
tttcatttga ttatgattat gaaggtatga ccttcataac cttcgtccga aatccattat 420
atccaaagga aaataatgct tcgaaggacg aaggattttg atatttaaca ttttatgttg 480
ccttgttctt aattcatagc atttgagaac aagtccccaa caccaatctt tatctttact 540
atattaaagc accagttcaa cgatcgtctc gtgtcaatat tattaaaaaa ctcctacatt 600
tctttataat caacccgcac tcttataatc tcttctctta ctactataat aagagagttt 660
atgtacaaaa taaggtgaaa ttatgtataa gtgttctgga ccttggttgt tggctcatat 720
tcacacaacc taatcaatag aaaacatatg ttttattaaa acaaaattta tcatatatat 780
atatatatat atatatatat atatatatat atataatata aaccgtagca atgcacaggc 840
atatgactag tggcaactta ataccatgtg tgtattaaga tgaataagag gtatccaaat 900
aaataacttg ttcgcttacg tctggatcga aaggggttgg aaacgattaa atctcttcct 960
agtcaaaatt aaatagaagg agatttaatc gatttctccc aatccccttc gatccaggtg 1020

```
caaccgaata agtccttaaa tgttgaggaa cacgaaacaa ccatgcattg gcatgtaaag   1080
ctccaagaat tcgttgtatc cttaacaact cacagaacat caaccaaaat tgcacgtcaa   1140
gggtattggg taagaaacaa tcaaacaaat cctctctgtg tgcaaagaaa cacggtgagt   1200
catgccgaga tcatactcat ctgatataca tgcttacagc tcacaagaca ttacaaacaa   1260
ctcatattgc attacaaaga tcgtttcatg aaaaataaaa taggccggaa caggacaaaa   1320
atccttgacg tgtaaagtaa atttacaaca aaaaaaaagc catatgtcaa gctaaatcta   1380
attcgtttta cgtagatcaa caacctgtag aaggcaacaa aactgagcca cgcagaagta   1440
cagaatgatt ccagatgaac catcgacgtg ctacgtaaag agagtgacga gtcatataca   1500
tttggcaaga aaccatgaag ctgcctacag ccgtctcggt ggcataagaa cacaagaaat   1560
tgtgttaatt aatcaaagct ataaataacg ctcgcatgcc tgtgcacttc tccatcacca   1620
ccactgggtc ttcagaccat tagctttatc tactccagag cgcagaagaa cccgatcgac   1680
accggatcct aaaccatgag ggtgttgctc gttgccctcg ctctcctggc tctcgctgcg   1740
agcgccacct cccaggtgca gctccaggag tccggcggcg gcctcgtgca gccgggcggc   1800
tccctccgcc tgagctgcgc cgcgtccggc aacatcttca gcatcaacac gatgggctgg   1860
tacaggcagg cccccggcaa gcagcgggag ctcgtggcct ccatcaccac gggcggcacc   1920
acgaactacg aggacagcgt caagggccgc ttcaccatct ccagggacaa cgccaagaag   1980
acggtgtacc tccagatgaa ccgcctgaag ccggaggaca cggcggtcta ctactgcaac   2040
caccgcaggt cctacagcgg cagggactac cccgtgtacg gcatggacta ctggggcaag   2100
ggcaccctcg tgaccgtgtc ctccaaggac gagctgtaac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
atgttactag atcgggaatt gttaattaag tctaactcga gttactggta cgtatacagg   2460
gttccttgcg tgaagaaggg tggcctgcgg ttcaccatta acggtcacga ctacttccag   2520
ctagtactgg tgaccaacgt cgcggcggca gggtcaatca agtccatgga ggttatgggt   2580
tccaacacag cggattggat gccgatggca cgtaactggg gcgcccaatg gcactcactg   2640
gcctacctca ccggtcaagg tctatccttt agggtcacca acacagatga ccaaacgctc   2700
gtcttcacca acgtcgtgcc accaggatgg aagtttggcc agacatttgc aagcaagctg   2760
cagttcaagt gagaggagaa gcctgaattg ataccggagc gtttcttttg ggagtaacat   2820
ctctggttgc ctagcaaaca tatgattgta tataagtttc gttgtgcgtt tattctttcg   2880
gtgtgtaaaa taacatacat gctttcctga tattttcttg tatatatgta cacacacacg   2940
acaaatcctt ccatttctat tattattgaa caatttaatt gcgagggcga gtacttgtct   3000
gtttaccttt tttttttcag atggcatttt atagtttaac ctttcatgga ccggcagtag   3060
ttctaaccat gaatgaaaag aaatcatagt ccacaccacg cagggacatt gtggtcattt   3120
tagacaagac gatttgatta atgtcttgta tgatatggtc gacagtgagg actaacaaac   3180
atatggcata ttttattacc ggcgagttaa ataaatttat gtcacagtaa taaactgcct   3240
aataaatgca cgccagaaaa tataatgata aaaaaaagaa aagatacata agtccattgc   3300
ttctactttt ttaaaaatta aatccaacat tttctatttt ttggtataaa cttggaagta   3360
```

ctagttggat atgcaaaatc atctaacctc catatatttc atcaatttgt ttactttaca 3420
tatgggagag gatagtatgt caaagaaaat gacaacaagc ttacaagttt cttattttaa 3480
aagttccgct aacttatcaa gcatagtgtg ccacgcaaaa ctgacaacaa accaacaaat 3540
ttaaggagcg cctaacttat catctatgac ataccgcaca aaatgataac atactagaga 3600
aactttattg cacaaaagga aatttatcca taaggcaaag gaacatctta aggctttgga 3660
tatacattta ccaacaagca ttgtttgtat taccccctaaa gcgcaagaca tgtcatccat 3720
gagtcatagt gtgtatatct caacattgca aagctacctt ttttctatta tacttttcgc 3780
attataggct agatattatc tatacatgtc aacaaactct atccctacgt catatctgaa 3840
gattcttttc ttcactatat aagttggctt ccctgtcatt gaactcacat caaccagccc 3900
aagtttccaa taacatcctc aaatagctgg atcctaaacc atgagggtgt tgctcgttgc 3960
cctcgctctc ctggctctcg ctgcgagcgc cacctcccag gttcagctgc aggaaagcgg 4020
tggcggactg gtgcagccag gtggcagcct caggctgagc tgcgctgcta gcggcaatat 4080
ttttagcatt aacacaatgg gttggtatag acaggctcct ggcaagcagc gtgagctcgt 4140
tgccagcatt accacgggtg gtacaaccaa ttatgaagat agcgtgaagg gtcgttttac 4200
cattagcagg gacaatgcta agaagaccgt ttacctccag atgaacaggc tgaagccaga 4260
agataccgcc gtgtattact gcaaccacag gagaagctat agcggaagag attatcctgt 4320
ttacggtatg gactactggg gcaagggaac cctggttacc gtgagcagca aggacgagct 4380
gtaacctagg tccccgaatt tccccgatcg ttcaaacatt tggcaataaa gtttcttaag 4440
attgaatcct gttgccggtc ttgcgatgat tatcatataa tttctgttga attacgttaa 4500
gcatgtaata attaacatgt aatgcatgac gttatttatg agatgggttt ttatgattag 4560
agtcccgcaa ttatacattt aatacgcgat agaaaacaaa atatagcgcg caaactagga 4620
taaattatcg cgcgcggtgt catctatgtt actagatcgg gaattggaat tcctgcagtg 4680
cagcgtgacc cggtcgtgcc cctctctaga gataatgagc attgcatgtc taagttataa 4740
aaaattacca catatttttt ttgtcacact tgtttgaagt gcagtttatc tatctttata 4800
catatattta aactttactc tacgaataat ataatctata gtactacaat aatatcagtg 4860
ttttagagaa tcatataaat gaacagttag acatggtcta aaggacaatt gagtattttg 4920
acaacaggac tctacagttt tatcttttta gtgtgcatgt gttctccttt ttttttgcaa 4980
atagcttcac ctatataata cttcatccat tttattagta catccattta gggtttaggg 5040
ttaatggttt ttatagacta atttttttag tacatctatt ttattctatt ttagcctcta 5100
aattaagaaa actaaaactc tattttagtt tttttattta ataatttaga tataaaatag 5160
aataaaataa agtgactaaa aattaaacaa ataccctta agaaattaaa aaaactaagg 5220
aaacattttt cttgtttcga gtagataatg ccagcctgtt aaacgccgtc gacgagtcta 5280
acggacacca accagcgaac cagcagcgtc gcgtcgggcc aagcgaagca gacggcacgg 5340
catctctgtc gctgcctctg gacccctctc gagagttccg ctccaccgtt ggacttgctc 5400
cgctgtcggc atccagaaat tgcgtggcgg agcggcagac gtgagccggc acggcaggcg 5460
gcctcctcct cctctcacgg cacggcagct acgggggatt cctttcccac cgctccttcg 5520
ctttcccttc ctcgcccgcc gtaataaata gacacccccct ccacaccctc tttccccaac 5580
ctcgtgttgt tcggagcgca cacacacaca accagatctc ccccaaatcc acccgtcggc 5640
acctccgctt caaggtacgc cgctcgtcct cccccccccc ccctctctac cttctctaga 5700
tcggcgttcc ggtccatggt tagggcccgg tagttctact tctgttcatg tttgtgttag 5760
atccgtgttt gtgttagatc cgtgctgcta gcgttcgtac acggatgcga cctgtacgtc 5820
agacacgttc tgattgctaa cttgccagtg tttctctttg gggaatcctg ggatggctct 5880
agccgttccg cagacgggat cgatttcatg attttttttg tttcgttgca tagggtttgg 5940
tttgcccttt tcctttattt caatatatgc cgtgcacttg tttgtcgggt catcttttca 6000
tgcttttttt tgtcttggtt gtgatgatgt ggtctggttg ggcggtcgtt ctagatcgga 6060
gtagaattct gtttcaaact acctggtgga tttattaatt ttggatctgt atgtgtgtgc 6120
catacatatt catagttacg aattgaagat gatggatgga aatatcgatc taggataggt 6180
atacatgttg atgcgggttt tactgatgca tatacagaga tgctttttgt tcgcttggtt 6240
gtgatgatgt ggtgtggttg ggcggtcgtt cattcgttct agatcggagt agaatactgt 6300
ttcaaactac ctggtgtatt tattaatttt ggaactgtat gtgtgtgtca tacatcttca 6360
tagttacgag tttaagatgg atggaaatat cgatctagga taggtataca tgttgatgtg 6420
ggttttactg atgcatatac atgatggcat atgcagcatc tattcatatg ctctaacctt 6480
gagtacctat ctattataat aaacaagtat gttttataat tattttgatc ttgatatact 6540
tggatgatgg catatgcagc agctatatgt ggattttttt agccctgcct tcatacgcta 6600
tttatttgct tggtactgtt tcttttgtcg atgctcaccc tgttgtttgg tgttacttct 6660
gcagatccag atctaaacca tgcagaaact cattaactca gtgcaaaact atgcctgggg 6720
cagcaaaacg gcgttgactg aactttatgg tatggaaaat ccgtccagcc agccgatggc 6780
cgagctgtgg atgggcgcac atccgaaaag cagttcacga gtgcagaatg ccgccggaga 6840
tatcgtttca ctgcgtgatg tgattgagag tgataaatcg actctgctcg gagaggccgt 6900
tgccaaacgc tttggcgaac tgcctttcct gttcaaagta ttatgcgcag cacagccact 6960
ctccattcag gttcatccaa acaaacacaa ttctgaaatc ggttttgcca aagaaaatgc 7020
cgcaggtatc ccgatggatg ccgccgagcg taactataaa gatcctaacc acaagccgga 7080
gctggttttt gcgctgacgc ctttccttgc gatgaacgcg tttcgtgaat tttccgagat 7140
tgtctcccta ctccagccgg tcgcaggtgc acatccggcg attgctcact tttacaaca 7200 gcctgatgcc gaacgtttaa gcgaactgtt cgccagcctg ttgaatatgc agggtgaaga 7260
aaaatcccgc gcgctggcga ttttaaaatc ggccctcgat agccagcagg gtgaaccgtg 7320
gcaaacgatt cgtttaattt ctgaatttta cccggaagac agcggtctgt tctccccgct 7380
attgctgaat gtggtgaaat tgaaccctgg cgaagcgatg ttcctgttcg ctgaaacacc 7440
gcacgcttac ctgcaaggcg tggcgctgga agtgatggca aactccgata acgtgctgcg 7500
tgcgggtctg acgcctaaat acattgatat tccggaactg gttgccaatg tgaaattcga 7560
agccaaaccg gctaaccagt tgttgaccca gccggtgaaa caaggtgcag aactggactt 7620
cccgattcca gtggatgatt ttgccttctc gctgcatgac cttagtgata aagaaaccac 7680
cattagccag cagagtgccg ccattttgtt ctgcgtcgaa ggcgatgcaa cgttgtggaa 7740
aggttctcag cagttacagc ttaaaccggg tgaatcagcg tttattgccg ccaacgaatc 7800
accggtgact gtcaaaggcc acggccgttt agcgcgtgtt tacaacaagc tgtaagagct 7860
tactgaaaaa attaacatct cttgctaagc tgggagctct agatccccga atttccccga 7920
tcgttcaaac atttggcaat aaagtttctt aagattgaat cctgttgccg gtcttgcgat 7980
gattatcata taatttctgt tgaattacgt taagcatgta ataattaaca tgtaatgcat 8040
gacgttattt atgagatggg tttttatgat tagagtcccg caattataca tttaatacgc 8100
gatagaaaac aaaatatagc gcgcaaacta ggataaatta tcgcgcgcgg tgtcatctat 8160
gttactagat cgggaattgg cgagctcgaa ttaattcagt acattaaaaa cgtccgcaat 8220
gtgttattaa gttgtctaag cgtcaatttg tttacaccac aatatatcct gcca 8274

<210> SEQ ID NO 171
<211> LENGTH: 8280
<212> TYPE: DNA
<213> ORGANISM: Artificial Sequence
<220> FEATURE:
<223> OTHER INFORMATION: Synthetic construct, pAG4997

<400> SEQUENCE: 171
gtttacccgc caatatatcc tgtcaaacac tgatagttta aactgaaggc gggaaacgac 60
aacctgatca tgagcggaga attaagggag tcacgttatg acccccgccg atgacgcggg 120
acaagccgtt ttacgtttgg aactgacaga accgcaacgt tgaaggagcc actcagccta 180
agcggccgca ttggacttaa ttaagtgagg ccggccaagc gtcgatttaa atgtaccaca 240
tggcgcgcca actatcatgc gatcgcttca tgtctaactc gagttactgg tacgtaccaa 300
atccatggaa tcaaggtacc aaagtaatca tattatttta tgtgtgaatc ttctttactt 360
tttcatttga ttatgattat gaaggtatga ccttcataac cttcgtccga aatccattat 420
atccaaagga aaataatgct tcgaaggacg aaggattttg atatttaaca ttttatgttg 480
ccttgttctt aattcatagc atttgagaac aagtccccaa caccaatctt tatctttact 540
atattaaagc accagttcaa cgatcgtctc gtgtcaatat tattaaaaaa ctcctacatt 600
tctttataat caacccgcac tcttataatc tcttctctta ctactataat aagagagttt 660
atgtacaaaa taaggtgaaa ttatgtataa gtgttctgga ccttggttgt tggctcatat 720
tcacacaacc taatcaatag aaaacatatg ttttattaaa acaaaattta tcatatatat 780
atatatatat atatatatat atatatatat atataatata aaccgtagca atgcacaggc 840
atatgactag tggcaactta ataccatgtg tgtattaaga tgaataagag gtatccaaat 900
aaataacttg ttcgcttacg tctggatcga aaggggttgg aaacgattaa atctcttcct 960
agtcaaaatt aaatagaagg agatttaatc gatttctccc aatccccttc gatccaggtg 1020
caaccgaata agtccttaaa tgttgaggaa cacgaaacaa ccatgcattg gcatgtaaag 1080
ctccaagaat tcgttgtatc cttaacaact cacagaacat caaccaaaat tgcacgtcaa 1140
gggtattggg taagaaacaa tcaaacaaat cctctctgtg tgcaaagaaa cacggtgagt 1200
catgccgaga tcatactcat ctgatataca tgcttacagc tcacaagaca ttacaaacaa 1260
ctcatattgc attacaaaga tcgtttcatg aaaaataaaa taggccggaa caggacaaaa 1320
atccttgacg tgtaaagtaa atttacaaca aaaaaaaagc catatgtcaa gctaaatcta 1380
attcgtttta cgtagatcaa caacctgtag aaggcaacaa aactgagcca cgcagaagta 1440
cagaatgatt ccagatgaac catcgacgtg ctacgtaaag agagtgacga gtcatataca 1500
tttggcaaga aaccatgaag ctgcctacag ccgtctcggt ggcataagaa cacaagaaat 1560
tgtgttaatt aatcaaagct ataaataacg ctcgcatgcc tgtgcacttc tccatcacca 1620
ccactgggtc ttcagaccat tagctttatc tactccagag cgcagaagaa cccgatcgac 1680
accggatcct aaaccatgag ggtgttgctc gttgccctcg ctctcctggc tctcgctgcg 1740
agcgccacct cccaggtgca gctccaggag ttcggcggcg gcctcgtgca gccgggcggc 1800
tccctccgcc tgagctgcgc cgcgtccggc aggacgggct ccagctacgc gatgggctgg 1860
ttcaggcagg cgcccggcaa ggagagggag ttcgtggcgg ccatctcgtg gagcggcggc 1920
agcaccgact acgctgactc cgtcaagggc cgcttcacca tcagcaggga caacgcgaag 1980
aacacgatgt acctccagat gaactccctg aagccggagg acaccgccgt gtactactgc 2040
gcggtcgacc gcaacctctt caagctgagg gtggccgtcc aggagtacac caacctcggc 2100
cagggcaccc aggtgaccgt gtcctccaag gacgagctgt aacctaggtc cccgaatttc 2160
cccgatcgtt caaacatttg gcaataaagt ttcttaagat tgaatcctgt tgccggtctt 2220
gcgatgatta tcatataatt tctgttgaat tacgttaagc atgtaataat taacatgtaa 2280
tgcatgacgt tatttatgag atgggttttt atgattagag tcccgcaatt atacatttaa 2340
tacgcgatag aaaacaaaat atagcgcgca aactaggata aattatcgcg cgcggtgtca 2400
tctatgttac tagatcggga attgttaatt aagtctaact cgagttactg gtacgtatac 2460
agggttcctt gcgtgaagaa gggtggcctg cggttcacca ttaacggtca cgactacttc 2520
cagctagtac tggtgaccaa cgtcgcggcg gcagggtcaa tcaagtccat ggaggttatg 2580
ggttccaaca cagcggattg gatgccgatg gcacgtaact ggggcgccca atggcactca 2640
ctggcctacc tcaccggtca aggtctatcc tttagggtca ccaacacaga tgaccaaacg 2700
ctcgtcttca ccaacgtcgt gccaccagga tggaagtttg gccagacatt tgcaagcaag 2760
ctgcagttca agtgagagga gaagcctgaa ttgataccgg agcgtttctt ttgggagtaa 2820
catctctggt tgcctagcaa acatatgatt gtatataagt ttcgttgtgc gtttattctt 2880
tcggtgtgta aaataacata catgctttcc tgatattttc ttgtatatat gtacacacac 2940
acgacaaatc cttccatttc tattattatt gaacaattta attgcgaggg cgagtacttg 3000
tctgtttacc tttttttttt cagatggcat tttatagttt aacctttcat ggaccggcag 3060
tagttctaac catgaatgaa aagaaatcat agtccacacc acgcagggac attgtggtca 3120
ttttagacaa gacgatttga ttaatgtctt gtatgatatg gtcgacagtg aggactaaca 3180
aacatatggc atattttatt accggcgagt taaataaatt tatgtcacag taataaactg 3240
cctaataaat gcacgccaga aaatataatg ataaaaaaaa gaaaagatac ataagtccat 3300
tgcttctact tttttaaaaa ttaaatccaa cattttctat tttttggtat aaacttggaa 3360
gtactagttg gatatgcaaa atcatctaac ctccatatat ttcatcaatt tgtttacttt 3420
acatatggga gaggatagta tgtcaaagaa aatgacaaca agcttacaag tttcttattt 3480
taaaagttcc gctaacttat caagcatagt gtgccacgca aaactgacaa caaaccaaca 3540
aatttaagga gcgcctaact tatcatctat gacataccgc acaaaatgat aacatactag 3600
agaaacttta ttgcacaaaa ggaaatttat ccataaggca aaggaacatc ttaaggcttt 3660
ggatatacat ttaccaacaa gcattgtttg tattacccct aaagcgcaag acatgtcatc 3720
catgagtcat agtgtgtata tctcaacatt gcaaagctac ctttttttcta ttatactttt 3780
cgcattatag gctagatatt atctatacat gtcaacaaac tctatcccta cgtcatatct 3840
gaagattctt ttcttcacta tataagttgg cttccctgtc attgaactca catcaaccag 3900
cccaagtttc caataacatc ctcaaatagc tggatcctaa accatgaggg tgttgctcgt 3960
tgccctcgct ctcctggctc tcgctgcgag cgccacctcc caggttcagc tccaggagtt 4020
tggtggcgga ctggtgcagc caggtggcag cctcaggctg agctgcgctg ctagcggtag 4080
aaccggcagc agctatgcta tgggatggtt tagacaggct ccaggcaagg agcgtgaatt 4140
tgttgctgcc attagctgga gcggaggtag caccgattat gctgacagcg tgaagggcag 4200
gtttaccatt agcagagata atgccaagaa caccatgtac ctccagatga atagcctgaa 4260

-continued

```
gccagaggat accgctgttt attactgcgc cgtggaccgt aatctcttta agctgagggt   4320
tgctgtgcag gaatacacca acctcggcca gggaacccag gttaccgtga gcagcaagga   4380
cgagctgtaa cctaggtccc cgaatttccc cgatcgttca aacatttggc aataaagttt   4440
cttaagattg aatcctgttg ccggtcttgc gatgattatc atataatttc tgttgaatta   4500
cgttaagcat gtaataatta acatgtaatg catgacgtta tttatgagat gggtttttat   4560
gattagagtc ccgcaattat acatttaata cgcgatagaa aacaaaatat agcgcgcaaa   4620
ctaggataaa ttatcgcgcg cggtgtcatc tatgttacta gatcgggaat tggaattcct   4680
gcagtgcagc gtgacccggt cgtgcccctc tctagagata atgagcattg catgtctaag   4740
ttataaaaaa ttaccacata ttttttttgt cacacttgtt tgaagtgcag tttatctatc   4800
tttatacata tatttaaact ttactctacg aataatataa tctatagtac tacaataata   4860
tcagtgtttt agagaatcat ataaatgaac agttagacat ggtctaaagg acaattgagt   4920
attttgacaa caggactcta cagttttatc tttttagtgt gcatgtgttc tccttttttt   4980
ttgcaaatag cttcacctat ataatacttc atccatttta ttagtacatc catttagggt   5040
ttagggttaa tggtttttat agactaattt ttttagtaca tctattttat tctattttag   5100
cctctaaatt aagaaaacta aaactctatt ttagtttttt tatttaataa tttagatata   5160
aaatagaata aaataaagtg actaaaaatt aaacaaatac cctttaagaa attaaaaaaa   5220
ctaaggaaac atttttcttg tttcgagtag ataatgccag cctgttaaac gccgtcgacg   5280
agtctaacgg acaccaacca gcgaaccagc agcgtcgcgt cgggccaagc gaagcagacg   5340
gcacggcatc tctgtcgctg cctctggacc cctctcgaga gttccgctcc accgttggac   5400
ttgctccgct gtcggcatcc agaaattgcg tggcggagcg gcagacgtga gccggcacgg   5460
caggcggcct cctcctcctc tcacggcacg gcagctacgg gggattcctt tcccaccgct   5520
ccttcgcttt cccttcctcg cccgccgtaa taaatagaca ccccctccac accctctttc   5580
cccaacctcg tgttgttcgg agcgcacaca cacacaacca gatctccccc aaatccaccc   5640
gtcggcacct ccgcttcaag gtacgccgct cgtcctcccc cccccccct ctctaccttc   5700
tctagatcgg cgttccggtc catggttagg gcccggtagt tctacttctg ttcatgtttg   5760
tgttagatcc gtgtttgtgt tagatccgtg ctgctagcgt tcgtacacgg atgcgacctg   5820
tacgtcagac acgttctgat tgctaacttg ccagtgtttc tctttgggga atcctgggat   5880
ggctctagcc gttccgcaga cgggatcgat ttcatgattt tttttgtttc gttgcatagg   5940
gtttggtttg cccttttcct ttatttcaat atatgccgtg cacttgtttg tcgggtcatc   6000
ttttcatgct tttttttgtc ttggttgtga tgatgtggtc tggttgggcg gtcgttctag   6060
atcggagtag aattctgttt caaactacct ggtggattta ttaattttgg atctgtatgt   6120
gtgtgccata catattcata gttacgaatt gaagatgatg gatggaaata tcgatctagg   6180
ataggtatac atgttgatgc gggttttact gatgcatata cagagatgct tttgttcgc    6240
ttggttgtga tgatgtggtg tggttgggcg gtcgttcatt cgttctagat cggagtagaa   6300
tactgtttca aactacctgg tgtatttatt aattttggaa ctgtatgtgt gtgtcataca   6360
tcttcatagt tacgagttta agatggatgg aaatatcgat ctaggatagg tatacatgtt   6420
gatgtgggtt ttactgatgc atatacatga tggcatatgc agcatctatt catatgctct   6480
aaccttgagt acctatctat tataataaac aagtatgttt tataattatt ttgatcttga   6540
tatacttgga tgatggcata tgcagcagct atatgtggat ttttttagcc ctgccttcat   6600
acgctattta tttgcttggt actgtttctt ttgtcgatgc tcaccctgtt gtttggtgtt   6660
```

```
acttctgcag atccagatct aaaccatgca gaaactcatt aactcagtgc aaaactatgc   6720

ctggggcagc aaaacggcgt tgactgaact ttatggtatg gaaaatccgt ccagccagcc   6780

gatggccgag ctgtggatgg gcgcacatcc gaaaagcagt tcacgagtgc agaatgccgc   6840

cggagatatc gtttcactgc gtgatgtgat tgagagtgat aaatcgactc tgctcggaga   6900

ggccgttgcc aaacgctttg gcgaactgcc tttcctgttc aaagtattat gcgcagcaca   6960

gccactctcc attcaggttc atccaaacaa acacaattct gaaatcggtt ttgccaaaga   7020

aaatgccgca ggtatcccga tggatgccgc cgagcgtaac tataaagatc ctaaccacaa   7080

gccggagctg gtttttgcgc tgacgccttt ccttgcgatg aacgcgtttc gtgaattttc   7140

cgagattgtc tccctactcc agccggtcgc aggtgcacat ccggcgattg ctcacttttt   7200

acaacagcct gatgccgaac gtttaagcga actgttcgcc agcctgttga atatgcaggg   7260

tgaagaaaaa tcccgcgcgc tggcgatttt aaaatcggcc ctcgatagcc agcagggtga   7320

accgtggcaa acgattcgtt taatttctga attttacccg gaagacagcg gtctgttctc   7380

cccgctattg ctgaatgtgg tgaaattgaa ccctggcgaa gcgatgttcc tgttcgctga   7440

aacaccgcac gcttacctgc aaggcgtggc gctggaagtg atggcaaact ccgataacgt   7500

gctgcgtgcg ggtctgacgc ctaaatacat tgatattccg gaactggttg ccaatgtgaa   7560

attcgaagcc aaaccggcta accagttgtt gacccagccg gtgaaacaag gtgcagaact   7620

ggacttcccg attccagtgg atgattttgc cttctcgctg catgacctta gtgataaaga   7680

aaccaccatt agccagcaga gtgccgccat tttgttctgc gtcgaaggcg atgcaacgtt   7740

gtggaaaggt tctcagcagt tacagcttaa accgggtgaa tcagcgttta ttgccgccaa   7800

cgaatcaccg gtgactgtca aaggccacgg ccgtttagcg cgtgtttaca acaagctgta   7860

agagcttact gaaaaaatta acatctcttg ctaagctggg agctctagat ccccgaattt   7920

ccccgatcgt tcaaacattt ggcaataaag tttcttaaga ttgaatcctg ttgccggtct   7980

tgcgatgatt atcatataat ttctgttgaa ttacgttaag catgtaataa ttaacatgta   8040

atgcatgacg ttatttatga gatgggtttt tatgattaga gtcccgcaat tatacattta   8100

atacgcgata gaaaacaaaa tatagcgcgc aaactaggat aaattatcgc gcgcggtgtc   8160

atctatgtta ctagatcggg aattggcgag ctcgaattaa ttcagtacat taaaaacgtc   8220

cgcaatgtgt tattaagttg tctaagcgtc aatttgttta caccacaata tatcctgcca   8280
```

```
<210> SEQ ID NO 172
<211> LENGTH: 8274
<212> TYPE: DNA
<213> ORGANISM: Artificial Sequence
<220> FEATURE:
<223> OTHER INFORMATION: Synthetic construct,  pAG4998

<400> SEQUENCE: 172

gtttacccgc caatatatcc tgtcaaacac tgatagttta aactgaaggc gggaaacgac     60

aacctgatca tgagcggaga attaagggag tcacgttatg acccccgccg atgacgcggg    120

acaagccgtt ttacgtttgg aactgacaga accgcaacgt tgaaggagcc actcagccta    180

agcggccgca ttggacttaa ttaagtgagg ccggccaagc gtcgatttaa atgtaccaca    240

tggcgcgcca actatcatgc gatcgcttca tgtctaactc gagttactgg tacgtaccaa    300

atccatggaa tcaaggtacc aaagtaatca tattatttta tgtgtgaatc ttctttactt    360

tttcatttga ttatgattat gaaggtatga ccttcataac cttcgtccga aatccattat    420
```

-continued

```
atccaaagga aaataatgct tcgaaggacg aaggattttg atatttaaca ttttatgttg    480
ccttgttctt aattcatagc atttgagaac aagtccccaa caccaatctt tatctttact    540
atattaaagc accagttcaa cgatcgtctc gtgtcaatat tattaaaaaa ctcctacatt    600
tctttataat caacccgcac tcttataatc tcttctctta ctactataat aagagagttt    660
atgtacaaaa taaggtgaaa ttatgtataa gtgttctgga ccttggttgt tggctcatat    720
tcacacaacc taatcaatag aaaacatatg ttttattaaa acaaaattta tcatatatat    780
atatatatat atatatatat atatatatat atataatata aaccgtagca atgcacaggc    840
atatgactag tggcaactta ataccatgtg tgtattaaga tgaataagag gtatccaaat    900
aaataacttg ttcgcttacg tctggatcga aaggggttgg aaacgattaa atctcttcct    960
agtcaaaatt aaatagaagg agatttaatc gatttctccc aatccccttc gatccaggtg   1020
caaccgaata agtccttaaa tgttgaggaa cacgaaacaa ccatgcattg gcatgtaaag   1080
ctccaagaat tcgttgtatc cttaacaact cacagaacat caaccaaaat tgcacgtcaa   1140
gggtattggg taagaaacaa tcaaacaaat cctctctgtg tgcaaagaaa cacggtgagt   1200
catgccgaga tcatactcat ctgatataca tgcttacagc tcacaagaca ttacaaacaa   1260
ctcatattgc attacaaaga tcgtttcatg aaaaataaaa taggccggaa caggacaaaa   1320
atccttgacg tgtaaagtaa atttacaaca aaaaaaaagc catatgtcaa gctaaatcta   1380
attcgtttta cgtagatcaa caacctgtag aaggcaacaa aactgagcca cgcagaagta   1440
cagaatgatt ccagatgaac catcgacgtg ctacgtaaag agagtgacga gtcatataca   1500
tttggcaaga aaccatgaag ctgcctacag ccgtctcggt ggcataagaa cacaagaaat   1560
tgtgttaatt aatcaaagct ataaataacg ctcgcatgcc tgtgcacttc tccatcacca   1620
ccactgggtc ttcagaccat tagctttatc tactccagag cgcagaagaa cccgatcgac   1680
accggatcct aaaccatgag ggtgttgctc gttgccctcg ctctcctggc tctcgctgcg   1740
agcgccacct cccaggtgca gctccaggcc tccggcggcg gcctcgtgca ggcgggcggc   1800
tccctccgcc tgagctgcgc cgcgtccggc aggaccttca acagctacgc ttggggctgg   1860
ttcaggcagg cgccgggcaa ggagcgcggc ttcgtggcca ggatctcctt cagcggcggc   1920
cacacctact actccgacag cgtcaagggc cgcttcacga tcagcaggga caacgccaag   1980
aactccgtgt acctccagat gaacagcctg aagcccgagg acacggccgt ctactactgc   2040
gcggcggacc cgaccccata cggcctccgc aacgagagga actaccacta ctggggccag   2100
ggcacccagg tgaccgtgtc ctccaaggac gagctgtaac ctaggtcccc gaatttcccc   2160
gatcgttcaa acatttggca ataaagtttc ttaagattga atcctgttgc cggtcttgcg   2220
atgattatca tataatttct gttgaattac gttaagcatg taataattaa catgtaatgc   2280
atgacgttat ttatgagatg ggtttttatg attagagtcc cgcaattata catttaatac   2340
gcgatagaaa acaaaatata gcgcgcaaac taggataaat tatcgcgcgc ggtgtcatct   2400
atgttactag atcgggaatt gttaattaag tctaactcga gttactggta cgtatacagg   2460
gttccttgcg tgaagaaggg tggcctgcgg ttcaccatta acggtcacga ctacttccag   2520
ctagtactgg tgaccaacgt cgcggcggca gggtcaatca agtccatgga ggttatgggt   2580
tccaacacag cggattggat gccgatggca cgtaactggg gcgcccaatg gcactcactg   2640
gcctacctca ccggtcaagg tctatccttt agggtcacca acacagatga ccaaacgctc   2700
gtcttcacca acgtcgtgcc accaggatgg aagtttggcc agacatttgc aagcaagctg   2760
cagttcaagt gagaggagaa gcctgaattg ataccggagc gtttcttttg ggagtaacat   2820
```

```
ctctggttgc ctagcaaaca tatgattgta tataagtttc gttgtgcgtt tattctttcg   2880
gtgtgtaaaa taacatacat gctttcctga tattttcttg tatatatgta cacacacacg   2940
acaaatcctt ccatttctat tattattgaa caatttaatt gcgagggcga gtacttgtct   3000
gtttaccttt ttttttcag atggcatttt atagtttaac ctttcatgga ccggcagtag   3060
ttctaaccat gaatgaaaag aaatcatagt ccacaccacg cagggacatt gtggtcattt   3120
tagacaagac gatttgatta atgtcttgta tgatatggtc gacagtgagg actaacaaac   3180
atatggcata ttttattacc ggcgagttaa ataaatttat gtcacagtaa taaactgcct   3240
aataaatgca cgccagaaaa tataatgata aaaaaaagaa aagatacata agtccattgc   3300
ttctactttt ttaaaaatta aatccaacat tttctatttt ttggtataaa cttggaagta   3360
ctagttggat atgcaaaatc atctaacctc catatatttc atcaatttgt ttactttaca   3420
tatgggagag gatagtatgt caaagaaaat gacaacaagc ttacaagttt cttattttaa   3480
aagttccgct aacttatcaa gcatagtgtg ccacgcaaaa ctgacaacaa accaacaaat   3540
ttaaggagcg cctaacttat catctatgac ataccgcaca aaatgataac atactagaga   3600
aactttattg cacaaaagga aatttatcca taaggcaaag gaacatctta aggctttgga   3660
tatacattta ccaacaagca ttgtttgtat taccccctaaa gcgcaagaca tgtcatccat   3720
gagtcatagt gtgtatatct caacattgca aagctacctt ttttctatta tacttttcgc   3780
attataggct agatattatc tatacatgtc aacaaactct atccctacgt catatctgaa   3840
gattcttttc ttcactatat aagttggctt ccctgtcatt gaactcacat caaccagccc   3900
aagtttccaa taacatcctc aaatagctgg atcctaaacc atgagggtgt tgctcgttgc   3960
cctcgctctc ctggctctcg ctgcgagcgc cacctcccag gttcagctcc aggcttcggg   4020
cggcgggctc gtccaggcgg gcggctcgct caggctctcg tgcgcggcgt cggggcggac   4080
tttcaacagc tacgcttggg gctggttcag gcaggcgccg ggcaaggagc gcggcttcgt   4140
ggccaggatc tccttcagcg gcggccacac ctactactcc gacagcgtca agggccgctt   4200
cacgatctcc agggacaacg ccaagaacag cgtgtacctc cagatgaact ccctgaagcc   4260
cgaggacacg gccgtctact actgcgcggc ggacccgacg ccctacggcc tcaggaacga   4320
gcggaactac cattactggg ggcagggcac gcaggtcact gtctcttcga aggacgagct   4380
gtaacctagg tccccgaatt tccccgatcg ttcaaacatt tggcaataaa gtttcttaag   4440
attgaatcct gttgccggtc ttgcgatgat tatcatataa tttctgttga attacgttaa   4500
gcatgtaata attaacatgt aatgcatgac gttatttatg agatgggttt ttatgattag   4560
agtcccgcaa ttatacattt aatacgcgat agaaaacaaa atatagcgcg caaactagga   4620
taaattatcg cgcgcggtgt catctatgtt actagatcgg gaattggaat tcctgcagtg   4680
cagcgtgacc cggtcgtgcc cctctctaga gataatgagc attgcatgtc taagttataa   4740
aaaattacca catatttttt ttgtcacact tgtttgaagt gcagtttatc tatctttata   4800
catatattta aactttactc tacgaataat ataatctata gtactacaat aatatcagtg   4860
ttttagagaa tcatataaat gaacagttag acatggtcta aaggacaatt gagtattttg   4920
acaacaggac tctacagttt tatctttta gtgtgcatgt gttctccttt ttttttgcaa   4980
atagcttcac ctatataata cttcatccat tttattagta catccattta gggtttaggg   5040
ttaatggttt ttatagacta attttttag tacatctatt ttattctatt ttagcctcta   5100
aattaagaaa actaaaactc tattttagtt tttttattta ataatttaga tataaaatag   5160
```

-continued

```
aataaaataa agtgactaaa aattaaacaa ataccettta agaaattaaa aaaactaagg   5220
aaacattttt cttgtttcga gtagataatg ccagcctgtt aaacgccgtc gacgagtcta   5280
acggacacca accagcgaac cagcagcgtc gcgtcgggcc aagcgaagca gacggcacgg   5340
catctctgtc gctgcctctg gacccctctc gagagttccg ctccaccgtt ggacttgctc   5400
cgctgtcggc atccagaaat tgcgtggcgg agcggcagac gtgagccggc acggcaggcg   5460
gcctcctcct cctctcacgg cacggcagct acgggggatt cctttcccac cgctccttcg   5520
ctttcccttc ctcgcccgcc gtaataaata gacacccect ccacaccctc tttccccaac   5580
ctcgtgttgt tcggagcgca cacacacaca accagatctc ccccaaatcc acccgtcggc   5640
acctccgctt caaggtacgc cgctcgtcct cccccccccc ccctctctac cttctctaga   5700
tcggcgttcc ggtccatggt tagggcccgg tagttctact tctgttcatg tttgtgttag   5760
atccgtgttt gtgttagatc cgtgctgcta gcgttcgtac acggatgcga cctgtacgtc   5820
agacacgttc tgattgctaa cttgccagtg tttctctttg gggaatcctg ggatggctct   5880
agccgttccg cagacgggat cgatttcatg attttttttg tttcgttgca tagggtttgg   5940
tttgcccttt tcctttattt caatatatgc cgtgcacttg tttgtcgggt catcttttca   6000
tgcttttttt tgtcttggtt gtgatgatgt ggtctggttg ggcggtcgtt ctagatcgga   6060
gtagaattct gtttcaaact acctggtgga tttattaatt ttggatctgt atgtgtgtgc   6120
catacatatt catagttacg aattgaagat gatggatgga aatatcgatc taggataggt   6180
atacatgttg atgcgggttt tactgatgca tatacagaga tgctttttgt tcgcttggtt   6240
gtgatgatgt ggtgtggttg ggcggtcgtt cattcgttct agatcggagt agaatactgt   6300
ttcaaactac ctggtgtatt tattaatttt ggaactgtat gtgtgtgtca tacatcttca   6360
tagttacgag tttaagatgg atggaaatat cgatctagga taggtataca tgttgatgtg   6420
ggttttactg atgcatatac atgatggcat atgcagcatc tattcatatg ctctaacctt   6480
gagtacctat ctattataat aaacaagtat gttttataat tattttgatc ttgatatact   6540
tggatgatgg catatgcagc agctatatgt ggattttttt agccctgcct tcatacgcta   6600
tttatttgct tggtactgtt tcttttgtcg atgctcaccc tgttgtttgg tgttacttct   6660
gcagatccag atctaaacca tgcagaaact cattaactca gtgcaaaact atgcctgggg   6720
cagcaaaacg gcgttgactg aactttatgg tatggaaaat ccgtccagcc agccgatggc   6780
cgagctgtgg atgggcgcac atccgaaaag cagttcacga gtgcagaatg ccgccggaga   6840
tatcgtttca ctgcgtgatg tgattgagag tgataaatcg actctgctcg gagaggccgt   6900
tgccaaacgc tttggcgaac tgcctttcct gttcaaagta ttatgcgcag cacagccact   6960
ctccattcag gttcatccaa acaaacacaa ttctgaaatc ggttttgcca aagaaaatgc   7020
cgcaggtatc ccgatggatg ccgccgagcg taactataaa gatcctaacc acaagccgga   7080
gctggttttt gcgctgacgc ctttccttgc gatgaacgcg tttcgtgaat tttccgagat   7140
tgtctcccta ctccagccgg tcgcaggtgc acatccggcg attgctcact tttacaaca    7200
gcctgatgcc gaacgtttaa gcgaactgtt cgccagcctg ttgaatatgc agggtgaaga   7260
aaaatcccgc gcgctggcga ttttaaaatc ggccctcgat agccagcagg gtgaaccgtg   7320
gcaaacgatt cgtttaattt ctgaatttta cccggaagac agcggtctgt tctccccgct   7380
attgctgaat gtggtgaaat tgaaccctgg cgaagcgatg ttcctgttcg ctgaaacacc   7440
gcacgcttac ctgcaaggcg tggcgctgga agtgatggca aactccgata acgtgctgcg   7500
tgcgggtctg acgcctaaat acattgatat tccggaactg gttgccaatg tgaaattcga   7560
```

agccaaaccg gctaaccagt tgttgaccca gccggtgaaa caaggtgcag aactggactt 7620
cccgattcca gtggatgatt ttgccttctc gctgcatgac cttagtgata aagaaaccac 7680
cattagccag cagagtgccg ccattttgtt ctgcgtcgaa ggcgatgcaa cgttgtggaa 7740
aggttctcag cagttacagc ttaaaccggg tgaatcagcg tttattgccg ccaacgaatc 7800
accggtgact gtcaaaggcc acggccgttt agcgcgtgtt tacaacaagc tgtaagagct 7860
tactgaaaaa attaacatct cttgctaagc tgggagctct agatccccga atttccccga 7920
tcgttcaaac atttggcaat aaagtttctt aagattgaat cctgttgccg gtcttgcgat 7980
gattatcata taatttctgt tgaattacgt taagcatgta ataattaaca tgtaatgcat 8040
gacgttattt atgagatggg tttttatgat tagagtcccg caattataca tttaatacgc 8100
gatagaaaac aaaatatagc gcgcaaacta ggataaatta tcgcgcgcgg tgtcatctat 8160
gttactagat cgggaattgg cgagctcgaa ttaattcagt acattaaaaa cgtccgcaat 8220
gtgttattaa gttgtctaag cgtcaatttg tttacaccac aatatatcct gcca 8274

<210> SEQ ID NO 173
<211> LENGTH: 372
<212> TYPE: DNA
<213> ORGANISM: Artificial Sequence
<220> FEATURE:
<223> OTHER INFORMATION: Synthetic construct, chIL101A11A coding seq

<400> SEQUENCE: 173
caggttcagc tgcaggaaag cggtggcgga ctggtgcagc caggtggcag cctcaggctg 60
agctgcgctg ctagcggcaa tatttttagc attaacacaa tgggttggta tagacaggct 120
cctggcaagc agcgtgagct cgttgccagc attaccacgg gtggtacaac caattatgaa 180
gatagcgtga agggtcgttt taccattagc agggacaatg ctaagaagac cgtttacctc 240
cagatgaaca ggctgaagcc agaagatacc gccgtgtatt actgcaacca caggagaagc 300
tatagcggaa gagattatcc tgtttacggt atggactact ggggcaaggg aaccctggtt 360
accgtgagca gc 372

<210> SEQ ID NO 174
<211> LENGTH: 372
<212> TYPE: DNA
<213> ORGANISM: Artificial Sequence
<220> FEATURE:
<223> OTHER INFORMATION: Synthetic construct, chIL101A11B coding seq

<400> SEQUENCE: 174
caggtgcagc tccaggagtc cggcggcggc ctcgtgcagc cgggcggctc cctccgcctg 60
agctgcgccg cgtccggcaa catcttcagc atcaacacga tgggctggta caggcaggcc 120
cccggcaagc agcgggagct cgtggcctcc atcaccacgg gcggcaccac gaactacgag 180
gacagcgtca agggccgctt caccatctcc agggacaacg ccaagaagac ggtgtacctc 240
cagatgaacc gcctgaagcc ggaggacacg gcggtctact actgcaacca ccgcaggtcc 300
tacagcggca gggactaccc cgtgtacggc atggactact ggggcaaggg caccctcgtg 360
accgtgtcct cc 372

<210> SEQ ID NO 175
<211> LENGTH: 375
<212> TYPE: DNA
<213> ORGANISM: Artificial Sequence
<220> FEATURE:

<223> OTHER INFORMATION: Synthetic construct, chIL101F11A coding seq

<400> SEQUENCE: 175
caggttcagc tccaggagtt tggtggcgga ctggtgcagc caggtggcag cctcaggctg 60
agctgcgctg ctagcggtag aaccggcagc agctatgcta tgggatggtt tagacaggct 120
ccaggcaagg agcgtgaatt tgttgctgcc attagctgga gcggaggtag caccgattat 180
gctgacagcg tgaagggcag gtttaccatt agcagagata atgccaagaa caccatgtac 240
ctccagatga atagcctgaa gccagaggat accgctgttt attactgcgc cgtggaccgt 300
aatctcttta agctgagggt tgctgtgcag gaatacacca acctcggcca gggaacccag 360
gttaccgtga gcagc 375

<210> SEQ ID NO 176
<211> LENGTH: 375
<212> TYPE: DNA
<213> ORGANISM: Artificial Sequence
<220> FEATURE:
<223> OTHER INFORMATION: Synthetic construct, chIL101F11B coding seq

<400> SEQUENCE: 176
caggtgcagc tccaggagtt cggcggcggc ctcgtgcagc cgggcggctc cctccgcctg 60
agctgcgccg cgtccggcag gacgggctcc agctacgcga tgggctggtt caggcaggcg 120
cccggcaagg agagggagtt cgtggcggcc atctcgtgga gcggcggcag caccgactac 180
gctgactccg tcaagggccg cttcaccatc agcagggaca acgcgaagaa cacgatgtac 240
ctccagatga actccctgaa gccggaggac accgccgtgt actactgcgc ggtcgaccgc 300
aacctcttca agctgagggt ggccgtccag gagtacacca acctcggcca gggcacccag 360
gtgaccgtgt cctcc 375

<210> SEQ ID NO 177
<211> LENGTH: 372
<212> TYPE: DNA
<213> ORGANISM: Artificial Sequence
<220> FEATURE:
<223> OTHER INFORMATION: Synthetic construct, chIL101H1A coding seq

<400> SEQUENCE: 177
caggttcagc tccaggcttc gggcggcggg ctcgtccagg cgggcggctc gctcaggctc 60
tcgtgcgcgg cgtcggggcg gactttcaac agctacgctt ggggctggtt caggcaggcg 120
ccgggcaagg agcgcggctt cgtggccagg atctccttca gcggcggcca cacctactac 180
tccgacagcg tcaagggccg cttcacgatc tccagggaca acgccaagaa cagcgtgtac 240
ctccagatga actccctgaa gcccgaggac acggccgtct actactgcgc ggcggacccg 300
acgccctacg gcctcaggaa cgagcggaac taccattact gggggcaggg cacgcaggtc 360
actgtctctt cg 372

<210> SEQ ID NO 178
<211> LENGTH: 372
<212> TYPE: DNA
<213> ORGANISM: Artificial Sequence
<220> FEATURE:
<223> OTHER INFORMATION: Synthetic construct, chIL101H1B coding seq

<400> SEQUENCE: 178
caggtgcagc tccaggcctc cggcggcggc ctcgtgcagg cgggcggctc cctccgcctg 60
agctgcgccg cgtccggcag gaccttcaac agctacgctt ggggctggtt caggcaggcg 120

```
ccgggcaagg agcgcggctt cgtggccagg atctccttca gcggcggcca cacctactac    180

tccgacagcg tcaagggccg cttcacgatc agcagggaca acgccaagaa ctccgtgtac    240

ctccagatga acagcctgaa gcccgaggac acggccgtct actactgcgc ggcggacccg    300

accccatacg gcctccgcaa cgagaggaac taccactact ggggccaggg cacccaggtg    360

accgtgtcct cc                                                         372


<210> SEQ ID NO 179
<211> LENGTH: 147
<212> TYPE: PRT
<213> ORGANISM: Artificial Sequence
<220> FEATURE:
<223> OTHER INFORMATION: Synthetic construct,
      xGZein27ss:chIL10sdAb1H1:KDEL

<400> SEQUENCE: 179

Met Arg Val Leu Leu Val Ala Leu Ala Leu Leu Ala Leu Ala Ala Ser
1               5                   10                  15

Ala Thr Ser Gln Val Gln Leu Gln Ala Ser Gly Gly Gly Leu Val Gln
            20                  25                  30

Ala Gly Gly Ser Leu Arg Leu Ser Cys Ala Ala Ser Gly Arg Thr Phe
        35                  40                  45

Asn Ser Tyr Ala Trp Gly Trp Phe Arg Gln Ala Pro Gly Lys Glu Arg
    50                  55                  60

Gly Phe Val Ala Arg Ile Ser Phe Ser Gly Gly His Thr Tyr Tyr Ser
65                  70                  75                  80

Asp Ser Val Lys Gly Arg Phe Thr Ile Ser Arg Asp Asn Ala Lys Asn
                85                  90                  95

Ser Val Tyr Leu Gln Met Asn Ser Leu Lys Pro Glu Asp Thr Ala Val
            100                 105                 110

Tyr Tyr Cys Ala Ala Asp Pro Thr Pro Tyr Gly Leu Arg Asn Glu Arg
        115                 120                 125

Asn Tyr His Tyr Trp Gly Gln Gly Thr Gln Val Thr Val Ser Ser Lys
    130                 135                 140

Asp Glu Leu
145


<210> SEQ ID NO 180
<211> LENGTH: 8
<212> TYPE: PRT
<213> ORGANISM: Artificial Sequence
<220> FEATURE:
<223> OTHER INFORMATION: Synthetic construct, counter selection peptide
      1

<400> SEQUENCE: 180

Asp Asp Glu Leu Asn Ile Gln Leu
1               5


<210> SEQ ID NO 181
<211> LENGTH: 8
<212> TYPE: PRT
<213> ORGANISM: Artificial Sequence
<220> FEATURE:
<223> OTHER INFORMATION: Synthetic construct, counter selection peptide
      2

<400> SEQUENCE: 181

Val Leu Pro Arg Ala Met Gln Thr
1               5
```

<210> SEQ ID NO 182
<211> LENGTH: 8
<212> TYPE: PRT
<213> ORGANISM: Artificial Sequence
<220> FEATURE:
<223> OTHER INFORMATION: Synthetic construct, counter selection peptide
3

<400> SEQUENCE: 182

Glu Lys Met Asp Glu Asn Gly Ile
1 5

<210> SEQ ID NO 183
<211> LENGTH: 8
<212> TYPE: PRT
<213> ORGANISM: Artificial Sequence
<220> FEATURE:
<223> OTHER INFORMATION: Synthetic construct, counter selection peptide
4

<400> SEQUENCE: 183

Glu Pro Thr Cys Leu His Phe Ser
1 5

<210> SEQ ID NO 184
<211> LENGTH: 7
<212> TYPE: PRT
<213> ORGANISM: Artificial Sequence
<220> FEATURE:
<223> OTHER INFORMATION: Synthetic construct, counter selection peptide
5

<400> SEQUENCE: 184

Asp Gln Met Gly Asp Leu Leu
1 5

<210> SEQ ID NO 185
<211> LENGTH: 7
<212> TYPE: PRT
<213> ORGANISM: Artificial Sequence
<220> FEATURE:
<223> OTHER INFORMATION: Synthetic construct, counter selection peptide
6

<400> SEQUENCE: 185

Asp Gln Leu His Ser Leu Leu
1 5

<210> SEQ ID NO 186
<211> LENGTH: 8
<212> TYPE: PRT
<213> ORGANISM: Artificial Sequence
<220> FEATURE:
<223> OTHER INFORMATION: Synthetic construct, counter selection peptide
7

<400> SEQUENCE: 186

Val Met Pro Lys Ala Glu Ser Asp
1 5

<210> SEQ ID NO 187
<211> LENGTH: 8
<212> TYPE: PRT
<213> ORGANISM: Artificial Sequence
<220> FEATURE:
<223> OTHER INFORMATION: Synthetic construct, counter selection peptide
8

<400> SEQUENCE: 187

Val Met Pro Gln Ala Glu Asn His
1 5

<210> SEQ ID NO 188
<211> LENGTH: 8
<212> TYPE: PRT
<213> ORGANISM: Artificial Sequence
<220> FEATURE:
<223> OTHER INFORMATION: Synthetic construct, counter selection peptide

<400> SEQUENCE: 188

Ser Lys Leu Gln Glu Arg Gly Val
1 5

<210> SEQ ID NO 189
<211> LENGTH: 8
<212> TYPE: PRT
<213> ORGANISM: Artificial Sequence
<220> FEATURE:
<223> OTHER INFORMATION: Synthetic construct, counter selection peptide 10

<400> SEQUENCE: 189

Ser Glu Leu Gln Glu Arg Gly Val
1 5

<210> SEQ ID NO 190
<211> LENGTH: 8
<212> TYPE: PRT
<213> ORGANISM: Artificial Sequence
<220> FEATURE:
<223> OTHER INFORMATION: Synthetic construct, counter selection peptide 11

<400> SEQUENCE: 190

Glu Asn Ser Cys Ile His Phe Pro
1 5

<210> SEQ ID NO 191
<211> LENGTH: 8
<212> TYPE: PRT
<213> ORGANISM: Artificial Sequence
<220> FEATURE:
<223> OTHER INFORMATION: Synthetic construct, counter selection peptide 12

<400> SEQUENCE: 191

Asp Ser Ser Cys Ile His Leu Pro
1 5

<210> SEQ ID NO 192
<211> LENGTH: 7
<212> TYPE: PRT
<213> ORGANISM: Artificial Sequence
<220> FEATURE:
<223> OTHER INFORMATION: Synthetic construct, counter selection peptide 13

<400> SEQUENCE: 192

Asp Gln Leu Asn Ser Met Leu
1 5

<210> SEQ ID NO 193
<211> LENGTH: 8
<212> TYPE: PRT

<213> ORGANISM: Artificial Sequence
<220> FEATURE:
<223> OTHER INFORMATION: Synthetic construct, counter selection peptide
      14

<400> SEQUENCE: 193

Asn Met Leu Gln Glu Arg Gly Val
1               5

<210> SEQ ID NO 194
<211> LENGTH: 8
<212> TYPE: PRT
<213> ORGANISM: Artificial Sequence
<220> FEATURE:
<223> OTHER INFORMATION: Synthetic construct, counter selection peptide
      15

<400> SEQUENCE: 194

Asp Ser Ser Cys Thr His Phe Pro
1               5

<210> SEQ ID NO 195
<211> LENGTH: 7
<212> TYPE: PRT
<213> ORGANISM: Artificial Sequence
<220> FEATURE:
<223> OTHER INFORMATION: Synthetic construct; counter selection peptide
      16

<400> SEQUENCE: 195

Asp Asp Leu Glu Ile Gly Leu
1               5

<210> SEQ ID NO 196
<211> LENGTH: 12
<212> TYPE: PRT
<213> ORGANISM: Artificial Sequence
<220> FEATURE:
<223> OTHER INFORMATION: Synthetic construct, counter selection peptide
      17

<400> SEQUENCE: 196

Val Leu Pro Thr Ala Ile Ala Asp Met Thr Glu Glu
1               5                   10

<210> SEQ ID NO 197
<211> LENGTH: 8
<212> TYPE: PRT
<213> ORGANISM: Artificial Sequence
<220> FEATURE:
<223> OTHER INFORMATION: Synthetic construct, counter selection peptide
      18

<400> SEQUENCE: 197

Thr Gln Met Glu Gly Lys Gly Pro
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic construct, counter selection peptide
      19

<400> SEQUENCE: 198

Asn Gln Cys Cys Arg Phe Val
1               5

<210> SEQ ID NO 199
<211> LENGTH: 6
<212> TYPE: PRT
<213> ORGANISM: Artificial Sequence
<220> FEATURE:
<223> OTHER INFORMATION: Synthetic construct, IEGRMD linker

<400> SEQUENCE: 199

Ile Glu Gly Arg Met Asp
1               5

<210> SEQ ID NO 200
<211> LENGTH: 20
<212> TYPE: DNA
<213> ORGANISM: Artificial Sequence
<220> FEATURE:
<223> OTHER INFORMATION: Synthetic construct, forward primer 3661

<400> SEQUENCE: 200
cgtgcccaag ttcagttaca 20

<210> SEQ ID NO 201
<211> LENGTH: 22
<212> TYPE: DNA
<213> ORGANISM: Artificial Sequence
<220> FEATURE:
<223> OTHER INFORMATION: Synthetic construct, [00171] reverse primer 3662

<400> SEQUENCE: 201
ttgcaacaag ttctctttgc tt 22

<210> SEQ ID NO 202
<211> LENGTH: 372
<212> TYPE: DNA
<213> ORGANISM: Artificial Sequence
<220> FEATURE:
<223> OTHER INFORMATION: Synthetic cosntruct, Nb1A11

<400> SEQUENCE: 202
caagttcagt tacaggaaag cgggggaggt ttagttcagc ctgggggttc attgaggttg 60
agttgtgcag caagtggaaa tattttttct attaatacta tgggatggta tagacaagct 120
ccaggaaagc aaagagaact tgttgcaagt attactactg gaggaactac aaattacgaa 180
gatagtgtta aaggaagatt cactatttca agagataatg ctaagaaaac agtttatctt 240
cagatgaata gattgaagcc agaagataca gcagtttact actgtaatca tagaagatca 300
tactctggta gagattatcc tgtttatggt atggattatt ggggaaaagg gacattagtt 360
acagttagca gc 372

<210> SEQ ID NO 203
<211> LENGTH: 676
<212> TYPE: DNA
<213> ORGANISM: Artificial Sequence
<220> FEATURE:
<223> OTHER INFORMATION: Synthetic construct, Nb1A11:AtUBQ10i

<400> SEQUENCE: 203
caagttcagt tacaggaaag cgggggaggt ttagttcagc ctgggggttc attgaggttg 60
agttgtgcag caagtggaaa tattttttct attaatacta tgggatggta tagacaagct 120
ccaggtaaat ttctgtgttc cttattctct caaaatcttc gattttgttt tcgttcgatc 180

-continued

```
ccaatttcgt atatgttctt tggtttagat tctgttaatc ttagatcgaa gacgattttc    240

tgggtttgat cgttagatat catcttaatt ctcgattagg gtttcataga tatcatccga    300

tttgttcaaa taatttgagt tttgtcgaat aattactctt cgatttgtga tttctatcta    360

gatctggtgt tagtttctag tttgtgcgat cgaatttgtc gattaatctg agtttttctg    420

attaacagga aagcaaagag aacttgttgc aagtattact actggaggaa ctacaaatta    480

cgaagatagt gttaaaggaa gattcactat ttcaagagat aatgctaaga aaacagttta    540

tcttcagatg aatagattga agccagaaga tacagcagtt tactactgta atcatagaag    600

atcatactct ggtagagatt atcctgttta tggtatggat tattggggaa aagggacatt    660

agttacagtt agcagc                                                    676
```

<210> SEQ ID NO 204
<211> LENGTH: 1466
<212> TYPE: DNA
<213> ORGANISM: Artificial Sequence
<220> FEATURE:
<223> OTHER INFORMATION: Synthetic construct, prNbUbi1

<400> SEQUENCE: 204

```
catgaaagtc cacatcatca gctcgtccca aacatcacta ctagacccaa ctcgttcaat     60

cttctcgact acaacaaatg aaatccgctc atcaaggtgt ctgaggctga tctcaataaa    120

tggagggact aattgtatgg atcgaaatct gccccaaaat atttagggta aggtacattg    180

aagaaagagt catcgaggtc gatcaggaaa cgatcgagat gttaacaatg gtcgatgtcg    240

agcaccgcat gtagagttgt aacacctagt ttttagaata ggataataca aagaatattc    300

tattggatat cctttacact tatattatta gagtttgtta ggaaaatgac ccacataaat    360

aggaaaaaag acaatgaatg gagacaggtg acatttatct gatgagaaca gacttttgat    420

agaagatatt ttctctctca ctaagataca aacactacat tttcatcaag attcttgttc    480

atatcattgt acacttttct atcaaatctg aaataattta aatattctag gatttgtctg    540

tcactcatca ttgtcagacg ggataatcat gtactcatcc tttttggca aaccactttt    600

tctatttact taaatgccat ttattgatat ctattgctag tcattcctcc accgttgctc    660

atactttttt gcaatagtat gcatgttgat atcaatccac caccaaatct tctaacatta    720

atcatatttt cacaacttac atttataaat attattatta actaagttta actcactatt    780

atataaactc aattgtttta ctcgaaagtt acactattat attgagaatt acgtttccaa    840

actttttaag catttattgt gtaaccataa gagactttga ttttttaaaa attatttaga    900

ttttattaat gagaatggca caacattatg gtcaactatg tatttcatca ttaactaaat    960

agttagcact ttgattcttt cacatgaatt atgaatttat gatgggctca aattaaaatt   1020

aaattattca caaaaactta tttttatatt ctacgacacc cacttttcta gctttttccc   1080

gaaggggcgt gagagtgtca cacacgctcc aaatttccca accaaacaag gaaagggcag   1140

agaaagatag ctttagcgtg ttgttttggt gcactacacg tcattaggac acgtgtcatg   1200

atataatagg ccaatcccac gaggcggttt cgtcttgagt cggccatagt gtccataaat   1260

gagggctctc cgtcggtttc cccatcattc atcagattta tcttctatac ttcatcgcct   1320

tcatatttct ctctcaaggt ttgagaattt cttcaatttc tcgctttagc agttcttttt   1380

tattgaatca acgatttcgg catctaaagt cctaattttg aagttcattg ctttaattgt   1440

ttgttgttga ttttatatta ttacag                                        1466
```

<210> SEQ ID NO 205
<211> LENGTH: 90
<212> TYPE: DNA
<213> ORGANISM: Artificial Sequence
<220> FEATURE:
<223> OTHER INFORMATION: Synthetic construct, ssPR1a

<400> SEQUENCE: 205
atgggatttg ttctcttttc acaattgcct tcatttcttc ttgtctctac acttctctta 60
ttcctagtaa tatcccactc ttgccgtgcc 90

<210> SEQ ID NO 206
<211> LENGTH: 102
<212> TYPE: DNA
<213> ORGANISM: Artificial Sequence
<220> FEATURE:
<223> OTHER INFORMATION: Synthetic construct, myc:6xHis:KDEL

<400> SEQUENCE: 206
acttctggac caggaggaca aggagctgaa caaaagttga tttctgaaga ggatcttgga 60
gctcatcatc atcatcatca tggagcttct aaggatgaac tt 102

<210> SEQ ID NO 207
<211> LENGTH: 149
<212> TYPE: PRT
<213> ORGANISM: Llama glama
<220> FEATURE:
<221> NAME/KEY: MISC_FEATURE
<222> LOCATION: (1)..(149)
<223> OTHER INFORMATION: Llama Il-10

<400> SEQUENCE: 207

Glu Asn Ser Cys Ala His Phe Pro Ala Ser Leu Pro His Met Leu Arg
1 5 10 15

Glu Leu Arg Ala Ala Phe Gly Arg Val Lys Thr Phe Phe Gln Met Lys
20 25 30

Asp Gln Leu Asp Asn Met Leu Leu Thr Arg Ser Leu Leu Glu Asp Phe
35 40 45

Lys Gly Tyr Leu Gly Cys Gln Ala Leu Ser Glu Met Ile Gln Phe Tyr
50 55 60

Leu Glu Glu Val Met Pro Gln Ala Glu Asn His Gly Pro Asp Ile Lys
65 70 75 80

Glu His Val Asn Ser Leu Gly Glu Lys Leu Lys Thr Leu Arg Leu Arg
85 90 95

Leu Arg Arg Cys His Arg Phe Leu Pro Cys Glu Asn Lys Ser Lys Ala
100 105 110

Val Glu Gln Val Arg Gly Val Phe Ser Lys Leu Gln Glu Lys Gly Val
115 120 125

Tyr Lys Ala Met Ser Glu Phe Asp Ile Phe Ile Asn Tyr Ile Glu Ala
130 135 140

Tyr Met Thr Met Lys
145

<210> SEQ ID NO 208
<211> LENGTH: 154
<212> TYPE: PRT
<213> ORGANISM: Artificial Sequence
<220> FEATURE:
<223> OTHER INFORMATION: Synthetic construct, 40-IL-bR2-1H5 (FIG.4)

<400> SEQUENCE: 208

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Asn Ser Tyr
            20                  25                  30

Ala Trp Gly Trp Phe Arg Gln Ala Pro Gly Lys Glu Arg Gly Phe Val
        35                  40                  45

Ala Arg Ile Ser Phe Ser Gly Gly His Thr Tyr Tyr Ser Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Lys Pro Glu Asp Thr Ala Val Tyr Tyr Cys
                85                  90                  95

Ala Ala Asp Pro Thr Pro Tyr Gly Leu Arg Asn Glu Arg Asn Tyr His
            100                 105                 110

Tyr Trp Gly Gln Gly Thr Gln Val Thr Val Ser Ser Thr Ser Gly Pro
        115                 120                 125

Gly Gly Gln Gly Ala Glu Gln Lys Leu Ile Ser Glu Glu Asp Leu Gly
    130                 135                 140

Ala His His His His His His Gly Ala Ser
145                 150
```

<210> SEQ ID NO 209
<211> LENGTH: 7
<212> TYPE: PRT
<213> ORGANISM: Artificial Sequence
<220> FEATURE:
<223> OTHER INFORMATION: Synthetic construct, 68-IL-bR2-1D9_ AA 28 - 34

<400> SEQUENCE: 209

```
Arg Leu Ser Ile Asn Val Met
1               5
```

<210> SEQ ID NO 210
<211> LENGTH: 4
<212> TYPE: PRT
<213> ORGANISM: Artificial Sequence
<220> FEATURE:
<223> OTHER INFORMATION: Synthetic construct, 68-IL-bR2-1D9_AA 54-57

<400> SEQUENCE: 210

```
Asn Ser Arg Ser
1
```

<210> SEQ ID NO 211
<211> LENGTH: 5
<212> TYPE: PRT
<213> ORGANISM: Artificial Sequence
<220> FEATURE:
<223> OTHER INFORMATION: Synthetic construct, 03-IL-bR2-1C1_AA 30-34

<400> SEQUENCE: 211

```
Ser Ile Asn Thr Met
1               5
```

<210> SEQ ID NO 212
<211> LENGTH: 7
<212> TYPE: PRT
<213> ORGANISM: Artificial Sequence
<220> FEATURE:
<223> OTHER INFORMATION: Synthetic construct, 03-IL-bR2-1C1 AA 97-103

<400> SEQUENCE: 212

Asn His Arg Arg Ser Tyr Ser
1 5

<210> SEQ ID NO 213
<211> LENGTH: 9
<212> TYPE: PRT
<213> ORGANISM: Artificial Sequence
<220> FEATURE:
<223> OTHER INFORMATION: Synthetic construct, 03-IL-bR2-1C1_AA105-112

<400> SEQUENCE: 213

Arg Asp Tyr Pro Val Tyr Gly Met Asp
1 5

<210> SEQ ID NO 214
<211> LENGTH: 5
<212> TYPE: PRT
<213> ORGANISM: Artificial Sequence
<220> FEATURE:
<223> OTHER INFORMATION: Synthetic construct, 35-IL-bR2-1C5_AA 30-34

<400> SEQUENCE: 214

Gly Ile Asn Val Met
1 5

<210> SEQ ID NO 215
<211> LENGTH: 5
<212> TYPE: PRT
<213> ORGANISM: Artificial Sequence
<220> FEATURE:
<223> OTHER INFORMATION: Synthetic construct, 35-IL-bR2-1C5_AA 50 -54

<400> SEQUENCE: 215

Thr Val Thr Thr Gly
1 5

<210> SEQ ID NO 216
<211> LENGTH: 8
<212> TYPE: PRT
<213> ORGANISM: Artificial Sequence
<220> FEATURE:
<223> OTHER INFORMATION: Synthetic construct, 48-IL-bR2-1H6_AA 27-34

<400> SEQUENCE: 216

Ser Ile Ser Ser Ile Asp Gly Met
1 5

<210> SEQ ID NO 217
<211> LENGTH: 5
<212> TYPE: PRT
<213> ORGANISM: Artificial Sequence
<220> FEATURE:
<223> OTHER INFORMATION: Synthetic construct, 48-IL-bR2-1H6_AA 75-79

<400> SEQUENCE: 217

Asp Gln Thr Thr Leu
1 5

<210> SEQ ID NO 218
<211> LENGTH: 9
<212> TYPE: PRT
<213> ORGANISM: Artificial Sequence
<220> FEATURE:
<223> OTHER INFORMATION: Synthetic construct, 48-IL-bR2-1H6_AA 105 - 112

<400> SEQUENCE: 218

Val Pro Asp Trp Tyr Tyr Gly Met Asp 1 5

<210> SEQ ID NO 219
<211> LENGTH: 4
<212> TYPE: PRT
<213> ORGANISM: Artificial Sequence
<220> FEATURE:
<223> OTHER INFORMATION: Synthetic construct, 01-IL-bR2-2A8_AA 76-79

<400> SEQUENCE: 219

Gln Thr Thr Leu
1

<210> SEQ ID NO 220
<211> LENGTH: 7
<212> TYPE: PRT
<213> ORGANISM: Artificial Sequence
<220> FEATURE:
<223> OTHER INFORMATION: Synthetic construct, 85-IL-bR2-1E11_AA 102-108

<400> SEQUENCE: 220

Ala Ser Leu Ser Ile Tyr Arg
1 5

<210> SEQ ID NO 221
<211> LENGTH: 9
<212> TYPE: PRT
<213> ORGANISM: Artificial Sequence
<220> FEATURE:
<223> OTHER INFORMATION: Synthetic construct, 44-IL-bR2-1D6_AA 26 - 34

<400> SEQUENCE: 221

Glu Ser Ile Ser Ser Ile Asn Thr Met
1 5

<210> SEQ ID NO 222
<211> LENGTH: 4
<212> TYPE: PRT
<213> ORGANISM: Artificial Sequence
<220> FEATURE:
<223> OTHER INFORMATION: Synthetic construct, 44-IL-bR2-1D6_AA 99-102

<400> SEQUENCE: 222

Gly Val Pro Thr
1

<210> SEQ ID NO 223
<211> LENGTH: 11
<212> TYPE: PRT
<213> ORGANISM: Artificial Sequence
<220> FEATURE:
<223> OTHER INFORMATION: Synthetic construct, 44-IL-bR2-1D6_AA 104-113

<400> SEQUENCE: 223

Asp Asp Asp Ala Met Pro Ile Ser Trp Arg Phe
1 5 10

<210> SEQ ID NO 224
<211> LENGTH: 5
<212> TYPE: PRT
<213> ORGANISM: Artificial Sequence
<220> FEATURE:
<223> OTHER INFORMATION: Synthetic construct, 27-IL-bR2-1C4_AA 27 - 31

<400> SEQUENCE: 224

Phe Ser Leu Glu Asn
1 5

<210> SEQ ID NO 225
<211> LENGTH: 5
<212> TYPE: PRT
<213> ORGANISM: Artificial Sequence
<220> FEATURE:
<223> OTHER INFORMATION: Synthetic construct, 27-IL-bR2-1C4_AA 46 - 50

<400> SEQUENCE: 225

Glu Gly Leu Ser Cys
1               5

<210> SEQ ID NO 226
<211> LENGTH: 9
<212> TYPE: PRT
<213> ORGANISM: Artificial Sequence
<220> FEATURE:
<223> OTHER INFORMATION: Synthetic construct, 27-IL-bR2-1C4_AA 53-61

<400> SEQUENCE: 226

Ser Thr Asp Asp Ser Ile Phe Ser Val
1               5

<210> SEQ ID NO 227
<211> LENGTH: 8
<212> TYPE: PRT
<213> ORGANISM: Artificial Sequence
<220> FEATURE:
<223> OTHER INFORMATION: Synthetic construct, 27-IL-bR2-1C4_AA 98-105

<400> SEQUENCE: 227

Thr Ser Arg Gly Leu Gly Ser Cys
1               5

<210> SEQ ID NO 228
<211> LENGTH: 6
<212> TYPE: PRT
<213> ORGANISM: Artificial Sequence
<220> FEATURE:
<223> OTHER INFORMATION: Synthetic construct, 32-IL-bR2-1H4_AA 52 - 57

<400> SEQUENCE: 228

Thr Asn Ala Asp Arg Ile
1               5

<210> SEQ ID NO 229
<211> LENGTH: 5
<212> TYPE: PRT
<213> ORGANISM: Artificial Sequence
<220> FEATURE:
<223> OTHER INFORMATION: Synthetic construct, 32-IL-bR2-1H4_AA 98 - 102

<400> SEQUENCE: 229

Thr Asn Phe Tyr Ser
1               5

<210> SEQ ID NO 230
<211> LENGTH: 5
<212> TYPE: PRT
<213> ORGANISM: Artificial Sequence
<220> FEATURE:
<223> OTHER INFORMATION: Synthetic construct, 86-IL-bR2-1F11_AA 100-104

<400> SEQUENCE: 230

Arg Asn Leu Phe Lys
1               5

<210> SEQ ID NO 231
<211> LENGTH: 5
<212> TYPE: PRT
<213> ORGANISM: Artificial Sequence
<220> FEATURE:
<223> OTHER INFORMATION: Synthetic construct, 86-IL-bR2-1F11_AA 107-110

<400> SEQUENCE: 231

Val Ala Val Gln Glu
1 5

<210> SEQ ID NO 232
<211> LENGTH: 4
<212> TYPE: PRT
<213> ORGANISM: Artificial Sequence
<220> FEATURE:
<223> OTHER INFORMATION: Synthetic construct, 20-IL-bR2-1D3_AA 44 - 47

<400> SEQUENCE: 232

Gly Leu Glu Trp
1

<210> SEQ ID NO 233
<211> LENGTH: 4
<212> TYPE: PRT
<213> ORGANISM: Artificial Sequence
<220> FEATURE:
<223> OTHER INFORMATION: Synthetic construct, 20-IL-bR2-1D3_AA 52-55

<400> SEQUENCE: 233

Thr Trp Asn Val
1

<210> SEQ ID NO 234
<211> LENGTH: 8
<212> TYPE: PRT
<213> ORGANISM: Artificial Sequence
<220> FEATURE:
<223> OTHER INFORMATION: Synthetic construct, 20-IL-bR2-1D3_AA 100-107

<400> SEQUENCE: 234

Gly Ile Ala Pro Arg Arg Tyr Tyr
1 5

<210> SEQ ID NO 235
<211> LENGTH: 9
<212> TYPE: PRT
<213> ORGANISM: Artificial Sequence
<220> FEATURE:
<223> OTHER INFORMATION: Synthetic construct, 49-IL-bR2-1A7_AA 27 - 35

<400> SEQUENCE: 235

Asn Ile Tyr Asp Ile Asn Thr Met Ala
1 5

<210> SEQ ID NO 236
<211> LENGTH: 13
<212> TYPE: PRT
<213> ORGANISM: Artificial Sequence
<220> FEATURE:
<223> OTHER INFORMATION: Synthetic construct, 49-IL-bR2-1A7_AA 97-109

<400> SEQUENCE: 236

Asn Val Lys Thr Gly Arg Gly Arg Asn Leu Tyr Ser Asp
1 5 10

<210> SEQ ID NO 237
<211> LENGTH: 8
<212> TYPE: PRT
<213> ORGANISM: Artificial Sequence
<220> FEATURE:
<223> OTHER INFORMATION: Synthetic construct, 24-IL-bR2-1H3_AA 27 - 34

<400> SEQUENCE: 237

Ser Ile Ser Ser Ile Asp Thr Met
1               5

<210> SEQ ID NO 238
<211> LENGTH: 4
<212> TYPE: PRT
<213> ORGANISM: Artificial Sequence
<220> FEATURE:
<223> OTHER INFORMATION: Synthetic construct, 24-IL-bR2-1H3_AA 98-101

<400> SEQUENCE: 238

Val Val Val Ser
1

<210> SEQ ID NO 239
<211> LENGTH: 6
<212> TYPE: PRT
<213> ORGANISM: Artificial Sequence
<220> FEATURE:
<223> OTHER INFORMATION: Synthetic construct, 24-IL-bR2-1H3_AA 103 - 108

<400> SEQUENCE: 239

Thr Leu Ile Ala Gly Ser
1               5

<210> SEQ ID NO 240
<211> LENGTH: 10
<212> TYPE: PRT
<213> ORGANISM: Artificial Sequence
<220> FEATURE:
<223> OTHER INFORMATION: Synthetic construct, 58-IL-bR2-1B8-_AA 26-35

<400> SEQUENCE: 240

Glu Ser Ile Asp Thr Phe Asp Ile Ile Asp
1               5                   10

<210> SEQ ID NO 241
<211> LENGTH: 18
<212> TYPE: PRT
<213> ORGANISM: Artificial Sequence
<220> FEATURE:
<223> OTHER INFORMATION: Synthetic construct, 58-IL-bR2-1B8_AA 46 - 61

<400> SEQUENCE: 241

Asp Gln Arg Glu Leu Val Ala Gln Met Leu Pro Val Gly Ala Thr Thr
1               5                   10                  15

Tyr Ala

<210> SEQ ID NO 242
<211> LENGTH: 11
<212> TYPE: PRT
<213> ORGANISM: Artificial Sequence
<220> FEATURE:
<223> OTHER INFORMATION: Synthetic construct, 58-IL-bR2-1B8_AA 97-107

<400> SEQUENCE: 242

His Ser Ile Asn Arg Asp His Asn Ile Trp Cys
1               5                   10

```
<210> SEQ ID NO 243
<211> LENGTH: 6
<212> TYPE: PRT
<213> ORGANISM: Artificial Sequence
<220> FEATURE:
<223> OTHER INFORMATION: Synthetic construct, 10-IL-bR2-1B2_AA 27 - 32

<400> SEQUENCE: 243

Val Ile Pro Asp Ala Ser
1               5


<210> SEQ ID NO 244
<211> LENGTH: 7
<212> TYPE: PRT
<213> ORGANISM: Artificial Sequence
<220> FEATURE:
<223> OTHER INFORMATION: Synthetic construct, 10-IL-bR2-1B2_AA 52-59

<400> SEQUENCE: 244

Val Gly Pro Thr Asn Ile Leu
1               5


<210> SEQ ID NO 245
<211> LENGTH: 6
<212> TYPE: PRT
<213> ORGANISM: Artificial Sequence
<220> FEATURE:
<223> OTHER INFORMATION: Synthetic construct, 10-IL-bR2-1B2_AA75-80

<400> SEQUENCE: 245

Gly Gly Asp Thr Ile Ser
1               5


<210> SEQ ID NO 246
<211> LENGTH: 8
<212> TYPE: PRT
<213> ORGANISM: Artificial Sequence
<220> FEATURE:
<223> OTHER INFORMATION: Synthetic construct, 10-IL-bR2-1B2_AA 97-104

<400> SEQUENCE: 246

Asn Leu Leu Gln Ser Gly Thr Asn
1               5


<210> SEQ ID NO 247
<211> LENGTH: 5
<212> TYPE: PRT
<213> ORGANISM: Artificial Sequence
<220> FEATURE:
<223> OTHER INFORMATION: Synthetic construct, 12-IL-bR2-1D2_AA 30-34

<400> SEQUENCE: 247

Ser Arg Asn Thr Met
1               5


<210> SEQ ID NO 248
<211> LENGTH: 4
<212> TYPE: PRT
<213> ORGANISM: Artificial Sequence
<220> FEATURE:
<223> OTHER INFORMATION: Synthetic construct, 12-IL-bR2-1D2_AA 55-58

<400> SEQUENCE: 248

Asp Ile Thr Asn
1
```

-continued

```
<210> SEQ ID NO 249
<211> LENGTH: 5
<212> TYPE: PRT
<213> ORGANISM: Artificial Sequence
<220> FEATURE:
<223> OTHER INFORMATION: Synthetic construct, 76-IL-bR2-1D10_AA 99-103

<400> SEQUENCE: 249

Ile Arg Gly Val Asn
1               5
```